US012747257B2

(12) United States Patent
Wang et al.

(10) Patent No.: US 12,747,257 B2

(45) Date of Patent: Sep. 29, 2026

(54) POLYHYDROXYLATED CYCLOPENTANE DERIVATIVES AND METHODS OF USE

(71) Applicant: Sanegene Bio USA Inc., Cambridge, MA (US)

(72) Inventors: Weimin Wang, Cambridge, MA (US); Xiaochuan Cai, Cambridge, MA (US)

(73) Assignee: Sanegene Bio USA Inc., Woburn, MA (US)

(*) Notice: Subject to any disclaimer, the term of this patent is extended or adjusted under 35 U.S.C. 154(b) by 100 days.

(21) Appl. No.: 17/960,202

(22) Filed: Oct. 5, 2022

(65) Prior Publication Data

US 2023/0227480 A1 Jul. 20, 2023

Related U.S. Application Data

(60) Provisional application No. 63/252,358, filed on Oct. 5, 2021.

(51) Int. Cl.

*C07F 9/22* (2006.01)

*C07H 21/00* (2006.01)

(52) U.S. Cl.

CPC ............. *C07F 9/222* (2013.01); *C07H 21/00* (2013.01)

(58) Field of Classification Search

CPC ......... C07F 9/222; C07H 21/00; C07H 15/18; C07H 21/02; C07H 21/04

See application file for complete search history.

(56) References Cited

U.S. PATENT DOCUMENTS

| | | | | |
|---|---|---|---|---|
| 12,465,647 | B2 * | 11/2025 | Wang | A61K 47/549 |
| 2009/0239814 | A1 | 9/2009 | Manoharan et al. | |
| 2009/0247608 | A1 | 10/2009 | Manoharan et al. | |
| 2012/0136042 | A1 | 5/2012 | Manoharan et al. | |
| 2013/0158824 | A1 | 6/2013 | Nassouri et al. | |
| 2019/0160176 | A1 * | 5/2019 | Heyes | A61P 9/00 |
| 2023/0138928 | A1 * | 5/2023 | Wang | C07H 13/00 514/44 A |

FOREIGN PATENT DOCUMENTS

| | | | | |
|---|---|---|---|---|
| WO | WO-2009073809 A2 | 6/2009 | | |
| WO | WO-2009082607 A2 | 7/2009 | | |
| WO | WO-2012089352 A1 | 7/2012 | | |
| WO | WO-2012101095 A1 | 8/2012 | | |
| WO | WO-2015006740 A2 | 1/2015 | | |
| WO | WO-2016100401 A1 | 6/2016 | | |
| WO | WO-2017214112 A1 | 12/2017 | | |
| WO | WO-2018039364 A1 | 3/2018 | | |
| WO | WO-2018045317 A1 | 3/2018 | | |
| WO | WO-2019092660 A1 | 5/2019 | | |
| WO | WO-2019211799 A1 | 11/2019 | | |
| WO | WO2020093061 A1 | 5/2020 | | |
| WO | WO2021113820 A1 | 6/2021 | | |
| WO | WO-2023274395 A1 * | 1/2023 | | A61K 31/713 |

OTHER PUBLICATIONS

Ozcan, G.; et al. "Preclinical and clinical development of siRNA-based therapeutics" 2015, Advanced Drug Delivery Reviews, vol. 87, pp. 108-119. (Year: 2015).*

Damha, M. J.; et al. "An improved procedure for derivatization of controlled-pore glass beads for solid-phase oligonucleotide synthesis" 1990, Nucleic Acids Research, vol. 18, pp. 3813-3821. (Year: 1990).*

Manoharan, M.; et al. "Unique Gene-Silencing and Structural Properties of 2'-Fluoro-Modified siRNAs" 2011, Angewandte Chemie International Edition, vol. 50, pp. 2189-2406. (Year: 2011).*

Wolfrum, C.; et al. "Mechanisms and optimization of in vivo delivery of lipophilic siRNAs" 2007, Nature Biotechnology, vol. 25, pp. 1149-1157. (Year: 2007).*

Ashley, C. E.; et al. "Delivery of Small Interfering RNA by Peptide-Targeted Mesoporous Silica Nanoparticle-Supported Lipid Bilayers" 2012, ACS Nano, vol. 6, pp. 2174-2188. (Year: 2012).*

English language translation of WO 2023274395 A1; translated Aug. 1, 2024. (Year: 2023).*

Rajeev, K. G.; et al. ":Hepatocyte-Specific Delivery of siRNAs Conjugated to Novel Non-nucleosidic Trivalent N-Acetylgalactosamine Elicits Robust Gene Silencing in Vivo" 2015 ChemBioChem, vol. 16, pp. 903-908. (Year: 2015).*

Winkler et al. "Oligonucleotide conjugates for therapeutic applications", Ther Deliv. Jul. 2013; 4(7): 791-809.

Antle Vincent D. et al. "Substrate Specificity of Human Glycinamide Ribonucleotide Transformylase", Archives of Biochemistry and Biophysics, . vol. 370, No. 2, Oct. 1, 1999, pp. 231-235.

(Continued)

*Primary Examiner* — Andrea Olson

*Assistant Examiner* — Benjamin M Brandsen

(74) *Attorney, Agent, or Firm* — Fenwick & West LLP; Chen Chen; Nina Gu

(57) ABSTRACT

The present disclosure provides linker compounds of Formula (I) or (II):

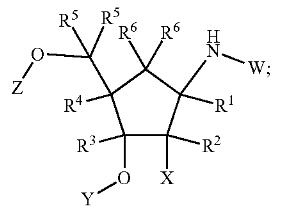

(I)

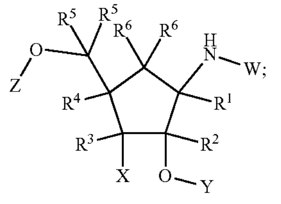

(II)

pharmaceutically acceptable salts thereof, and related scaffolds and conjugates. The present disclosure also relates to uses of the linker compounds, scaffolds, and conjugates, e.g., in delivering nucleic acid and/or treating or preventing diseases.

19 Claims, 1 Drawing Sheet

(56) References Cited

OTHER PUBLICATIONS

Biggadike Keith et al. "Synthesis of fluorinated carbocyclic nucleosides: preparation of (±))-carbocyclic-FMAU and some congeners", Journal of the Chemical Society, Chemical Communications, No. 4, Jan. 1, 1987, pp. 251-254.
Busch, Florian et al. "Dissecting the Differences between the [alpha] and [beta] Anomers of the Oxidative DNA Lesion FaPydG", Chemistry—A European Journal, John Wiley & Sons, Inc, DE, vol. 14, No. 7, Jan. 14, 2008, pp. 2125-2132.
Caperelli C.A. et al. "Carbocyclic substrates for de Novo purine biosynthesis. Enantiospecific synthesis and enantiospecificity of enzymatic utilization", Journal of Biological Chemistry, vol. 267, No. 14, May 1, 1992, pp. 9783-9787.
Jadhav, Satish et al. "Solid-Supported Porphyrins Useful for the Synthesis of Conjugates with Oligomeric Biomolecules", Bioconjugate Chemistry, vol. 27, No. 4, Apr. 20, 2016, pp. 1023-1029.
Lehmann, Thomas E et al. "Triple-Helix Formation by Pyrimidine Oligonucleotides Containing Nonnatural Nucleosides with Extended Aromatic Nucleobases: Intercalation from the major groove as a method for recognizing C.G and T.A base pairs", Helvetica Chimica Acta, Verlag Helvetica Chimica Acta, Hoboken, USA, vol. 80, No. 6, 1997, pp. 2002-2022.
Mueller Heiko et al. "Synthesis of a Stabilized Version of the Imidazolone DNA Lesion", Chembiochem, vol. 9, No. 10, Jul. 2, 2008, pp. 1617-1622.
Palmer C F et al. "Electrophilic substitution of a 2-azabicyclo[2.2.1]hept-5-en-3-one as a potential route to 3-deoxycarbocyclic nucleosides", Journal of the Chemical Society, Perkin Transactions 1, Royal Society of Chemistry, Cambridge, UK, Jan. 1, 1991, pp. 484-486.
Rydzik Anna M. et al.: "Access to 1 '-Amino Carbocyclic Phosphoramidite to Enable Postsynthetic Functionalization of Oligonucleotides", Organic Letters, vol. 23, No. 17, Aug. 23, 2021, pp. 6735-6739.

* cited by examiner

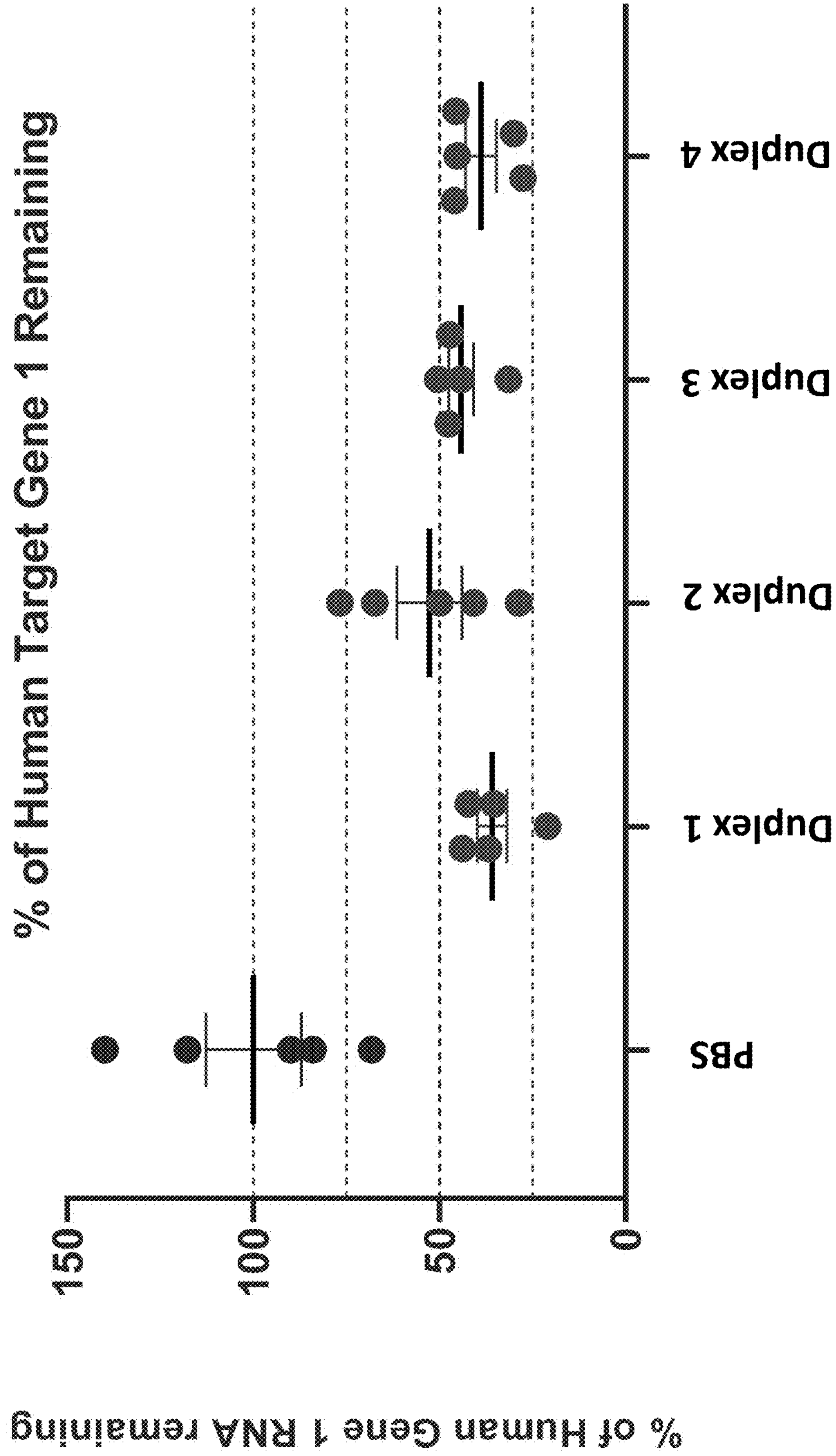
% of Human Target Gene 1 Remaining
150
100
50
0
PBS
Duplex 1
Duplex 2
Duplex 3
Duplex 4
% of Human Gene 1 RNA remaining

POLYHYDROXYLATED CYCLOPENTANE DERIVATIVES AND METHODS OF USE

RELATED APPLICATION

This application claims priority to, and the benefit of, U.S. Application No. 63/252,358, filed on Oct. 5, 2021, the entire contents of which are incorporated herein by reference.

BACKGROUND

Efficient delivery of genetic materials such as RNA to cells in vivo requires specific targeting and protection from the extracellular environment, particularly serum proteins. One method of achieving specific targeting is to conjugate a targeting moiety to the nucleic acid (e.g., oligonucleotide). The targeting moiety helps direct the nucleic acid to the site of interest. A targeting moiety can improve delivery by receptor-mediated endocytosis. This process is initiated via activation of a cell-surface or membrane receptor following binding of a specific ligand to the receptor. Many receptor-mediated endocytotic systems are known, including those that recognize sugars such as galactose, mannose, mannose-6-phosphate, peptides and proteins such as transferrin, asialoglycoprotein, vitamin B12, insulin, and epidermal growth factor (EGF). The asialoglycoprotein receptor (ASGP-R) is a high capacity receptor and is highly abundant on hepatocytes. The ASGP-R shows a high affinity for N-Acetyl-D-Galactosylamine (GalNAc) than D-Gal. Recently, certain carbohydrate conjugates have been shown to be a valuable alternative to liposomes for nucleic acid delivery. Moreover, after successful delivery into cells, the stability of the nucleic acid in the cellular environment is important for achieving the desirable therapeutic effects.

Thus, there continues to be a need for novel linkers and conjugates for nucleic acid delivery. The present disclosure addresses this need.

SUMMARY

In some aspects, the present disclosure provides a compound of Formula (I) or (II):

(I)

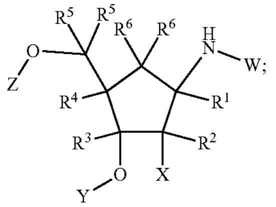

(II)

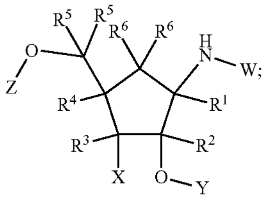

or a pharmaceutically acceptable salt thereof, wherein:

W is H, $C_1$-$C_6$ alkyl optionally substituted with one or more halogen, or an amino substitution group;

X is H, halogen, or —$OR^X$;

$R^X$ is H, $C_1$-$C_6$ alkyl, or —($C_1$-$C_6$ alkyl)-($C_6$-$C_{10}$ aryl), wherein the $C_1$-$C_6$ alkyl or —($C_1$-$C_6$ alkyl)-($C_6$-$C_{10}$ aryl) is optionally substituted with one or more $R^{Xa}$;

each $R^{Xa}$ independently is halogen, $C_1$-$C_6$ alkyl, or —O—($C_1$-$C_6$ alkyl), wherein the $C_1$-$C_6$ alkyl or —O—($C_1$-$C_6$ alkyl) is optionally substituted with one or more halogen;

Y is H, $C_1$-$C_6$ alkyl optionally substituted with one or more halogen, —$P(R^Y)_2$, —$P(OR^Y)(N(R^Y)_2)$, —$P(=O)(OR^Y)R^Y$, —$P(=S)(OR^Y)R^Y$, —$P(=O)(SR^Y)R^Y$, —$P(=S)(SR^Y)R^Y$, —$P(=O)(OR^Y)_2$, —$P(=S)(OR^Y)_2$, —$P(=O)(SR^Y)_2$, —$P(=S)(SR^Y)_2$, or a hydroxy protecting group;

each $R^Y$ independently is H or $C_1$-$C_6$ alkyl optionally substituted with one or more halogen or cyano;

Z is H, or $C_1$-$C_6$ alkyl optionally substituted with one or more halogen, —$P(R^Z)_2$, —$P(OR^Z)(N(R^Z)_2)$, —$P(=O)(OR^Z)R^Z$, —$P(=S)(OR^Z)R^Z$, —$P(=O)(SR^Z)R^Z$, —$P(=S)(SR^Z)R^Z$, —$P(=O)(OR^Z)_2$, —$P(=S)(OR^Z)_2$, —$P(=O)(SR^Z)_2$, —$P(=S)(SR^Z)_2$, or a hydroxy protecting group; each $R^Z$ independently is H or $C_1$-$C_6$ alkyl optionally substituted with one or more halogen or cyano;

or Y and Z in Formula (I), together form —$Si(R^L)_2$—O—$Si(R^L)_2$—, wherein each $R^L$ independently is H or $C_1$-$C_6$ alkyl;

$R^1$ is H, halogen, or $C_1$-$C_6$ alkyl optionally substituted with one or more halogen;

$R^2$ is H, halogen, or $C_1$-$C_6$ alkyl optionally substituted with one or more halogen;

$R^3$ is H, halogen, or $C_1$-$C_6$ alkyl optionally substituted with one or more halogen;

$R^4$ is H, halogen, or $C_1$-$C_6$ alkyl optionally substituted with one or more halogen;

each $R^5$ independently is H, halogen, or $C_1$-$C_6$ alkyl optionally substituted with one or more halogen; and each $R^6$ independently is H, halogen, or $C_1$-$C_6$ alkyl optionally substituted with one or more halogen.

In some aspects, the present disclosure provides a scaffold or a pharmaceutically acceptable salt thereof, wherein the scaffold comprises:

(i) a Ligand; and (ii) a Linker Unit, wherein the Linker Unit is:

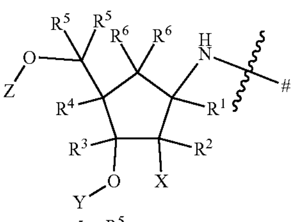

or

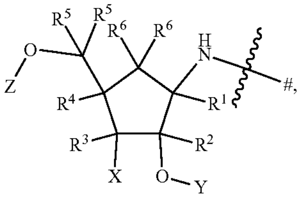

wherein variables $R^1$, $R^2$, $R^3$, $R^4$, $R^5$, $R^6$, X, Y, and Z are described herein, and # indicates an attachment to the Ligand.

In some aspects, the present disclosure provides a scaffold or a pharmaceutically acceptable salt thereof, wherein the scaffold comprises:

(i) one or more Nucleic Acid Agent; and (ii) one or more Linker Unit, wherein each Linker Unit independently is:

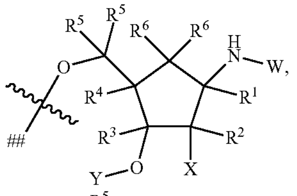

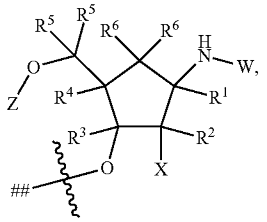

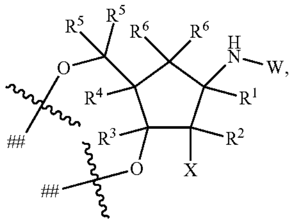

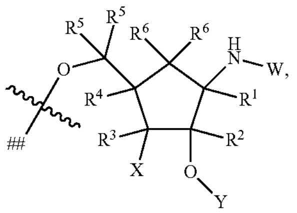

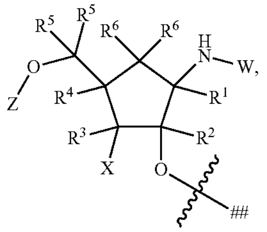

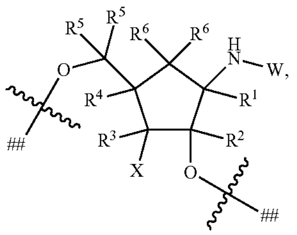

wherein variables $R^1$, $R^2$, $R^3$, $R^4$, $R^5$, $R^6$, W, X, Y, and Z are described herein, and ## indicates an attachment to the Nucleic Acid Agent.

In some aspects, the present disclosure provides a conjugate or a pharmaceutically acceptable salt thereof, wherein the conjugate comprises:

(i) one or more Nucleic Acid Agent;

(ii) one or more Ligand; and (iii) one or more Linker Unit, wherein each Linker Unit independently is:

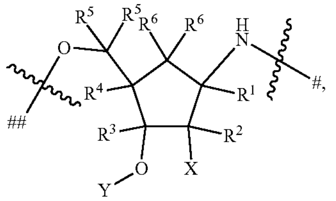

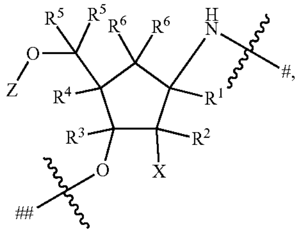

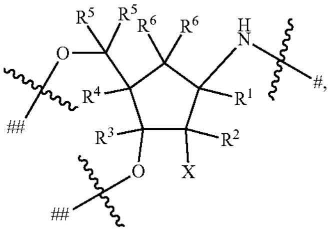

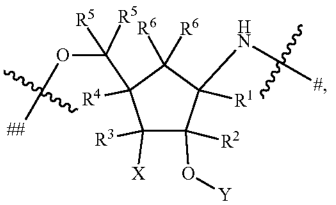

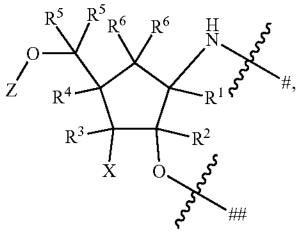

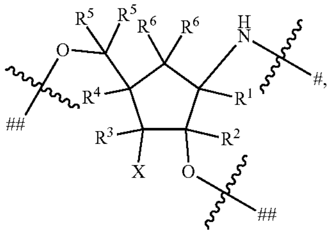

wherein variables $R^1$, $R^2$, $R^3$, $R^4$, $R^5$, $R^6$, X, Y, and Z are described herein, # indicates an attachment to the Ligand, and ## indicates an attachment to the Nucleic Acid Agent.

In some aspects, the present disclosure provides a compound being an isotopic derivative of a compound disclosed herein.

In some aspects, the present disclosure provides a pharmaceutical composition comprising a compound, scaffold, or conjugate described herein.

In some aspects, the present disclosure provides a method of modulating the expression of a target gene in a subject, comprising administering to the subject a conjugate described herein.

In some aspects, the present disclosure provides a method of delivering a Nucleic Acid Agent to a subject, comprising administering to the subject a conjugate described herein.

In some aspects, the present disclosure provides a method of treating or preventing a disease in a subject in need thereof, comprising administering to the subject a therapeutically effective amount of a conjugate described herein.

In some aspects, the present disclosure provides a use of a conjugate described herein in the manufacture of a medicament for modulating the expression of a target gene in a subject.

In some aspects, the present disclosure provides a use of a conjugate described herein in the manufacture of a medicament for delivering a Nucleic Acid Agent to a subject.

In some aspects, the present disclosure provides a use of a conjugate described herein in the manufacture of a medicament for treating or preventing a disease in a subject in need thereof.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims.

BRIEF DESCRIPTION OF DRAWINGS

FIG. 1 is a graph showing the gene silencing activity of siRNA duplexes in liver on day 5 after a single 0.5 mg/kg s.c. injection of CD-1 female mice, followed by HDI dosing on day 4 (human gene 1 plasmid, 10 μg).

DETAILED DESCRIPTION

The present disclosure provides compounds, linkers, scaffolds, and conjugates described herein for nucleic acid delivery. The present disclosure also relates to uses of the compounds, linkers, scaffolds, and conjugates, e.g., in delivering nucleic acid and/or treating or preventing diseases.

Linker Compounds of the Present Disclosure

In some aspects, the present disclosure provides a compound of Formula (I) or (II):

(I)

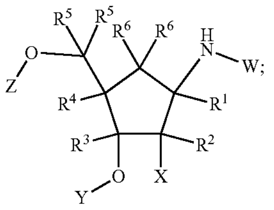

-continued (II)

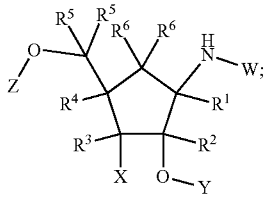

or a pharmaceutically acceptable salt thereof, wherein:

W is H, $C_1$-$C_6$ alkyl optionally substituted with one or more halogen, or an amino substitution group;

X is H, halogen, or —$OR^X$;

$R^X$ is H, $C_1$-$C_6$ alkyl, or —($C_1$-$C_6$ alkyl)-($C_6$-$C_{10}$ aryl), wherein the $C_1$-$C_6$ alkyl or —($C_1$-$C_6$ alkyl)-($C_6$-$C_{10}$ aryl) is optionally substituted with one or more $R^{Xa}$;

each $R^{Xa}$ independently is halogen, $C_1$-$C_6$ alkyl, or —O—($C_1$-$C_6$ alkyl), wherein the $C_1$-$C_6$ alkyl or —O—($C_1$-$C_6$ alkyl) is optionally substituted with one or more halogen;

Y is H, $C_1$-$C_6$ alkyl optionally substituted with one or more halogen, —$P(R^Y)_2$, —$P(OR^Y)(N(R^Y)_2)$, —$P(=O)(OR^Y)R^Y$, —$P(=S)(OR^Y)R^Y$, —$P(=O)(SR^Y)R^Y$, —$P(=S)(SR^Y)R^Y$, —$P(=O)(OR^Y)_2$, —$P(=S)(OR^Y)_2$, —$P(=O)(SR^Y)_2$, —$P(=S)(SR^Y)_2$, or a hydroxy protecting group;

each $R^Y$ independently is H or $C_1$-$C_6$ alkyl optionally substituted with one or more halogen or cyano;

Z is H, or $C_1$-$C_6$ alkyl optionally substituted with one or more halogen, —$P(R^Z)_2$, —$P(OR^Z)(N(R^Z)_2)$, —$P(=O)(OR^Z)R^Z$, —$P(=S)(OR^Z)R^Z$, —$P(=O)(SR^Z)R^Z$, —$P(=S)(SR^Z)R^Z$, —$P(=O)(OR^Z)_2$, —$P(=S)(OR^Z)_2$, —$P(=O)(SR^Z)_2$, —$P(=S)(SR^Z)_2$, or a hydroxy protecting group;

each $R^Z$ independently is H or $C_1$-$C_6$ alkyl optionally substituted with one or more halogen or cyano;

or Y and Z in Formula (I), together form —$Si(R^L)_2$—O—$Si(R^L)_2$—, wherein each $R^L$ independently is H or $C_1$-$C_6$ alkyl;

$R^1$ is H, halogen, or $C_1$-$C_6$ alkyl optionally substituted with one or more halogen;

$R^2$ is H, halogen, or $C_1$-$C_6$ alkyl optionally substituted with one or more halogen;

$R^3$ is H, halogen, or $C_1$-$C_6$ alkyl optionally substituted with one or more halogen;

$R^4$ is H, halogen, or $C_1$-$C_6$ alkyl optionally substituted with one or more halogen;

each $R^5$ independently is H, halogen, or $C_1$-$C_6$ alkyl optionally substituted with one or more halogen; and each $R^6$ independently is H, halogen, or $C_1$-$C_6$ alkyl optionally substituted with one or more halogen.

It is understood that, for a compound of the present disclosure, variables W, X, $R^X$, $R^{Xa}$Y, $R^Y$, Z, $R^Z$, $R^L$, $R^1$, $R^2$, $R^3$, $R^4$, $R^5$, and $R^6$ can each be, where applicable, selected from the groups described herein, and any group described herein for any of variables W, X, $R^X$, $R^{Xa}$, Y, $R^Y$, Z, $R^Z$, $R^L$, $R^1$, $R^2$, $R^3$, $R^4$, $R^5$, and $R^6$ can be combined, where applicable, with any group described herein for one or more of the remainder of variables W, X, $R^X$, $R^{Xa}$, Y, $R^Y$, Z, $R^Z$, $R^L$, $R^1$, $R^2$, $R^3$, $R^4$, $R^5$, and $R^6$.

Variable W, X $R^X$, $R^{Xa}$, Y, $R^Y$, Z, $R^Z$, and $R^L$

In some embodiments, W is H.

In some embodiments, W is $C_1$-$C_6$ alkyl (e.g., methyl, ethyl, n-propyl, i-propyl, n-butyl, i-butyl, s-butyl, t-butyl, pentyl, or hexyl) optionally substituted with one or more halogen (e.g., F, Cl, Br, or I).

In some embodiments, W is $C_1$-$C_6$ alkyl (e.g., methyl, ethyl, n-propyl, i-propyl, n-butyl, i-butyl, s-butyl, t-butyl, pentyl, or hexyl).

In some embodiments, W is methyl, ethyl, or propyl.

In some embodiments, W is an amino substitution group, i.e., a group suitable for substituting a hydrogen of an amino moiety, such as an amino protecting group.

In some embodiments, W is an amino protecting group, including, but not limited to, fluorenylmethyloxycarbonyl (Fmoc), tert-butyloxycarbonyl (BOC), benzyloxycarbonyl (Cbz), optionally substituted acyl, trifluoroacetyl (TFA), benzyl, triphenylmethyl (Tr), 4,4'-dimethoxytrityl (DMTr), or toluenesulfonyl (Ts).

In some embodiments, W is optionally substituted acyl (e.g., —C(=O)($C_1$-$C_{30}$ alkyl), wherein the $C_1$-$C_{30}$ alkyl is optionally substituted).

In some embodiments, W is substituted acyl (e.g.,

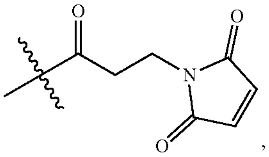

,

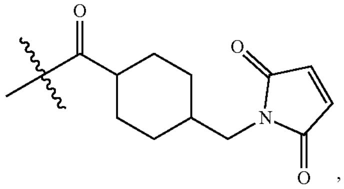

, or

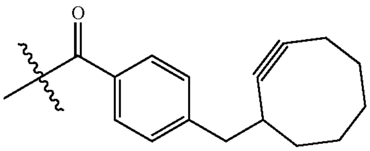

).

In some embodiments, W is trifluoroacetyl (TFA).

In some embodiments, W is optionally substituted thioacyl (e.g., —C(=S)($C_1$-$C_{30}$ alkyl), wherein the $C_1$-$C_{30}$ alkyl is optionally substituted).

In some embodiments, W is substituted thioacyl (e.g.,

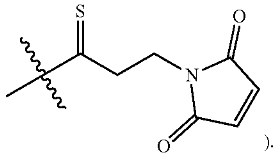 [SMILES: *C(=S)CCN1C(=O)C=CC1=O]

).

In some embodiments, W is an amino substitution group, i.e., a group suitable for substituting a hydrogen of an amino moiety, such as —C(=O)($C_1$-$C_{30}$ alkyl), —C(=O)NH($C_1$-$C_{30}$ alkyl), —C(=S)($C_1$-$C_{30}$ alkyl), or —C(=S)NH($C_1$-$C_{30}$ alkyl), wherein the $C_1$-$C_{30}$ alkyl is optionally substituted. In some embodiments, W is —C(=O)($C_1$-$C_{25}$ alkyl), —C(=O)NH($C_1$-$C_{25}$ alkyl), —C(=S)($C_1$-$C_{25}$ alkyl), or —C(=S)NH($C_1$-$C_{25}$ alkyl), wherein the $C_1$-$C_{25}$ alkyl is optionally substituted.

In some embodiments, W is —C(=O)NH($C_1$-$C_{30}$ alkyl), wherein the $C_1$-$C_{30}$ alkyl is optionally substituted.

In some embodiments, W is —C(=S)NH($C_1$-$C_{30}$ alkyl), wherein the $C_1$-$C_{30}$ alkyl is optionally substituted.

In some embodiments, X is H.

In some embodiments, X is not H.

In some embodiments, X is halogen (e.g., F, Cl, Br, or I).

In some embodiments, X is F or Cl.

In some embodiments, X is F.

In some embodiments, X is —$OR^X$.

In some embodiments, X is —OH.

In some embodiments, X is not —OH.

In some embodiments, X is —O—($C_1$-$C_6$ alkyl) (e.g., wherein the $C_1$-$C_6$ alkyl is methyl, ethyl, n-propyl, i-propyl, n-butyl, i-butyl, s-butyl, t-butyl, pentyl, or hexyl) optionally substituted with one or more $R^{Xa}$.

In some embodiments, X is —O—($C_1$-$C_6$ alkyl) (e.g., wherein the $C_1$-$C_6$ alkyl is methyl, ethyl, n-propyl, i-propyl, n-butyl, i-butyl, s-butyl, t-butyl, pentyl, or hexyl).

In some embodiments, X is —$OCH_3$.

In some embodiments, X is —O—($C_1$-$C_6$ alkyl)-O—($C_1$-$C_6$ alkyl) (e.g., wherein the $C_1$-$C_6$ alkyl is methyl, ethyl, n-propyl, i-propyl, n-butyl, i-butyl, s-butyl, t-butyl, pentyl, or hexyl) optionally substituted with one or more $R^{Xa}$.

In some embodiments, X is —O—($C_1$-$C_6$ alkyl)-O—($C_1$-$C_6$ alkyl) (e.g., wherein the $C_1$-$C_6$ alkyl is methyl, ethyl, n-propyl, i-propyl, n-butyl, i-butyl, s-butyl, t-butyl, pentyl, or hexyl).

In some embodiments, X is —$OCH_2CH_2OCH_3$.

In some embodiments, X is —O—($C_1$-$C_6$ alkyl)-($C_6$-$C_{10}$ aryl) optionally substituted with one or more $R^{Xa}$.

In some embodiments, X is —O—($C_1$-$C_6$ alkyl)-($C_6$-$C_{10}$ aryl).

In some embodiments, X is

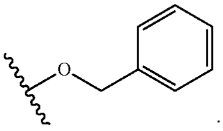 [SMILES: *OCc1ccccc1]

.

In some embodiments, X is

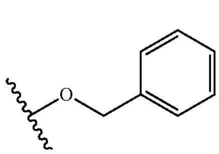 [SMILES: *OCc1ccccc1]

optionally substituted with one or more $R^{Xa}$.

In some embodiments, X is

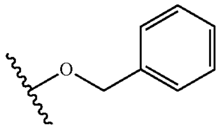 [SMILES: *OCc1ccccc1]

optionally substituted with one or more halogen.

In some embodiments, X is

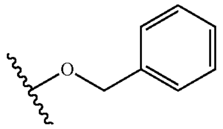 [SMILES: *OCc1ccccc1]

optionally substituted with one or more $C_1$-$C_6$ alkyl or —O—($C_1$-$C_6$ alkyl), wherein the $C_1$-$C_6$ alkyl or —O—($C_1$-$C_6$ alkyl) is optionally substituted with one or more halogen.

In some embodiments, $R^X$ is H.

In some embodiments, $R^X$ is not H.

In some embodiments, $R^X$ is $C_1$-$C_6$ alkyl (e.g., methyl, ethyl, n-propyl, i-propyl, n-butyl, i-butyl, s-butyl, t-butyl, pentyl, or hexyl) optionally substituted with one or more $R^{Xa}$.

In some embodiments, $R^X$ is $C_1$-$C_6$ alkyl (e.g., methyl, ethyl, n-propyl, i-propyl, n-butyl, i-butyl, s-butyl, t-butyl, pentyl, or hexyl) optionally substituted with one or more halogen (e.g., F, Cl, Br, or I) or —O—($C_1$-$C_6$ alkyl) (e.g., wherein the $C_1$-$C_6$ alkyl is methyl, ethyl, n-propyl, i-propyl, n-butyl, i-butyl, s-butyl, t-butyl, pentyl, or hexyl) optionally substituted with one or more halogen.

In some embodiments, $R^X$ is $C_1$-$C_6$ alkyl (e.g., methyl, ethyl, n-propyl, i-propyl, n-butyl, i-butyl, s-butyl, t-butyl, pentyl, or hexyl).

In some embodiments, $R^X$ is methyl, ethyl, or propyl.

In some embodiments, $R^X$ is methyl.

In some embodiments, $R^X$ is $C_1$-$C_6$ alkyl (e.g., methyl, ethyl, n-propyl, i-propyl, n-butyl, i-butyl, s-butyl, t-butyl, pentyl, or hexyl) substituted with one or more halogen (e.g., F, Cl, Br, or I).

In some embodiments, $R^X$ is $C_1$-$C_6$ alkyl (e.g., methyl, ethyl, n-propyl, i-propyl, n-butyl, i-butyl, s-butyl, t-butyl, pentyl, or hexyl) substituted with one or more —O—($C_1$-$C_6$ alkyl) (e.g., wherein the $C_1$-$C_6$ alkyl is methyl, ethyl, n-propyl, i-propyl, n-butyl, i-butyl, s-butyl, t-butyl, pentyl, or hexyl), wherein the —O—($C_1$-$C_6$ alkyl) is optionally substituted with one or more halogen.

In some embodiments, $R^X$ is —($C_1$-$C_6$ alkyl)-($C_6$-$C_{10}$ aryl) optionally substituted with one or more $R^{Xa}$.

In some embodiments, $R^X$ is —($C_1$-$C_6$ alkyl)-($C_6$-$C_{10}$ aryl) optionally substituted with one or more halogen (e.g., F, Cl, Br, or I), $C_1$-$C_6$ alkyl (e.g., methyl, ethyl, n-propyl, i-propyl, n-butyl, i-butyl, s-butyl, t-butyl, pentyl, or hexyl), or —O—($C_1$-$C_6$ alkyl) (e.g., wherein the $C_1$-$C_6$ alkyl is methyl, ethyl, n-propyl, i-propyl, n-butyl, i-butyl, s-butyl, t-butyl, pentyl, or hexyl), wherein the $C_1$-$C_6$ alkyl or —O—($C_1$-$C_6$ alkyl) is optionally substituted with one or more halogen.

In some embodiments, $R^X$ is —($C_1$-$C_6$ alkyl)-($C_6$-$C_{10}$ aryl).

In some embodiments, at least one $R^{Xa}$ is halogen (e.g., F, Cl, Br, or I).

In some embodiments, at least one $R^{Xa}$ is F or Cl.

In some embodiments, at least one $R^{Xa}$ is $C_1$-$C_6$ alkyl (e.g., methyl, ethyl, n-propyl, i-propyl, n-butyl, i-butyl, s-butyl, t-butyl, pentyl, or hexyl) optionally substituted with one or more halogen (e.g., F, Cl, Br, or I).

In some embodiments, at least one $R^{Xa}$ is $C_1$-$C_6$ alkyl (e.g., methyl, ethyl, n-propyl, i-propyl, n-butyl, i-butyl, s-butyl, t-butyl, pentyl, or hexyl).

In some embodiments, at least one $R^{Xa}$ is $C_1$-$C_6$ alkyl (e.g., methyl, ethyl, n-propyl, i-propyl, n-butyl, i-butyl, s-butyl, t-butyl, pentyl, or hexyl) substituted with one or more halogen (e.g., F, Cl, Br, or I).

In some embodiments, at least one $R^{Xa}$ is —O—($C_1$-$C_6$ alkyl) optionally substituted with one or more halogen (e.g., F, Cl, Br, or I).

In some embodiments, at least one $R^{Xa}$ is —O—($C_1$-$C_6$ alkyl).

In some embodiments, at least one $R^{Xa}$ is —O—($C_1$-$C_6$ alkyl) substituted with one or more halogen (e.g., F, Cl, Br, or I).

In some embodiments, Y is H.

In some embodiments, Y is not H.

In some embodiments, Y is $C_1$-$C_6$ alkyl (e.g., methyl, ethyl, n-propyl, i-propyl, n-butyl, i-butyl, s-butyl, t-butyl, pentyl, or hexyl) optionally substituted with one or more halogen (e.g., F, Cl, Br, or I).

In some embodiments, Y is $C_1$-$C_6$ alkyl (e.g., methyl, ethyl, n-propyl, i-propyl, n-butyl, i-butyl, s-butyl, t-butyl, pentyl, or hexyl).

In some embodiments, Y is methyl, ethyl, or propyl.

In some embodiments, Y is —P($R^Y$)$_2$, —P($OR^Y$)(N($R^Y$)$_2$), —P(═O)($OR^Y$)$R^Y$, —P(═S)($OR^Y$)$R^Y$, —P(═O)($R^Y$)$R^Y$, —P(═S)($SR^Y$)$R^Y$, —P(═O)($R^Y$)$_2$, —P(═S)($OR^Y$)$_2$, —P(═O)($SR^Y$)$_2$, —P(═S)($SR^Y$)$_2$.

In some embodiments, Y is —P($R^Y$)$_2$.

In some embodiments, Y is —$PH_2$.

In some embodiments, Y is —P($OR^Y$)(N($R^Y$)$_2$).

In some embodiments, Y is —P(OH)($NH_2$).

In some embodiments, Y is —P(O($C_1$-$C_6$ alkyl))(N($C_1$-$C_6$ alkyl)$_2$), wherein the $C_1$-$C_6$ alkyl is optionally substituted with one or more halogen or cyano.

In some embodiments, Y is —P(═O)($OR^Y$)$R^Y$.

In some embodiments, Y is —P(═O)(OH)($C_1$-$C_6$ alkyl), wherein the $C_1$-$C_6$ alkyl is optionally substituted with one or more halogen or cyano.

In some embodiments, Y is —P(═S)($OR^Y$)$R^Y$.

In some embodiments, Y is —P(═S)(OH)($C_1$-$C_6$ alkyl), wherein the $C_1$-$C_6$ alkyl is optionally substituted with one or more halogen or cyano.

In some embodiments, Y is —P(═O)($SR^Y$)$R^Y$.

In some embodiments, Y is —P(═O)(SH)($C_1$-$C_6$ alkyl), wherein the $C_1$-$C_6$ alkyl is optionally substituted with one or more halogen or cyano.

In some embodiments, Y is —P(═S)($SR^Y$)$R^Y$.

In some embodiments, Y is —P(═S)(SH)($C_1$-$C_6$ alkyl), wherein the $C_1$-$C_6$ alkyl is optionally substituted with one or more halogen or cyano.

In some embodiments, Y is —P(═O)($OR^Y$)$_2$.

In some embodiments, Y is —P(═O)(OH)$_2$.

In some embodiments, Y is —P(═S)($OR^Y$)$_2$.

In some embodiments, Y is —P(═S)(OH)$_2$.

In some embodiments, Y is —P(═O)($SR^Y$)$_2$.

In some embodiments, Y is —P(═O)(SH)$_2$.

In some embodiments, Y is —P(═S)($SR^Y$)$_2$.

In some embodiments, Y is —P(═S)(SH)$_2$.

In some embodiments, Y is a hydroxy protecting group.

In some embodiments, Y is silyl (e.g., trimethylsilyl, triethylsilyl, tert-butyldimethylsilyl, tert-butyldiphenylsilyl, or triisopropylsilyl).

In some embodiments, Y is triphenylmethyl (Tr) or 4,4'-dimethoxytrityl (DMTr).

In some embodiments, Y is optionally substituted acyl (e.g., optionally substituted acetyl) or benzyl.

In some embodiments, Y is not a hydroxy protecting group.

In some embodiments, at least one $R^Y$ is H.

In some embodiments, each $R^Y$ is H.

In some embodiments, at least one $R^Y$ is $C_1$-$C_6$ alkyl (e.g., methyl, ethyl, n-propyl, i-propyl, n-butyl, i-butyl, s-butyl, t-butyl, pentyl, or hexyl) optionally substituted with one or more halogen (e.g., F, Cl, Br, or I) or cyano.

In some embodiments, each $R^Y$ is $C_1$-$C_6$ alkyl (e.g., methyl, ethyl, n-propyl, i-propyl, n-butyl, i-butyl, s-butyl, t-butyl, pentyl, or hexyl) optionally substituted with one or more halogen (e.g., F, Cl, Br, or I) or cyano.

In some embodiments, at least one $R^Y$ is H, and at least one $R^Y$ is $C_1$-$C_6$ alkyl (e.g., methyl, ethyl, n-propyl, i-propyl, n-butyl, i-butyl, s-butyl, t-butyl, pentyl, or hexyl) optionally substituted with one or more halogen or cyano.

In some embodiments, when X is —OH, then Y is not H or a hydroxy protecting group.

In some embodiments, when X is —OH, then Y is $C_1$-$C_6$ alkyl optionally substituted with one or more halogen, —$P(R^Y)_2$, —$P(OR^Y)(N(R^Y)_2)$, —$P(=O)(OR^Y)R^Y$, —$P(=S)(OR^Y)R^Y$, —$P(=O)(SR^Y)R^Y$, —$P(=S)(SR^Y)R^Y$, —$P(=O)(OR^Y)_2$, —$P(=S)(OR^Y)_2$, —$P(=O)(SR^Y)_2$, or —$P(=S)(SR_Y)_2$.

In some embodiments, when Y is H or a hydroxy protecting group, then X is not —OH.

In some embodiments, when Y is H or a hydroxy protecting group, then X is H, halogen, or —$OR^X$, and $R^X$ is $C_1$-$C_6$ alkyl or —($C_1$-$C_6$ alkyl)-($C_6$-$C_{10}$ aryl), wherein the $C_1$-$C_6$ alkyl or —($C_1$-$C_6$ alkyl)-($C_6$-$C_{10}$ aryl) is optionally substituted with one or more $R^{Xa}$.

In some embodiments, Z is H.

In some embodiments, Z is $C_1$-$C_6$ alkyl (e.g., methyl, ethyl, n-propyl, i-propyl, n-butyl, i-butyl, s-butyl, t-butyl, pentyl, or hexyl) optionally substituted with one or more halogen (e.g., F, Cl, Br, or I).

In some embodiments, Z is $C_1$-$C_6$ alkyl (e.g., methyl, ethyl, n-propyl, i-propyl, n-butyl, i-butyl, s-butyl, t-butyl, pentyl, or hexyl).

In some embodiments, Z is methyl, ethyl, or propyl.

In some embodiments, Z is —$P(R^Z)_2$, —$P(OR^Z)(N(R^Z)_2)$, —$P(=O)(OR^Z)R^Z$, —$P(=S)(OR^Z)R^Z$, —$P(=O)(SR^Z)R^Z$, —$P(=S)(SR^Z)R^Z$, —$P(=O)(OR^Z)_2$, —$P(=S)(OR^Z)_2$, —$P(=O)(SR^Z)_2$, —$P(=S)(SR^Z)_2$.

In some embodiments, Z is —$P(R^Z)_2$.

In some embodiments, Z is —$PH_2$.

In some embodiments, Z is —$P(OR^Z)(N(R^Z)_2)$.

In some embodiments, Z is —$P(OH)(NH_2)$.

In some embodiments, Z is —$P(O(C_1$-$C_6$ alkyl$))(N(C_1$-$C_6$ alkyl$)_2)$, wherein the $C_1$-$C_6$ alkyl is optionally substituted with one or more halogen or cyano.

In some embodiments, Z is —$P(=O)(OR^Z)R^Z$.

In some embodiments, Z is —$P(=O)(OH)(C_1$-$C_6$ alkyl), wherein the $C_1$-$C_6$ alkyl is optionally substituted with one or more halogen or cyano.

In some embodiments, Z is —$P(=S)(OR^Z)R^Z$.

In some embodiments, Z is —$P(=S)(OH)(C_1$-$C_6$ alkyl), wherein the $C_1$-$C_6$ alkyl is optionally substituted with one or more halogen or cyano.

In some embodiments, Z is —$P(=O)(SR^Z)R^Z$.

In some embodiments, Z is —$P(=O)(SH)(C_1$-$C_6$ alkyl), wherein the $C_1$-$C_6$ alkyl is optionally substituted with one or more halogen or cyano.

In some embodiments, Z is —$P(=S)(SR^Z)R^Z$.

In some embodiments, Z is —$P(=S)(SH)(C_1$-$C_6$ alkyl), wherein the $C_1$-$C_6$ alkyl is optionally substituted with one or more halogen or cyano.

In some embodiments, Z is —$P(=O)(OR^Z)_2$.

In some embodiments, Z is —$P(=O)(OH)_2$.

In some embodiments, Z is —$P(=S)(OR^Z)_2$.

In some embodiments, Z is —$P(=S)(OH)_2$.

In some embodiments, Z is —$P(=O)(SR^Z)_2$.

In some embodiments, Z is —$P(=O)(SH)_2$.

In some embodiments, Z is —$P(=S)(SR^Z)_2$.

In some embodiments, Z is —$P(=S)(SH)_2$.

In some embodiments, Z is a hydroxy protecting group.

In some embodiments, Z is silyl (e.g., trimethylsilyl, triethylsilyl, tert-butyldimethylsilyl, tert-butyldiphenylsilyl, or triisopropylsilyl).

In some embodiments, Z is triphenylmethyl (Tr) or 4,4'-dimethoxytrityl (DMTr).

In some embodiments, Z is substituted acyl (e.g., optionally substituted acetyl) or benzyl.

In some embodiments, at least one $R^Z$ is H.

In some embodiments, each $R^Z$ is H.

In some embodiments, at least one $R^Z$ is $C_1$-$C_6$ alkyl (e.g., methyl, ethyl, n-propyl, i-propyl, n-butyl, i-butyl, s-butyl, t-butyl, pentyl, or hexyl) optionally substituted with one or more halogen (e.g., F, Cl, Br, or I) or cyano.

In some embodiments, each $R^Z$ is $C_1$-$C_6$ alkyl (e.g., methyl, ethyl, n-propyl, i-propyl, n-butyl, i-butyl, s-butyl, t-butyl, pentyl, or hexyl) optionally substituted with one or more halogen (e.g., F, Cl, Br, or I) or cyano.

In some embodiments, at least one $R^Z$ is H, and at least one $R^Z$ is $C_1$-$C_6$ alkyl (e.g., methyl, ethyl, n-propyl, i-propyl, n-butyl, i-butyl, s-butyl, t-butyl, pentyl, or hexyl) optionally substituted with one or more halogen (e.g., F, Cl, Br, or I) or cyano.

In some embodiments, Y and Z in Formula (I) together form —$Si(R^L)_2$—O—$Si(R^L)_2$—.

In some embodiments, Y and Z in Formula (I) together form —$Si(C_1$-$C_6$ alkyl$)_2$-O—$Si(C_1$-$C_6$ alkyl$)_2$-.

In some embodiments, Y and Z in Formula (I) together form —$Si(C_1$-$C_6$ alkyl$)_2$-O—$SiH(C_1$-$C_6$ alkyl)-.

In some embodiments, Y and Z in Formula (I) together form —$SiH(C_1$-$C_6$ alkyl)-O—$SiH(C_1$-$C_6$ alkyl)-.

In some embodiments, Y and Z in Formula (I) together form —$Si(iPr)_2$-O—$Si(iPr)_2$-.

In some embodiments, at least one $R^L$ is H.

In some embodiments, each $R^L$ independently is $C_1$-$C_6$ alkyl.

In some embodiments, each $R^L$ independently is methyl, ethyl, or propyl (e.g., iPr).

Variables $R^1$, $R^2$, $R^3$, $R^4$, $R^5$, and $R^6$

In some embodiments, $R^1$ is H.

In some embodiments, $R^1$ is halogen (e.g., F, Cl, Br, or I).

In some embodiments, $R^1$ is F or Cl.

In some embodiments, $R^1$ is $C_1$-$C_6$ alkyl (e.g., methyl, ethyl, n-propyl, i-propyl, n-butyl, i-butyl, s-butyl, t-butyl, pentyl, or hexyl) optionally substituted with one or more halogen (e.g., F, Cl, Br, or I).

In some embodiments, $R^1$ is $C_1$-$C_6$ alkyl (e.g., methyl, ethyl, n-propyl, i-propyl, n-butyl, i-butyl, s-butyl, t-butyl, pentyl, or hexyl).

In some embodiments, $R^1$ is $C_1$-$C_6$ alkyl (e.g., methyl, ethyl, n-propyl, i-propyl, n-butyl, i-butyl, s-butyl, t-butyl, pentyl, or hexyl) substituted with one or more halogen (e.g., F, Cl, Br, or I).

In some embodiments, $R^2$ is H.

In some embodiments, $R^2$ is halogen (e.g., F, Cl, Br, or I).

In some embodiments, $R^2$ is F or Cl.

In some embodiments, $R^2$ is $C_1$-$C_6$ alkyl (e.g., methyl, ethyl, n-propyl, i-propyl, n-butyl, i-butyl, s-butyl, t-butyl, pentyl, or hexyl) optionally substituted with one or more halogen (e.g., F, Cl, Br, or I).

In some embodiments, $R^2$ is $C_1$-$C_6$ alkyl (e.g., methyl, ethyl, n-propyl, i-propyl, n-butyl, i-butyl, s-butyl, t-butyl, pentyl, or hexyl).

In some embodiments, $R^2$ is $C_1$-$C_6$ alkyl (e.g., methyl, ethyl, n-propyl, i-propyl, n-butyl, i-butyl, s-butyl, t-butyl, pentyl, or hexyl) substituted with one or more halogen (e.g., F, Cl, Br, or I).

In some embodiments, $R^3$ is H.

In some embodiments, $R^3$ is halogen (e.g., F, Cl, Br, or I).

In some embodiments, $R^3$ is F or Cl.

In some embodiments, $R^3$ is $C_1$-$C_6$ alkyl (e.g., methyl, ethyl, n-propyl, i-propyl, n-butyl, i-butyl, s-butyl, t-butyl, pentyl, or hexyl) optionally substituted with one or more halogen (e.g., F, Cl, Br, or I).

In some embodiments, $R^3$ is $C_1$-$C_6$ alkyl (e.g., methyl, ethyl, n-propyl, i-propyl, n-butyl, i-butyl, s-butyl, t-butyl, pentyl, or hexyl).

In some embodiments, $R^3$ is $C_1$-$C_6$ alkyl (e.g., methyl, ethyl, n-propyl, i-propyl, n-butyl, i-butyl, s-butyl, t-butyl, pentyl, or hexyl) substituted with one or more halogen (e.g., F, Cl, Br, or I).

In some embodiments, $R^4$ is H.

In some embodiments, $R^4$ is halogen (e.g., F, Cl, Br, or I).

In some embodiments, $R^4$ is F or Cl.

In some embodiments, $R^4$ is $C_1$-$C_6$ alkyl (e.g., methyl, ethyl, n-propyl, i-propyl, n-butyl, i-butyl, s-butyl, t-butyl, pentyl, or hexyl) optionally substituted with one or more halogen (e.g., F, Cl, Br, or I).

In some embodiments, $R^4$ is $C_1$-$C_6$ alkyl (e.g., methyl, ethyl, n-propyl, i-propyl, n-butyl, i-butyl, s-butyl, t-butyl, pentyl, or hexyl).

In some embodiments, $R^4$ is $C_1$-$C_6$ alkyl (e.g., methyl, ethyl, n-propyl, i-propyl, n-butyl, i-butyl, s-butyl, t-butyl, pentyl, or hexyl) substituted with one or more halogen (e.g., F, Cl, Br, or I).

In some embodiments, each $R^5$ is H.

In some embodiments, at least one $R^5$ is halogen (e.g., F, Cl, Br, or I) or $C_1$-$C_6$ alkyl (e.g., methyl, ethyl, n-propyl, i-propyl, n-butyl, i-butyl, s-butyl, t-butyl, pentyl, or hexyl) optionally substituted with one or more halogen (e.g., F, Cl, Br, or I).

In some embodiments, at least one $R^5$ is halogen (e.g., F, Cl, Br, or I).

In some embodiments, at least one $R^5$ is F or Cl.

In some embodiments, at least one $R^5$ is $C_1$-$C_6$ alkyl (e.g., methyl, ethyl, n-propyl, i-propyl, n-butyl, i-butyl, s-butyl, t-butyl, pentyl, or hexyl) optionally substituted with one or more halogen (e.g., F, Cl, Br, or I).

In some embodiments, at least one $R^5$ is $C_1$-$C_6$ alkyl (e.g., methyl, ethyl, n-propyl, i-propyl, n-butyl, i-butyl, s-butyl, t-butyl, pentyl, or hexyl).

In some embodiments, at least one $R^5$ is $C_1$-$C_6$ alkyl (e.g., methyl, ethyl, n-propyl, i-propyl, n-butyl, i-butyl, s-butyl, t-butyl, pentyl, or hexyl) substituted with one or more halogen (e.g., F, Cl, Br, or I).

In some embodiments, each $R^6$ is H.

In some embodiments, at least one $R^6$ is halogen (e.g., F, Cl, Br, or I) or $C_1$-$C_6$ alkyl (e.g., methyl, ethyl, n-propyl, i-propyl, n-butyl, i-butyl, s-butyl, t-butyl, pentyl, or hexyl) optionally substituted with one or more halogen (e.g., F, Cl, Br, or I).

In some embodiments, at least one $R^6$ is halogen (e.g., F, Cl, Br, or I).

In some embodiments, at least one $R^6$ is F or Cl.

In some embodiments, at least one $R^6$ is $C_1$-$C_6$ alkyl (e.g., methyl, ethyl, n-propyl, i-propyl, n-butyl, i-butyl, s-butyl, t-butyl, pentyl, or hexyl) optionally substituted with one or more halogen (e.g., F, Cl, Br, or I).

In some embodiments, at least one $R^6$ is $C_1$-$C_6$ alkyl (e.g., methyl, ethyl, n-propyl, i-propyl, n-butyl, i-butyl, s-butyl, t-butyl, pentyl, or hexyl).

In some embodiments, at least one $R^6$ is $C_1$-$C_6$ alkyl (e.g., methyl, ethyl, n-propyl, i-propyl, n-butyl, i-butyl, s-butyl, t-butyl, pentyl, or hexyl) substituted with one or more halogen (e.g., F, Cl, Br, or I).

In some embodiments, each of $R^1$, $R^2$, $R^3$, $R^4$, $R^5$, and $R^6$ is H.

Exemplary Embodiments of the Compounds

In some embodiments, the compound is of Formula (I'-1), (I'-2), (II'-1), or (II'-2):

(I'-1)

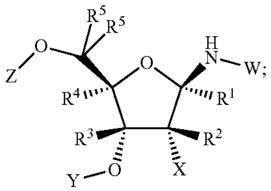

(I'-2)

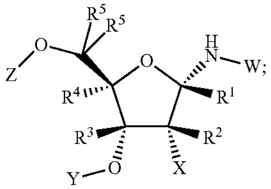

(II'-1)

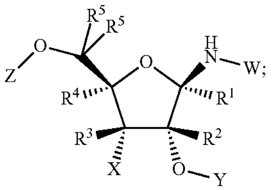

or (II'-2)

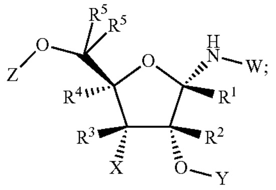

or a pharmaceutically acceptable salt thereof.

In some embodiments, the compound is of Formula (I-A) or (II-A):

(I-A)

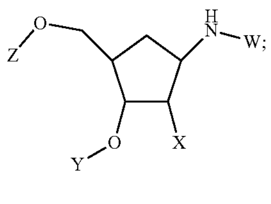

or

-continued (II-A)

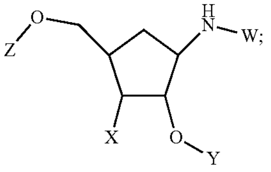

or a pharmaceutically acceptable salt thereof.

In some embodiments, the compound is of Formula (I-A'-1), (I-A'-2), (II-A'-1), or (II-A'-2):

(I-A'-1)

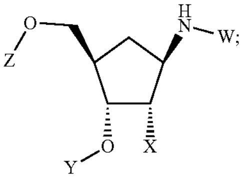

(I-A'-2)

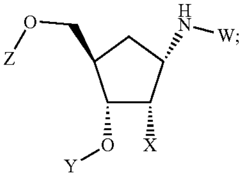

(II-A'-1)

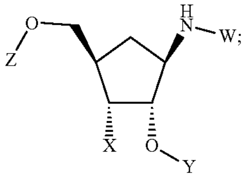

or (II-A'-2)

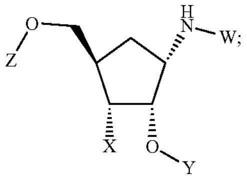

or a pharmaceutically acceptable salt thereof.

In some embodiments, the compound is of Formula (I-B) or (II-B):

(I-B)

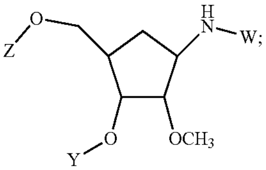

or (II-B)

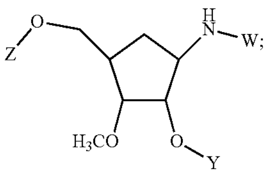

or a pharmaceutically acceptable salt thereof.

In some embodiments, the compound is of Formula (I-B'-1), (I-B'-2), (II-B'-1), or (II-B'-2):

(I-B'-1)

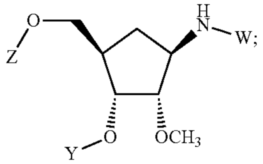

(I-B'-2)

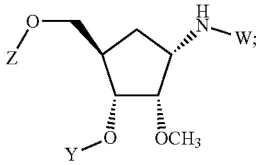

(II-B'-1)

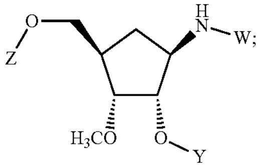

or (II-B'-2)

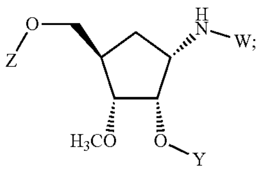

or a pharmaceutically acceptable salt thereof.

In some embodiments, Y is a hydroxy protecting group (e.g., silyl, Tr, DMTr, acyl, or benzyl), and Z is a hydroxy protecting group (e.g., silyl, Tr, DMTr, acyl, or benzyl); or Y and Z in Formula (I), (I'-1), (I'-2), (I-A), (I-A'-1), (I-A'-2), (I-B), (I-B'-1), or (I-B'-2) together form $—Si(R^L)_2—O—Si(R^L)_2—$, wherein each $R^L$ independently is H or $C_1$-$C_6$ alkyl.

In some embodiments, Y is a hydroxy protecting group (e.g., silyl, Tr, DMTr, acyl, or benzyl), and Z is a hydroxy protecting group (e.g., silyl, Tr, DMTr, acyl, or benzyl).

In some embodiments, Y and Z in Formula (I), (I'-1), (I'-2), (I-A), (I-A'-1), (I-A'-2), (I-B), (I-B'-1), or (I-B'-2) together form $—Si(R^L)_2—O—Si(R^L)_2—$, wherein each $R^L$ independently is H or $C_1$-$C_6$ alkyl.

In some embodiments, the compound is:

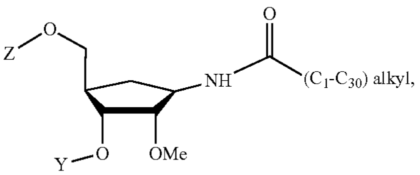

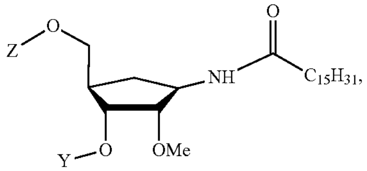

-continued

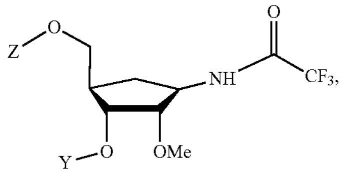

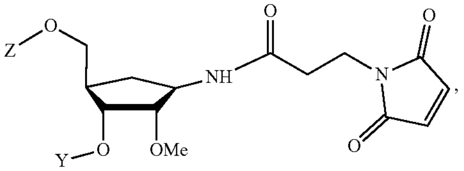

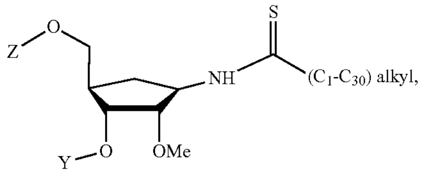

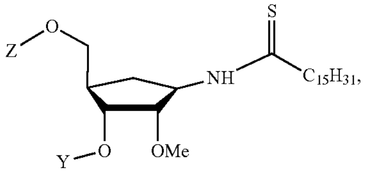

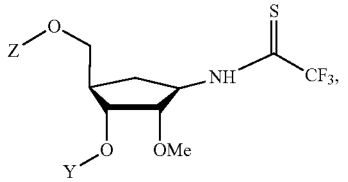

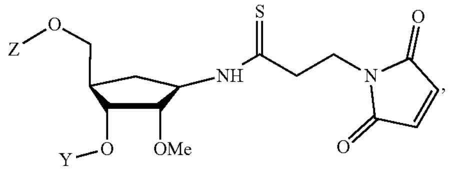

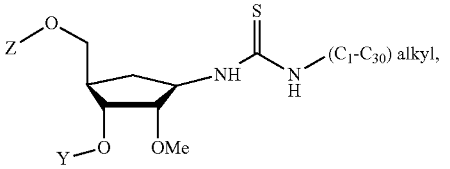

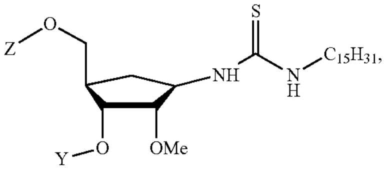

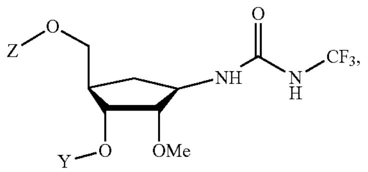

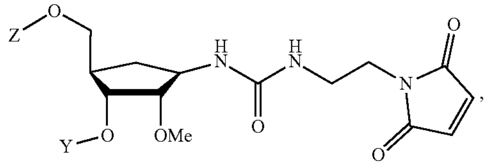

-continued

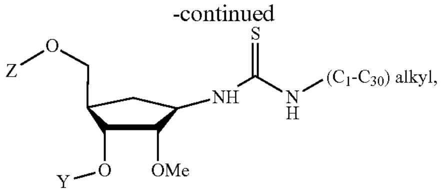

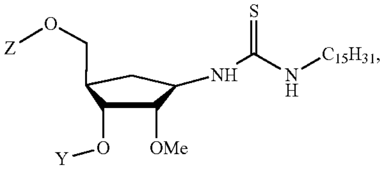

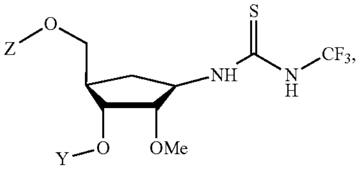

or

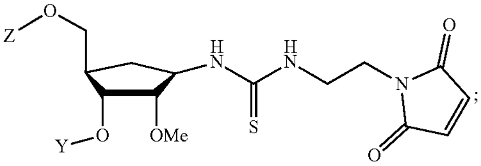

or a pharmaceutically acceptable salt thereof, wherein:

Y is —P($R^Y$)$_2$, —P($OR^Y$)(N($R^Y$)$_2$), —P(═O)($OR^Y$)$R^Y$, —P(═S)($OR^Y$)$R^Y$, —P(═O)($SR^Y$)$R^Y$, —P(═S)($SR^Y$)$R^Y$, —P(═O)($OR^Y$)$_2$, —P(═S)($OR^Y$)$_2$, —P(═O)($SR^Y$)$_2$, —P(═S)($SR^Y$)$_2$, or a hydroxy protecting group (e.g., silyl (e.g., trimethylsilyl, triethylsilyl, tert-butyldimethylsilyl, tert-butyldiphenylsilyl, or triisopropylsilyl), triphenylmethyl (Tr), 4,4'-dimethoxytrityl (DMTr), substituted acyl (e.g., optionally substituted acetyl), or benzyl);

each $R^Y$ independently is H or $C_1$-$C_6$ alkyl optionally substituted with one or more halogen or cyano;

Z is —P($R^Z$)$_2$, —P($OR^Z$)(N($R^Z$)$_2$), —P(═O)($OR^Z$)$R^Z$, —P(═S)($OR^Z$)$R^Z$, —P(═O)($SR^Z$)$R^Z$, —P(═S)($SR^Z$)$R^Z$, —P(═O)($OR^Z$)$_2$, —P(═S)($OR^Z$)$_2$, —P(═O)($SR^Z$)$_2$, —P(═S)($SR^Z$)$_2$, or a hydroxy protecting group (e.g., silyl (e.g., trimethylsilyl, triethylsilyl, tert-butyldimethylsilyl, tert-butyldiphenylsilyl, or triisopropylsilyl), triphenylmethyl (Tr), 4,4'-dimethoxytrityl (DMTr), substituted acyl (e.g., optionally substituted acetyl), or benzyl); and each $R^Z$ independently is H or $C_1$-$C_6$ alkyl optionally substituted with one or more halogen or cyano.

In some embodiments, the compound is:

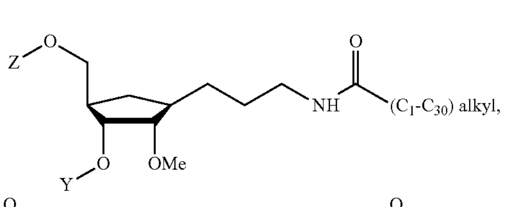

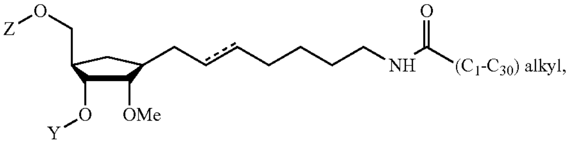

-continued
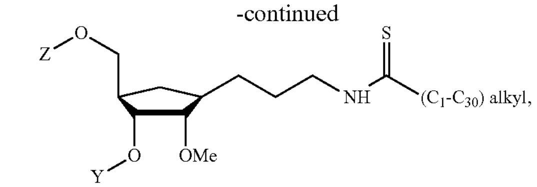
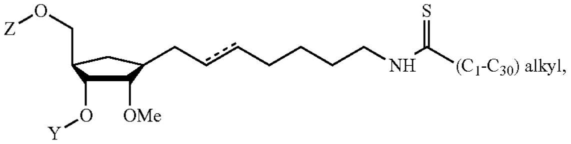
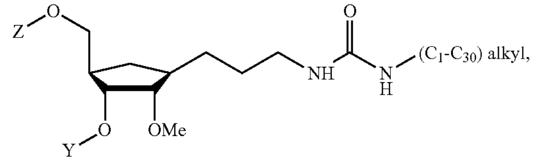
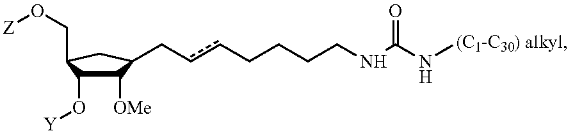
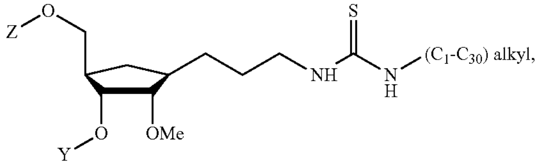
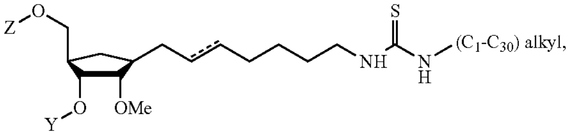
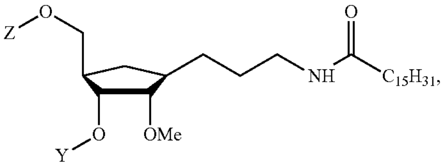
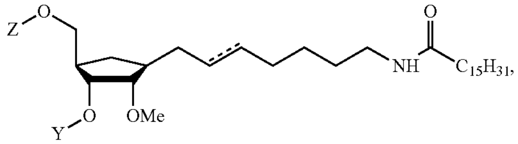
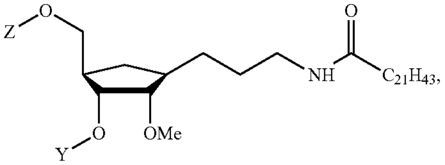
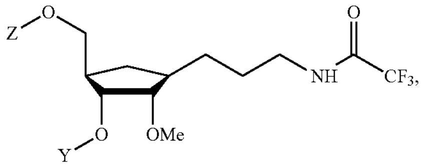
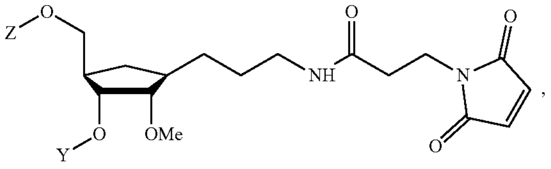
-continued
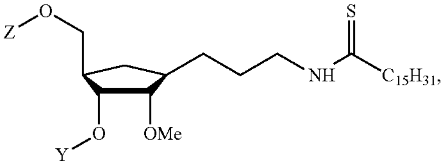
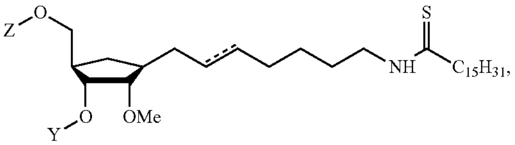
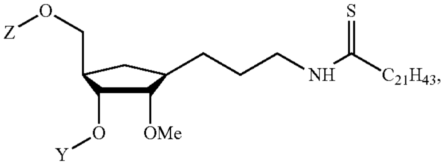
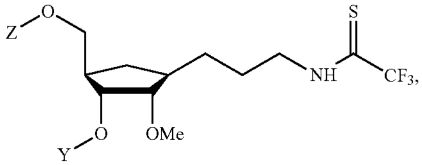
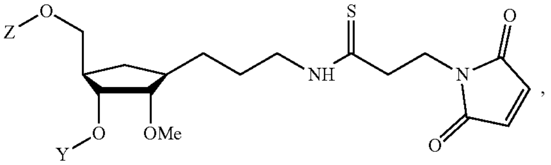
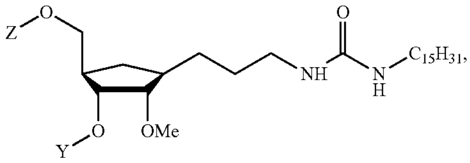
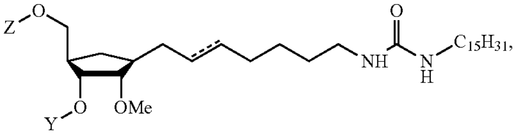
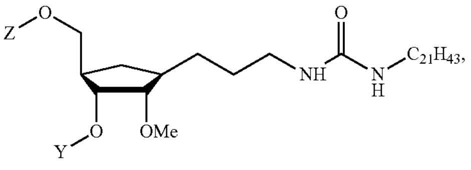
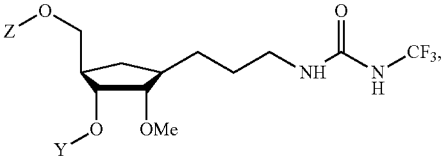
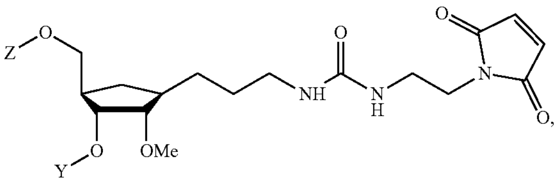

-continued

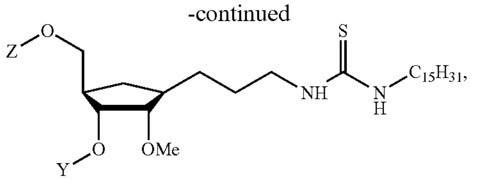

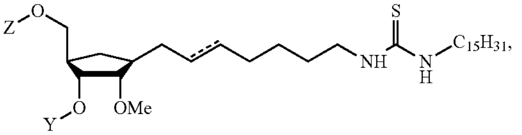

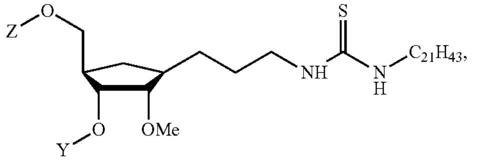

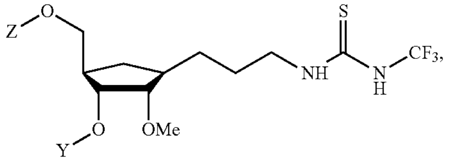

or

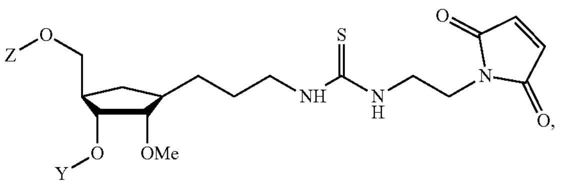

or a pharmaceutically acceptable salt thereof, wherein:

Y is —$P(R^Y)_2$, —$P(OR^Y)(N(R^Y)_2)$, —P(=O)($OR^Y$)$R^Y$, —P(=S)($OR^Y$)$R^Y$, —P(=O)($SR^Y$)$R^Y$, —P(=S)($SR^Y$)$R^Y$, —P(=O)$(OR^Y)_2$, —P(=S)$(OR^Y)_2$, —P(=O)$(SR^Y)_2$, —P(=S)$(SR^Y)_2$, or a hydroxy protecting group (e.g., silyl (e.g., trimethylsilyl, triethylsilyl, tert-butyldimethylsilyl, tert-butyldiphenylsilyl, or triisopropylsilyl), triphenylmethyl (Tr), 4,4'-dimethoxytrityl (DMTr), substituted acyl (e.g., optionally substituted acetyl), or benzyl);

each $R^Y$ independently is H or $C_1$-$C_6$ alkyl optionally substituted with one or more halogen or cyano;

Z is —$P(R^Z)_2$, —$P(OR^Z)(N(R^Z)_2)$, —P(=O)($OR^Z$)$R^Z$, —P(=S)($OR^Z$)$R^Z$, —P(=O)($SR^Z$)$R^Z$, —P(=S)($SR^Z$)$R^Z$, —P(=O)$(OR^Z)_2$, —P(=S)$(OR^Z)_2$, —P(=O)$(SR^Z)_2$, —P(=S)$(SR^Z)_2$, or a hydroxy protecting group (e.g., silyl (e.g., trimethylsilyl, triethylsilyl, tert-butyldimethylsilyl, tert-butyldiphenylsilyl, or triisopropylsilyl), triphenylmethyl (Tr), 4,4'-dimethoxytrityl (DMTr), substituted acyl (e.g., optionally substituted acetyl), or benzyl); and each $R^Z$ independently is H or $C_1$-$C_6$ alkyl optionally substituted with one or more halogen or cyano, and wherein the $C_1$-$C_{30}$ alkyl is optionally substituted.

In some embodiments, the compound is selected from the compounds described in Table L and pharmaceutically acceptable salts thereof.

TABLE L

| Compound No. | Structure |
|---|---|
| L-1 | 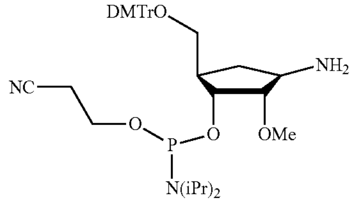 |
| L-2 | 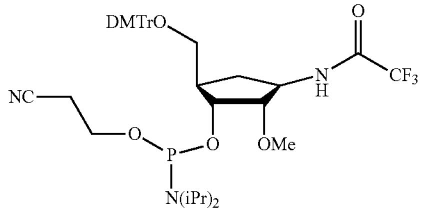 |
| L-3 | 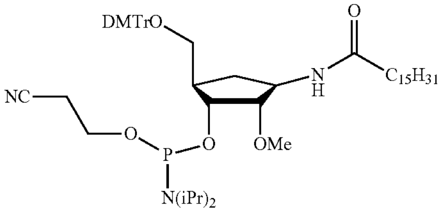 |
| L-4 | 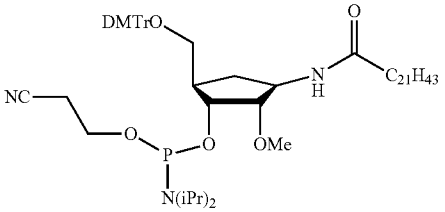 |
| L-5 | 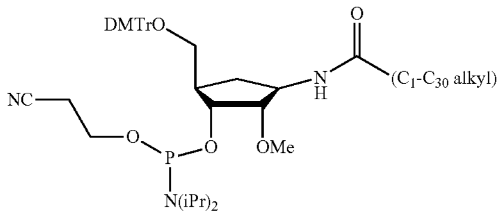 wherein the C1-C30 alkyl is optionally substituted |
| L-6 | 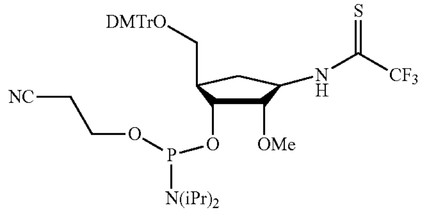 |

TABLE L-continued
| Compound No. | Structure |
| --- | --- |
| L-7 | 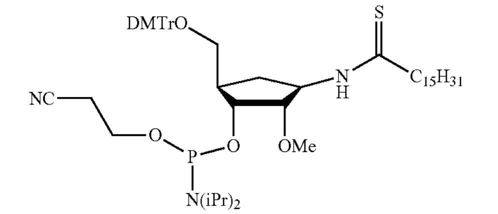 |
| L-8 | 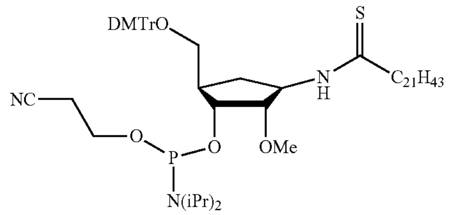 |
| L-9 | 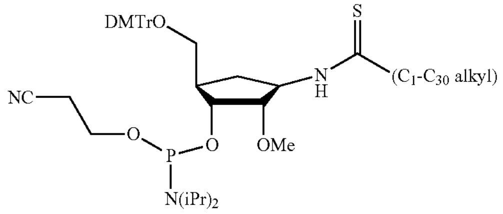<br>wherein the C1-C30 alkyl is optionally substituted |
| L-10 | 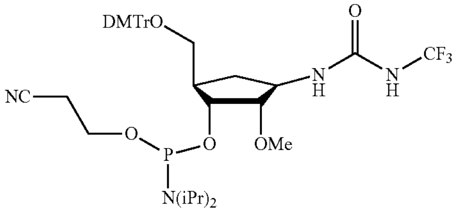 |
| L-11 | 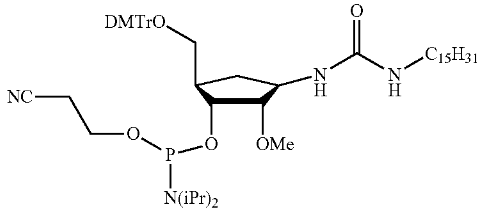 |
| L-12 | 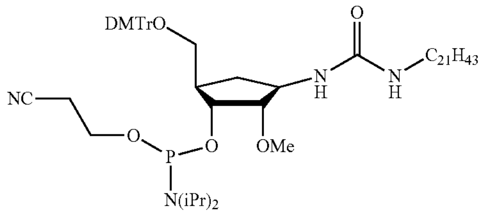 |
TABLE L-continued
| Compound No. | Structure |
| --- | --- |
| L-13 | 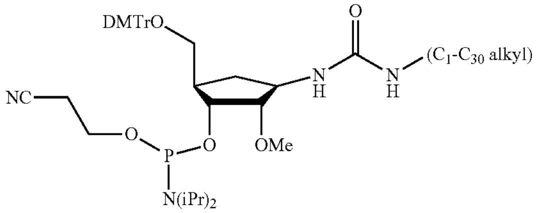<br>wherein the C1-C30 alkyl is optionally substituted |
| L-14 | 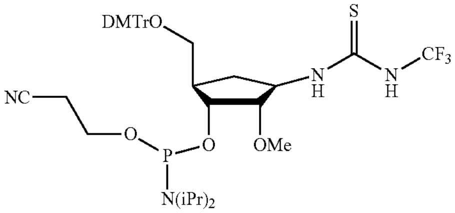 |
| L-15 | 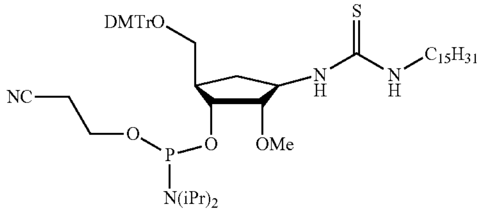 |
| L-16 | 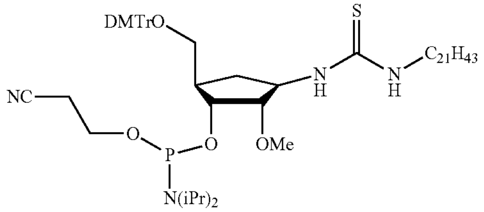 |
| L-17 | 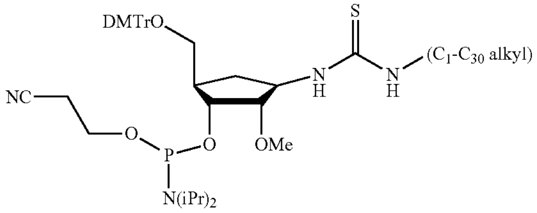<br>wherein the C1-C30 alkyl is optionally substituted |
| L-18 | 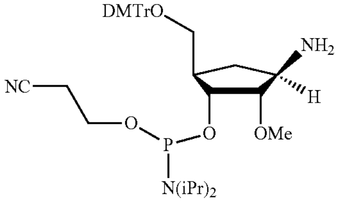 |

TABLE L-continued
| Compound No. | Structure |
| --- | --- |
| L-19 | 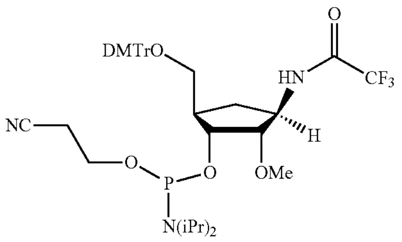 |
| L-20 | 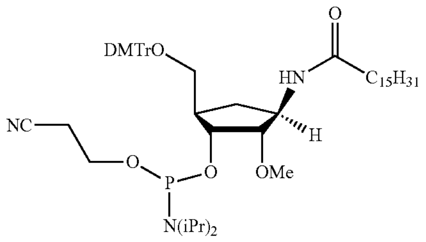 |
| L-21 | 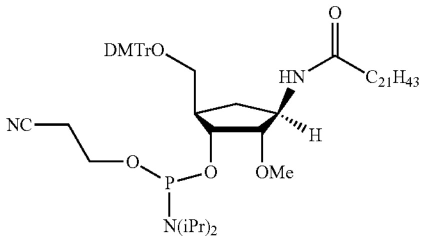 |
| L-22 | 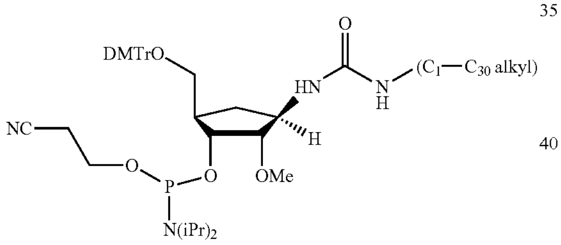<br>wherein the C1-C30 alkyl is optionally substituted |
| L-23 | 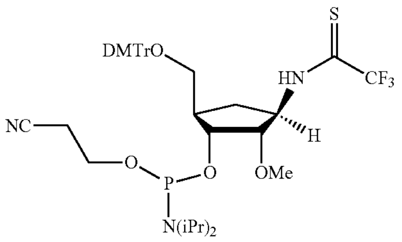 |
| L-24 | 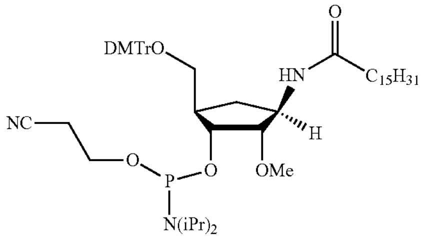 |
TABLE L-continued
| Compound No. | Structure |
| --- | --- |
| L-25 | 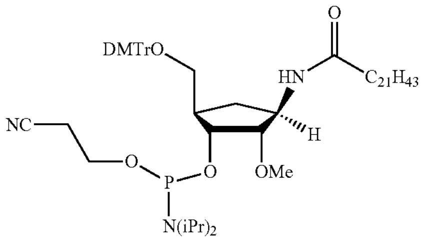 |
| L-26 | 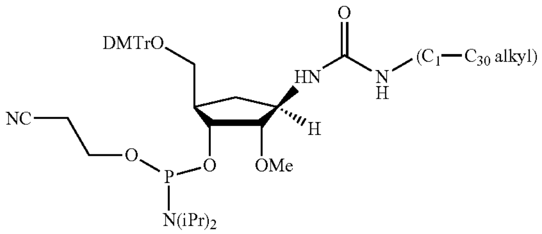<br>wherein the C1-C30 alkyl is optionally substituted |
| L-27 | 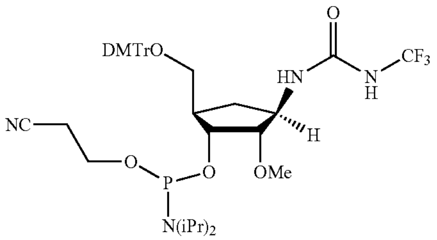 |
| L-28 | 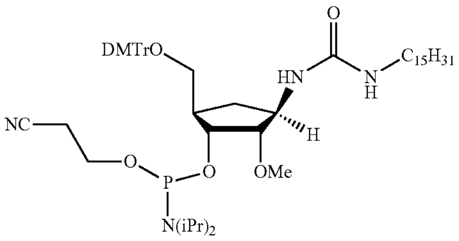 |
| L-29 | 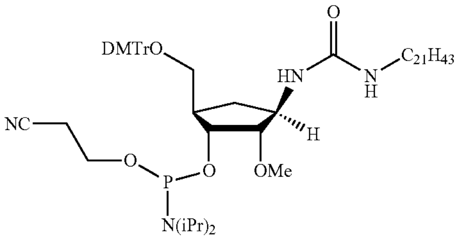 |
| L-30 | 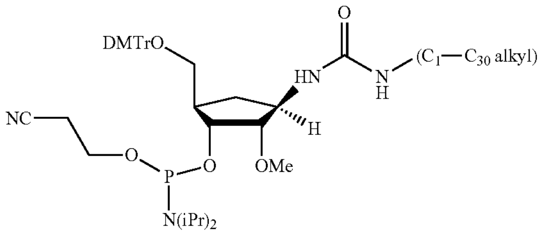<br>wherein the C1-C30 alkyl is optionally substituted |

TABLE L-continued
| Compound No. | Structure |
|---|---|
| L-31 | 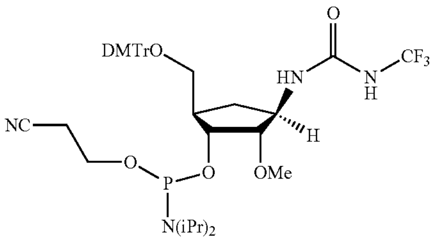 |
| L-32 | 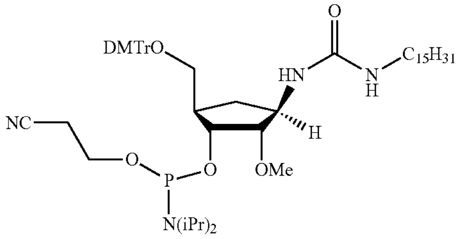 |
| L-33 | 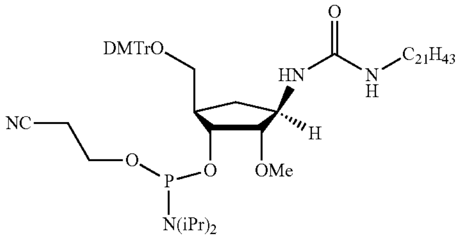 |
| L-34 | 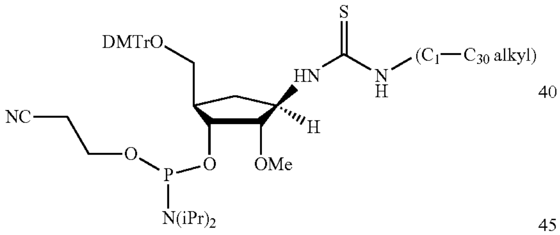<br>wherein the C1-C30 alkyl is optionally substituted |
| L-35 | 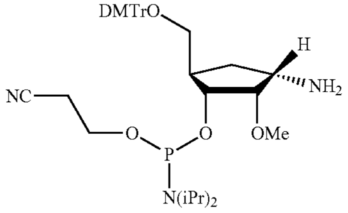 |
| L-36 | 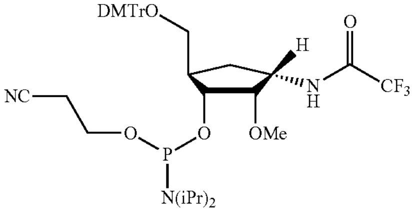 |
TABLE L-continued
| Compound No. | Structure |
|---|---|
| L-37 | 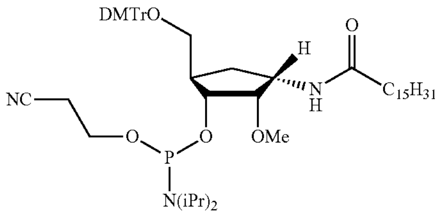 |
| L-38 | 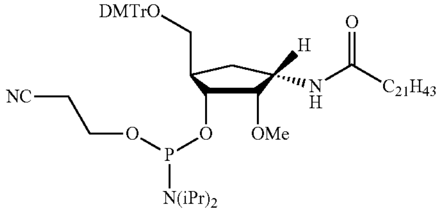 |
| L-39 | 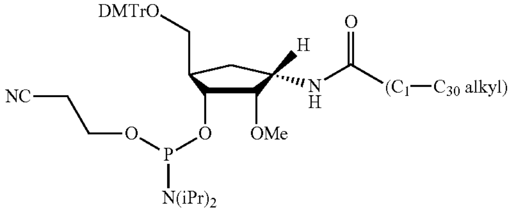<br>wherein the C1-C30 alkyl is optionally substituted |
| L-40 | 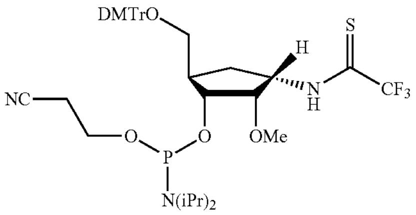 |
| L-41 | 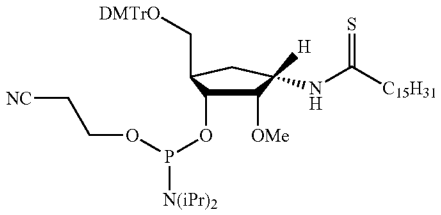 |
| L-42 | 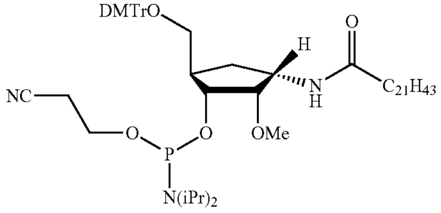 |

TABLE L-continued

| Compound No. | Structure |
|---|---|
| L-43 | 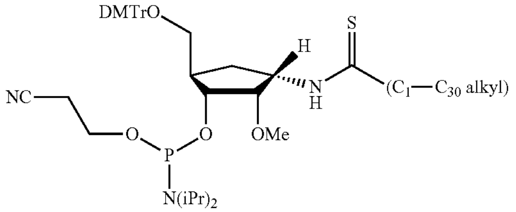<br>wherein the C1-C30 alkyl is optionally substituted |
| L-44 | 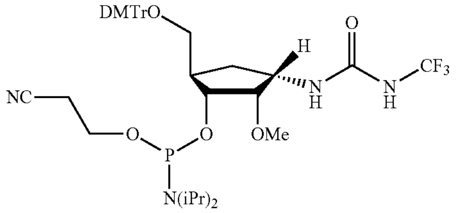 |
| L-45 | 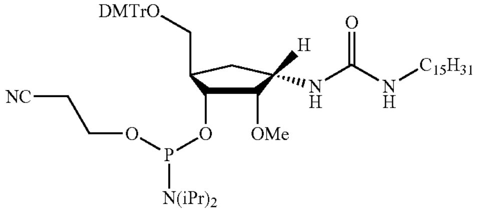 |
| L-46 | 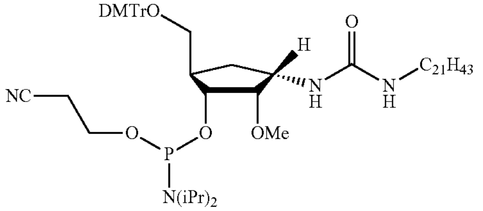 |
| L-47 | 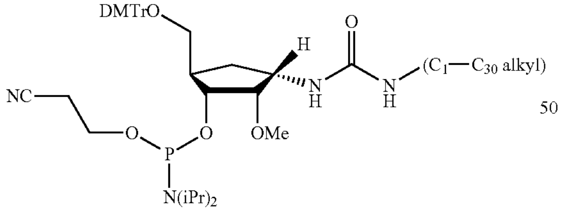<br>wherein the C1-C30 alkyl is optionally substituted |
| L-48 | 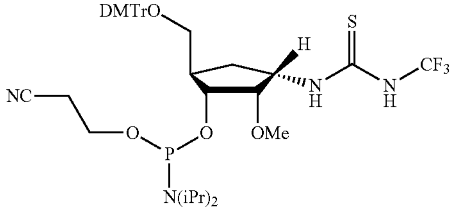 |
| L-49 | 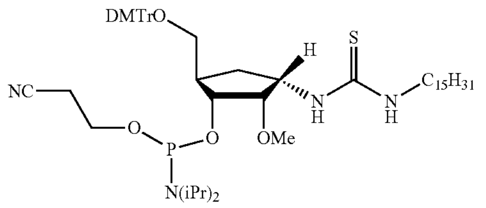 |
| L-50 | 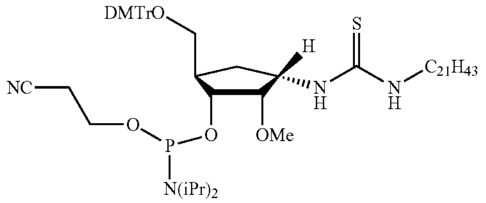 |
| L-51 | 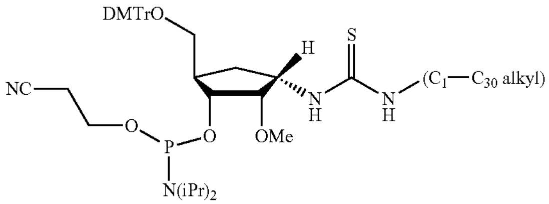<br>wherein the C1-C30 alkyl is optionally substituted |

In some aspects, the present disclosure provides a compound which is an isotopic derivative (e.g., isotopically labeled compound) of any one of the compounds of the Formulae disclosed herein.

It is understood that the isotopic derivative can be prepared using any of a variety of art-recognized techniques. For example, the isotopic derivative can generally be prepared by carrying out the procedures disclosed in the Schemes and/or in the Examples herein, by substituting an isotopically labeled reagent for a non-isotopically labeled reagent.

In some embodiments, the isotopic derivative is a deuterium labeled compound.

In some embodiments, the isotopic derivative is a deuterium labeled compound of any one of the compounds of the Formulae disclosed herein.

The term "isotopic derivative", as used herein, refers to a derivative of a compound in which one or more atoms are isotopically enriched or labelled. For example, an isotopic derivative of a compound of Formula (I) or (II) is isotopically enriched with regard to, or labelled with, one or more isotopes as compared to the corresponding compound of Formula (I) or (II). In some embodiments, the isotopic derivative is enriched with regard to, or labelled with, one or more atoms selected from $^{2}H$, $^{13}C$, $^{14}C$, $^{15}N$, $^{18}O$, $^{29}Si$, $^{32}P$, and $^{34}S$. In some embodiments, the isotopic derivative is a deuterium labeled compound (i.e., being enriched with $^{2}H$ with regard to one or more atoms thereof). In some embodiments, the compound is a $^{2}H$ labeled compound. In some embodiments, the compound is a $^{13}C$ labeled compound or a $^{14}C$ labeled compound. In some embodiments, the compound is a $^{18}F$ labeled compound. In some embodiments, the compound is a $^{123}I$ labeled compound, a $^{124}I$ labeled compound, a $^{125}I$ labeled compound, a $^{129}I$ labeled compound, a $^{131}$I labeled compound, a $^{135}$I labeled compound, or any combination thereof. In some embodiments, the compound is a $^{32}$P labeled compound or a $^{32}$P labeled compound. In some embodiments, the compound is a $^{33}$S labeled compound, a $^{34}$S labeled compound, a $^{35}$S labeled compound, a $^{16}$S labeled compound, or any combination thereof.

It is understood that the isotopic derivatives can be prepared using any of a variety of art-recognized techniques. For example, the isotopic derivatives can generally be prepared by carrying out the procedures disclosed in the Schemes and/or in the Examples described herein, by substituting an isotope labeled reagent for a non-isotope labeled reagent.

It is also understood that isotopical substitution may afford certain therapeutic advantages resulting from greater metabolic stability, e.g., increased in vivo half-life or reduced dosage requirements.

For the avoidance of doubt it is to be understood that, where in this specification a group is qualified by "described herein", the said group encompasses the first occurring and broadest definition as well as each and all of the particular definitions for that group.

It will be understood that while compounds disclosed herein may be presented in one particular configuration. Such particular configuration is not to be construed as limiting the disclosure to one or another isomer, tautomer, regioisomer or stereoisomer, nor does it exclude mixtures of isomers, tautomers, regioisomers or stereoisomers. In some embodiments, the presentation of a compound herein in a particular configuration intends to encompass, and to refer to, each of the available isomers, tautomers, regioisomers, and stereoisomers of the compound, or any mixture thereof; while the presentation further intends to refer to the specific configuration of the compound.

It will be understood that while compounds disclosed herein may be presented without specified configuration (e.g., without specified stereochemistry). Such presentation intends to encompass all available isomers, tautomers, regioisomers, and stereoisomers of the compound.

In some embodiments, the presentation of a compound herein without specified configuration intends to refer to each of the available isomers, tautomers, regioisomers, and stereoisomers of the compound, or any mixture thereof.

As used herein, the term "isomerism" means compounds that have identical molecular formulae but differ in the sequence of bonding of their atoms or in the arrangement of their atoms in space. Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of 32xidizing light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this disclosure may possess one or more asymmetric centers; such compounds can therefore be produced as individual I- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4$^{th}$ edition J. March, John Wiley and Sons, New York, 2001), for example by synthesis from optically active starting materials or by resolution of a racemic form. Some of the compounds of the disclosure may have geometric isomeric centers (E- and Z-isomers). It is to be understood that the present disclosure encompasses all optical, diastereoisomers and geometric isomers and mixtures thereof that possess inflammasome inhibitory activity.

As used herein, the term "chiral center" refers to a carbon atom bonded to four nonidentical substituents.

As used herein, the term "chiral isomer" means a compound with at least one chiral center. Compounds with more than one chiral center may exist either as an individual diastereomer or as a mixture of diastereomers, termed "diastereomeric mixture." When one chiral center is present, a stereoisomer may be 33xidizing33ati by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., Angew. Chem. 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

As used herein, the term "geometric isomer" means the diastereomers that owe their existence to hindered rotation about double bonds or a cycloalkyl linker (e.g., 1,3-cyclobutyl). These configurations are differentiated in their names by the prefixes cis and trans, or Z and E, which indicates that the groups are on the same or opposite side of the double bond in the molecule according to the Cahn-Ingold-Prelog rules.

It is to be understood that the compounds of the present disclosure may be depicted as different chiral isomers or geometric isomers. It is also to be understood that when compounds have chiral isomeric or geometric isomeric forms, all isomeric forms are intended to be included in the scope of the present disclosure, and the naming of the compounds does not exclude any isomeric forms, it being understood that not all isomers may have the same level of activity.

It is to be understood that the structures and other compounds discussed in this disclosure include all atropic isomers thereof. It is also to be understood that not all atropic isomers may have the same level of activity.

As used herein, the term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

As used herein, the term "tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where 34xidizing34ation is possible, a chemical equilibrium of the tautomers will be reached. The exact ratio of the tautomers depends on several factors, including temperature, solvent and pH. The concept of tautomers that are interconvertible by tautomerisations is called tautomerism. Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form. It will be understood that certain tautomers may have a higher level of activity than others.

It is to be understood that the compounds of any Formula described herein include the compounds themselves, as well as their salts, and their solvates, if applicable. A salt, for example, can be formed between an anion and a positively charged group (e.g., amino) on a substituted compound disclosed herein. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate).

As used herein, the term "pharmaceutically acceptable anion" refers to an anion suitable for forming a pharmaceutically acceptable salt. Likewise, a salt can also be formed between a cation and a negatively charged group (e.g., carboxylate) on a substituted compound disclosed herein. Suitable cations include sodium ion, potassium ion, magnesium ion, calcium ion, and an ammonium cation such as tetramethylammonium ion or diethylamine ion. The substituted compounds disclosed herein also include those salts containing quaternary nitrogen atoms.

It is to be understood that the compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

As used herein, the term "solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure origin to the reference compound.

As used herein, the term "derivative" refers to compounds that have a common core structure and are substituted with various groups as described herein.

As used herein, the term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonamides, tetrazoles, sulfonates and phosphonates. See, e.g., Patani and LaVoie, *Chem. Rev.* 96, 3147-3176, 1996.

It is also to be understood that certain compounds of any one of the Formulae disclosed herein may exist in solvated as well as unsolvated forms such as, for example, hydrated forms. A suitable pharmaceutically acceptable solvate is, for example, a hydrate such as hemi-hydrate, a mono-hydrate, a di-hydrate or a tri-hydrate. It is to be understood that the disclosure encompasses all such solvated forms that possess inflammasome inhibitory activity.

It is also to be understood that certain compounds of any one of the Formulae disclosed herein may exhibit polymorphism, and that the disclosure encompasses all such forms, or mixtures thereof, which possess inflammasome inhibitory activity. It is generally known that crystalline materials may be analysed using conventional techniques such as X-Ray Powder Diffraction analysis, Differential Scanning Calorimetry, Thermal Gravimetric Analysis, Diffuse Reflectance Infrared Fourier Transform (DRIFT) spectroscopy, Near Infrared (NTR) spectroscopy, solution and/or solid state nuclear magnetic resonance spectroscopy. The water content of such crystalline materials may be determined by Karl Fischer analysis.

Compounds of any one of the Formulae disclosed herein may exist in a number of different tautomeric forms and references to compounds of any one of the Formulae include all such forms. For the avoidance of doubt, where a compound can exist in one of several tautomeric forms, and only one is specifically described or shown, all others are nevertheless embraced by the Formulae disclosed herein. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

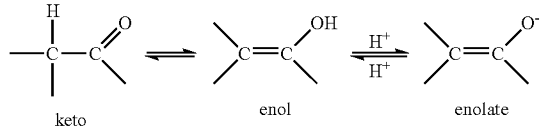

keto enol enolate

Compounds of any one of the Formulae disclosed herein containing an amine function may also form N-oxides. A reference herein to a compound of any one of the Formulae herein that contains an amine function also includes the N-oxide. Where a compound contains several amine functions, one or more than one nitrogen atom may be 37xidizin to form an N-oxide. Particular examples of N-oxides are the N-oxides of a tertiary amine or a nitrogen atom of a nitrogen-containing heterocycle. N-oxides can be formed by treatment of the corresponding amine with an 37xidizing agent such as hydrogen peroxide or a peracid (e.g. a peroxycarboxylic acid), see for example Advanced Organic Chemistry, by Jerry March, $4^{th}$ Edition, Wiley Interscience, pages. More particularly, N-oxides can be made by the procedure of L. W. Deady (Syn. Comm. 1977, 7, 509-514) in which the amine compound is reacted with meta-chloroperoxybenzoic acid (mCPBA), for example, in an inert solvent such as dichloromethane.

The compounds of any one of the Formulae disclosed herein may be administered in the form of a prodrug which is broken down in the human or animal body to release a compound of the disclosure. A prodrug may be used to alter the physical properties and/or the pharmacokinetic properties of a compound of the disclosure. A prodrug can be formed when the compound of the disclosure contains a suitable group or substituent to which a property-modifying group can be attached.

Accordingly, the present disclosure includes those compounds of any one of the Formulae disclosed herein as defined hereinbefore when made available by organic synthesis and when made available within the human or animal body by way of cleavage of a prodrug thereof. Accordingly, the present disclosure includes those compounds of any one of the Formulae disclosed herein that are produced by organic synthetic means and also such compounds that are produced in the human or animal body by way of metabolism of a precursor compound, that is a compound of any one of the Formulae disclosed herein may be a synthetically-produced compound or a metabolically-produced compound.

A suitable pharmaceutically acceptable prodrug of a compound of any one of the Formulae disclosed herein is one that is based on reasonable medical judgment as being suitable for administration to the human or animal body without undesirable pharmacological activities and without undue toxicity. Various forms of prodrug have been described, for example in the following documents: a) Methods in Enzymology, Vol. 42, p. 309-396, edited by K. Widder, et al. (Academic Press, 1985); b) Design of Pro-drugs, edited by H. Bundgaard, (Elsevier, 1985); c) A Textbook of Drug Design and Development, edited by Krogsgaard-Larsen and H. Bundgaard, Chapter 5 "Design and Application of Pro-drugs", by H. Bundgaard p. 113-191 (1991); d) H. Bundgaard, Advanced Drug Delivery Reviews, 8, 1-38 (1992); e) H. Bundgaard, et al., Journal of Pharmaceutical Sciences, 77, 285 (1988); f) N. Kakeya, et al., Chem. Pharm. Bull., 32, 692 (1984); g) T. Higuchi and V. Stella, "Pro-Drugs as Novel Delivery Systems", A.C.S. Symposium Series, Volume 14; and h) E. Roche (editor), "Bioreversible Carriers in Drug Design", Pergamon Press, 1987.

The in vivo effects of a compound of any one of the Formulae disclosed herein may be exerted in part by one or more metabolites that are formed within the human or animal body after administration of a compound of any one of the Formulae disclosed herein. As stated hereinbefore, the in vivo effects of a compound of any one of the Formulae disclosed herein may also be exerted by way of metabolism of a precursor compound (a prodrug).

Suitably, the present disclosure excludes any individual compounds not possessing the biological activity defined herein.

Scaffolds and Conjugates Containing the Linkers

As used herein, the term "scaffold" refers to a compound or complex that comprises a linker of the present disclosure, wherein the linker is covalently attached to either a ligand or a Nucleic Acid Agent.

As used herein, the term "conjugate" refers to a compound or complex that comprises a Nucleic Acid Agent being covalently attached to a Ligand via a linker of the present disclosure.

In some aspects, the present disclosure provides a scaffold or a pharmaceutically acceptable salt thereof, wherein the scaffold comprises:

(i) a Ligand; and (ii) a Linker Unit, wherein the Linker Unit is:

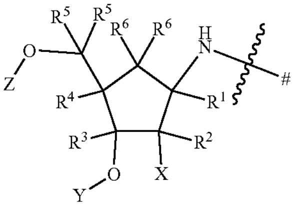

or

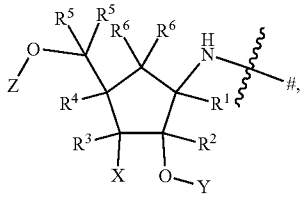

wherein variables $R^1$, $R^2$, $R^3$, $R^4$, $R^5$, $R^6$, X, Y, and Z are described herein, and # indicates an attachment to the Ligand.

In some aspects, the present disclosure provides a scaffold or a pharmaceutically acceptable salt thereof, wherein the scaffold comprises:

(i) one or more Nucleic Acid Agent; and (ii) one or more Linker Unit, wherein each Linker Unit independently is:

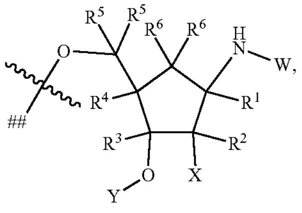

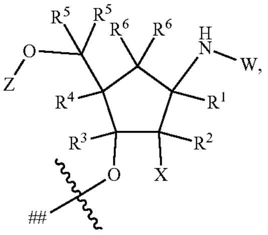

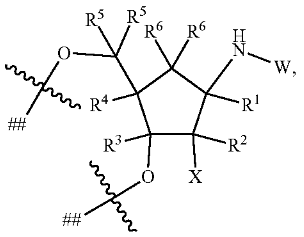

-continued

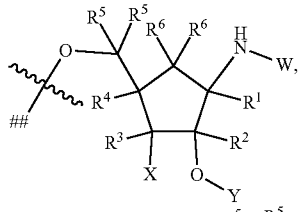

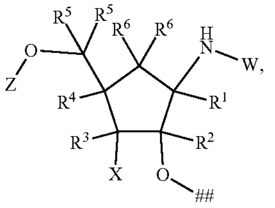

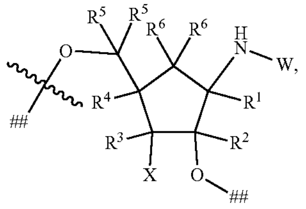

wherein variables $R^1$, $R^2$, $R^3$, $R^4$, $R^5$, $R^6$, W, X, Y, and Z are described herein, and ## indicates an attachment to the Nucleic Acid Agent.

In some embodiments, the attachment "##" is a direct attachment to the Nucleic Acid Agent, i.e., without any linking moiety.

In some embodiments, the attachment "##" is an indirect attachment to the Nucleic Acid Agent, i.e., there is a linking moiety between the Linker Unit and the Nucleic Acid Agent. In some embodiments, the linking moiety is a radical formed from any of the groups as defined for Y or Z herein. For example, the linking moiety is —$P(N(CH_3)_2)(O)$—, i.e., a radical formed from —$P(N(CH_3)_2)(OH)$. In some embodiments, the linking moiety is a radical formed from any of —$P(R^Y)_2$, —$P(OR^Y)(N(R^Y)_2)$, —$P(=O)(OR^Y)R^Y$, —$P(=S)(OR^Y)R^Y$, —$P(=O)(SR^Y)R^Y$, —$P(=S)(SR^Y)R^Y$, —$P(=O)(OR^Y)_2$, —$P(=S)(OR^Y)_2$, —$P(=O)(SR^Y)_2$, or —$P(=S)(SR^Y)_2$, or from any of —$P(R^Z)_2$, —$P(OR^Z)(N(R^Z)_2)$, —$P(=O)(OR^Z)R^Z$, —$P(=S)(OR^Z)R^Z$, —$P(=O)(SR^Z)R^Z$, —$P(=S)(SR^Z)R^Z$, —$P(=O)(OR^Z)_2$, —$P(=S)(OR^Z)_2$, —$P(=O)(SR^Z)_2$, or —$P(=S)(SR^Z)$.

In some embodiments, the scaffold comprises a double strand RNA (e.g., double strand siRNA).

In some embodiments, the scaffold comprises a double strand RNA (e.g., double strand siRNA) and one or more Linker Units.

In some embodiments, the scaffold comprises a double strand RNA (e.g., double strand siRNA) and from 1 to 10 Linker Units (e.g., from 1 to 10, from 1 to 9, from 1 to 8, from 1 to 7, from 1 to 6, from 1 to 5, from 1 to 4, or from 1 to 3 Linker Units), from 2 to 10 Linker Units (e.g., from 2 to 10, from 2 to 9, from 2 to 8, from 2 to 7, from 2 to 6, from 2 to 5, from 2 to 4, or from 2 to 3 Linker Units), from 3 to 10 Linker Units (e.g., from 3 to 10, from 3 to 9, from 3 to 8, from 3 to 7, from 3 to 6, from 3 to 5, or from 3 to 4 Linker Units), from 4 to 10 Linker Units (e.g., from 4 to 10, from 4 to 9, from 4 to 8, from 4 to 7, from 4 to 6, or from 4 to 5 Linker Units), from 5 to 10 Linker Units (e.g., from 5 to 10, from 5 to 9, from 5 to 8, from 5 to 7, or from 5 to 6 Linker Units), or from 6 to 10 Linker Units (e.g., from 6 to 10, from 6 to 9, from 6 to 8, or from 6 to 7 Linker Units).

In some embodiments, the scaffold comprises a double strand RNA (e.g., double strand siRNA) and 1 Linker Units, 2 Linker Units, 3 Linker Units, 4 Linker Units, 5 Linker Units, 6 Linker Units, 7 Linker Units, 8 Linker Units, 9 Linker Units, or 10 Linker Units.

In some embodiments, the scaffold comprises a double strand RNA (e.g., double strand siRNA) and one or more Linker Units, wherein:

one or more Linker Units (e.g., from 1 to 3 Linker Units) are consecutively or discretely attached to the sense strand (e.g., at the 3'- or 5'-terminal position) of the double strand RNA (e.g., double strand siRNA);

one or more nucleosides or nucleotides at one or more consecutive or discrete internal positions (positions between the 3'- and 5'-terminal positions) of the sense strand of the double strand RNA (e.g., double strand siRNA) are replaced with the one or more Linker Units (e.g., from 1 to 3 Linker Units);

one or more Linker Units (e.g., from 1 to 3 Linker Units) are consecutively or discretely attached to the antisense strand (e.g., at the 3'- or 5'-terminal position) of the double strand RNA (e.g., double strand siRNA); and/or one or more nucleosides or nucleotides at one or more consecutive or discrete internal position of the antisense strand are replaced with the one or more Linker Units (e.g., from 1 to 3 Linker Units).

In some embodiments, the scaffold comprises a double strand RNA (e.g., double strand siRNA) and one or more Linker Units, wherein:

one or more Linker Units (e.g., from 1 to 3 Linker Units) are consecutively or discretely attached to the sense strand (e.g., at the 3'- or 5'-terminal position) of the double strand RNA (e.g., double strand siRNA); and one or more nucleosides or nucleotides at one or more consecutive or discrete internal positions (positions between the 3'- and 5'-terminal positions) of the sense strand of the double strand RNA (e.g., double strand siRNA) are replaced with the one or more Linker Units (e.g., from 1 to 3 Linker Units).

In some embodiments, the scaffold comprises a double strand RNA (e.g., double strand siRNA) and one or more Linker Units, wherein:

one or more Linker Units (e.g., from 1 to 3 Linker Units) are consecutively or discretely attached to the antisense strand (e.g., at the 3'- or 5'-terminal position) of the double strand RNA (e.g., double strand siRNA); and one or more nucleosides or nucleotides at one or more consecutive or discrete internal position of the antisense strand are replaced with the one or more Linker Units (e.g., from 1 to 3 Linker Units).

In some embodiments, the one or more Linker Units (e.g., from 1 to 3 Linker Units) are consecutively or discretely attached to the sense strand (e.g., at the 3'- or 5'-terminal position) of the double strand RNA (e.g., double strand siRNA).

In some embodiments, the one or more Linker Units (e.g., from 1 to 3 Linker Units) are consecutively or discretely attached to the sense strand at the 3'-terminal position of the double strand RNA (e.g., double strand siRNA).

In some embodiments, the one or more Linker Units (e.g., from 1 to 3 Linker Units) are consecutively or discretely attached to the sense strand at the 5'-terminal position of the double strand RNA (e.g., double strand siRNA).

In some embodiments, one or more nucleosides or nucleotides at one or more consecutive or discrete internal positions of the sense strand of the double strand RNA (e.g., double strand siRNA) are replaced with the one or more Linker Units (e.g., from 1 to 3 Linker Units).

In some embodiments, the one or more Linker Units (e.g., from 1 to 3 Linker Units) are consecutively or discretely attached to the antisense strand (e.g., at the 3'- or 5'-terminal position) of the double strand RNA (e.g., double strand siRNA).

In some embodiments, the one or more Linker Units (e.g., from 1 to 3 Linker Units) are consecutively or discretely attached to the antisense strand at the 3'-terminal position of the double strand RNA (e.g., double strand siRNA).

In some embodiments, the one or more Linker Units (e.g., from 1 to 3 Linker Units) are consecutively or discretely attached to the antisense strand at the 5'-terminal position of the double strand RNA (e.g., double strand siRNA).

In some embodiments, one or more nucleosides or nucleotides at one or more consecutive or discrete internal positions of the antisense strand of the double strand RNA (e.g., double strand siRNA) are replaced with the one or more Linker Units (e.g., from 1 to 3 Linker Units).

In some embodiments, the scaffold is (Linker Unit)$_p$-((Nucleic Acid Agent)-(Linker Unit)$_s$)$_r$-(Nucleic Acid Agent)$_q$, wherein:

each Linker Unit is independent from another Linker Unit, and each Nucleic Acid Agent is independent from another Nucleic Acid Agent;

each r independently is an integer ranging from 0 to 10;

each s independently is an integer ranging from 0 to 10;

p is an integer ranging from 0 to 10;

q is 0 or 1; and the scaffold comprises at least one Linker Unit and at least one Nucleic Acid Agent.

In some embodiments, the scaffold is (Linker Unit)$_p$-((Nucleic Acid Agent)-(Linker Unit)$_s$)$_r$-(Nucleic Acid Agent).

In some embodiments, the scaffold is (Linker Unit)$_p$-((Nucleic Acid Agent)-(Linker Unit)$_s$)$_r$.

In some embodiments, the scaffold is (Linker Unit)$_p$-(Nucleic Acid Agent).

In some embodiments, the scaffold is (Nucleic Acid Agent)-(Linker Unit)$_s$-(Nucleic Acid Agent).

In some embodiments, the scaffold is

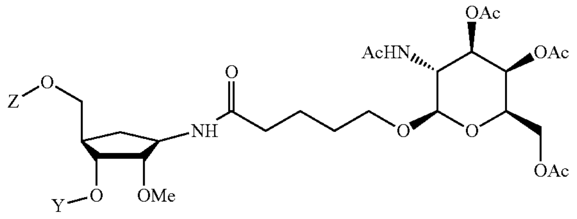

or a pharmaceutically acceptable salt thereof, wherein:

Y is —P(R$^Y$)$_2$, —P(OR$^Y$)(N(R$^Y$)$_2$), —P(=O)(OR$^Y$)R$^Y$, —P(=S)(OR$^Y$)R$^Y$, —P(=O)(SR$^Y$)R$^Y$, —P(=S)(SR$^Y$)R$^Y$, —P(=O)(OR$^Y$)$_2$, —P(=S)(OR$^Y$)$_2$, —P(=O)(SR$^Y$)$_2$, —P(=S)(SR$^Y$)$_2$, or a hydroxy protecting group (e.g., silyl (e.g., trimethylsilyl, triethylsilyl, tert-butyldimethylsilyl, tert-butyldiphenylsilyl, or triisopropylsilyl), triphenylmethyl (Tr), 4,4'-dimethoxytrityl (DMTr), substituted acyl (e.g., optionally substituted acetyl), or benzyl);

each R$^Y$ independently is H or $C_1$-$C_6$ alkyl optionally substituted with one or more halogen or cyano;

Z is —P(R$^Z$)$_2$, —P(OR$^Z$)(N(R$^Z$)$_2$), —P(=O)(OR$^Z$)R$^Z$, —P(=S)(OR$^Z$)R$^Z$, —P(=O)(SR$^Z$)R$^Z$, —P(=S)(SR$^Z$)R$^Z$, —P(=O)(OR$^Z$)$_2$, —P(=S)(OR$^Z$)$_2$, —P(=O)(SR$^Z$)$_2$, —P(=S)(SR$^Z$)$_2$, or a hydroxy protecting group (e.g., silyl (e.g., trimethylsilyl, triethylsilyl, tert-butyldimethylsilyl, tert-butyldiphenylsilyl, or triisopropylsilyl), triphenylmethyl (Tr), 4,4'-dimethoxytrityl (DMTr), substituted acyl (e.g., optionally substituted acetyl), or benzyl); and each R$^Z$ independently is H or $C_1$-$C_6$ alkyl optionally substituted with one or more halogen or cyano.

In some embodiments, the scaffold is formed by linking a Linker Unit based on any of the Linker Compounds described herein with a Ligand.

In some embodiments, the scaffold is formed by linking a Linker Unit based on any of the Linker Compounds selected from

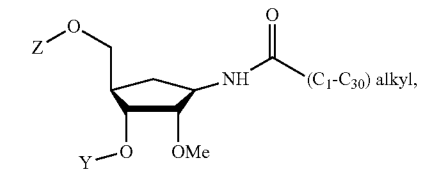

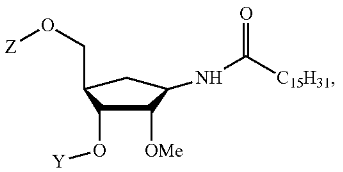

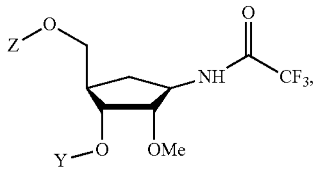

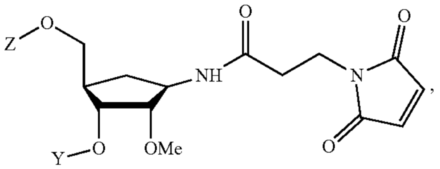

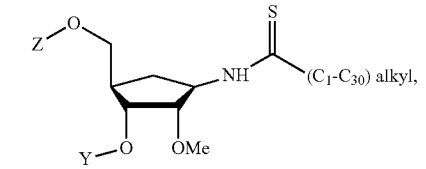

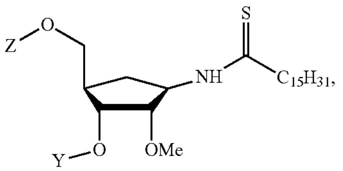

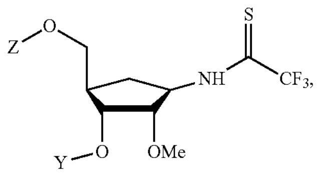

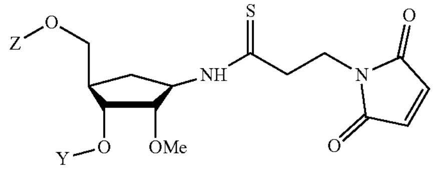

-continued
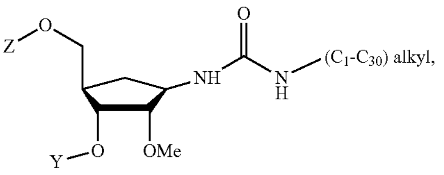
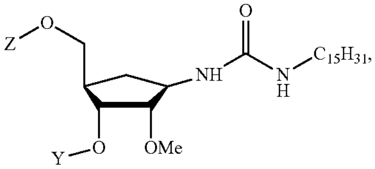
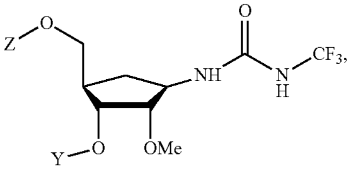
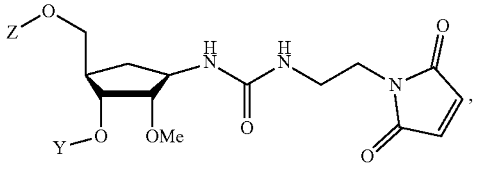
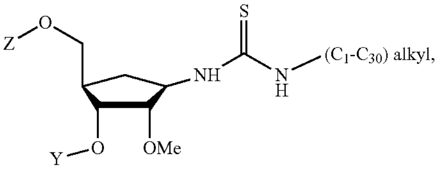
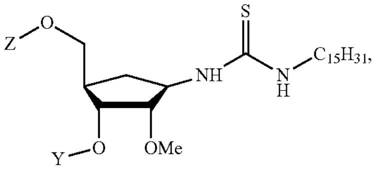
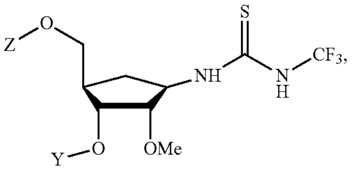
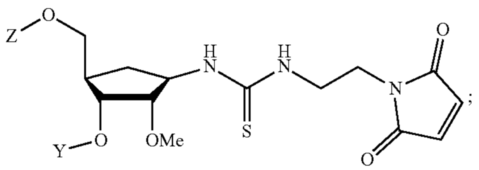
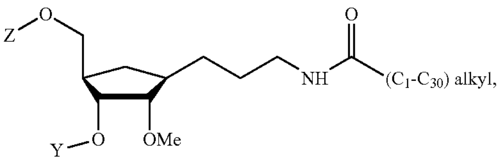
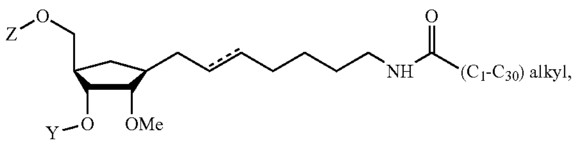
-continued
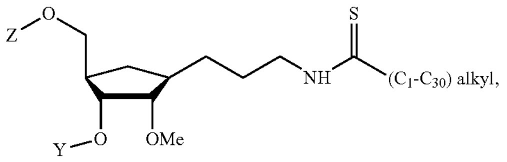
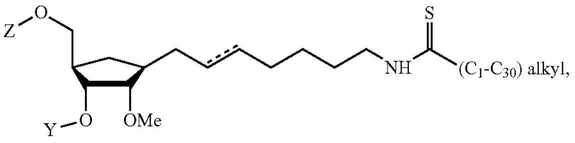
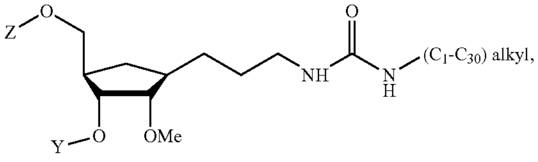
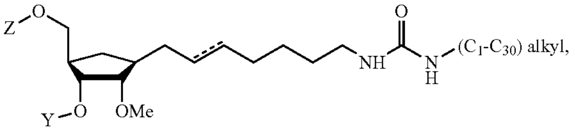
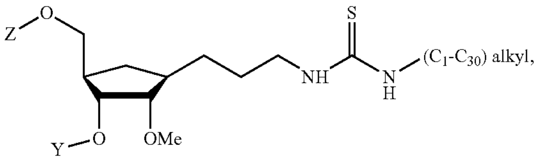
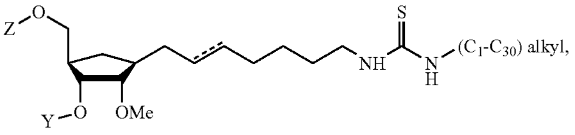
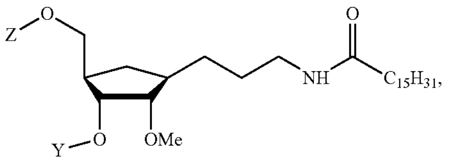
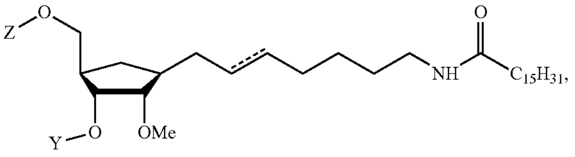
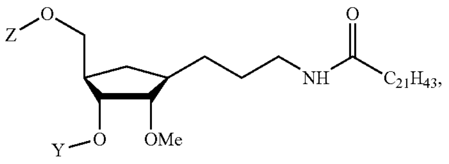
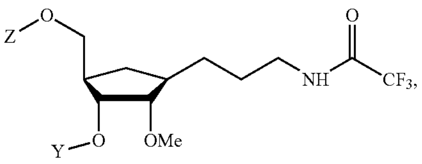
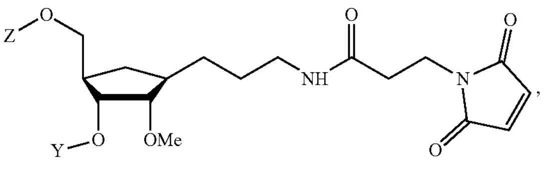

-continued
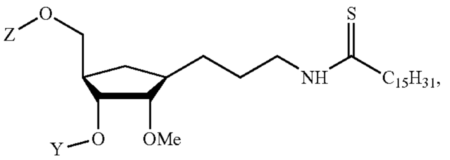
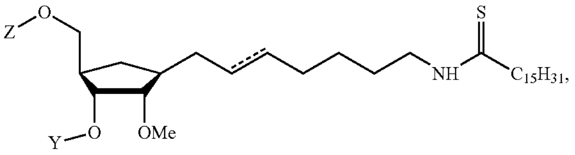
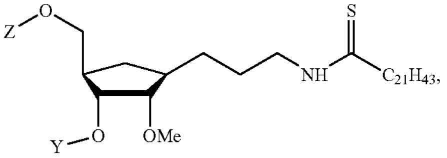
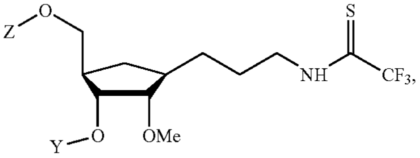
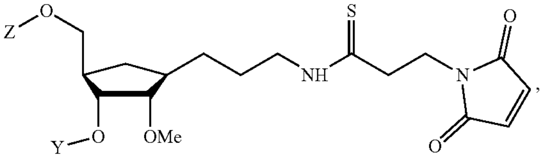
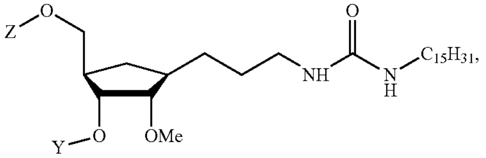
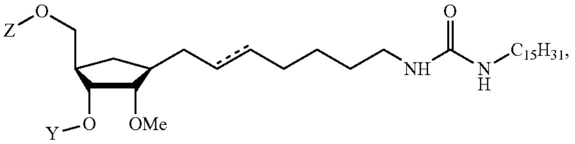
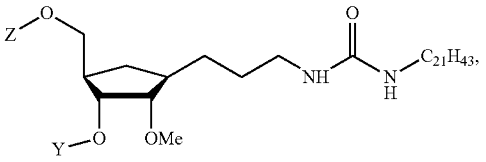
-continued
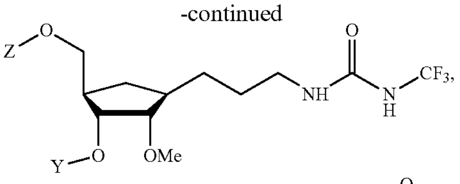
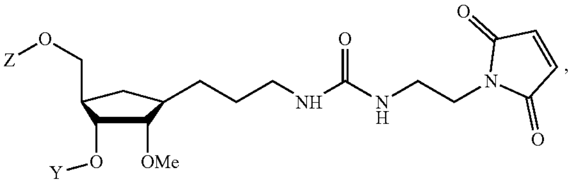
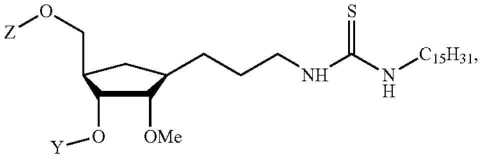
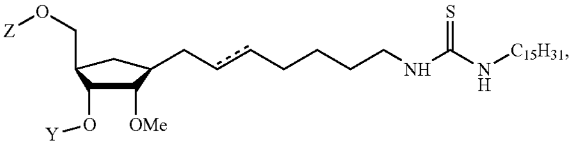
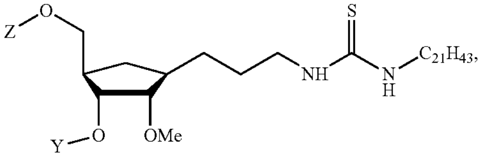
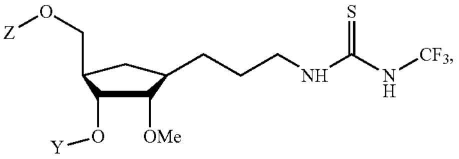
and
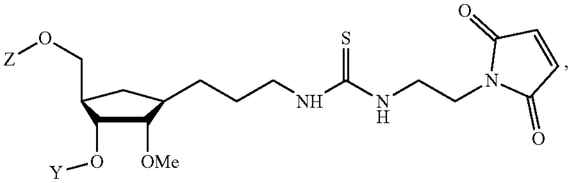
with a Ligand.
In some embodiments, the scaffold is formed by linking a Linker Unit based on any of the Linker Compounds selected from Table L with a Ligand.
In some embodiments, the scaffold is selected from the scaffolds described in Table Si.
TABLE S1
| Compound No. | Structure |
| --- | --- |
| S1-1 | 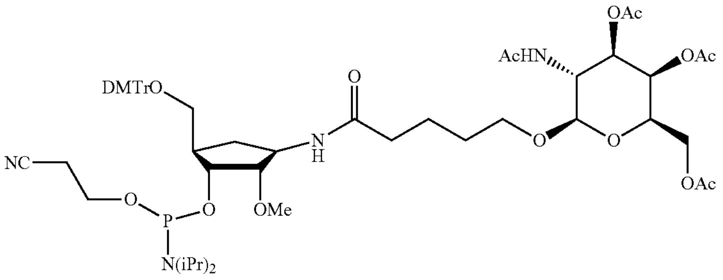 |

TABLE S1-continued
| Compound No. | Structure |
| --- | --- |
| S1-2 | 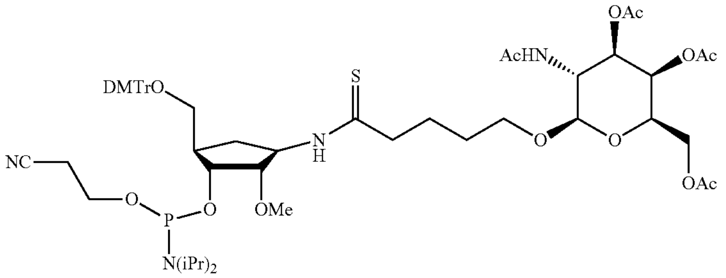 |
| S1-3 | 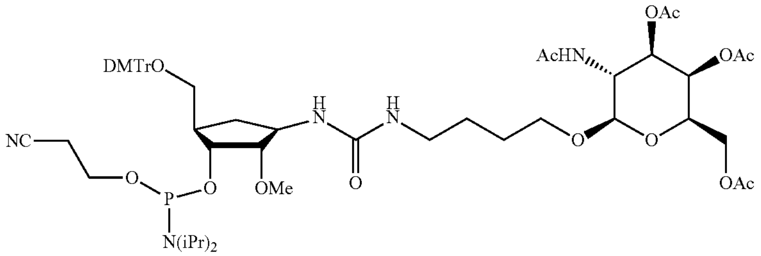 |
| S1-4 | 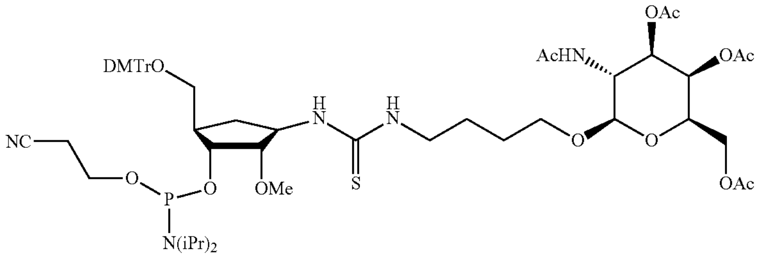 |
| S1-5 | 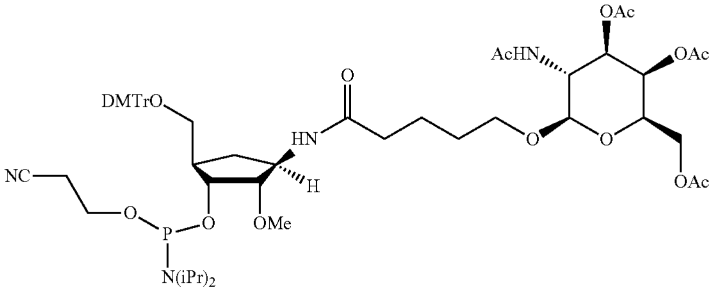 |
| S1-6 | 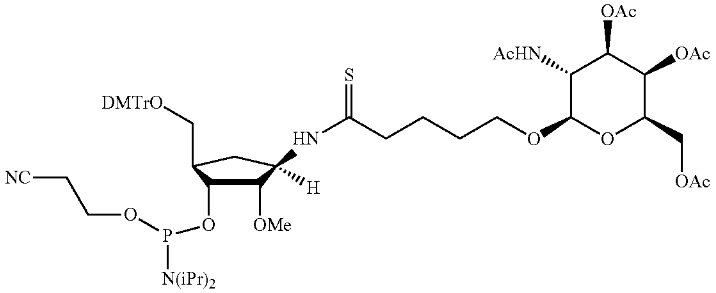 |

TABLE S1-continued
| Compound No. | Structure |
|---|---|
| S1-7 | 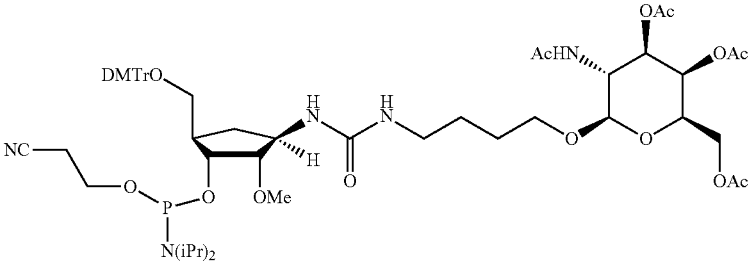 |
| S1-8 | 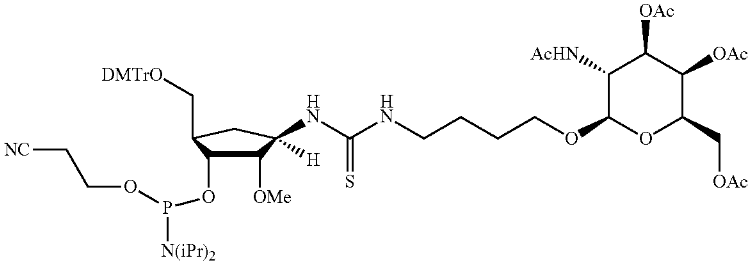 |
| S1-9 | 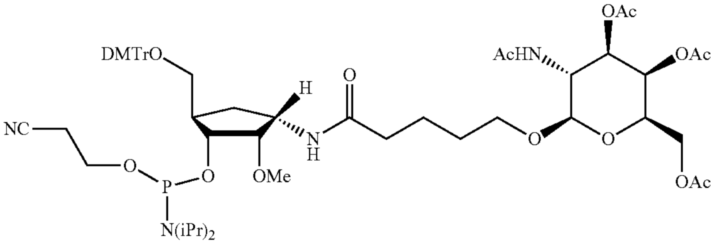 |
| S1-10 | 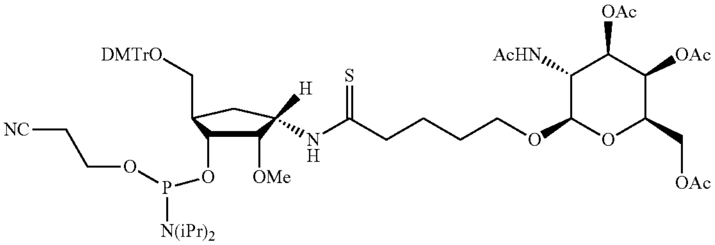 |
| S1-11 | 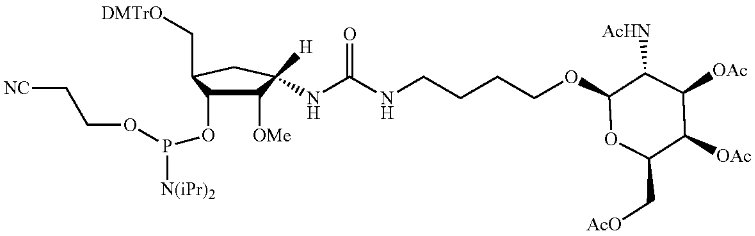 |
| S1-12 | 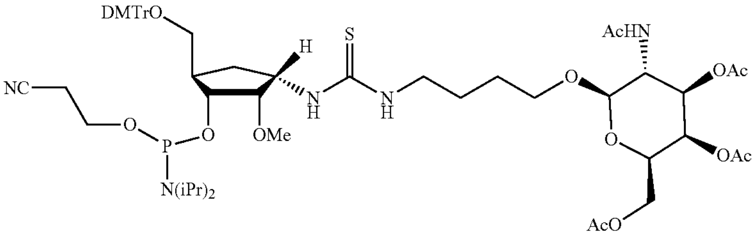 |

In some embodiments the scaffold is

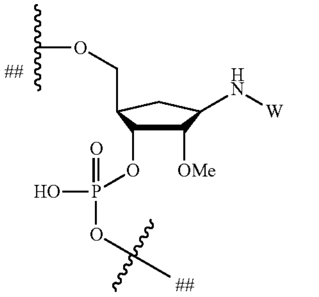

or

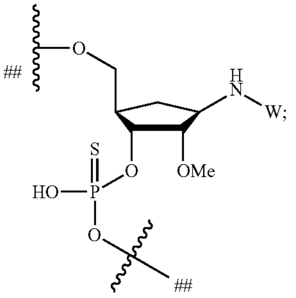

or a pharmaceutically acceptable salt thereof, wherein:

W is an amino substitution group (e.g., fluorenylmethyloxycarbonyl (Fmoc), tert-butyloxycarbonyl (BOC), benzyloxycarbonyl (Cbz), optionally substituted acyl, trifluoroacetyl (TFA), benzyl, triphenylmethyl (Tr), 4,4'-dimethoxytrityl (DMTr), or toluenesulfonyl (Ts), acyl (e.g., —C(═O)($C_1$-$C_{30}$ alkyl)), substituted acyl (e.g.,

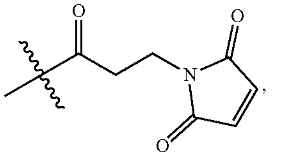

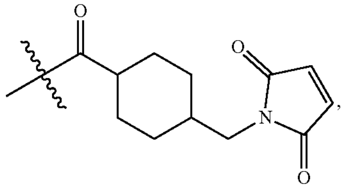

or

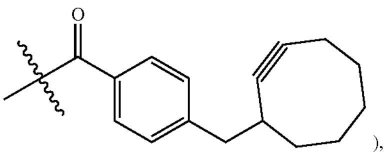 [SMILES: *C(=O)c1ccc(CC2C#CCCCCC2)cc1]

), trifluoroacetyl (TFA), —C(═O)($C_1$-$C_{30}$ alkyl), —C(═O)NH($C_1$-$C_{30}$ alkyl), —C(═S)($C_1$-$C_{30}$ alkyl), or —C(═S)NH($C_1$-$C_{30}$ alkyl), wherein the $C_1$-$C_{30}$ alkyl is optionally substituted)).

In some embodiments, the scaffold is formed by linking a Linker Unit based on any of the Linker Compounds described herein with a Nucleic Acid Agent.

In some embodiments, the scaffold is formed by linking a Linker Unit based on any of the Linker Compounds selected from

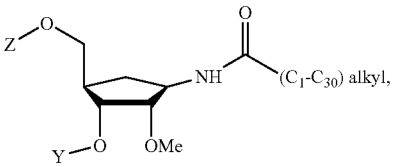

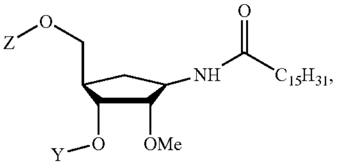

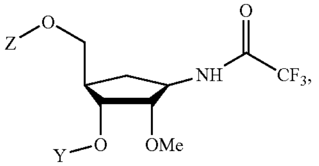

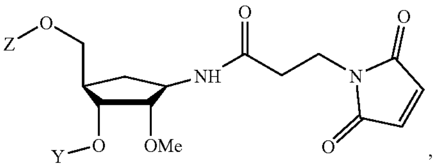

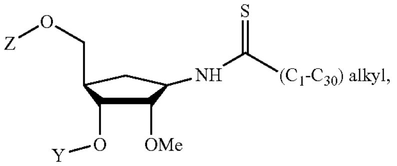

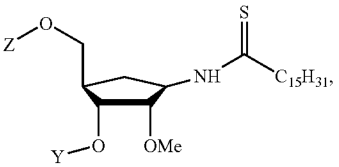

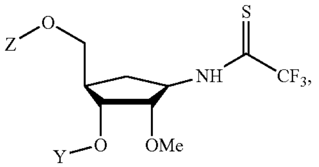

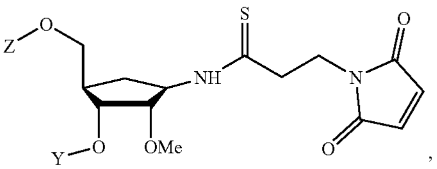

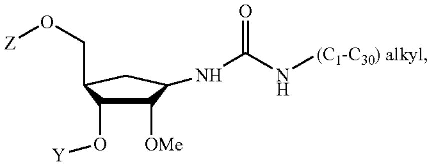

-continued
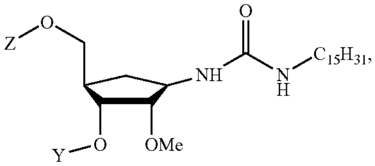
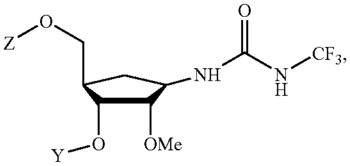
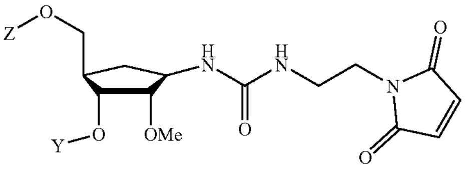
,
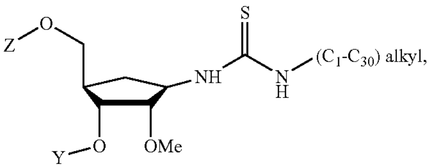
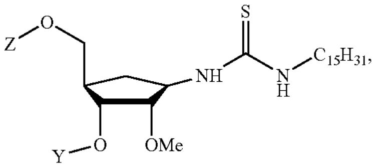
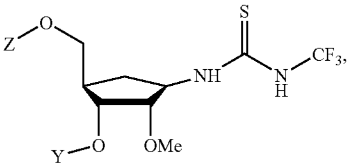
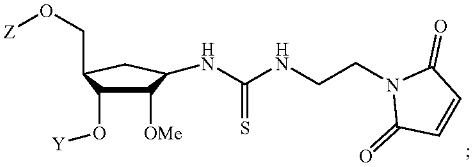
;
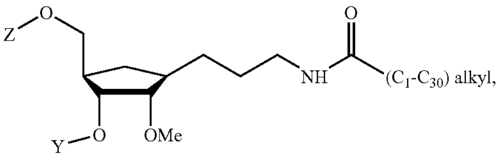
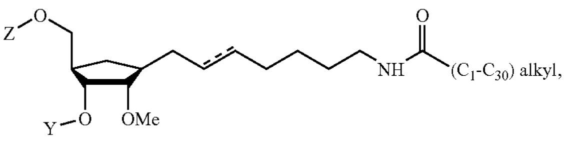
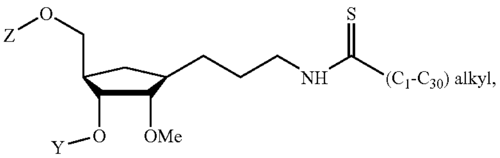
-continued
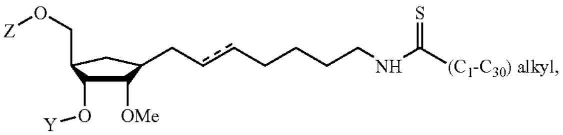
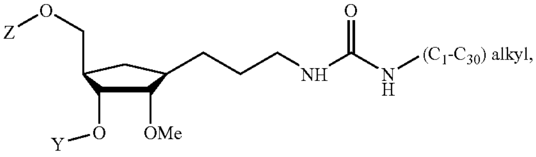
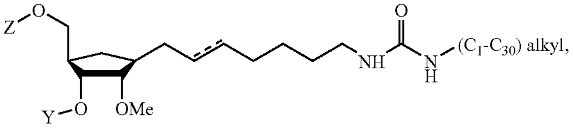
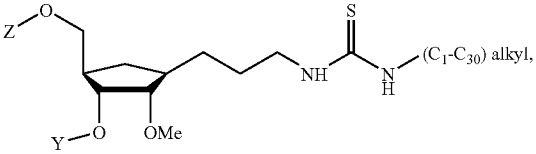
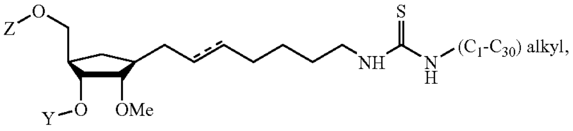
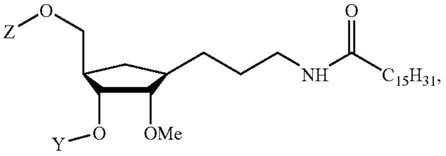
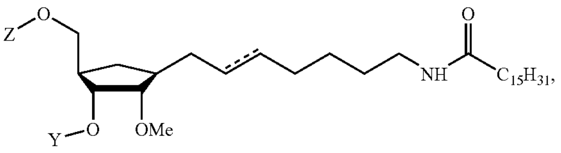
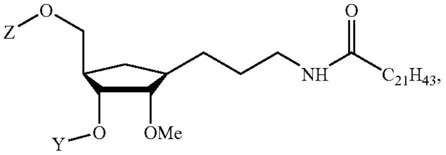
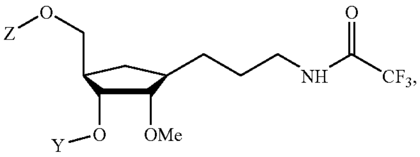
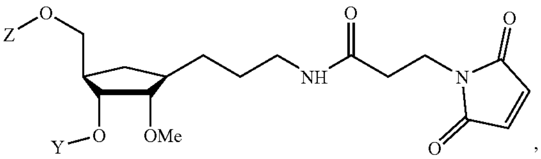
,
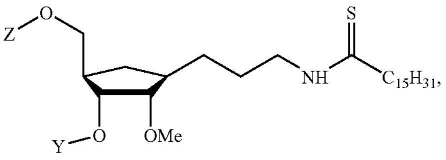

-continued
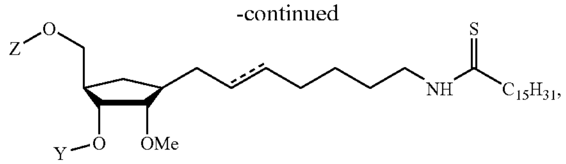
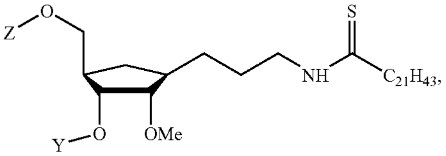
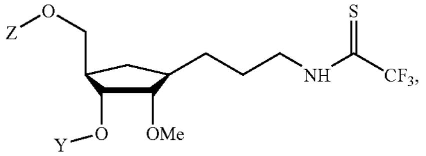
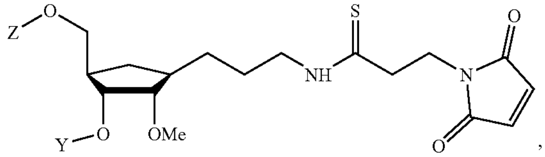
,
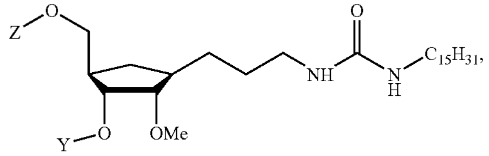
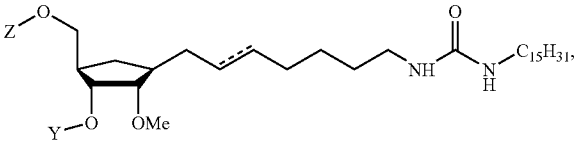
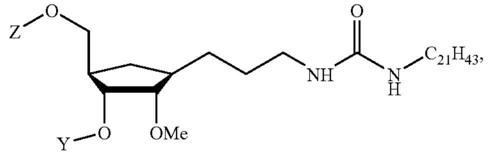
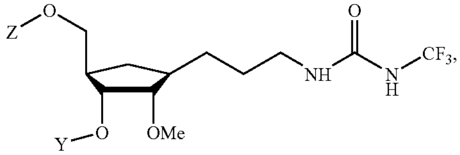
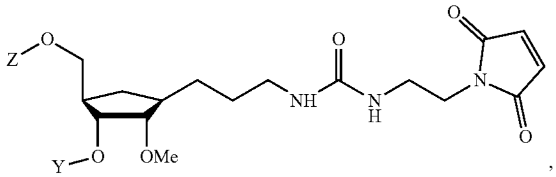
,
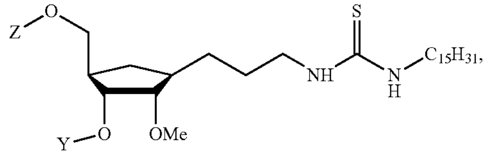
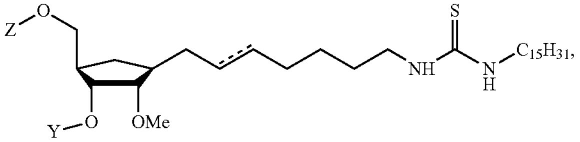
-continued
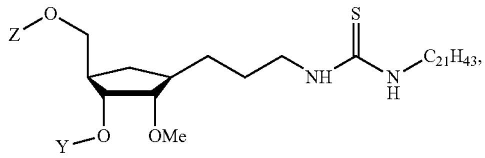
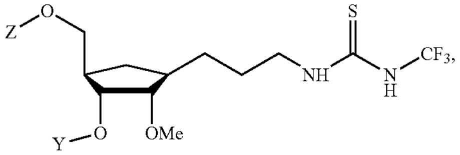
and
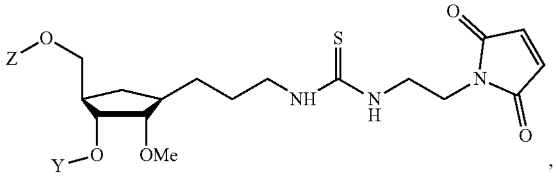
,
with a Nucleic Acid Agent.
In some embodiments, the scaffold is selected from the scaffolds described in Table S2.
TABLE S2
| Compound No. | Structure |
| --- | --- |
| S2-1 | 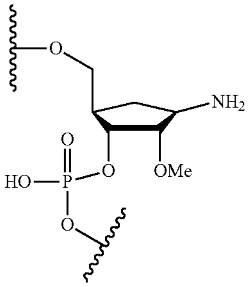 |
| S2-2 | 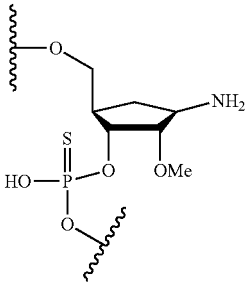 |
| S2-3 | 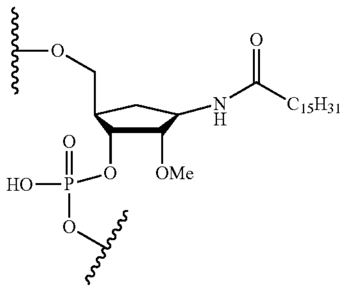 |

TABLE S2-continued
| Compound No. | Structure |
|---|---|
| S2-4 | 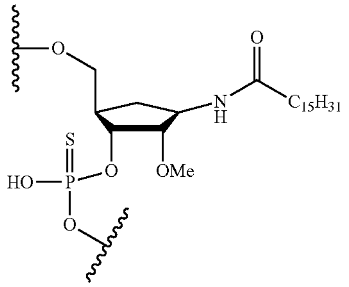 |
| S2-5 | 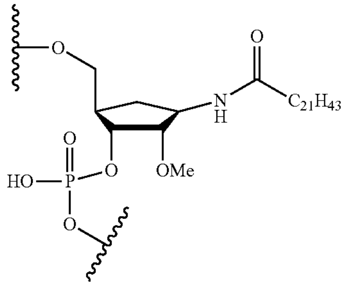 |
| S2-6 | 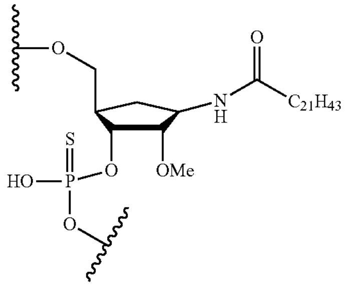 |
| S2-7 | 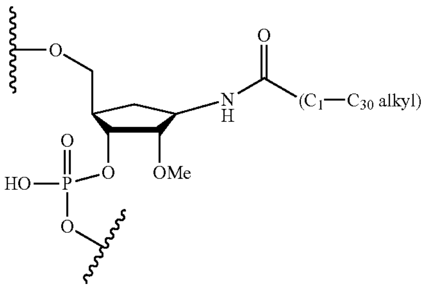 wherein the $C_1$-$C_{30}$ alkyl is optionally substituted |
| S2-8 | 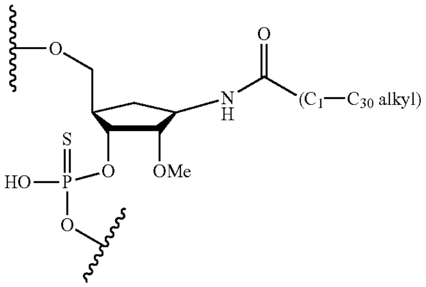 wherein the $C_1$-$C_{30}$ alkyl is optionally substituted |
TABLE S2-continued
| Compound No. | Structure |
|---|---|
| S2-9 | 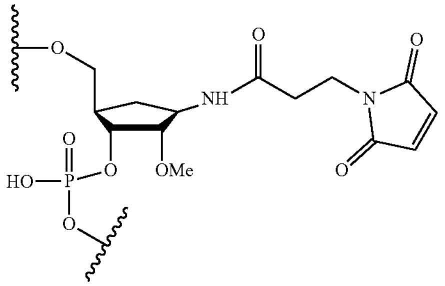 |
| S2-10 | 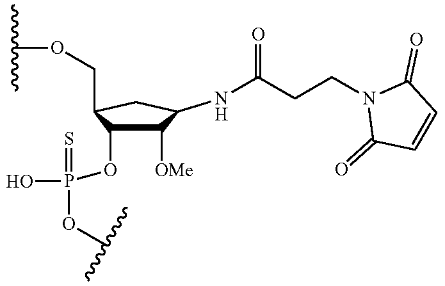 |
| S2-11 | 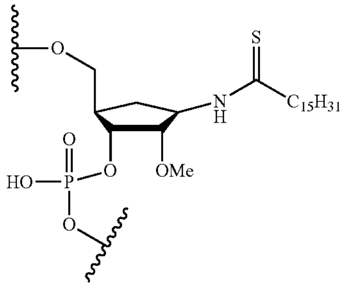 |
| S2-12 | 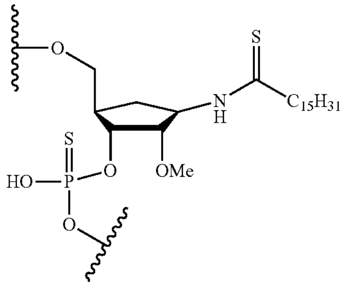 |
| S2-13 | 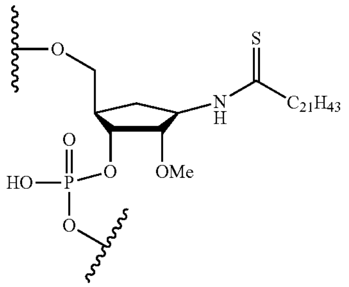 |

TABLE S2-continued
| Compound No. | Structure |
|---|---|
| S2-14 | 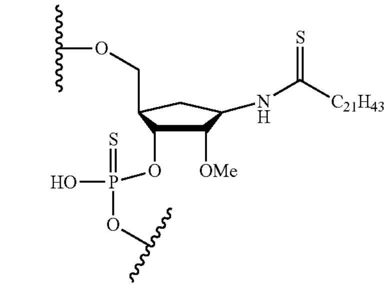 |
| S2-15 | 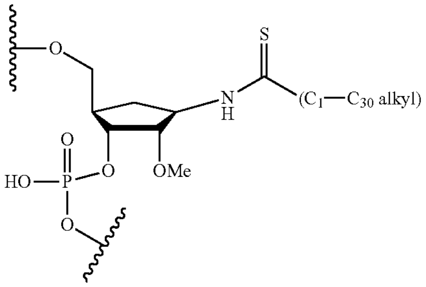<br>wherein the $C_1$-$C_{30}$ alkyl is optionally substituted |
| S2-16 | 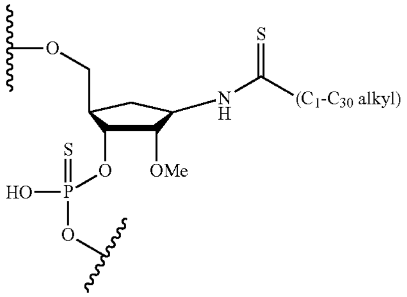<br>wherein the $C_1$-$C_{30}$ alkyl is optionally substituted |
| S2-17 | 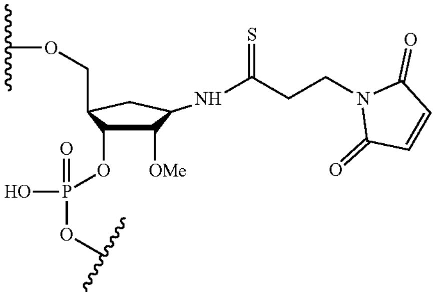 |
| S2-18 | 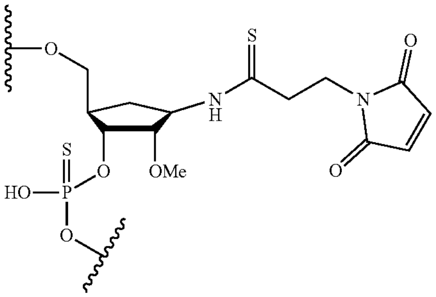 |
TABLE S2-continued
| Compound No. | Structure |
|---|---|
| S2-19 | 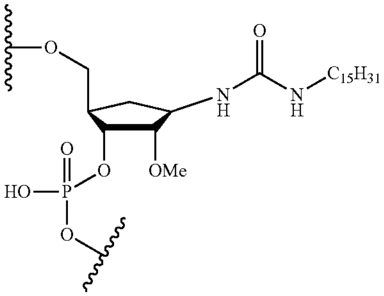 |
| S2-20 | 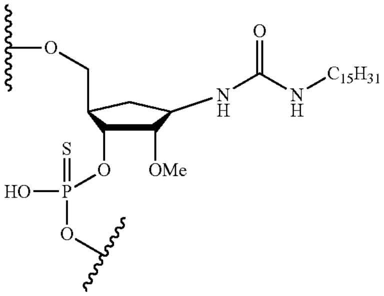 |
| S2-21 | 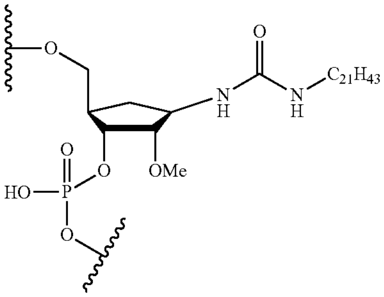 |
| S2-22 | 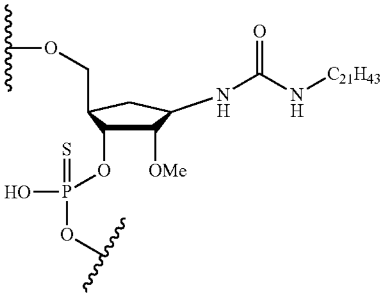 |
| S2-23 | 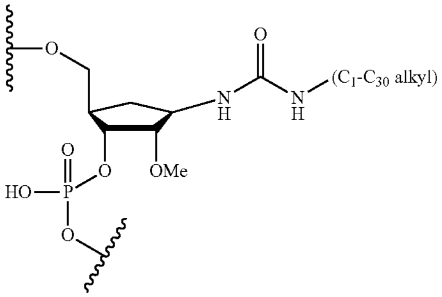<br>wherein the $C_1$-$C_{30}$ alkyl is optionally substituted |

TABLE S2-continued
| Compound No. | Structure |
| --- | --- |
| S2-24 | 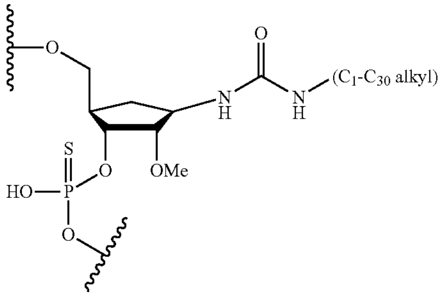 wherein the $C_1$-$C_{30}$ alkyl is optionally substituted |
| S2-25 | 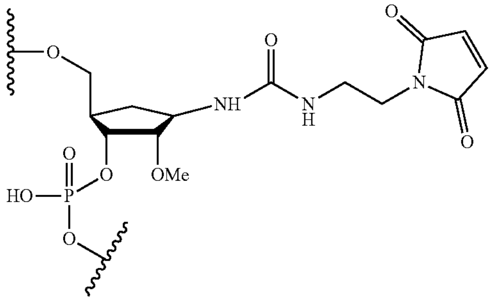 |
| S2-26 | 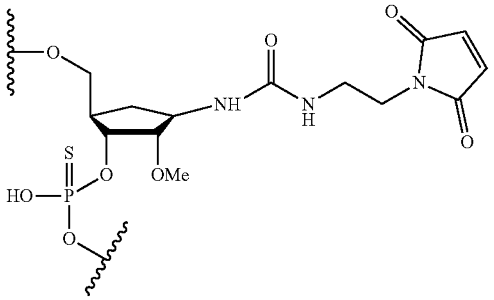 |
| S2-27 | 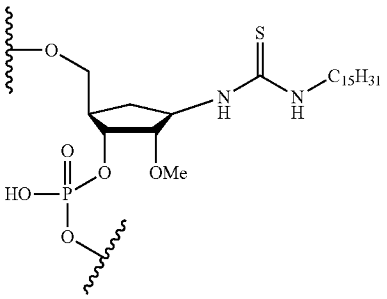 |
| S2-28 | 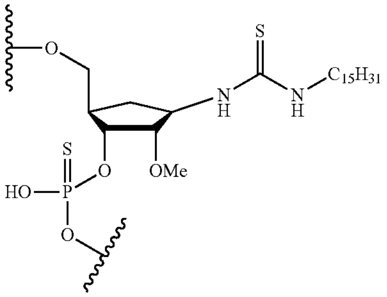 |
| S2-29 | 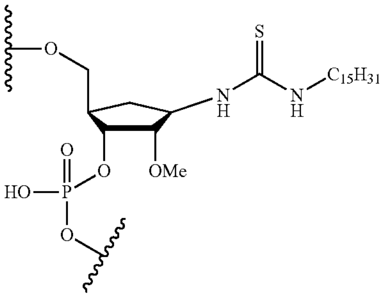 |
| S2-30 | 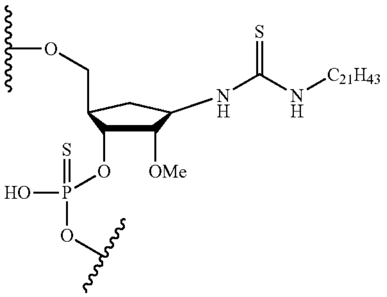 |
| S2-31 | 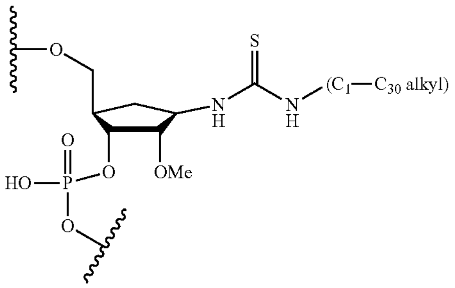 wherein the $C_1$-$C_{30}$ alkyl is optionally substituted |
| S2-32 | 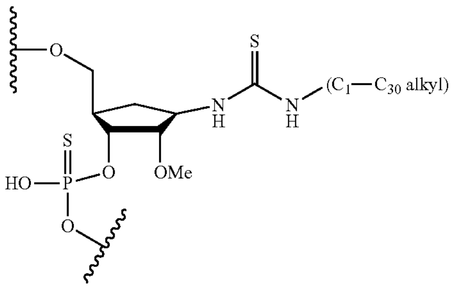 wherein the $C_1$-$C_{30}$ alkyl is optionally substituted |

TABLE S2-continued
| Compound No. | Structure |
| --- | --- |
| S2-33 | 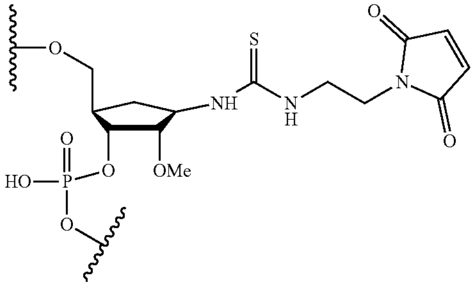 |
| S2-34 | 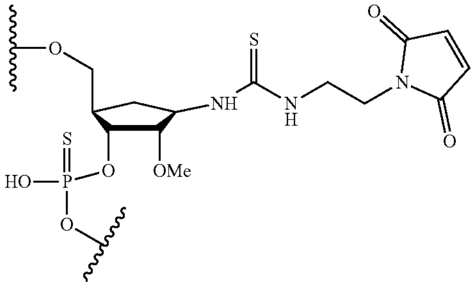 |
| S2-35 | 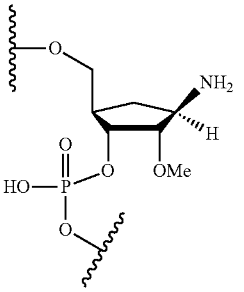 |
| S2-36 | 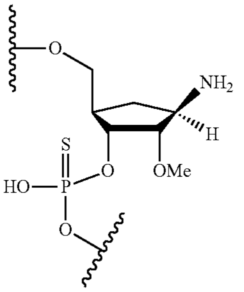 |
| S2-37 | 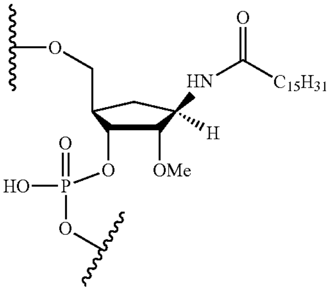 |
TABLE S2-continued
| Compound No. | Structure |
| --- | --- |
| S2-38 | 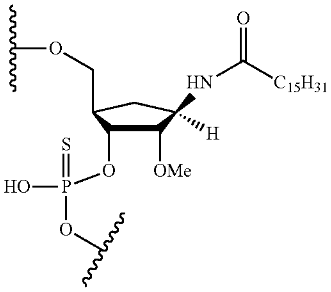 |
| S2-39 | 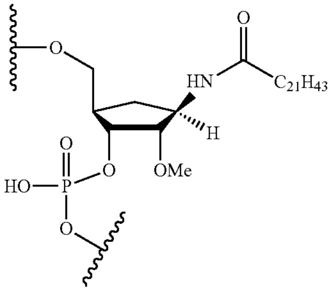 |
| S2-40 | 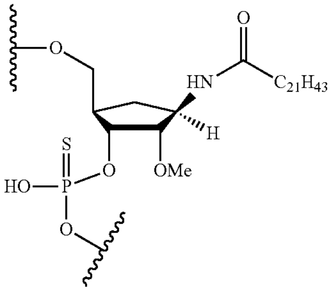 |
| S2-41 | 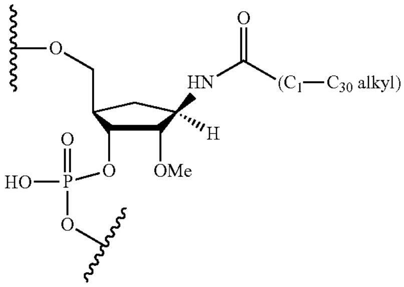 wherein the $C_1$-$C_{30}$ alkyl is optionally substituted |
| S2-42 | 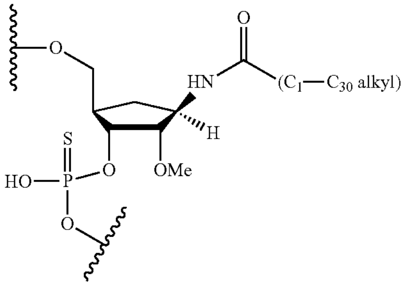 wherein the $C_1$-$C_{30}$ alkyl is optionally substituted |

TABLE S2-continued
| Compound No. | Structure |
| --- | --- |
| S2-43 | 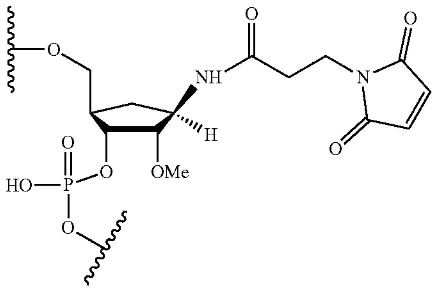 |
| S2-44 | 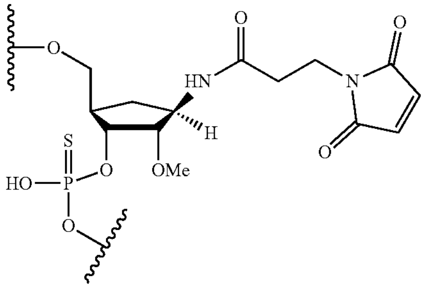 |
| S2-45 | 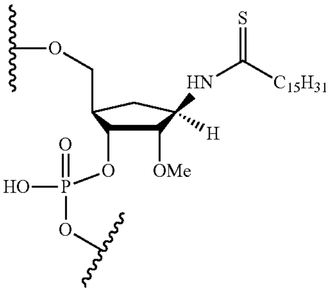 |
| S2-46 | 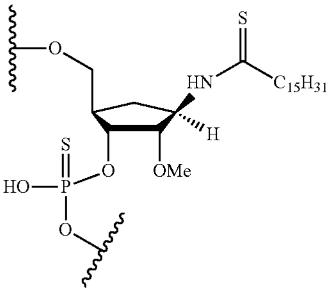 |
| S2-47 | 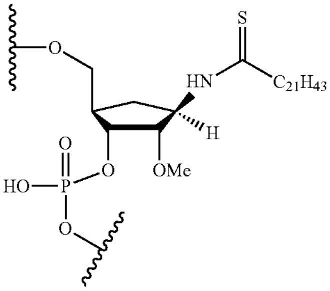 |
TABLE S2-continued
| Compound No. | Structure |
| --- | --- |
| S2-48 | 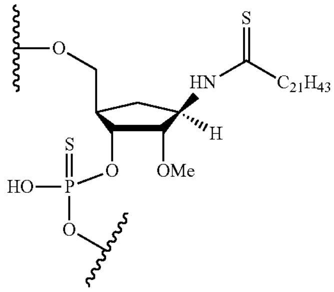 |
| S2-49 | 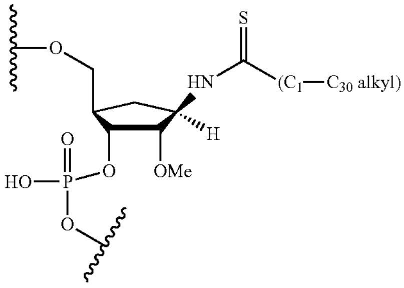<br>OMe wherein the $C_1$-$C_{30}$ alkyl is optionally substituted |
| S2-50 | 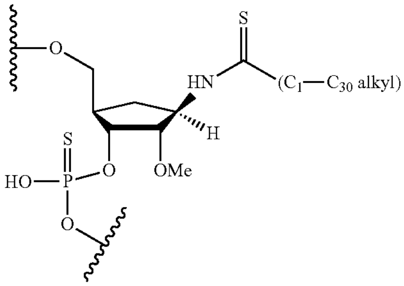<br>wherein the $C_1$-$C_{30}$ alkyl is optionally substituted |
| S2-51 | 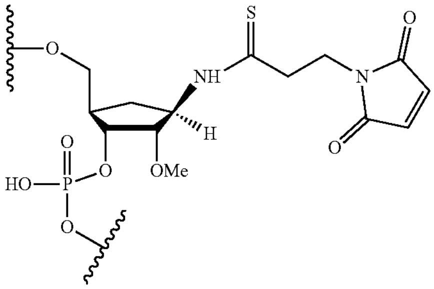 |
| S2-52 | 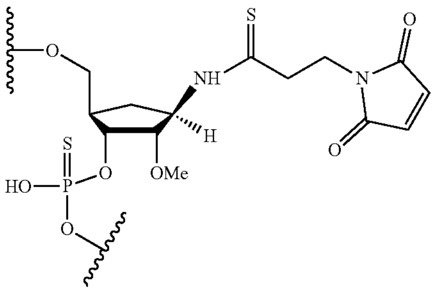 |

TABLE S2-continued
| Compound No. | Structure |
|---|---|
| S2-53 | 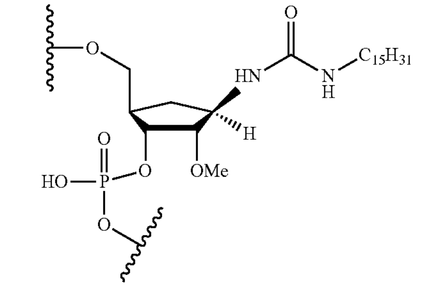 |
| S2-54 | 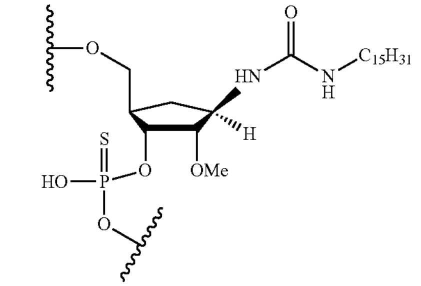 |
| S2-55 | 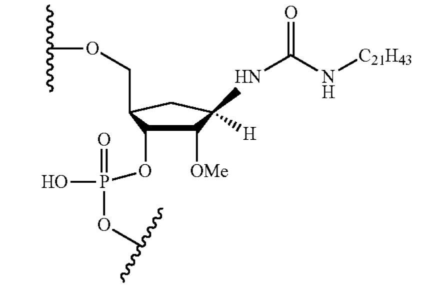 |
| S2-56 | 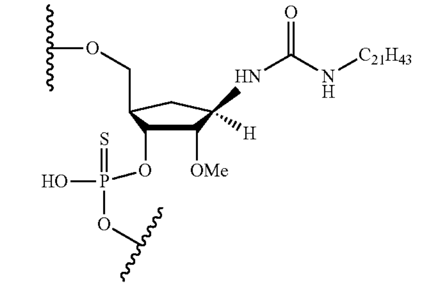 |
| S2-57 | 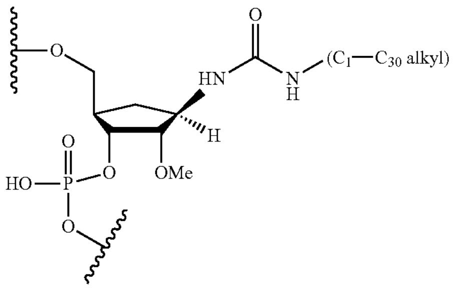 wherein the $C_1$-$C_{30}$ alkyl is optionally substituted |
| S2-58 | 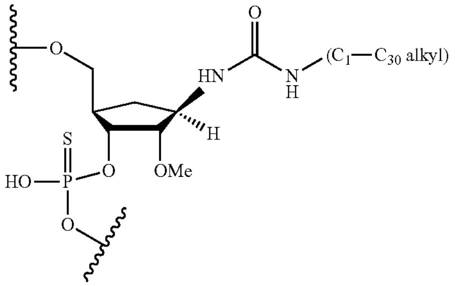 wherein the $C_1$-$C_{30}$ alkyl is optionally substituted |
| S2-59 | 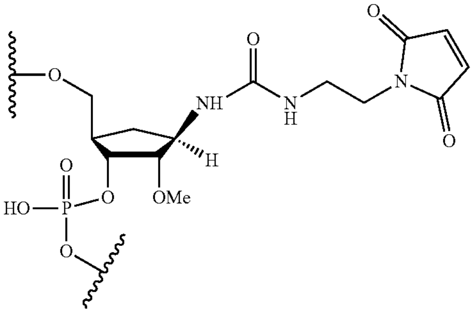 |
| S2-60 | 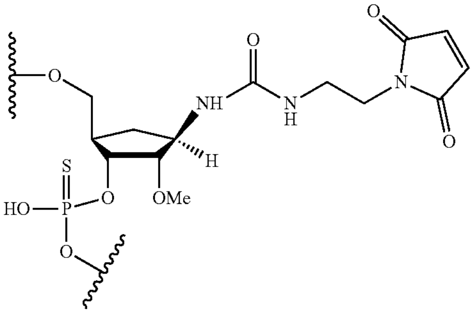 |
| S2-61 | 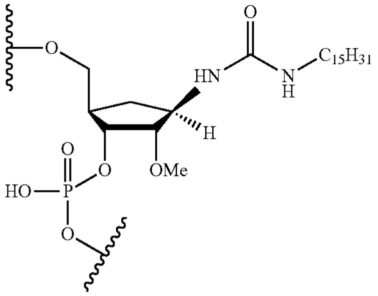 |
| S2-62 | 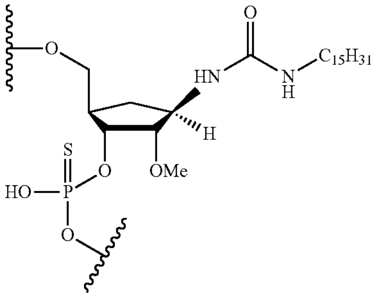 |

TABLE S2-continued
| Compound No. | Structure |
| --- | --- |
| S2-63 | 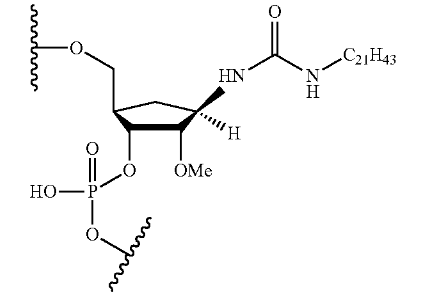 |
| S2-64 | 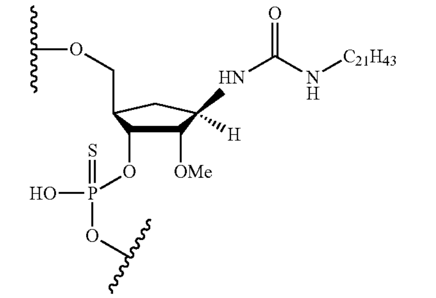 |
| S2-65 | 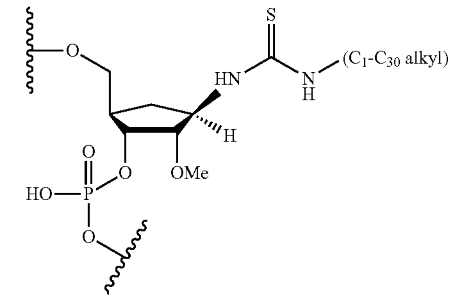 wherein the $C_1$-$C_{30}$ alkyl is optionally substituted |
| S2-66 | 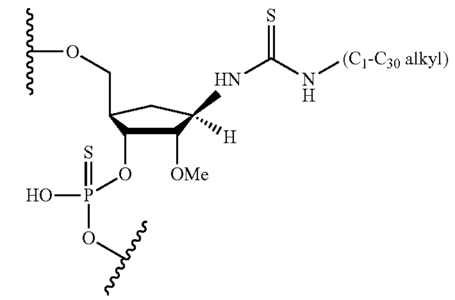 wherein the $C_1$-$C_{30}$ alkyl is optionally substituted |
TABLE S2-continued
| Compound No. | Structure |
| --- | --- |
| S2-67 | 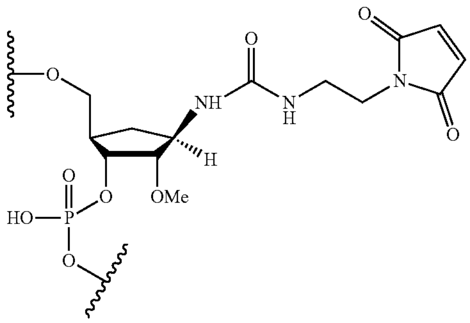 |
| S2-68 | 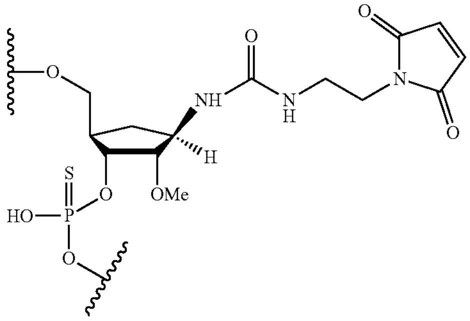 |
| S2-69 | 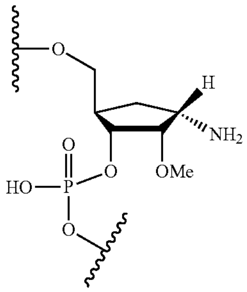 |
| S2-70 | 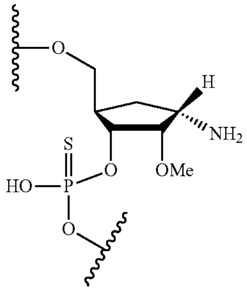 |
| S2-71 | 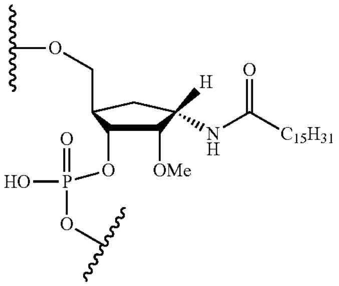 |

TABLE S2-continued
| Compound No. | Structure |
|---|---|
| S2-72 | 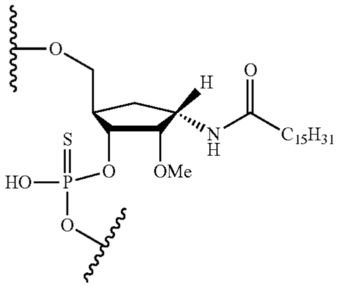 |
| S2-73 | 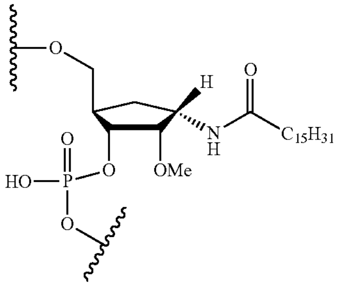 |
| S2-74 | 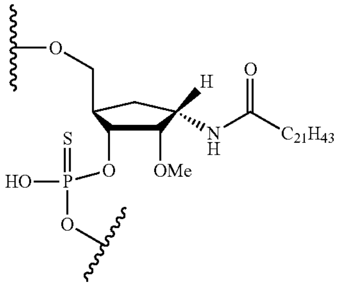 |
| S2-75 | 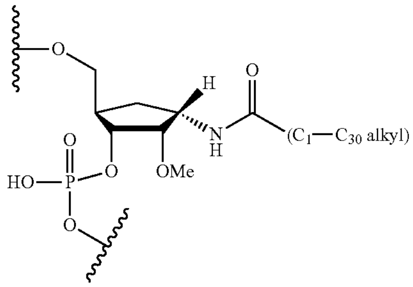 wherein the $C_1$-$C_{30}$ alkyl is optionally substituted |
| S2-76 | 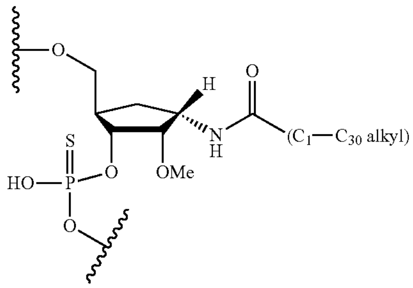 wherein the $C_1$-$C_{30}$ alkyl is optionally substituted |
TABLE S2-continued
| Compound No. | Structure |
|---|---|
| S2-77 | 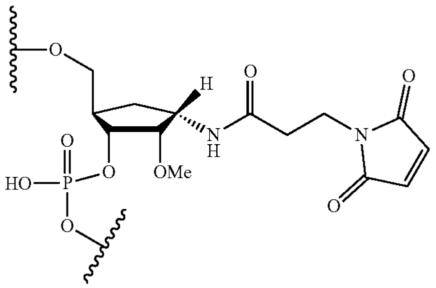 |
| S2-78 | 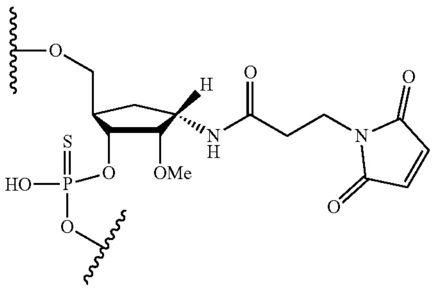 |
| S2-79 | 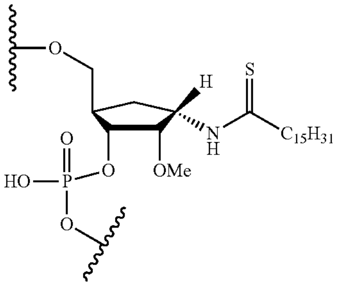 |
| S2-80 | 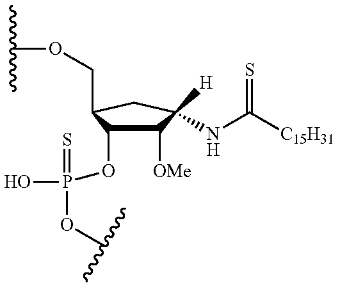 |
| S2-81 | 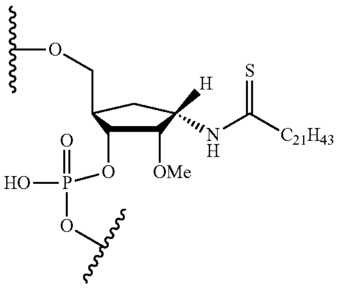 |

TABLE S2-continued
| Compound No. | Structure |
|---|---|
| S2-82 | 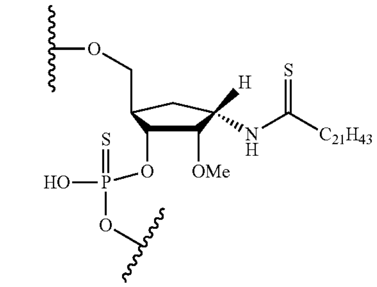 |
| S2-83 | 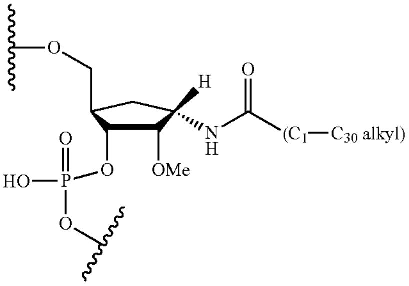 wherein the $C_1$-$C_{30}$ alkyl is optionally substituted |
| S2-84 | 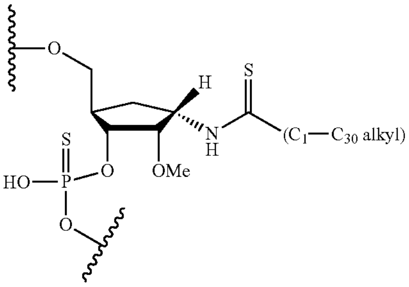 wherein the $C_1$-$C_{30}$ alkyl is optionally substituted |
| S2-85 | 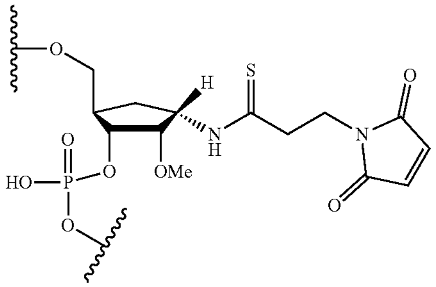 |
| S2-86 | 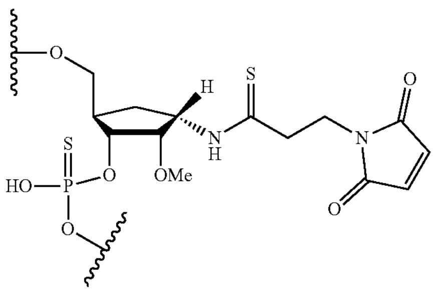 |
TABLE S2-continued
| Compound No. | Structure |
|---|---|
| S2-87 | 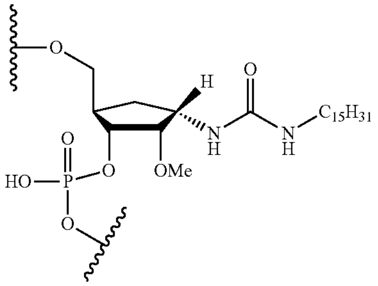 |
| S2-88 | 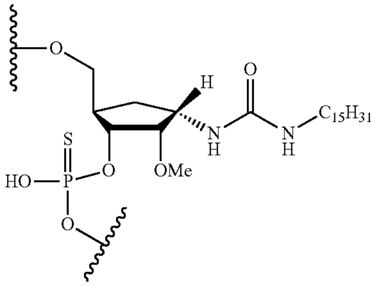 |
| S2-89 | 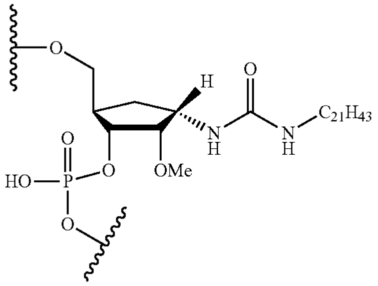 |
| S2-90 | 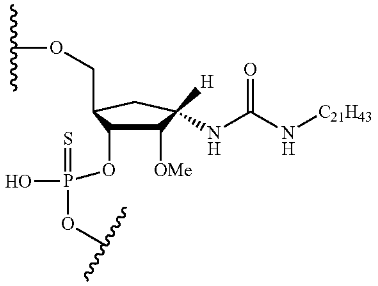 |
| S2-91 | 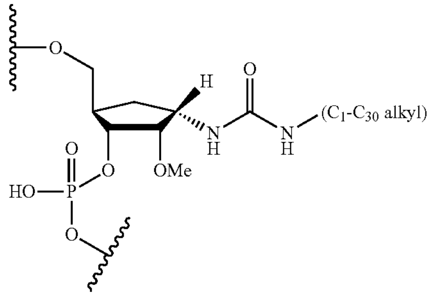 wherein the $C_1$-$C_{30}$ alkyl is optionally substituted |

TABLE S2-continued
| Compound No. | Structure |
| --- | --- |
| S2-92 | 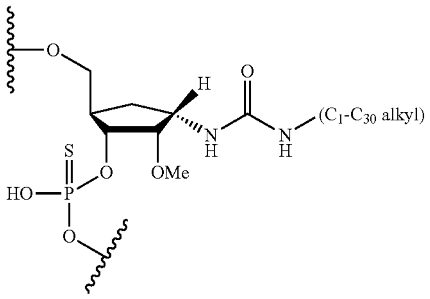 wherein the $C_1$-$C_{30}$ alkyl is optionally substituted |
| S2-93 | 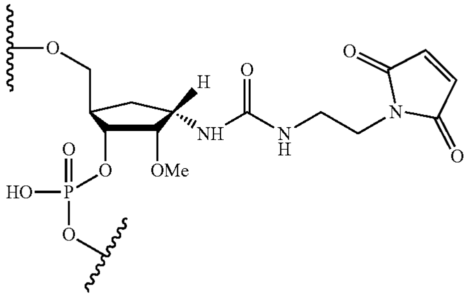 |
| S2-94 | 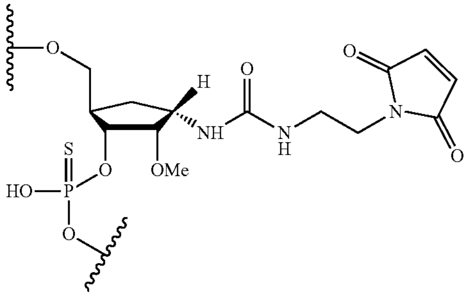 |
| S2-95 | 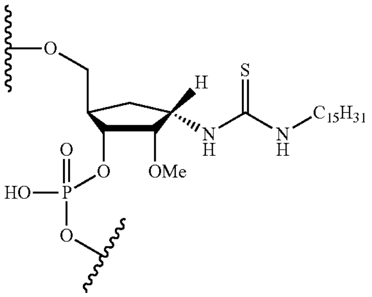 |
| S2-96 | 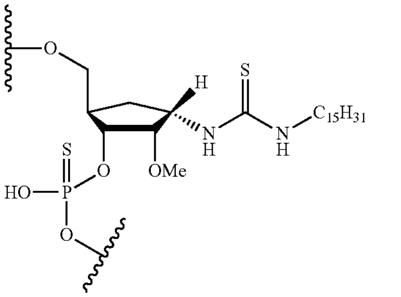 |
TABLE S2-continued
| Compound No. | Structure |
| --- | --- |
| S2-97 | 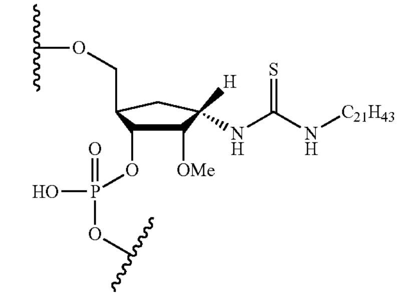 |
| S2-98 | 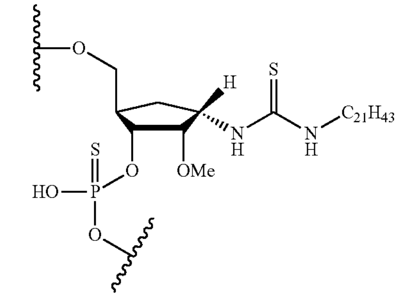 |
| S2-99 | 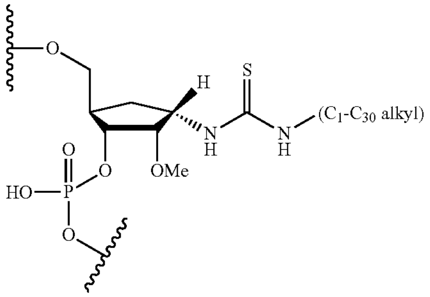 wherein the $C_1$-$C_{30}$ alkyl is optionally substituted |
| S2-100 | 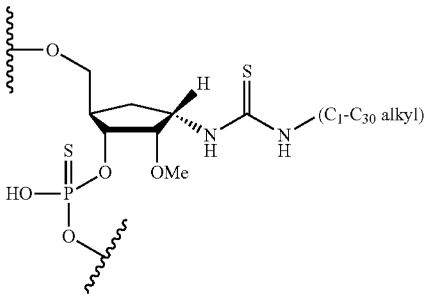 wherein the $C_1$-$C_{30}$ alkyl is optionally substituted |

TABLE S2-continued
| Compound No. | Structure |
|---|---|
| S2-101 | 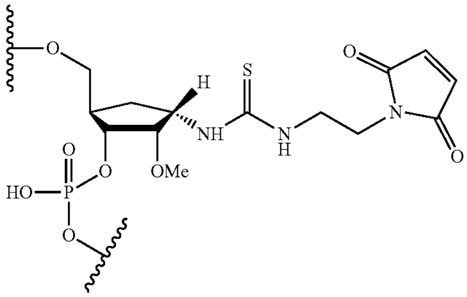 |
| S2-102 | 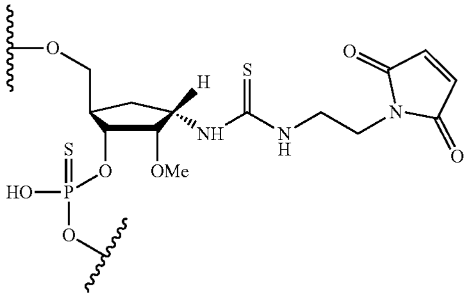 |
| S2-103 | 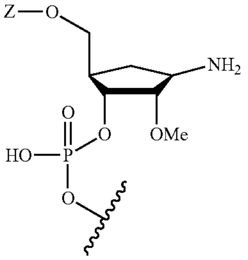 |
| S2-104 | 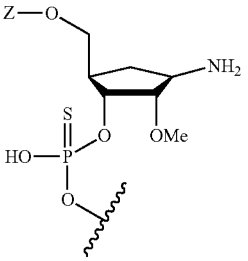 |
| S2-105 | 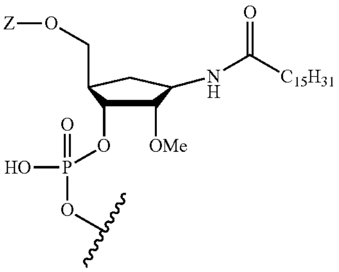 |
TABLE S2-continued
| Compound No. | Structure |
|---|---|
| S2-106 | 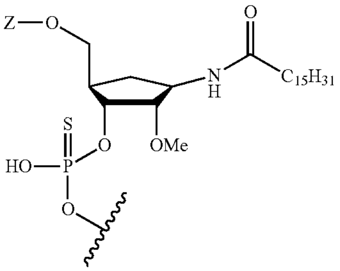 |
| S2-107 | 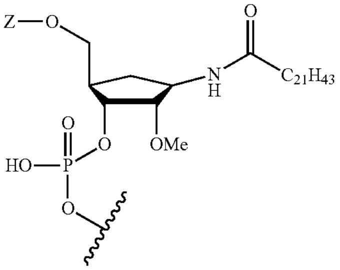 |
| S2-108 | 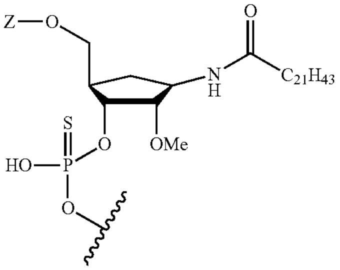 |
| S2-109 | 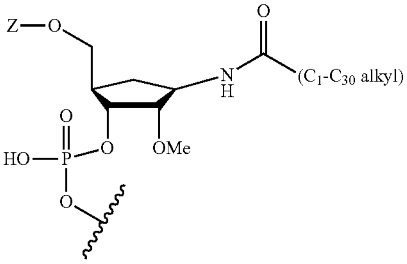 wherein the $C_1$-$C_{30}$ alkyl is optionally substituted |
| S2-110 | 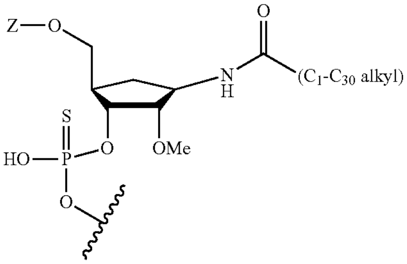 wherein the $C_1$-$C_{30}$ alkyl is optionally substituted |

TABLE S2-continued
| Compound No. | Structure |
| --- | --- |
| S2-111 | 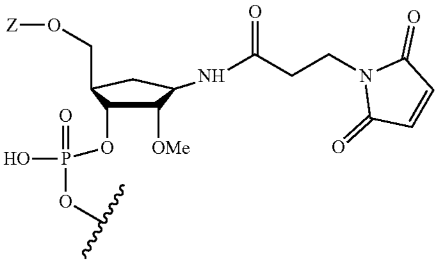 |
| S2-112 | 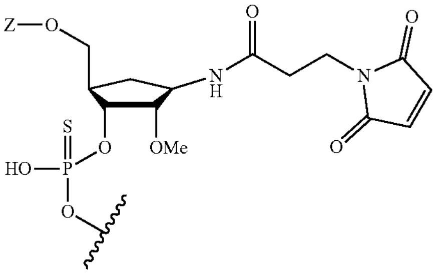 |
| S2-113 | 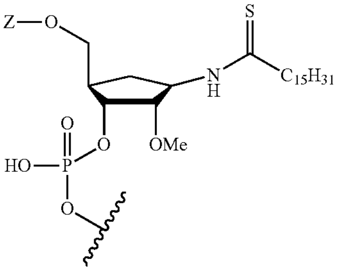 |
| S2-114 | 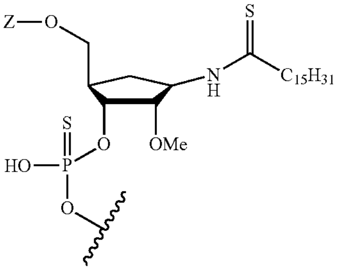 |
| S2-115 | 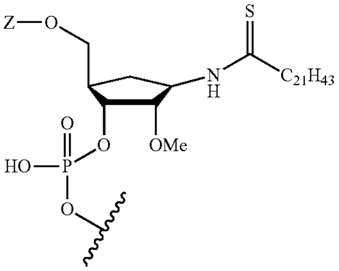 |
TABLE S2-continued
| Compound No. | Structure |
| --- | --- |
| S2-116 | 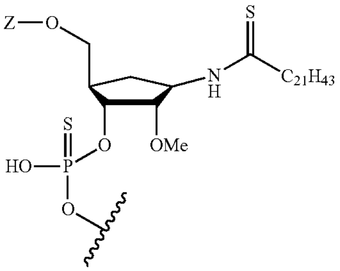 |
| S2-117 | 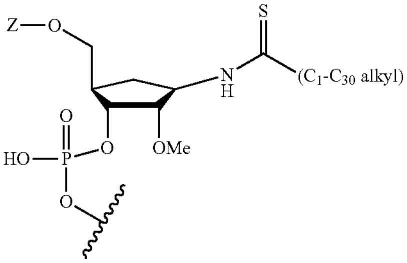 wherein the $C_1$-$C_{30}$ alkyl is optionally substituted |
| S2-118 | 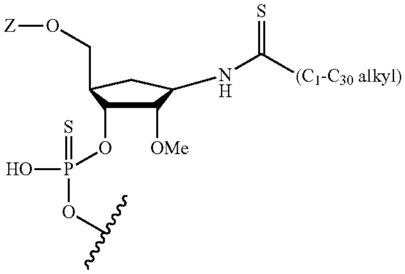 wherein the $C_1$-$C_{30}$ alkyl is optionally substituted |
| S2-119 | 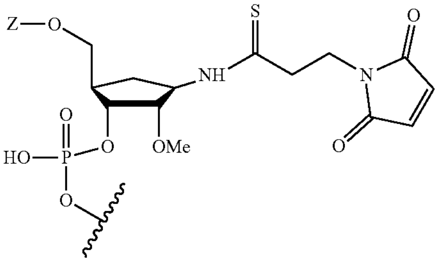 |
| S2-120 | 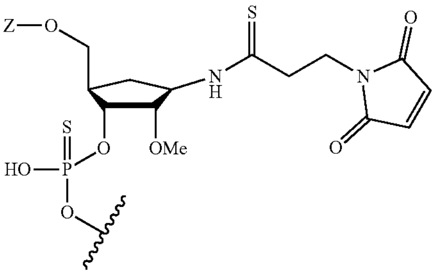 |

TABLE S2-continued
| Compound No. | Structure |
|---|---|
| S2-121 | 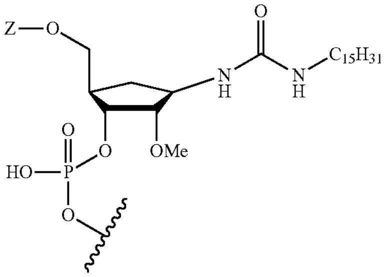 |
| S2-122 | 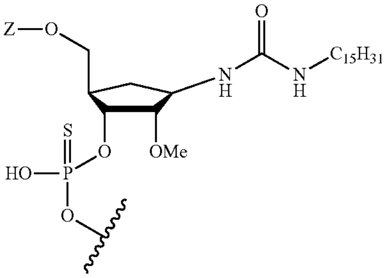 |
| S2-123 | 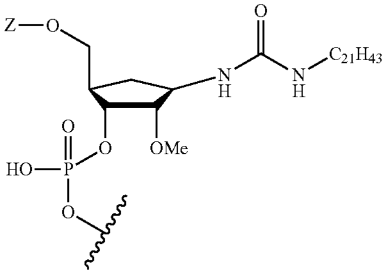 |
| S2-124 | 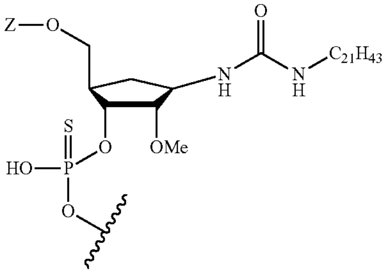 |
| S2-125 | 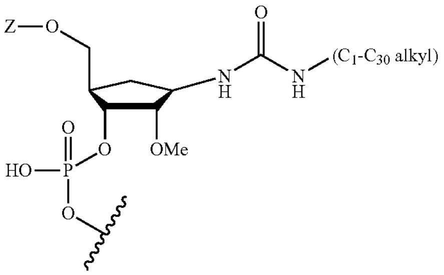 |
wherein the $C_1$-$C_{30}$ alkyl is optionally substituted
TABLE S2-continued
| Compound No. | Structure |
|---|---|
| S2-126 | 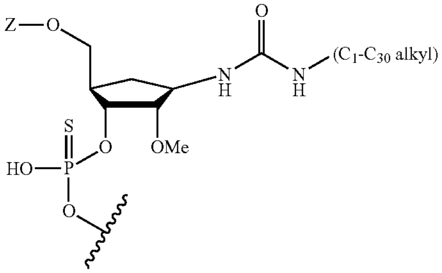 |
wherein the $C_1$-$C_{30}$ alkyl is optionally substituted
| Compound No. | Structure |
|---|---|
| S2-127 | 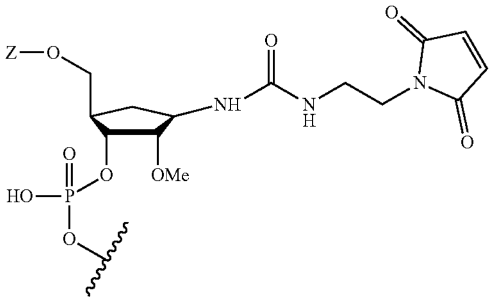 |
| S2-128 | 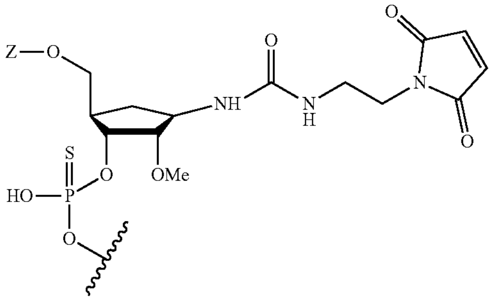 |
| S2-129 | 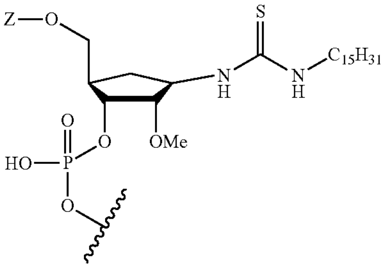 |
| S2-130 | 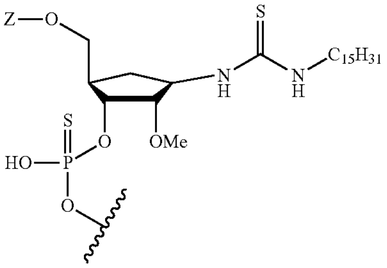 |

TABLE S2-continued
| Compound No. | Structure |
|---|---|
| S2-131 | 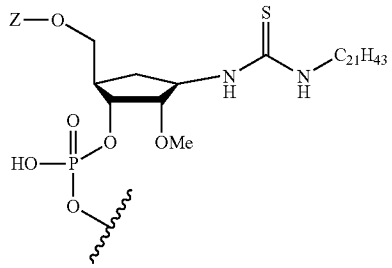 |
| S2-132 | 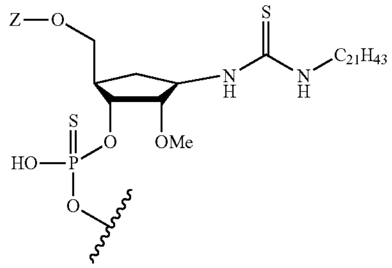 |
| S2-133 | 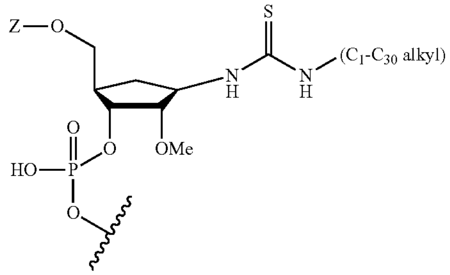<br>wherein the $C_1$-$C_{30}$ alkyl is optionally substituted |
| S2-134 | 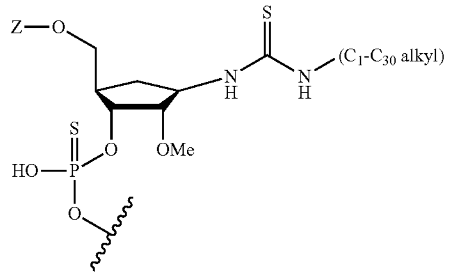<br>wherein the $C_1$-$C_{30}$ alkyl is optionally substituted |
| S2-135 | 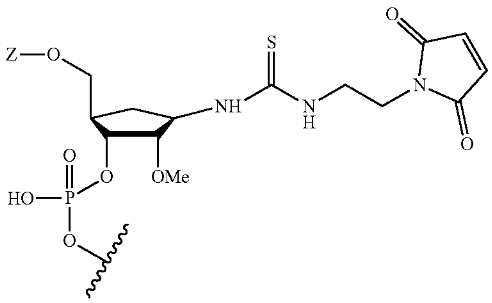 |
TABLE S2-continued
| Compound No. | Structure |
|---|---|
| S2-136 | 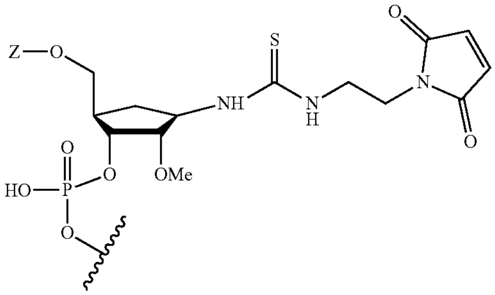 |
| S2-137 | 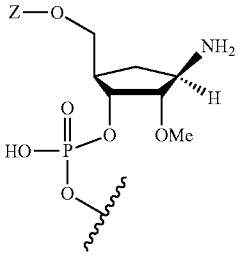 |
| S2-138 | 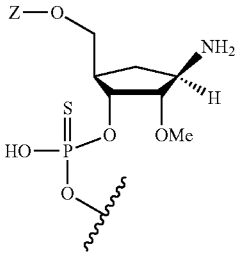 |
| S2-139 | 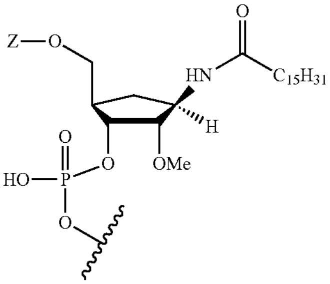 |
| S2-140 | 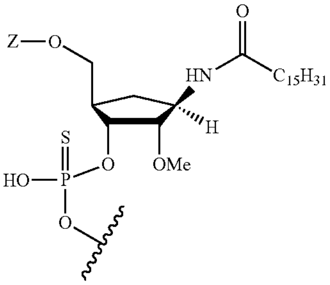 |

TABLE S2-continued
| Compound No. | Structure |
| --- | --- |
| S2-141 | 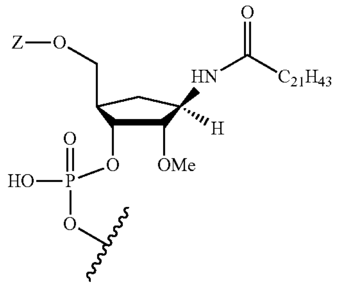 |
| S2-142 | 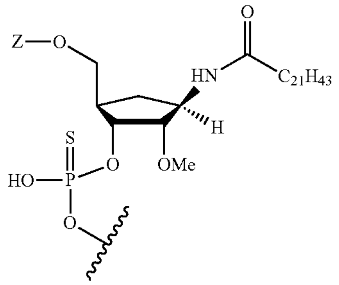 |
| S2-143 | 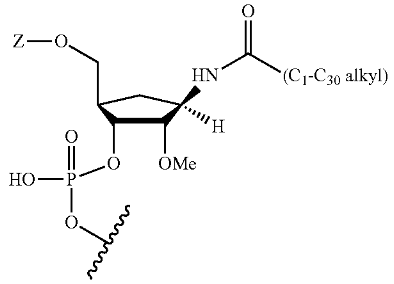<br>wherein the $C_1$-$C_{30}$ alkyl is optionally substituted |
| S2-144 | 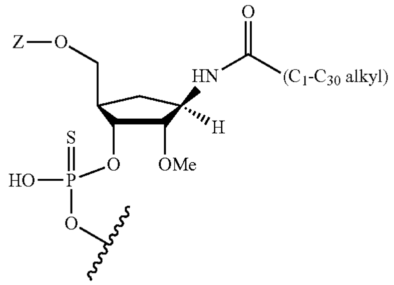<br>wherein the $C_1$-$C_{30}$ alkyl is optionally substituted |
| S2-145 | 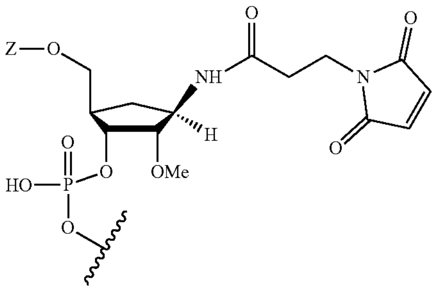 |
TABLE S2-continued
| Compound No. | Structure |
| --- | --- |
| S2-146 | 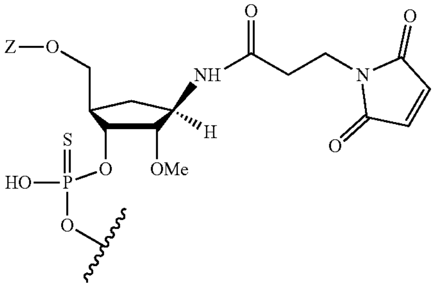 |
| S2-147 | 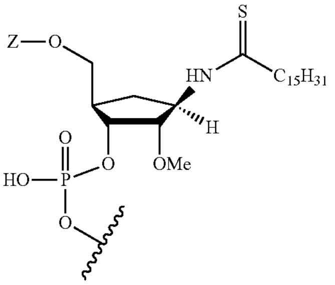 |
| S2-148 | 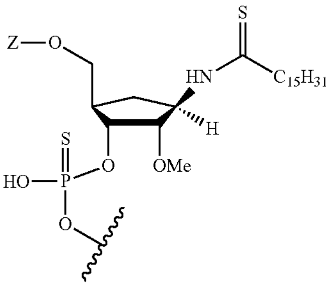 |
| S2-149 | 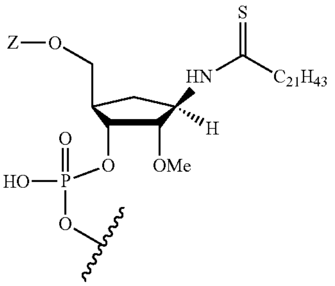 |
| S2-150 | 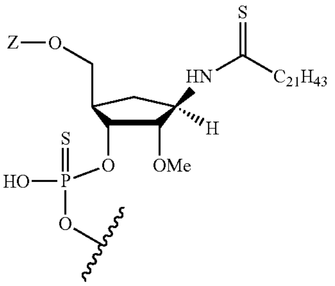 |

TABLE S2-continued
| Compound No. | Structure |
|---|---|
| S2-151 | 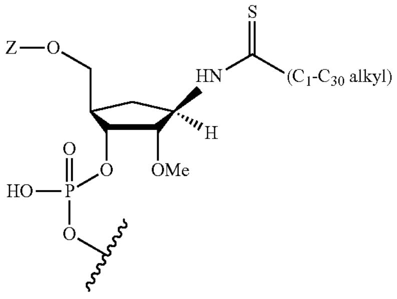 wherein the $C_1$-$C_{30}$ alkyl is optionally substituted |
| S2-152 | 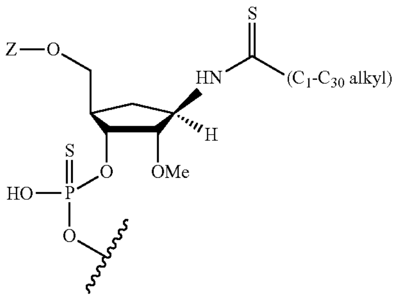 wherein the $C_1$-$C_{30}$ alkyl is optionally substituted |
| S2-153 | 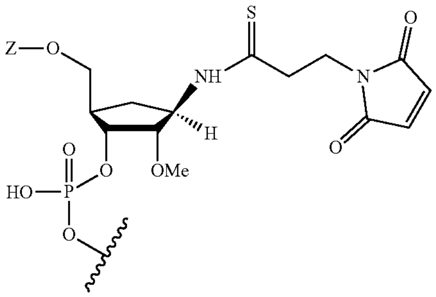 |
| S2-154 | 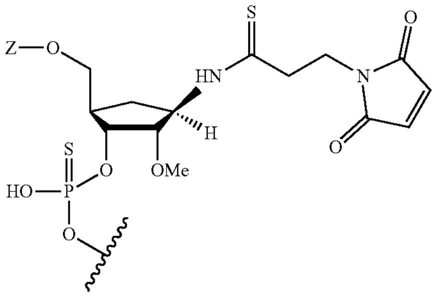 |
| S2-155 | 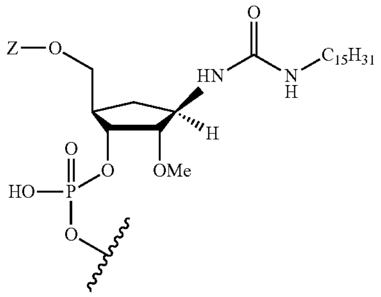 |
TABLE S2-continued
| Compound No. | Structure |
|---|---|
| S2-156 | 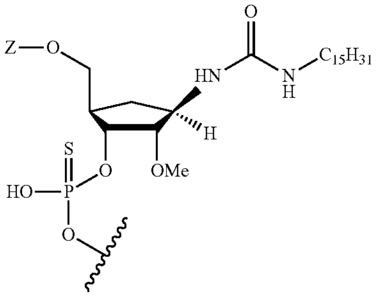 |
| S2-157 | 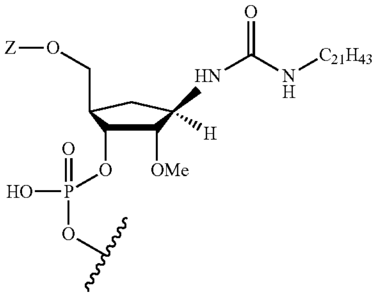 |
| S2-158 | 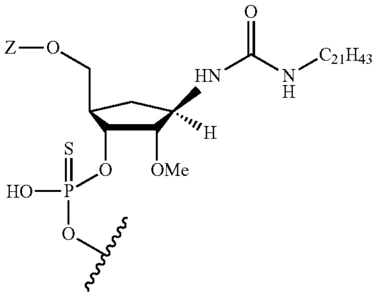 |
| S2-159 | 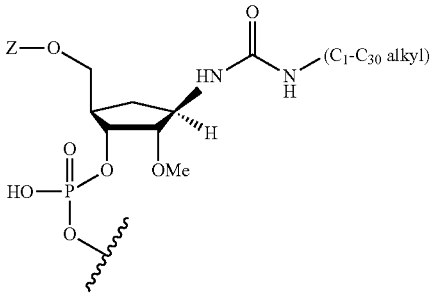 wherein the $C_1$-$C_{30}$ alkyl is optionally substituted |
| S2-160 | 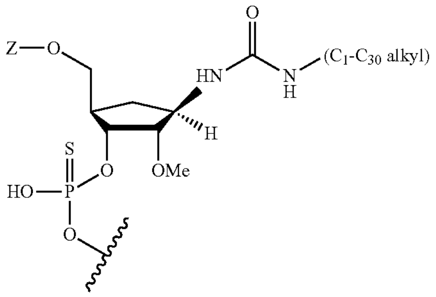 |

TABLE S2-continued
| Compound No. | Structure |
|---|---|
| | wherein the $C_1$-$C_{30}$ alkyl is optionally substituted |
| S2-161 | 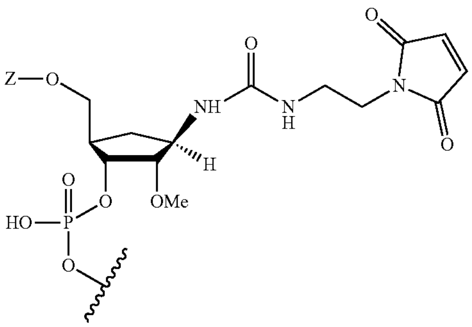 |
| S2-162 | 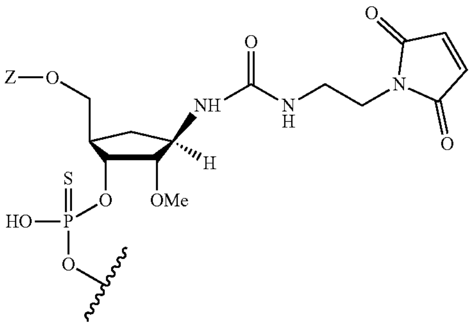 |
| S2-163 | 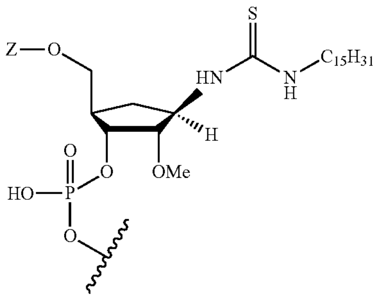 |
| S2-164 | 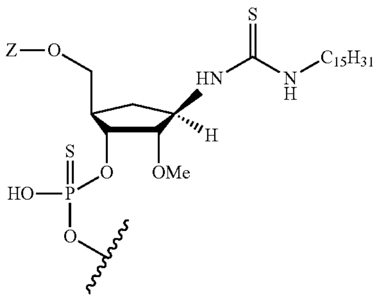 |
TABLE S2-continued
| Compound No. | Structure |
|---|---|
| S2-165 | 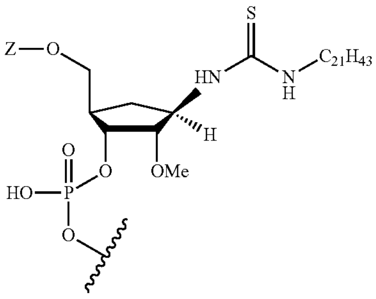 |
| S2-166 | 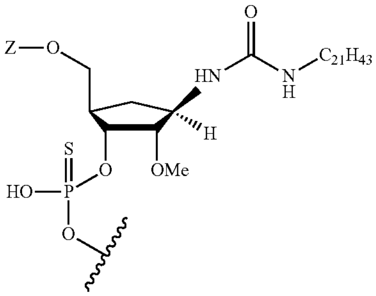 |
| S2-167 | 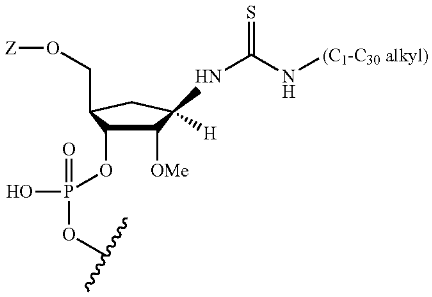<br>wherein the $C_1$-$C_{30}$ alkyl is optionally substituted |
| S2-168 | 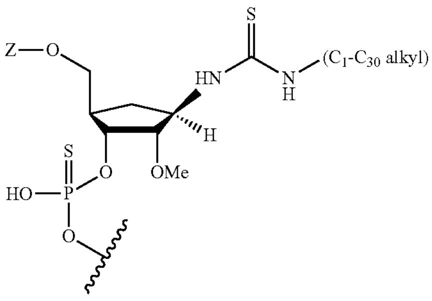<br>wherein the $C_1$-$C_{30}$ alkyl is optionally substituted |

TABLE S2-continued
| Compound No. | Structure |
|---|---|
| S2-169 | 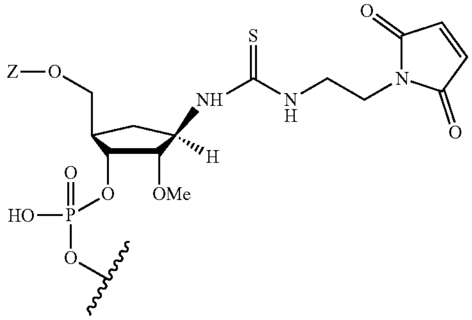 |
| S2-170 | 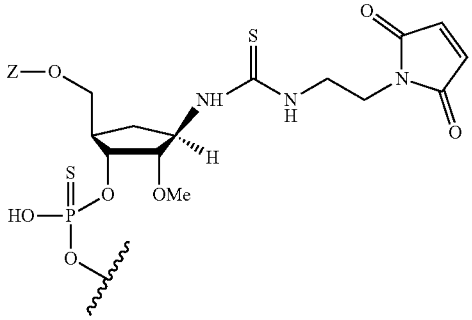 |
| S2-171 | 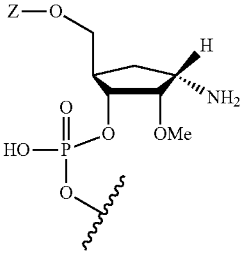 |
| S2-172 | 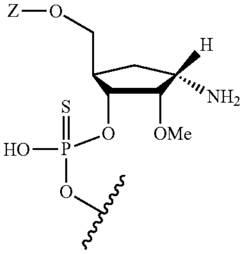 |
| S2-173 | 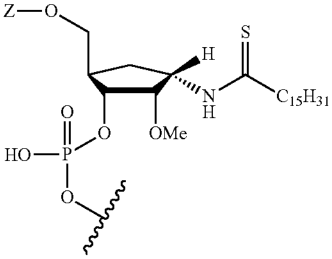 |
TABLE S2-continued
| Compound No. | Structure |
|---|---|
| S2-174 | 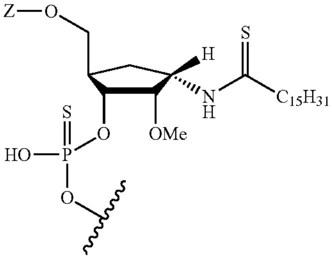 |
| S2-175 | 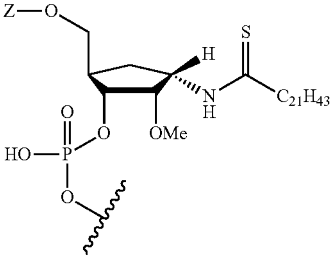 |
| S2-176 | 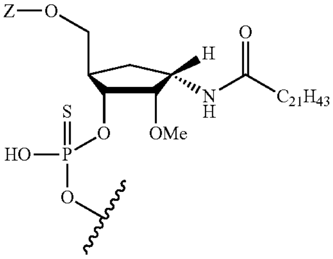 |
| S2-177 | 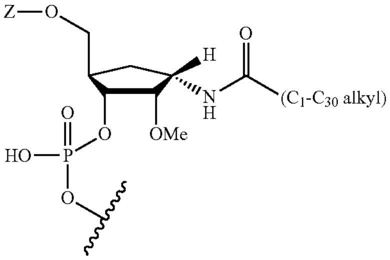 wherein the $C_1$-$C_{30}$ alkyl is optionally substituted |
| S2-178 | 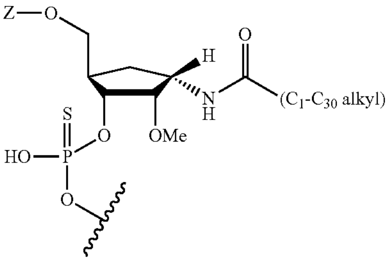 wherein the $C_1$-$C_{30}$ alkyl is optionally substituted |

TABLE S2-continued
| Compound No. | Structure |
| --- | --- |
| S2-179 | 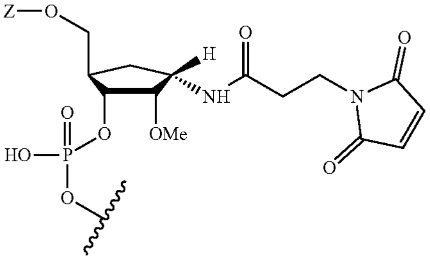 |
| S2-180 | 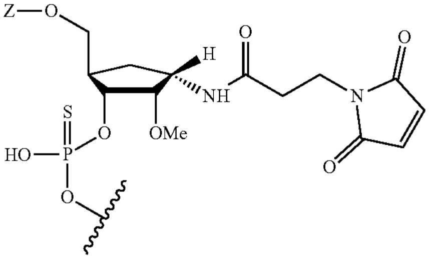 |
| S2-181 | 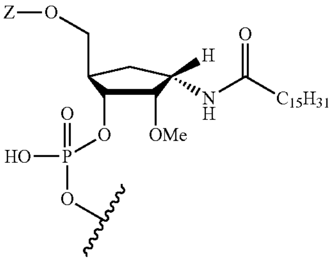 |
| S2-182 | 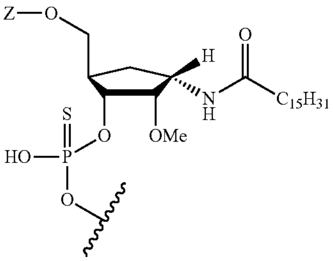 |
| S2-183 | 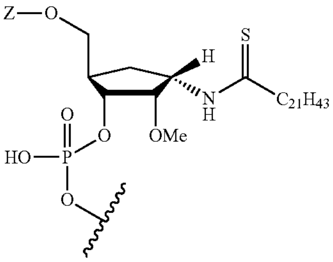 |
| S2-184 | 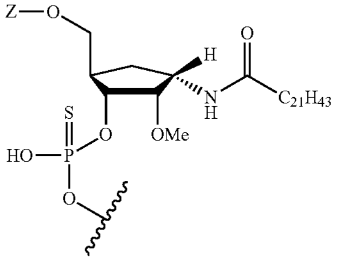 |
| S2-185 | 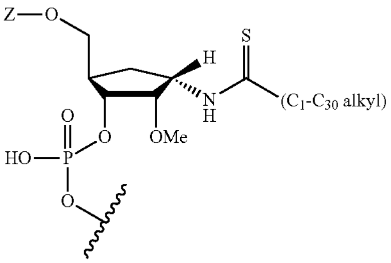 wherein the $C_1$-$C_{30}$ alkyl is optionally substituted |
| S2-186 | 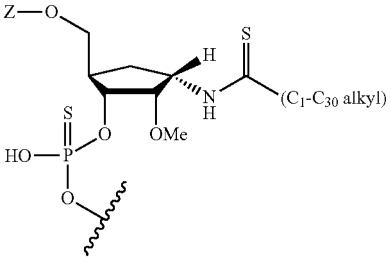 wherein the $C_1$-$C_{30}$ alkyl is optionally substituted |
| S2-187 | 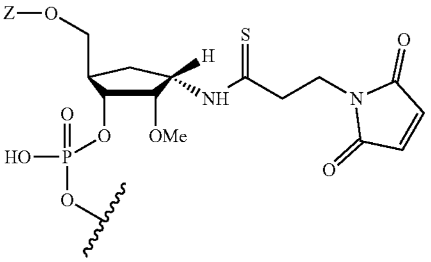 |
| S2-188 | 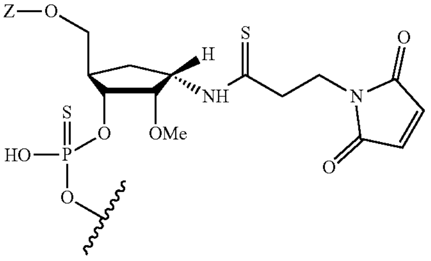 |

TABLE S2-continued
| Compound No. | Structure |
|---|---|
| S2-189 | 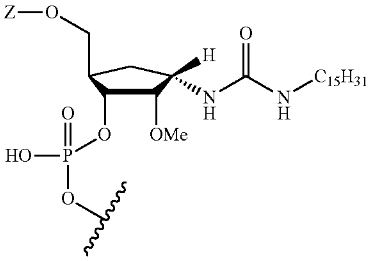 |
| S2-190 | 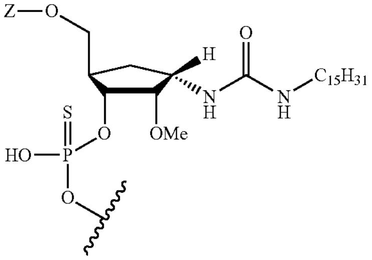 |
| S2-191 | 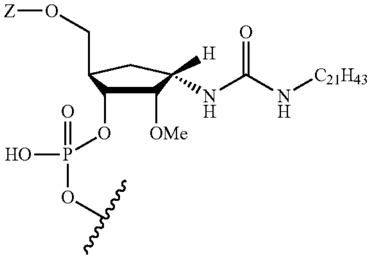 |
| S2-192 | 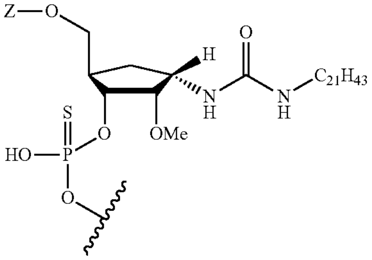 |
| S2-193 | 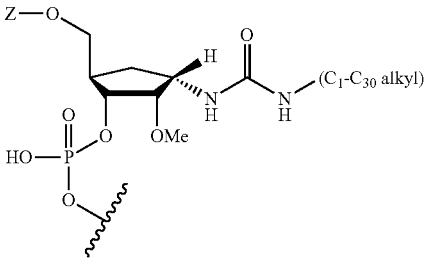<br>wherein the $C_1$-$C_{30}$ alkyl is optionally substituted |
| S2-194 | 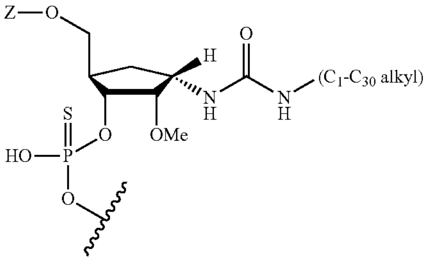<br>wherein the $C_1$-$C_{30}$ alkyl is optionally substituted |
| S2-195 | 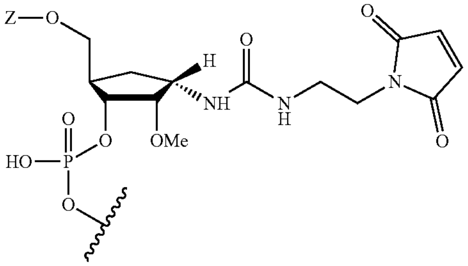 |
| S2-196 | 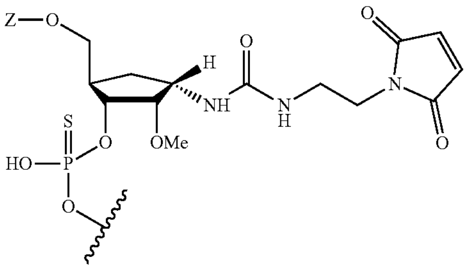 |
| S2-197 | 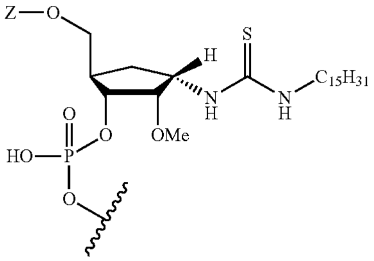 |
| S2-198 | 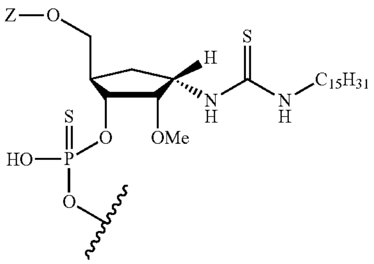 |

TABLE S2-continued
| Compound No. | Structure |
|---|---|
| S2-199 | 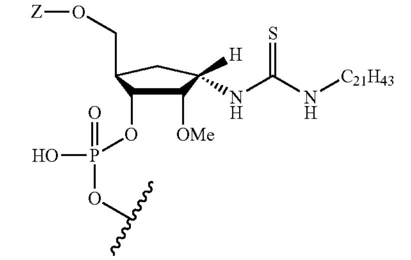 |
| S2-200 | 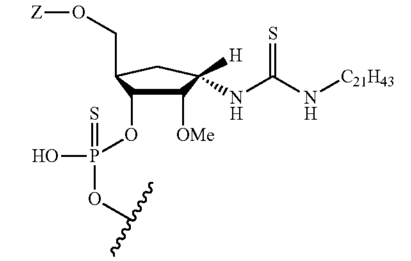 |
| S2-201 | 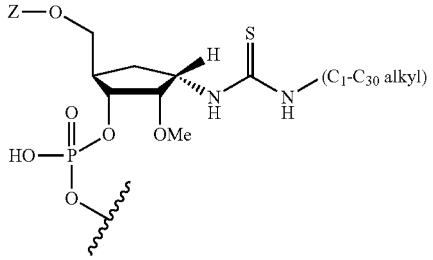<br>wherein the $C_1$-$C_{30}$ alkyl is optionally substituted |
| S2-202 | 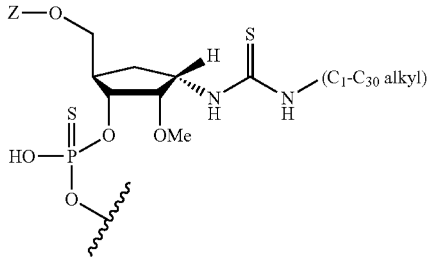<br>wherein the $C_1$-$C_{30}$ alkyl is optionally substituted |
| S2-203 | 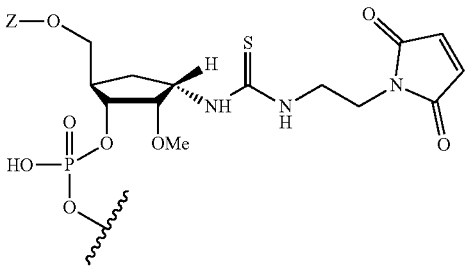 |
TABLE S2-continued
| Compound No. | Structure |
|---|---|
| S2-204 | 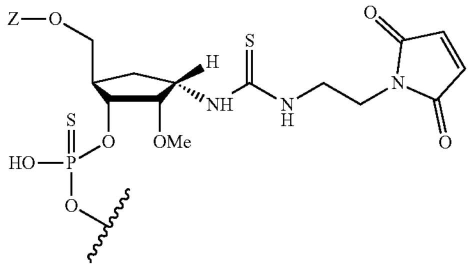 |
| S2-205 | 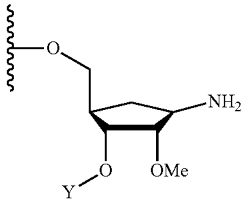 |
| S2-206 | 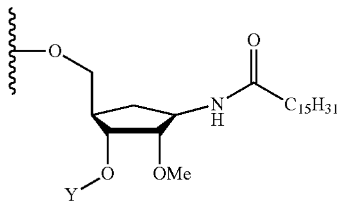 |
| S2-207 | 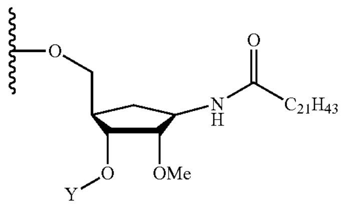 |
| S2-208 | 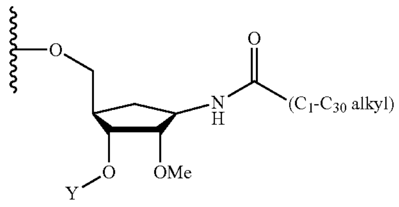<br>wherein the $C_1$-$C_{30}$ alkyl is optionally substituted |
| S2-209 | 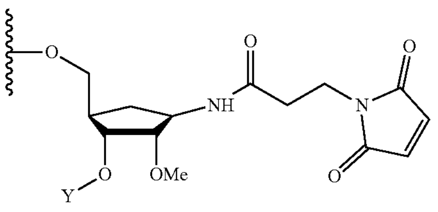 |
| S2-210 | 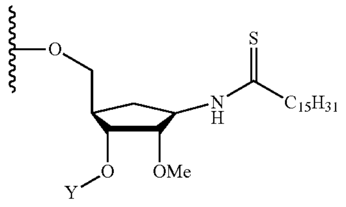 |

TABLE S2-continued
| Compound No. | Structure |
|---|---|
| S2-211 | 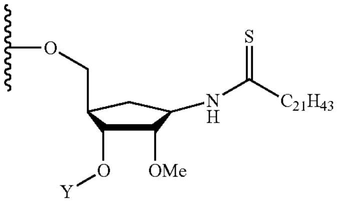 |
| S2-212 | 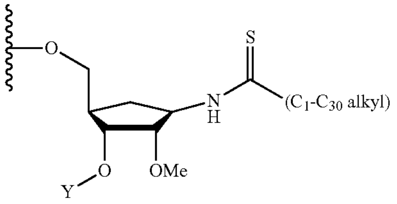 wherein the $C_1$-$C_{30}$ alkyl is optionally substituted |
| S2-213 | 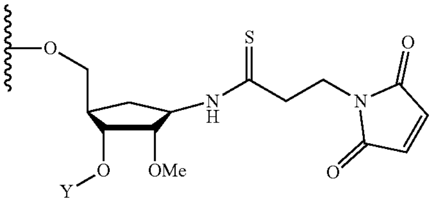 |
| S2-214 | 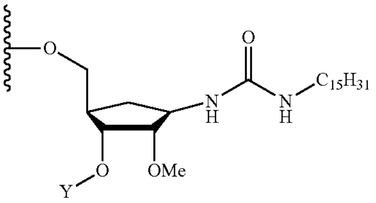 |
| S2-215 | 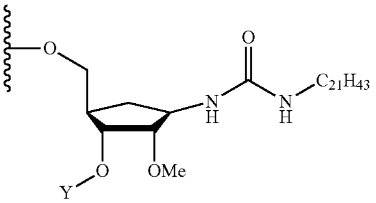 |
| S2-216 | 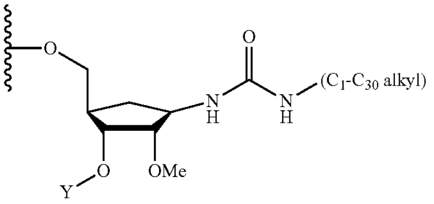 wherein the $C_1$-$C_{30}$ alkyl is optionally substituted |
TABLE S2-continued
| Compound No. | Structure |
|---|---|
| S2-217 | 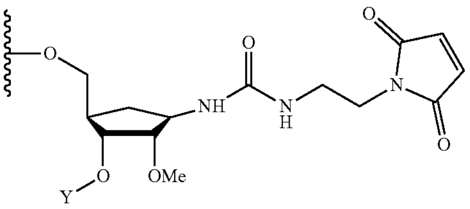 |
| S2-218 | 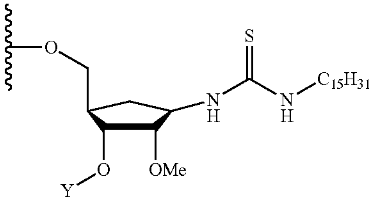 |
| S2-219 | 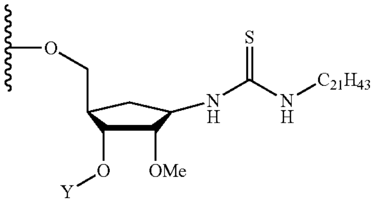 |
| S2-220 | 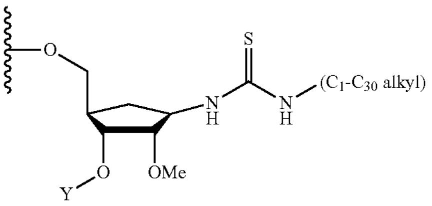 wherein the $C_1$-$C_{30}$ alkyl is optionally substituted |
| S2-221 | 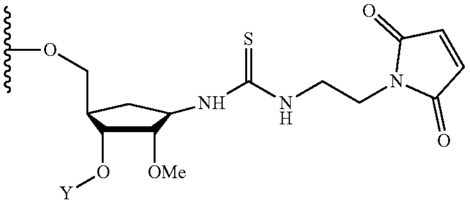 |
| S2-222 | 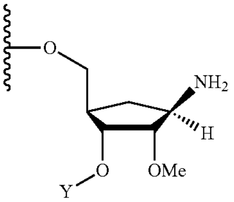 |
| S2-223 | 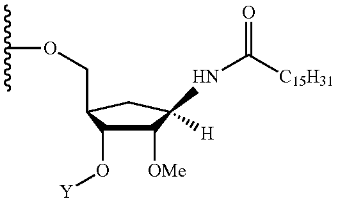 |

TABLE S2-continued
| Compound No. | Structure |
| --- | --- |
| S2-224 | 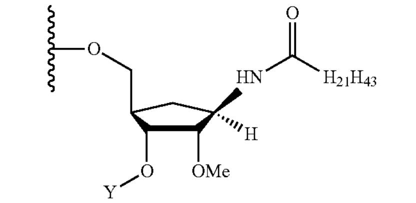 |
| S2-225 | 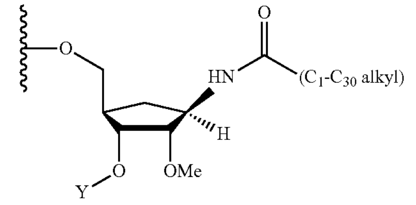 wherein the $C_1$-$C_{30}$ alkyl is optionally substituted |
| S2-226 | 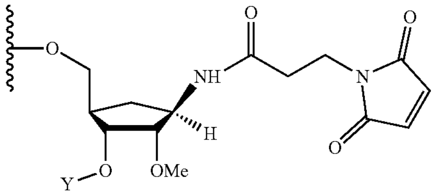 |
| S2-227 | 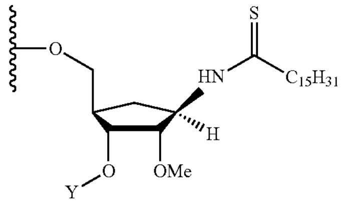 |
| S2-228 | 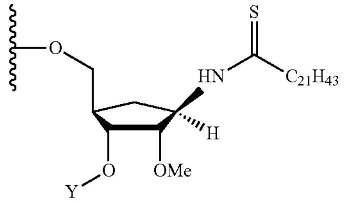 |
| S2-229 | 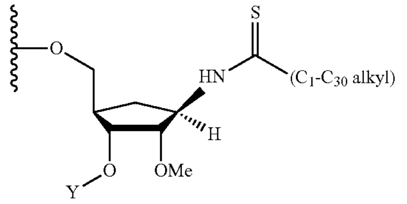 wherein the $C_1$-$C_{30}$ alkyl is optionally substituted |
| S2-230 | 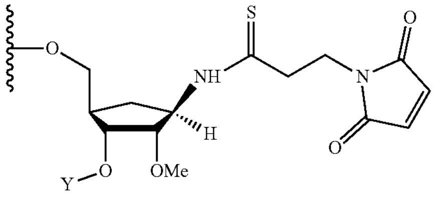 |
TABLE S2-continued
| Compound No. | Structure |
| --- | --- |
| S2-231 | 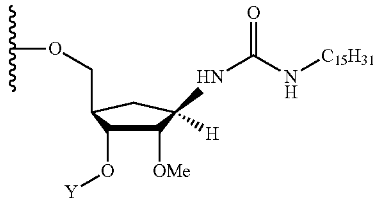 |
| S2-232 | 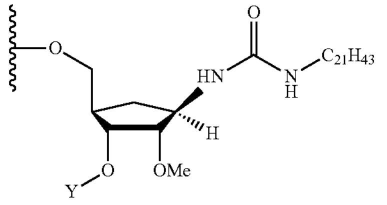 |
| S2-233 | 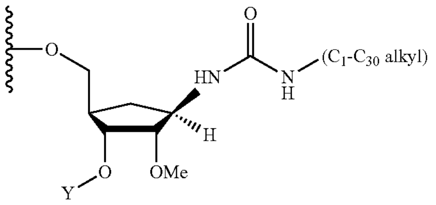 wherein the $C_1$-$C_{30}$ alkyl is optionally substituted |
| S2-234 | 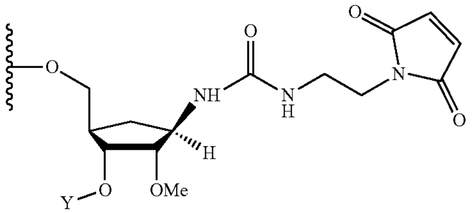 |
| S2-235 | 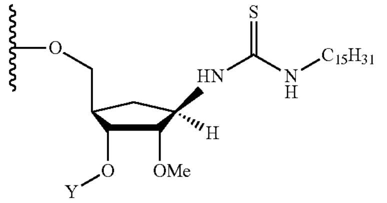 |
| S2-236 | 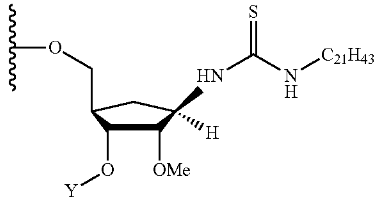 |
| S2-237 | 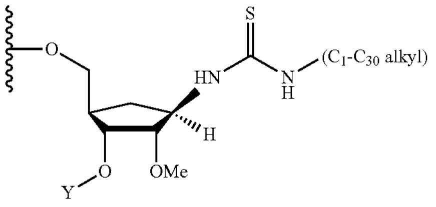 wherein the $C_1$-$C_{30}$ alkyl is optionally substituted |

TABLE S2-continued
| Compound No. | Structure |
|---|---|
| S2-238 | 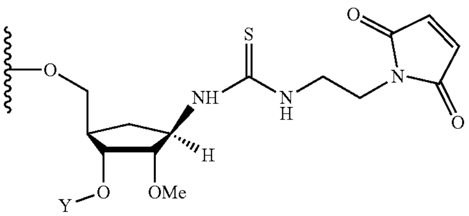 |
| S2-239 | 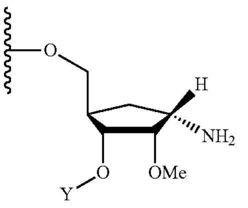 |
| S2-240 | 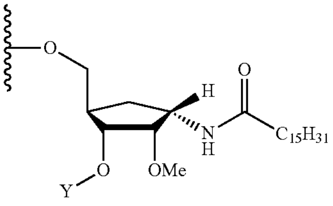 |
| S2-241 | 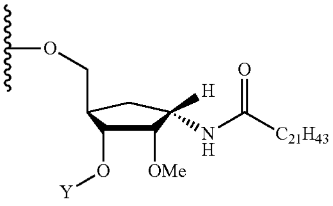 |
| S2-242 | 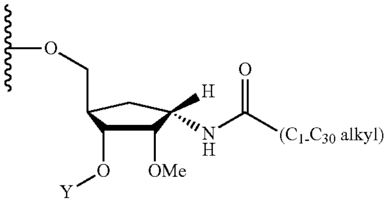 wherein the $C_1$-$C_{30}$ alkyl is optionally substituted |
| S2-243 | 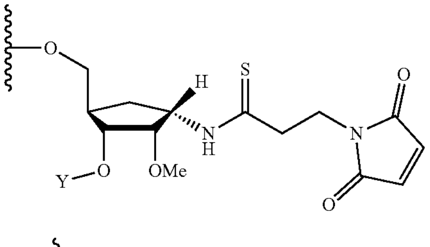 |
| S2-244 | 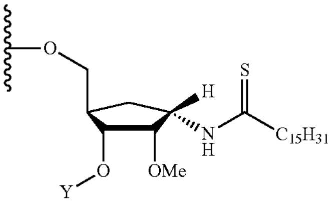 |
TABLE S2-continued
| Compound No. | Structure |
|---|---|
| S2-245 | 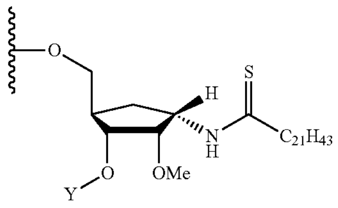 |
| S2-246 | 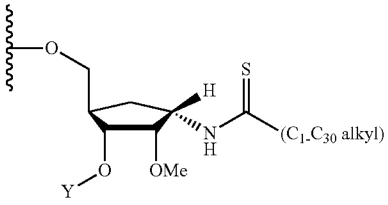 wherein the $C_1$-$C_{30}$ alkyl is optionally substituted |
| S2-247 | 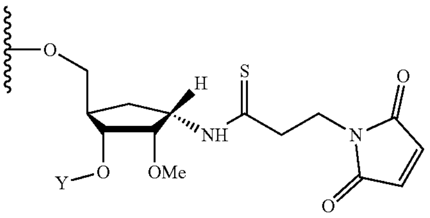 |
| S2-248 | 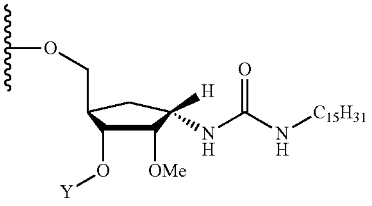 |
| S2-249 | 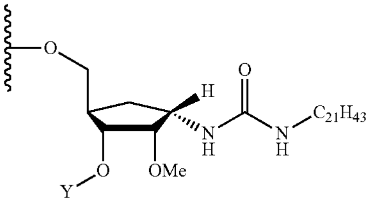 |
| S2-250 | 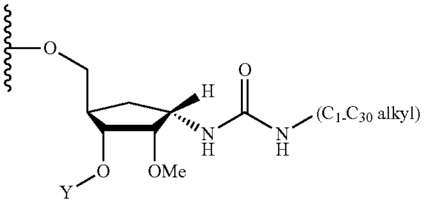 wherein the $C_1$-$C_{30}$ alkyl is optionally substituted |
| S2-251 | 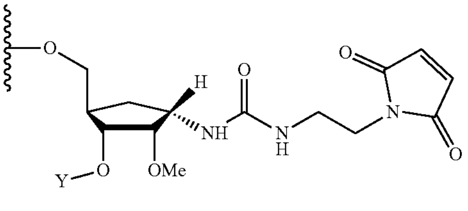 |

TABLE S2-continued

| Compound No. | Structure |
|---|---|
| S2-252 | 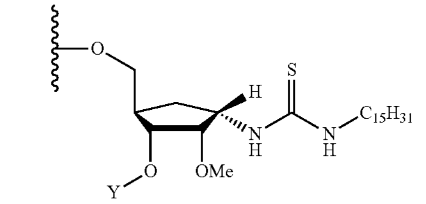 |
| S2-253 | 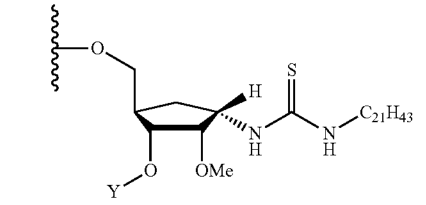 |
| S2-254 | 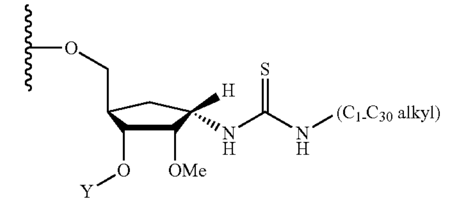 wherein the $C_1$-$C_{30}$ alkyl is optionally substituted |
| S2-255 | 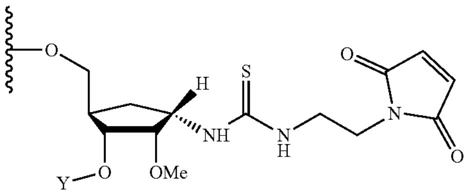 |

In some aspects, the present disclosure provides a conjugate or a pharmaceutically acceptable salt thereof, wherein the conjugate comprises:

(i) one or more Nucleic Acid Agent;

(ii) one or more Ligand; and (iii) one or more Linker Unit, wherein each Linker Unit independently is:

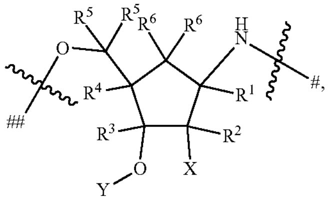

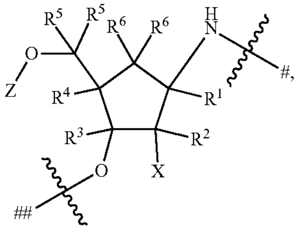

-continued

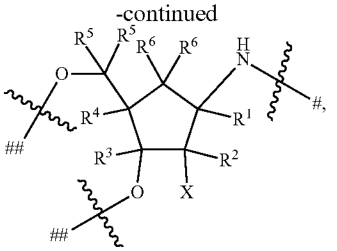

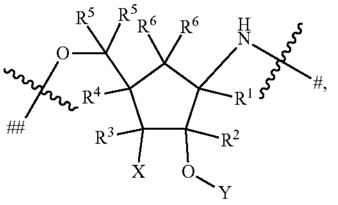

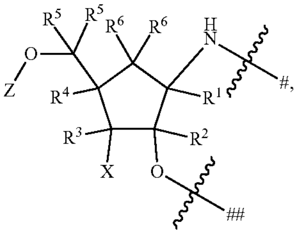

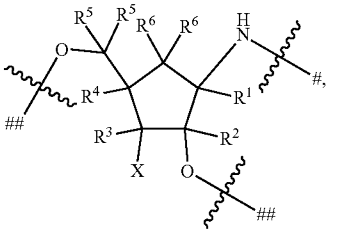

wherein variables $R^1$, $R^2$, $R^3$, $R^4$, $R^5$, $R^6$, X, Y, and Z are described herein, # indicates an attachment to the Ligand, and ## indicates an attachment to the Nucleic Acid Agent.

In some embodiments, the attachment "#" is a direct attachment to the Ligand, i.e., without any linking moiety.

In some embodiments, the attachment "#" is an indirect attachment to the Ligand, i.e., there is a linking moiety between the Linker Unit and the Ligand. In some embodiments, the linking moiety is a $C_1$-$C_{15}$ alkylene chain, wherein optionally one or more carbon atoms in the alkylene chain may be independently replaced with one or more —C(O)—, —C(O)O—, —OC(O)—, —C(O)NH—, —NHC(O)—, —NHC(O)NH—, —C(S)—, —C(S)O—, —OC(S)—, —C(S)NH—, —NHC(S)—, or —NHC(S)NH—, and wherein the alkylene chain is optionally substituted, for example, with one or more groups independently selected from $C_1$-$C_6$ alkyl, halogen, OH, $NH_2$, $C_1$-$C_6$ alkoxy, CN, and COOH. In some embodiments, the linking moiety is a branched alkylene chain comprising two, three, or more $C_1$-$C_{15}$ alkylene chains, wherein optionally one or more carbon atoms in each of the alkylene chain may be independently replaced with one or more —C(O)—, —C(O)O—, —OC(O)—, —C(O)NH—, —NHC(O)—, —NHC(O)NH—, —C(S)—, —C(S)O—, —OC(S)—, —C(S)NH—, —NHC(S)—, or —NHC(S)NH—, and wherein each of the alkylene chain is independently optionally substituted, for example, with one or more groups independently selected from $C_1$-$C_6$ alkyl, halogen, OH, $NH_2$, $C_1$-$C_6$ alkoxy, CN, and COOH. In some embodiments, the linking moiety is a branched alkylene chain comprising two $C_1$-$C_{15}$ alkylene chains. In some embodiments, the linking moiety is a branched alkylene chain comprising three $C_1$-$C_{15}$ alkylene chains. In some embodiments, the linking moiety is a branched alkylene chain comprising four $C_1$-$C_{15}$ alkylene chains.

In some embodiments, the attachment "##" is a direct attachment to the Nucleic Acid Agent, i.e., without any linking moiety.

In some embodiments, the attachment "##" is an indirect attachment to the Nucleic Acid Agent, i.e., there is a linking moiety between the Linker Unit and the Nucleic Acid Agent. In some embodiments, the linking moiety is a radical formed from any of the groups as defined for Y or Z herein. For example, the linking moiety is $—P(N(CH_3)_2)(O)—$, i.e., a radical formed from $—P(N(CH_3)_2)(OH)$. In some embodiments, the linking moiety is a radical formed from any of $—P(R^Y)_2$, $—P(OR^Y)(N(R^Y)_2)$, $—P(=O)(OR^Y)R^Y$, $—P(=S)(OR^Y)R^Y$, $—P(=O)(SR^Y)R^Y$, $—P(=S)(SR^Y)R^Y$, $—P(=O)(OR^Y)_2$, $—P(=S)(OR^Y)_2$, $—P(=O)(SR^Y)_2$, or $—P(=S)(SR^Y)_2$, or from any of $—P(R^Z)_2$, $—P(OR^Z)(N(R^Z)_2)$, $—P(=O)(OR^Z)R^Z$, $—P(=S)(OR^Z)R^Z$, $—P(=O)(SR^Z)R^Z$, $—P(=S)(SR^Z)R^Z$, $—P(=O)(OR^Z)_2$, $—P(=S)(OR^Z)_2$, $—P(=O)(SR^Z)_2$, or $—P(=S)(SR^Z)$.

In some embodiments, the conjugate comprises a double strand RNA (e.g., double strand siRNA), one or more Ligand, and one or more Linker Units.

In some embodiments, the conjugate comprises a double strand RNA (e.g., double strand siRNA) and from 1 to 10 Linker Units (e.g., from 1 to 10, from 1 to 9, from 1 to 8, from 1 to 7, from 1 to 6, from 1 to 5, from 1 to 4, or from 1 to 3 Linker Units), from 2 to 10 Linker Units (e.g., from 2 to 10, from 2 to 9, from 2 to 8, from 2 to 7, from 2 to 6, from 2 to 5, from 2 to 4, or from 2 to 3 Linker Units), from 3 to 10 Linker Units (e.g., from 3 to 10, from 3 to 9, from 3 to 8, from 3 to 7, from 3 to 6, from 3 to 5, or from 3 to 4 Linker Units), from 4 to 10 Linker Units (e.g., from 4 to 10, from 4 to 9, from 4 to 8, from 4 to 7, from 4 to 6, or from 4 to 5 Linker Units), from 5 to 10 Linker Units (e.g., from 5 to 10, from 5 to 9, from 5 to 8, from 5 to 7, or from 5 to 6 Linker Units), or from 6 to 10 Linker Units (e.g., from 6 to 10, from 6 to 9, from 6 to 8, or from 6 to 7 Linker Units).

In some embodiments, the conjugate comprises a double strand RNA (e.g., double strand siRNA) and 1 Linker Units, 2 Linker Units, 3 Linker Units, 4 Linker Units, 5 Linker Units, 6 Linker Units, 7 Linker Units, 8 Linker Units, 9 Linker Units, or 10 Linker Units.

In some embodiments, the conjugate comprises a double strand RNA (e.g., double strand siRNA), one or more Ligand, and one or more Linker Units, wherein:

- one or more Linker Units (e.g., from 1 to 3 Linker Units) are consecutively or discretely attached to the sense strand (e.g., at the 3'- or 5'-terminal position) of the double strand RNA (e.g., double strand siRNA);
- one or more nucleosides or nucleotides at one or more consecutive or discrete internal position of the sense strand of the double strand RNA (e.g., double strand siRNA) are replaced with the one or more Linker Units (e.g., from 1 to 3 Linker Units);
- one or more Linker Units (e.g., from 1 to 3 Linker Units) are consecutively or discretely attached to the antisense strand (e.g., at the 3'- or 5'-terminal position) of the double strand RNA (e.g., double strand siRNA); and/or
- one or more nucleosides or nucleotides at one or more consecutive or discrete internal position of the antisense strand are replaced with the one or more Linker Units (e.g., from 1 to 3 Linker Units).

In some embodiments, the conjugate comprises a double strand RNA (e.g., double strand siRNA), one or more Ligand, and one or more Linker Units, wherein:

- one or more Linker Units (e.g., from 1 to 3 Linker Units) are consecutively or discretely attached to the sense strand (e.g., at the 3'- or 5'-terminal position) of the double strand RNA (e.g., double strand siRNA); and
- one or more nucleosides or nucleotides at one or more consecutive or discrete internal position of the sense strand of the double strand RNA (e.g., double strand siRNA) are replaced with the one or more Linker Units (e.g., from 1 to 3 Linker Units).

In some embodiments, the conjugate comprises a double strand RNA (e.g., double strand siRNA), one or more Ligand, and one or more Linker Units, wherein:

- one or more Linker Units (e.g., from 1 to 3 Linker Units) are consecutively or discretely attached to the antisense strand (e.g., at the 3'- or 5'-terminal position) of the double strand RNA (e.g., double strand siRNA); and
- one or more nucleosides or nucleotides at one or more consecutive or discrete internal position of the antisense strand are replaced with the one or more Linker Units (e.g., from 1 to 3 Linker Units).

In some embodiments, the one or more Linker Units (e.g., from 1 to 3 Linker Units) is consecutively or discretely attached to the sense strand (e.g., at the 3'- or 5'-terminal position) of the double strand RNA (e.g., double strand siRNA).

In some embodiments, the one or more Linker Units (e.g., from 1 to 3 Linker Units) is consecutively or discretely attached to the sense strand 3'-terminal position of the double strand RNA (e.g., double strand siRNA).

In some embodiments, the one or more Linker Units (e.g., from 1 to 3 Linker Units) is consecutively or discretely attached to the sense strand 5'-terminal position of the double strand RNA (e.g., double strand siRNA).

In some embodiments, one or more nucleoside or nucleotide at one or more consecutive or discrete internal position of the sense strand of the double strand RNA (e.g., double strand siRNA) is replaced with the one or more Linker Units (e.g., from 1 to 3 Linker Units).

In some embodiments, the one or more Linker Units (e.g., from 1 to 3 Linker Units) is consecutively or discretely attached to the antisense strand (e.g., at the 3'- or 5'-terminal position) of the double strand RNA (e.g., double strand siRNA).

In some embodiments, the one or more Linker Units (e.g., from 1 to 3 Linker Units) is consecutively or discretely attached to the antisense strand at the 3'-terminal position of the double strand RNA (e.g., double strand siRNA).

In some embodiments, the one or more Linker Units (e.g., from 1 to 3 Linker Units) is consecutively or discretely attached to the antisense strand at the 5'-terminal position of the double strand RNA (e.g., double strand siRNA).

In some embodiments, one or more nucleoside or nucleotide at one or more consecutive or discrete internal position of the antisense strand of the double strand RNA (e.g., double strand siRNA) is replaced with the one or more Linker Units (e.g., from 1 to 3 Linker Units).

In some embodiments, the conjugate is (Linker Unit-$(\text{Ligand})_{0\text{-}1})_p$-((Nucleic Acid Agent)-(Linker Unit-$(\text{Ligand})_{0\text{-}1})_s)_r$-(Nucleic Acid Agent$)_q$, wherein:

- each Linker Unit is independent from another Linker Unit, each Nucleic Acid Agent is independent from another Nucleic Acid Agent, and each Ligand is independent from another Ligand;

each r independently is an integer ranging from 0 to 10;

each s independently is an integer ranging from 0 to 10;

p is an integer ranging from 0 to 10;

q is 0 or 1; and the conjugate comprises at least one Linker Unit, at least one Nucleic Acid Agent, and at least one Ligand.

In some embodiments, the conjugate is (Linker Unit-(Ligand)$_{0-1}$)$_p$-((Nucleic Acid Agent)-(Linker Unit-(Ligand)$_{0-1}$)$_s$)$_r$-(Nucleic Acid Agent).

In some embodiments, the conjugate is (Linker Unit-(Ligand)$_{0-1}$)$_p$-((Nucleic Acid Agent)-(Linker Unit-(Ligand)$_{0-1}$)$_s$)$_r$.

In some embodiments, the conjugate is (Linker Unit-(Ligand)$_{0-1}$)$_p$-(Nucleic Acid Agent).

In some embodiments, the conjugate is (Nucleic Acid Agent)-(Linker Unit-(Ligand)$_{0-1}$)$_s$-(Nucleic Acid Agent).

In some embodiments, the conjugate is selected from the conjugates described in Table C, wherein the Nucleic Acid Agent is attached at ##, and ## is a direct or indirect attachment described herein.

TABLE C

| Compound No. | Structure |
| --- | --- |
| C-1 | 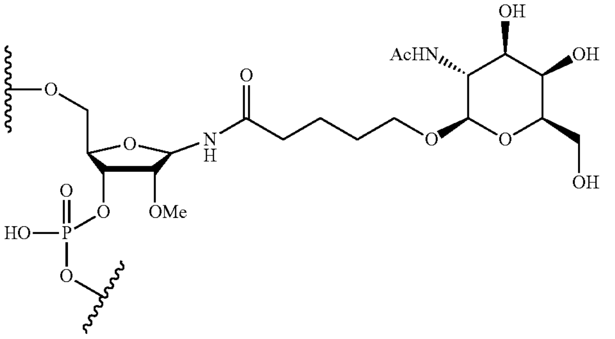 |
| C-2 | 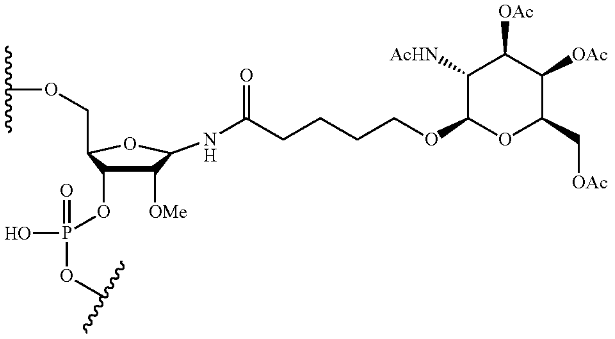 |
| C-3 | 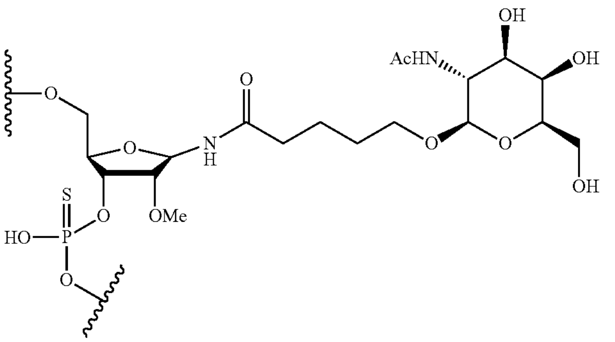 |

TABLE C-continued
| Compound No. | Structure |
| --- | --- |
| C-4 | 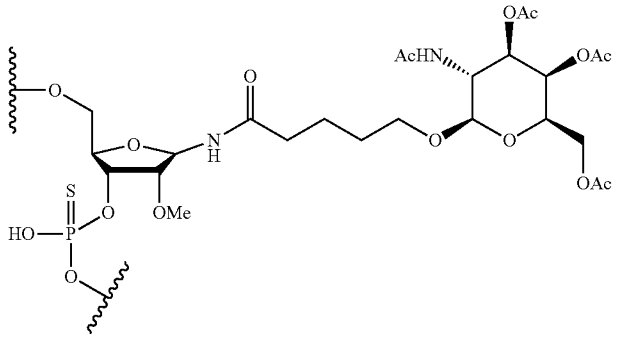 |
| C-5 | 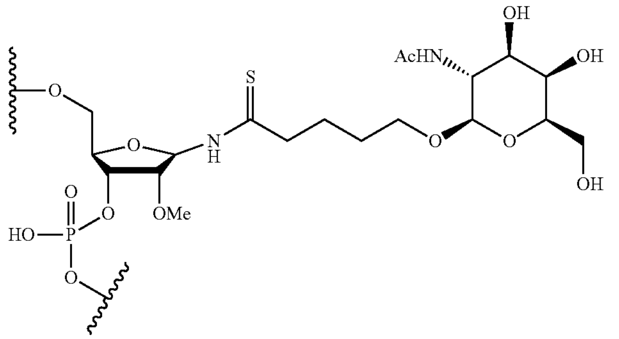 |
| C-6 | 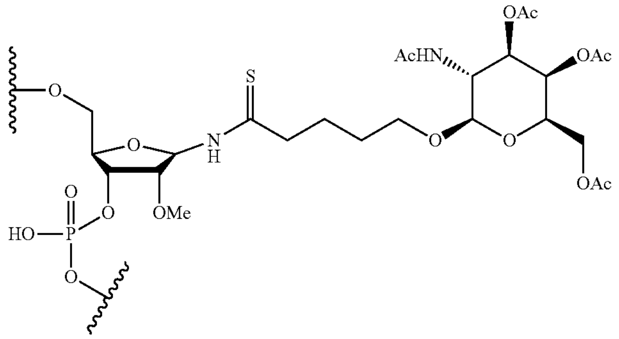 |
| C-7 | 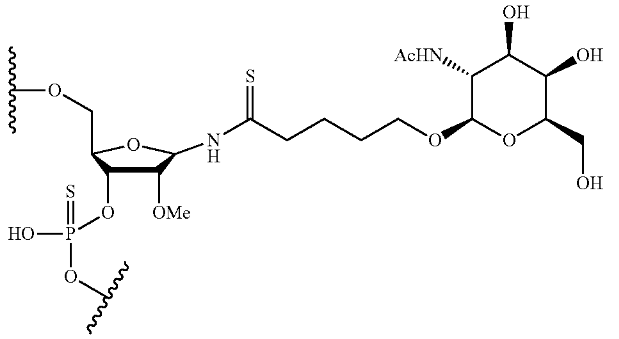 |

TABLE C-continued
| Compound No. | Structure |
| --- | --- |
| C-8 | 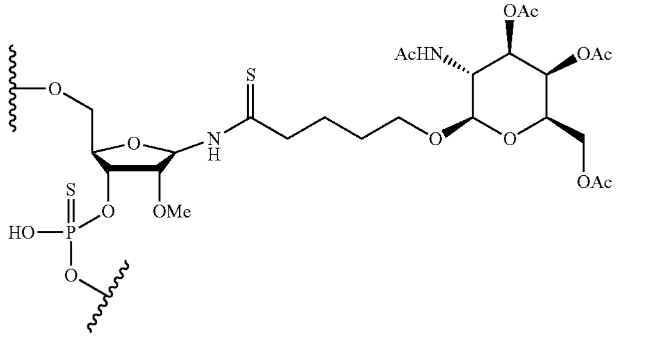 |
| C-9 | 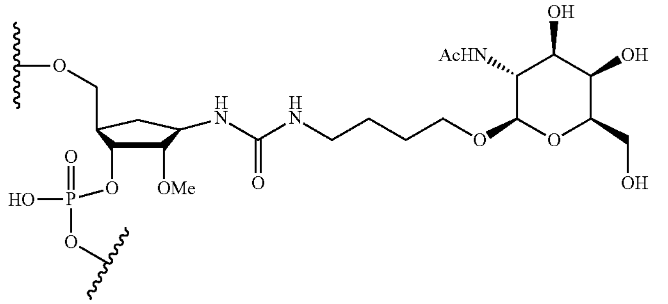 |
| C-10 | 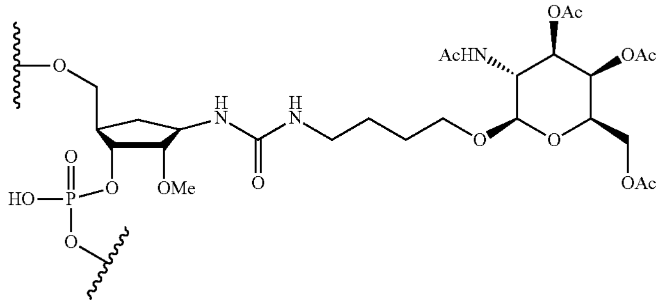 |
| C-11 | 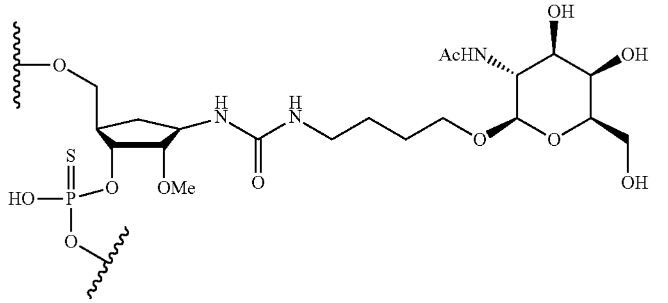 |
| C-12 | 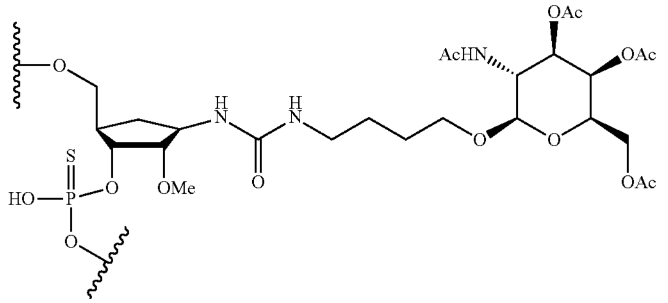 |

TABLE C-continued
| Compound No. | Structure |
| --- | --- |
| C-13 | 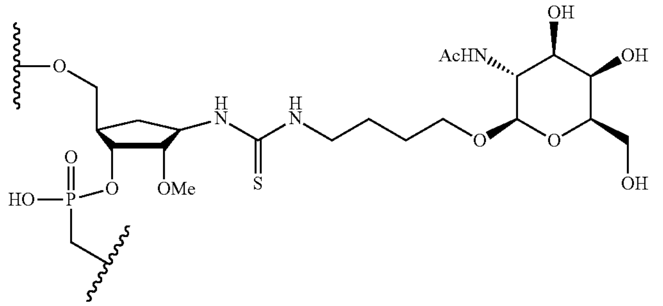 |
| C-14 | 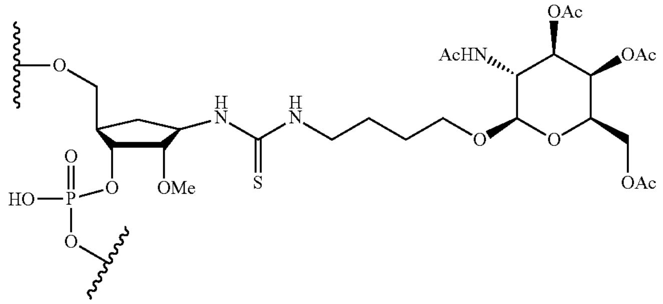 |
| C-15 | 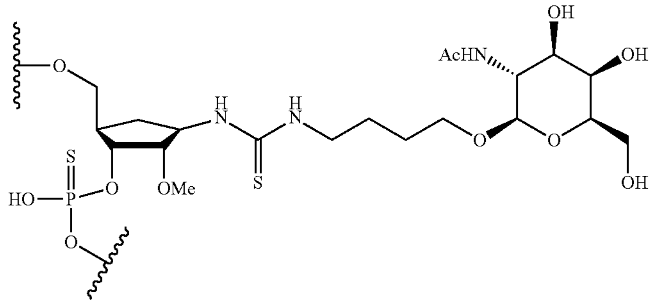 |
| C-16 | 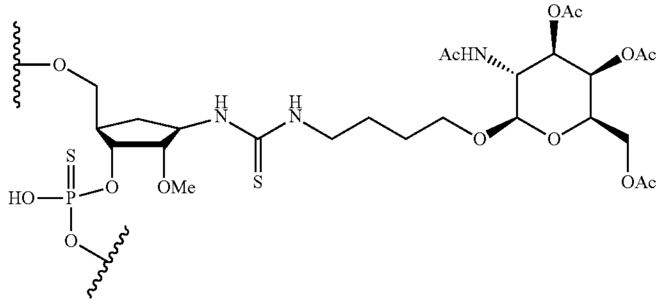 |
| C-17 | 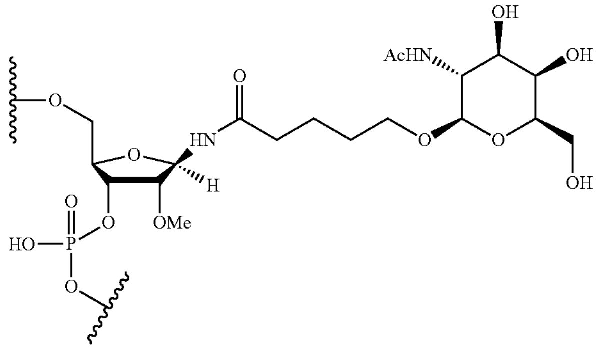 |

TABLE C-continued
| Compound No. | Structure |
| --- | --- |
| C-18 | 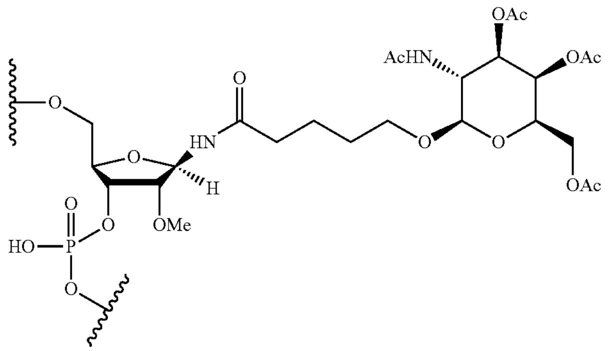 |
| C-19 | 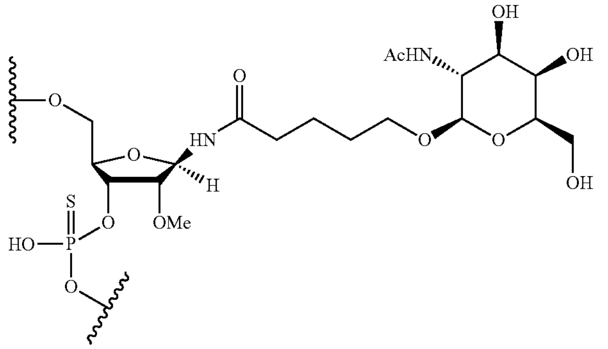 |
| C-20 | 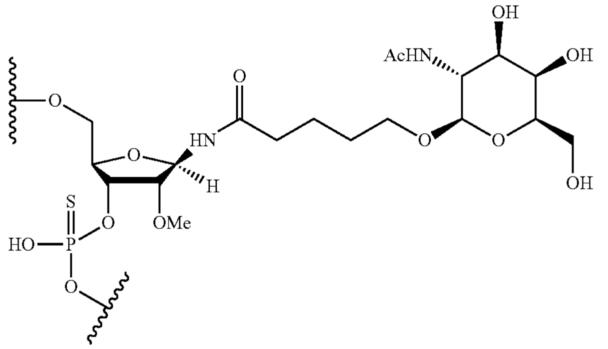 |
| C-21 | 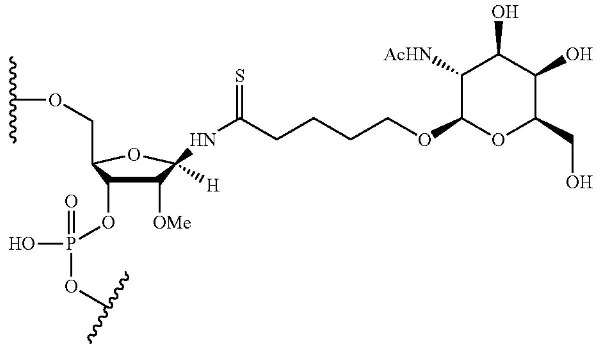 |

TABLE C-continued
| Compound No. | Structure |
|---|---|
| C-22 | 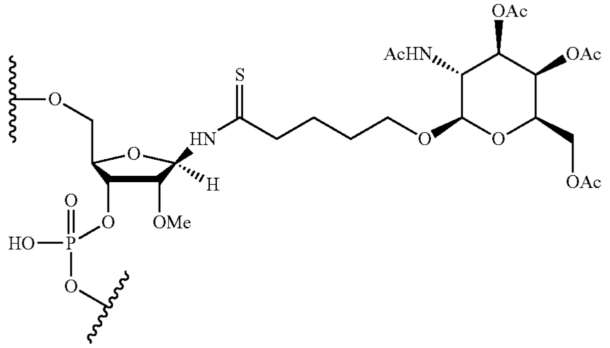 |
| C-23 | 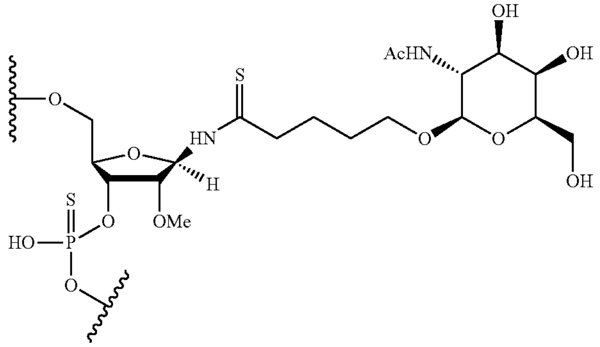 |
| C-24 | 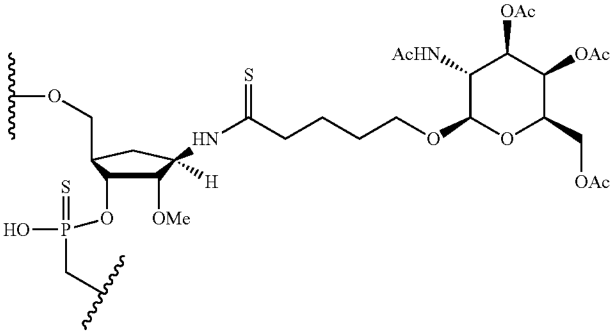 |
| C-25 | 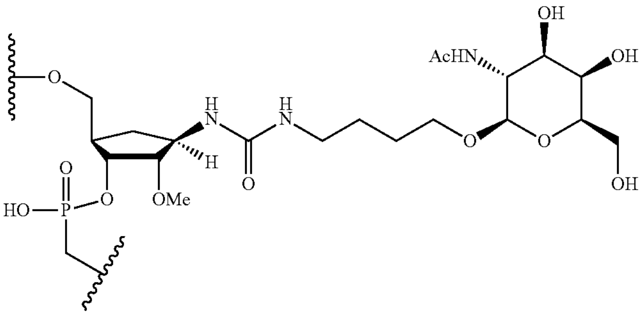 |

TABLE C-continued
| Compound No. | Structure |
| --- | --- |
| C-26 | 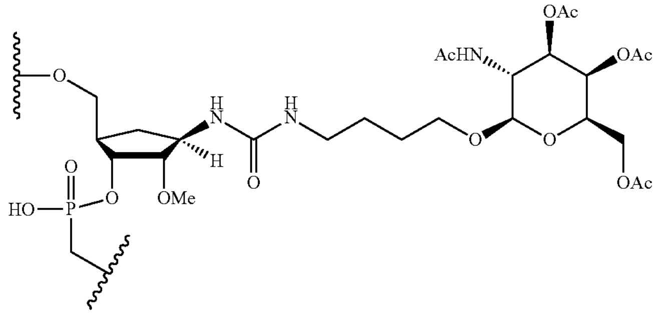 |
| C-27 | 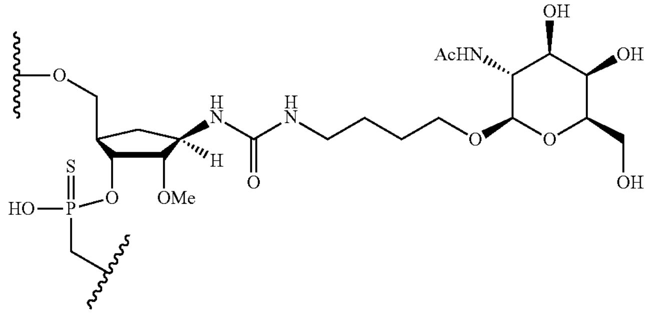 |
| C-28 | 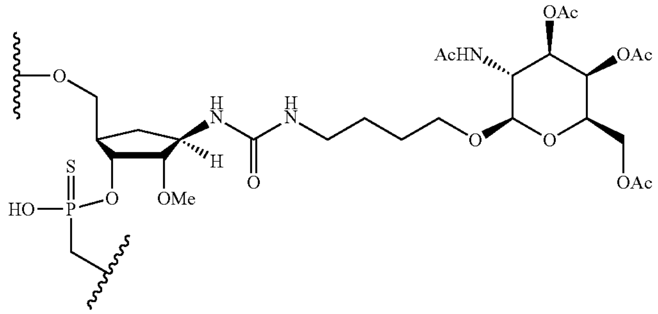 |
| C-29 | 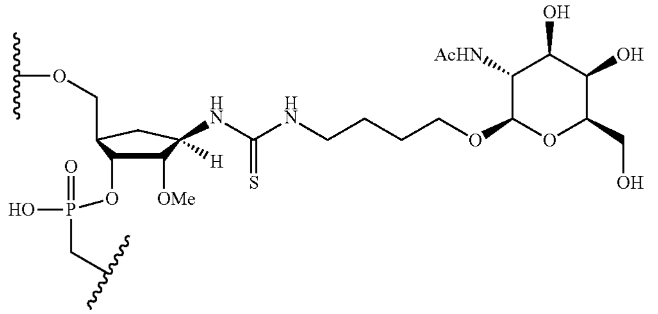 |
| C-30 | 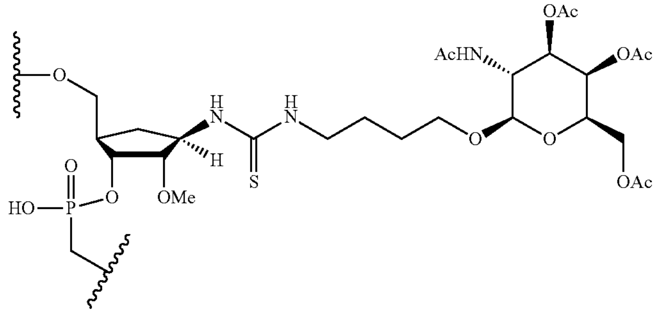 |

TABLE C-continued
| Compound No. | Structure |
|---|---|
| C-31 | 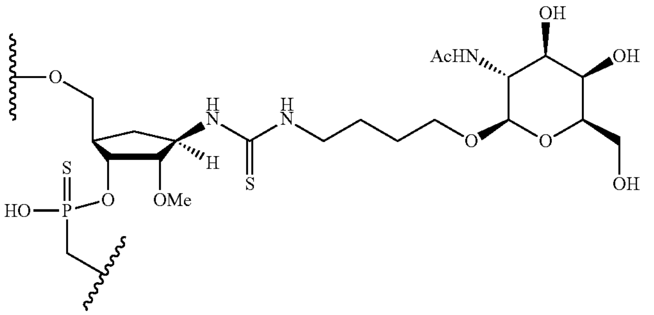 |
| C-32 | 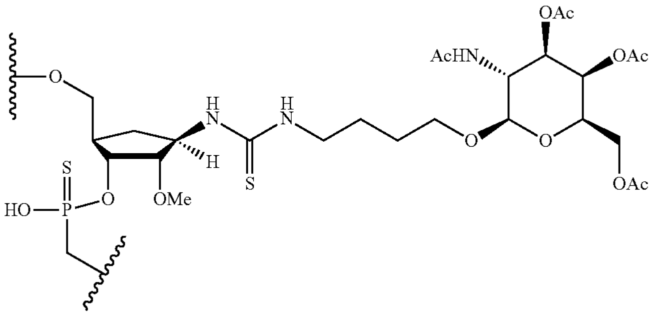 |
| C-33 | 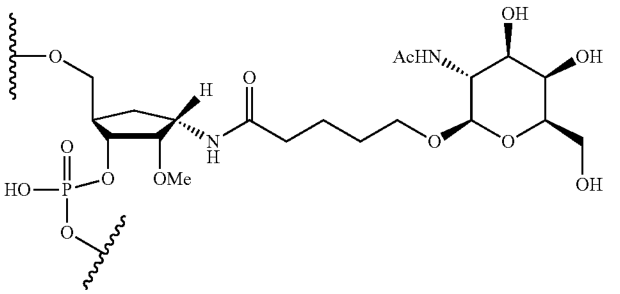 |
| C-34 | 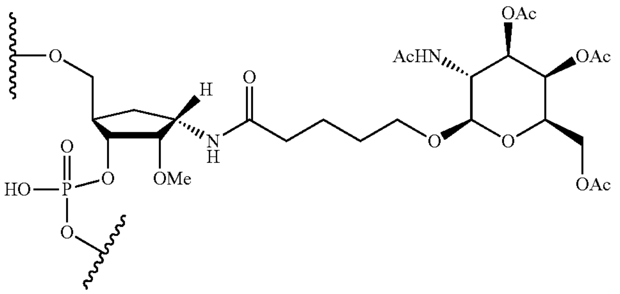 |
| C-35 | 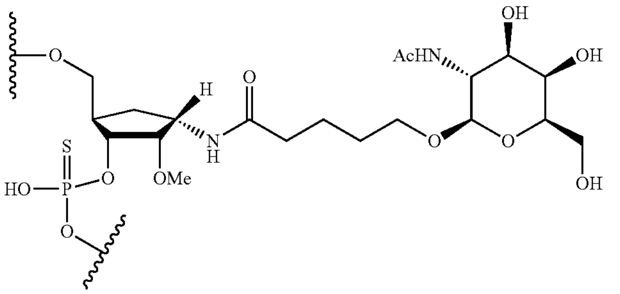 |

TABLE C-continued
| Compound No. | Structure |
| --- | --- |
| C-36 | 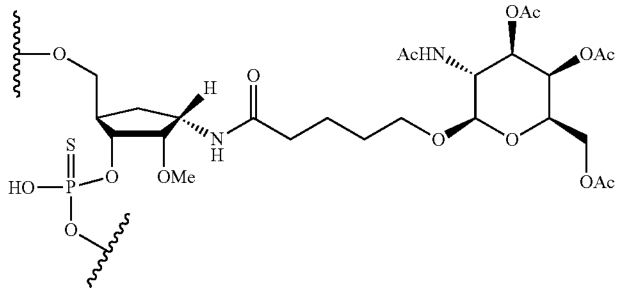 |
| C-37 | 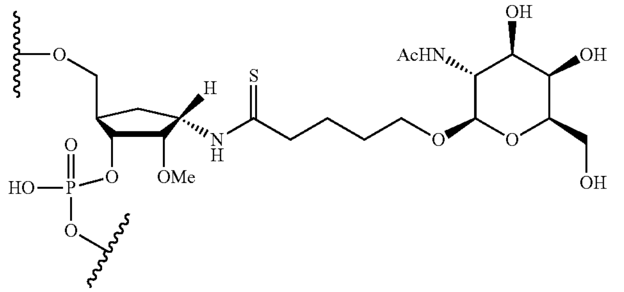 |
| C-38 | 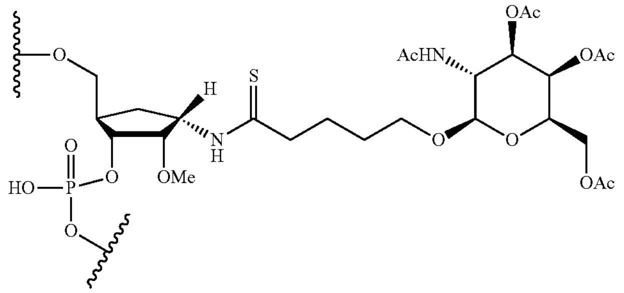 |
| C-39 | 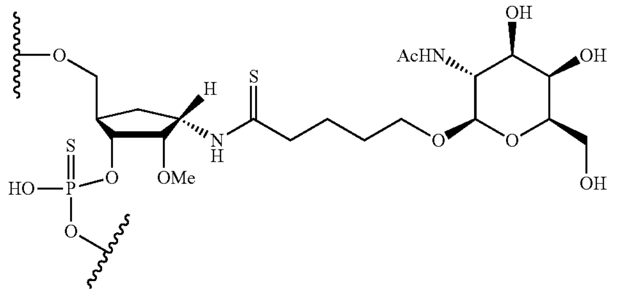 |
| C-40 | 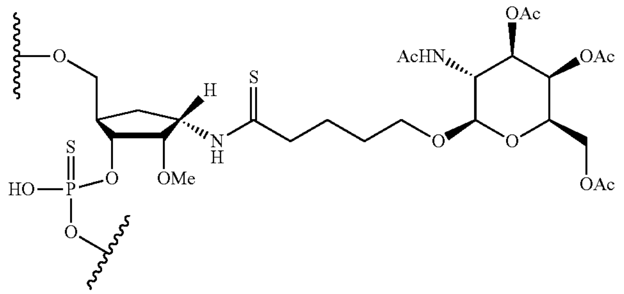 |

TABLE C-continued
| Compound No. | Structure |
| --- | --- |
| C-41 | 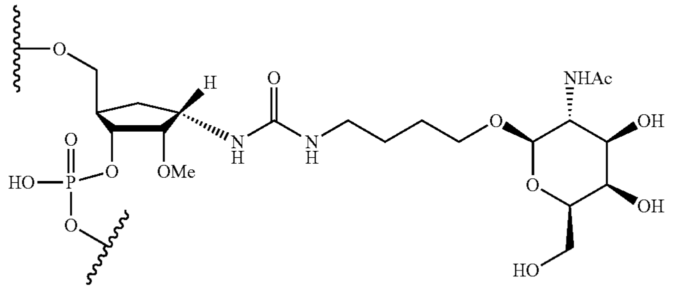 |
| C-42 | 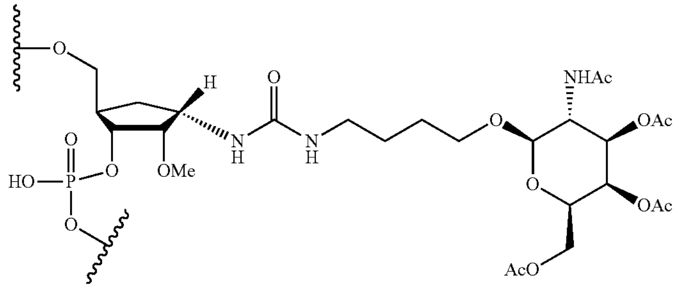 |
| C-43 | 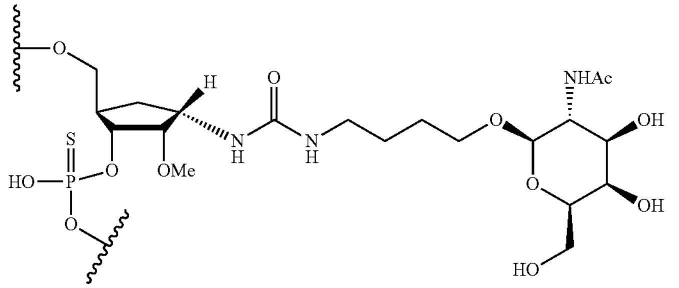 |
| C-44 | 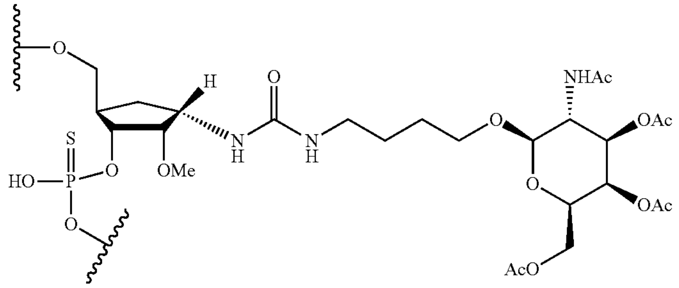 |
| C-45 | 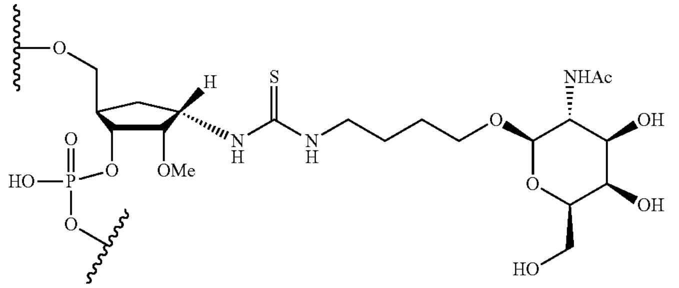 |

TABLE C-continued
| Compound No. | Structure |
| --- | --- |
| C-46 | 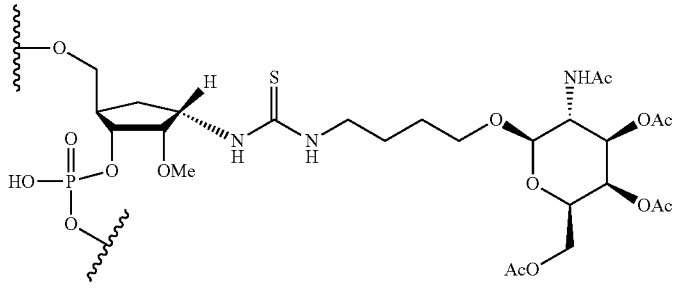 |
| C-47 | 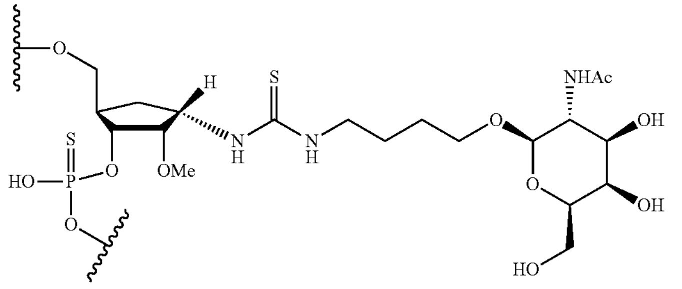 |
| C-48 | 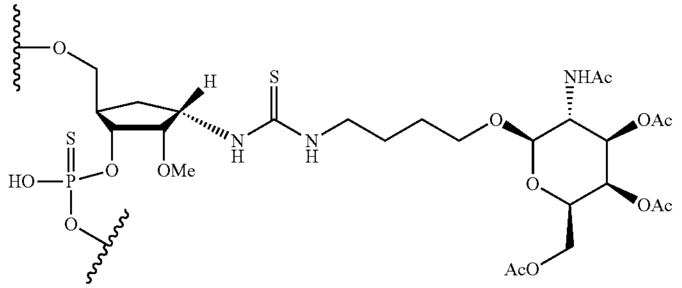 |
| C-49 | 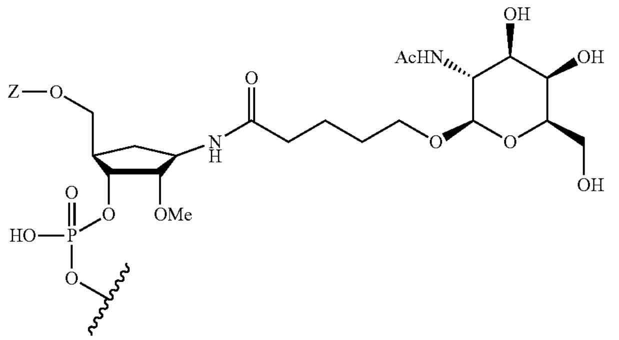 |
| C-50 | 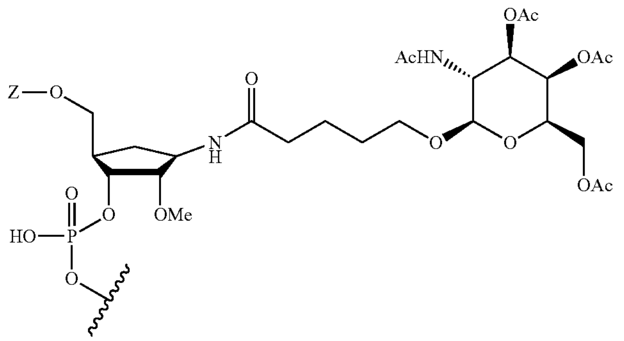 |

TABLE C-continued
| Compound No. | Structure |
|---|---|
| C-51 | 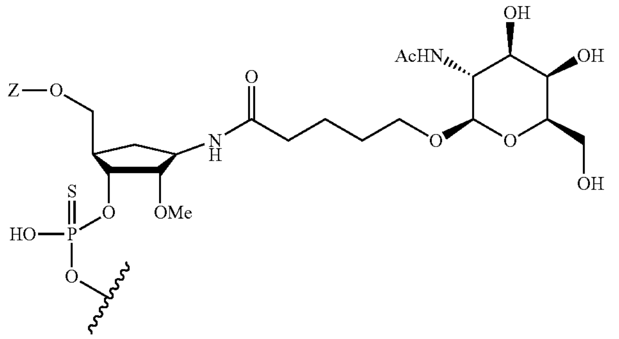 |
| C-52 | 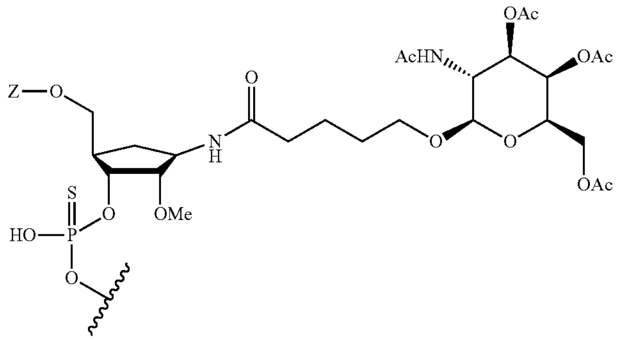 |
| C-53 | 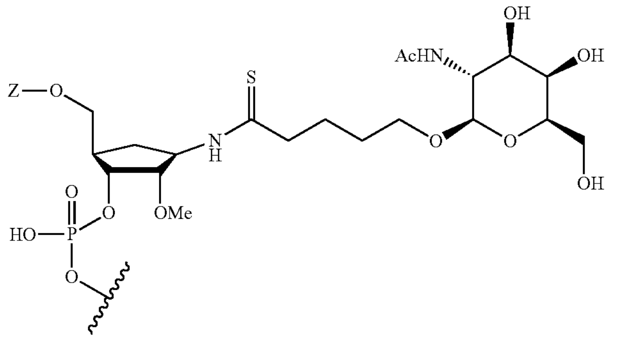 |
| C-54 | 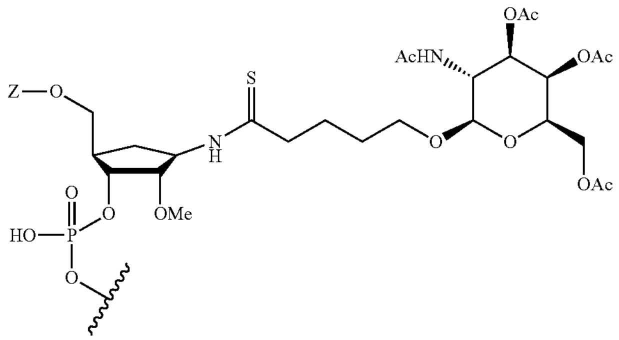 |

TABLE C-continued
| Compound No. | Structure |
| --- | --- |
| C-55 | 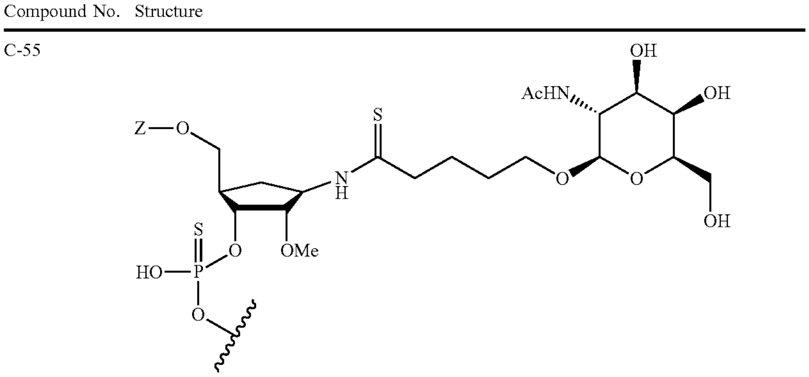 |
| C-56 | 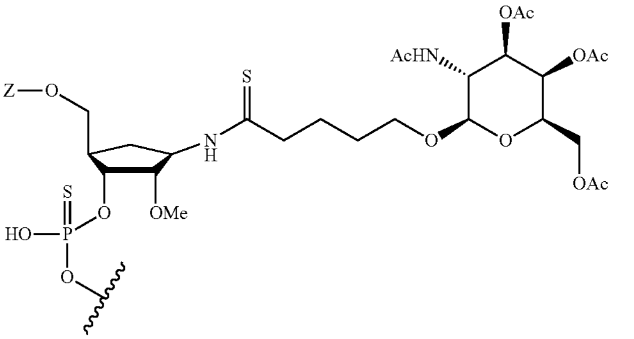 |
| C-57 | 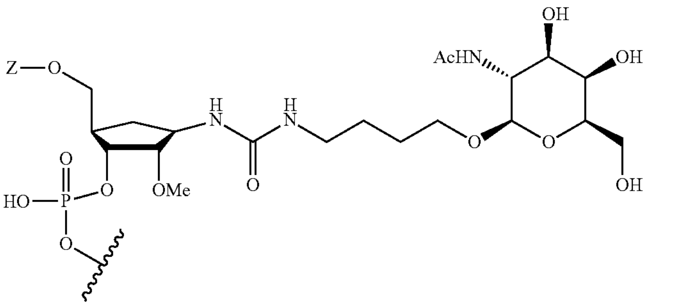 |
| C-58 | 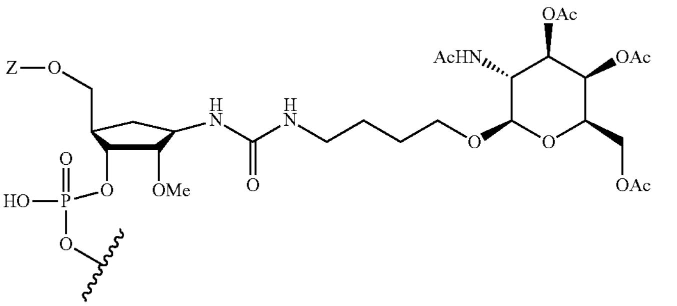 |
| C-59 | 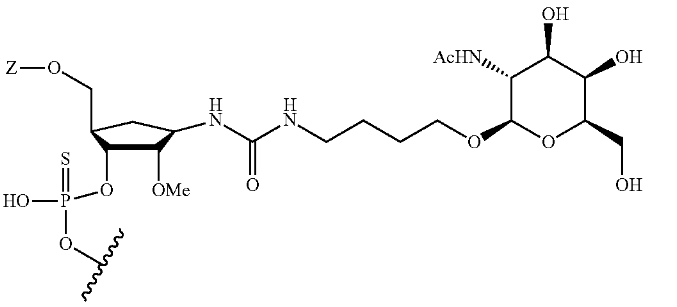 |

TABLE C-continued
| Compound No. | Structure |
| --- | --- |
| C-60 | 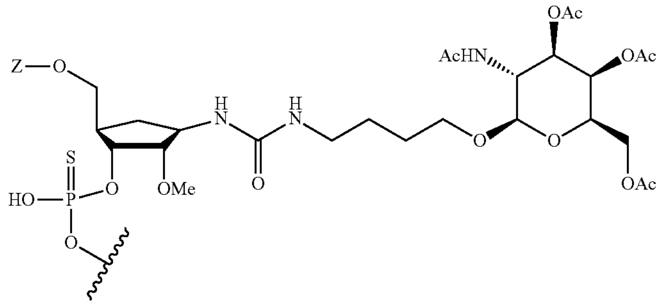 |
| C-61 | 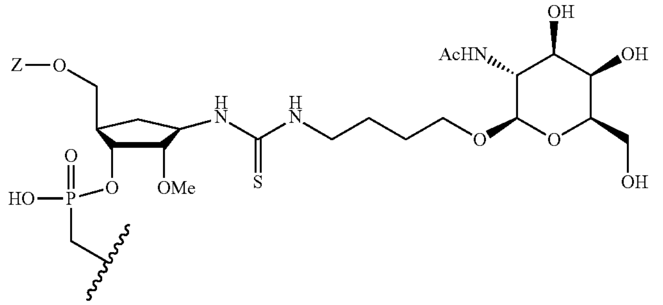 |
| C-62 | 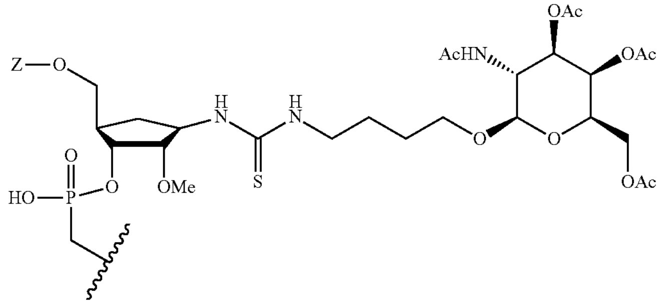 |
| C-63 | 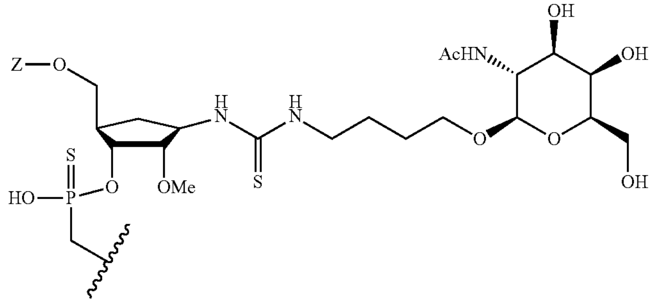 |
| C-64 | 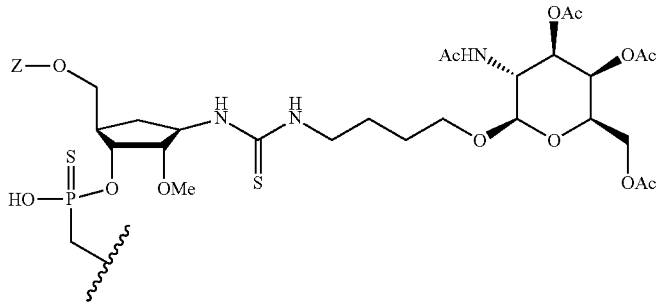 |

TABLE C-continued
| Compound No. | Structure |
|---|---|
| C-65 | 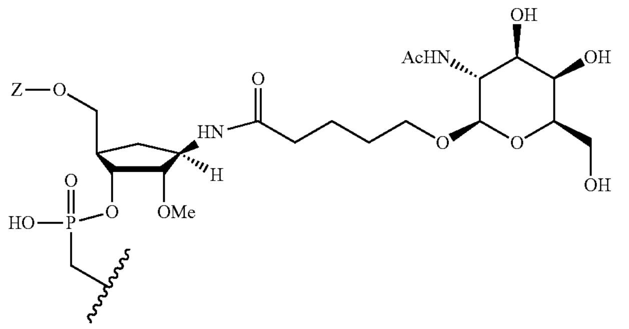 |
| C-66 | 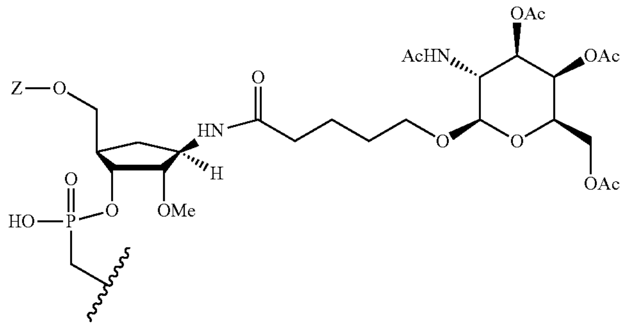 |
| C-67 | 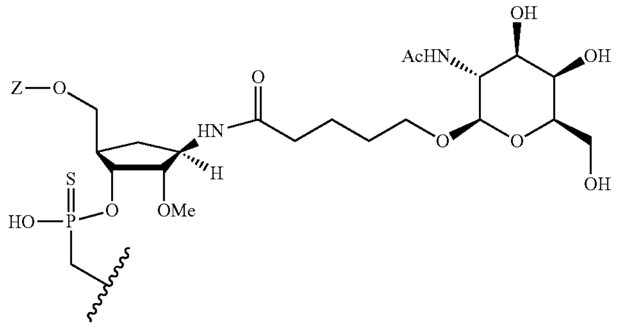 |
| C-68 | 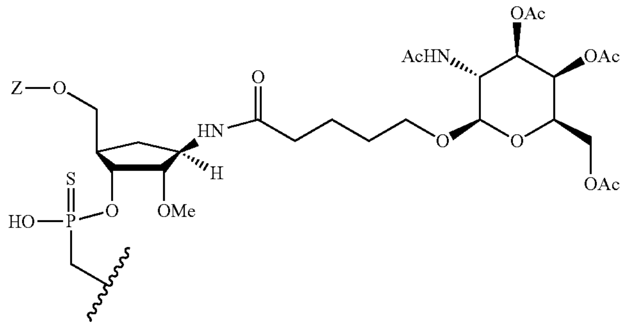 |

TABLE C-continued
| Compound No. | Structure |
| --- | --- |
| C-69 | 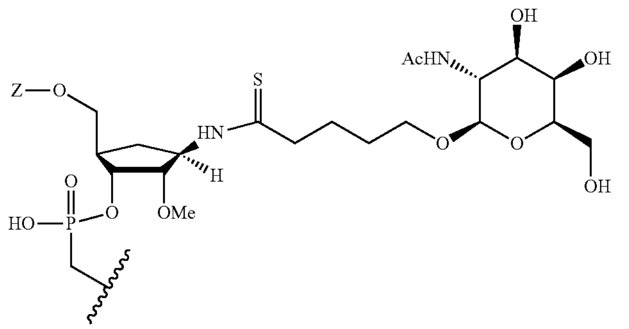 |
| C-70 | 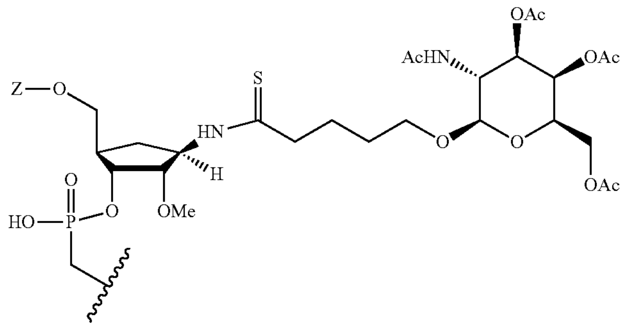 |
| C-71 | 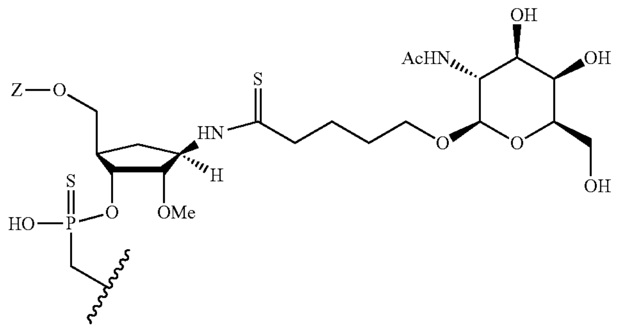 |
| C-72 | 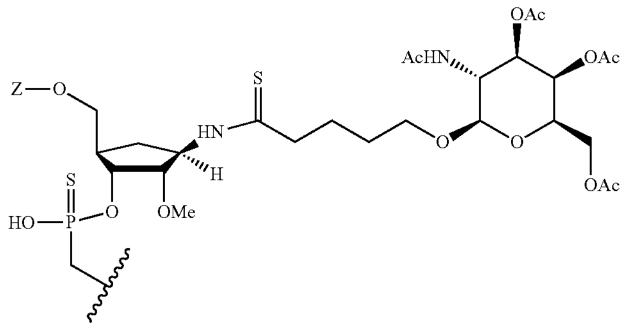 |

TABLE C-continued
| Compound No. | Structure |
| --- | --- |
| C-73 | 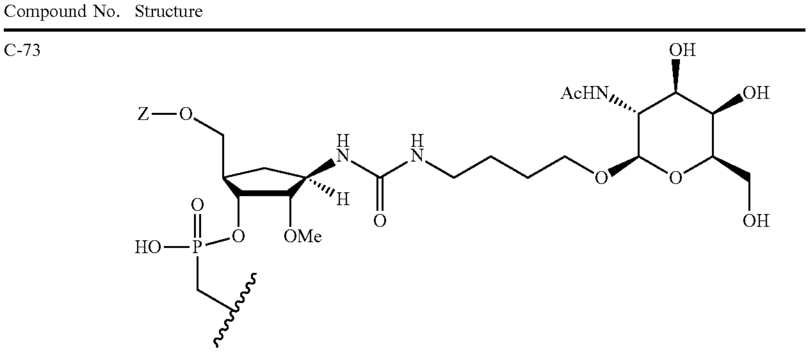 |
| C-74 | 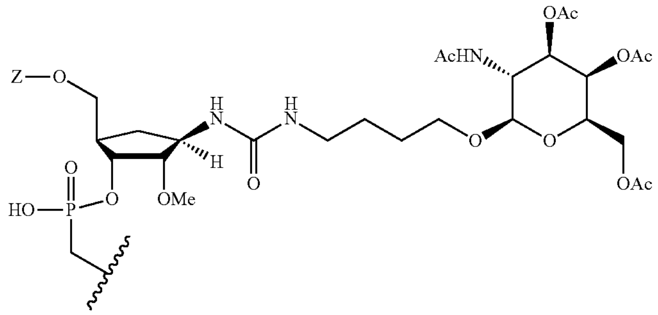 |
| C-75 | 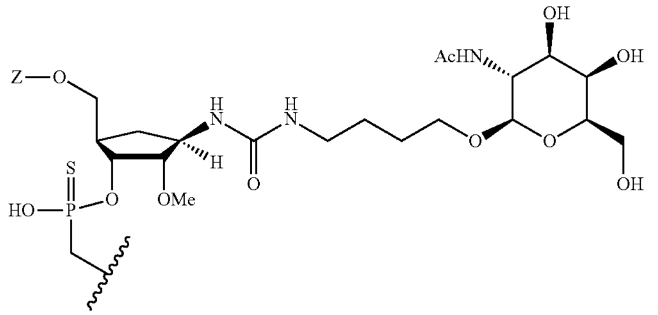 |
| C-76 | 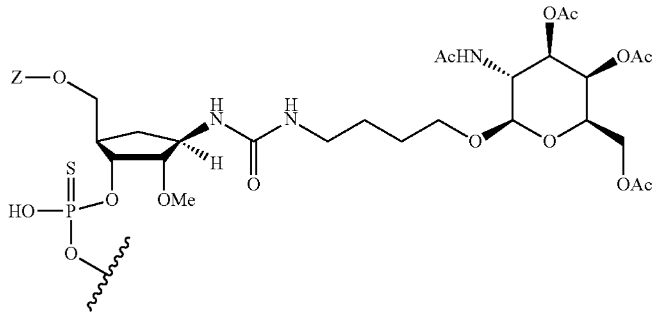 |
| C-77 | 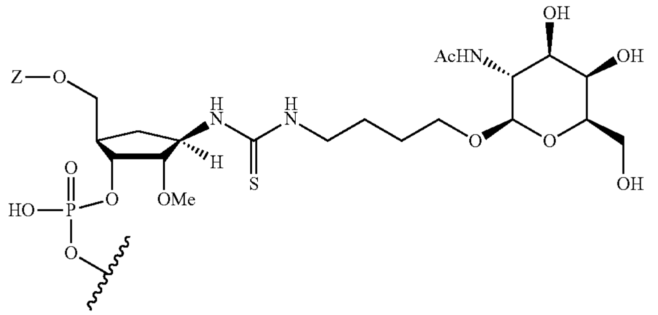 |

TABLE C-continued
| Compound No. | Structure |
| --- | --- |
| C-78 | 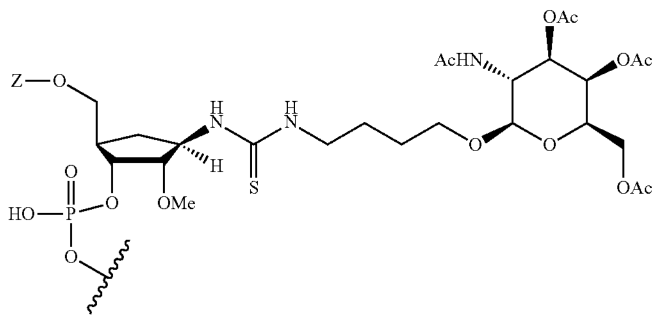 |
| C-79 | 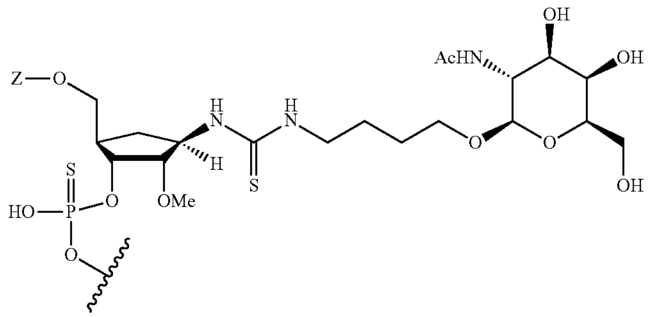 |
| C-80 | 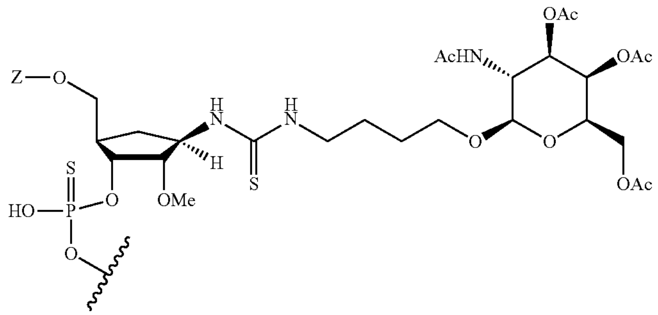 |
| C-81 | 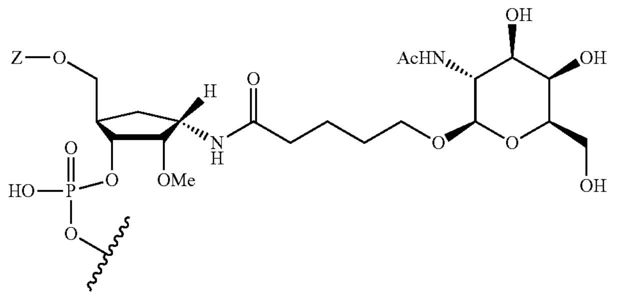 |
| C-82 | 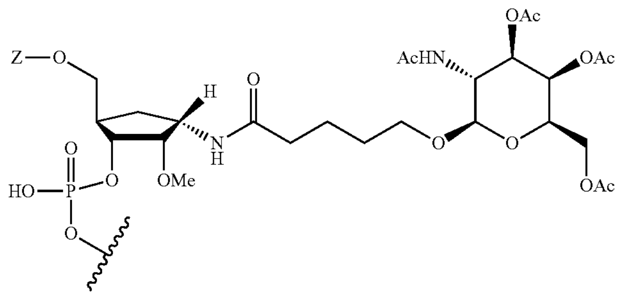 |

TABLE C-continued
| Compound No. | Structure |
| --- | --- |
| C-83 | 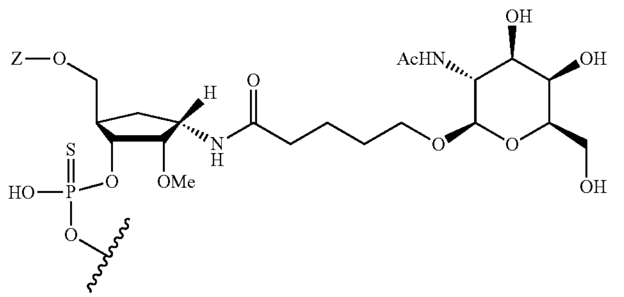 |
| C-84 | 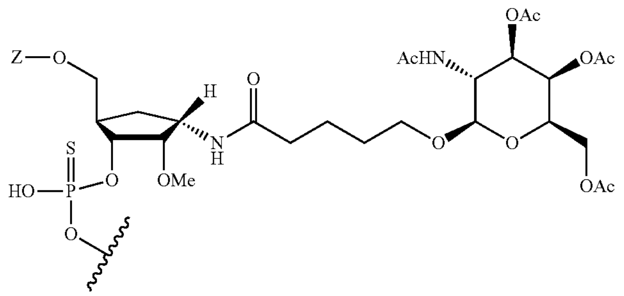 |
| C-85 | 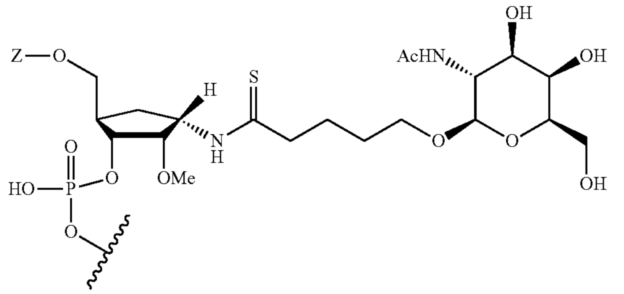 |
| C-86 | 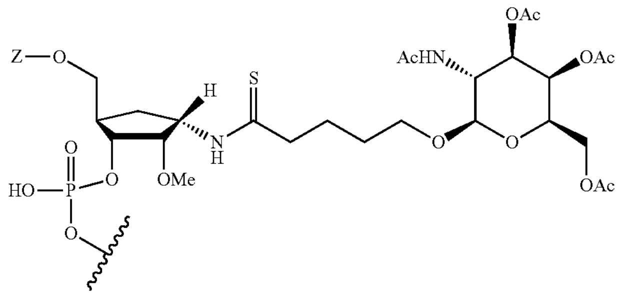 |
| C-87 | 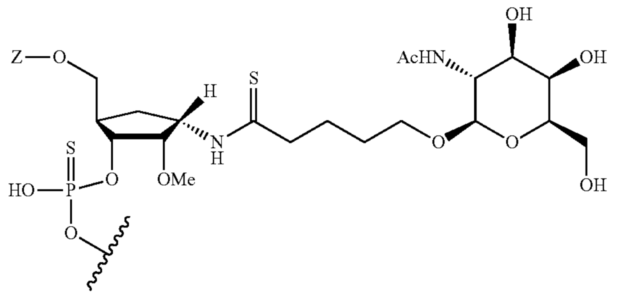 |

TABLE C-continued
| Compound No. | Structure |
| --- | --- |
| C-88 | 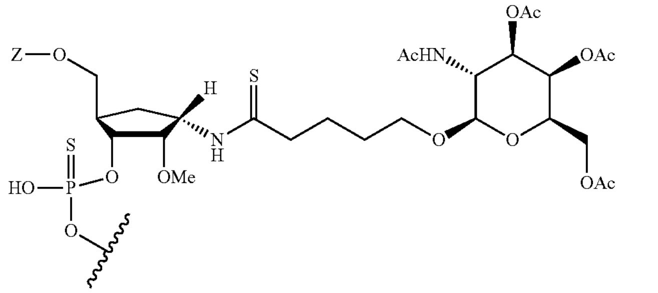 |
| C-89 | 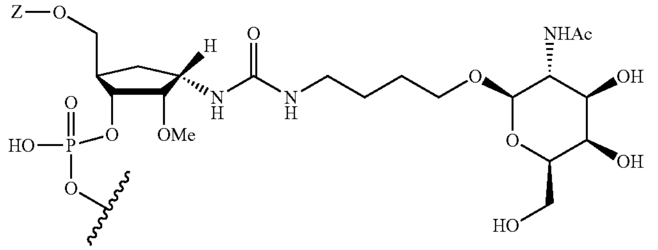 |
| C-90 | 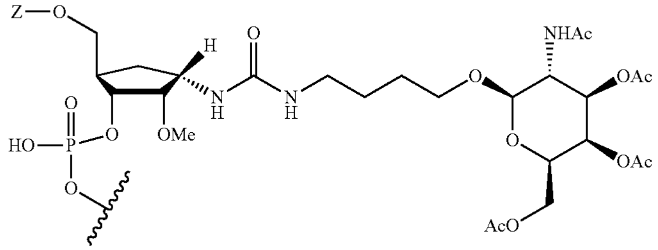 |
| C-91 | 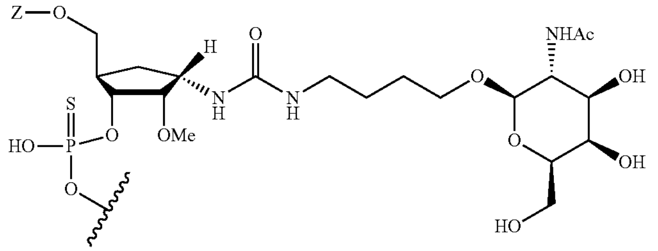 |
| C-92 | 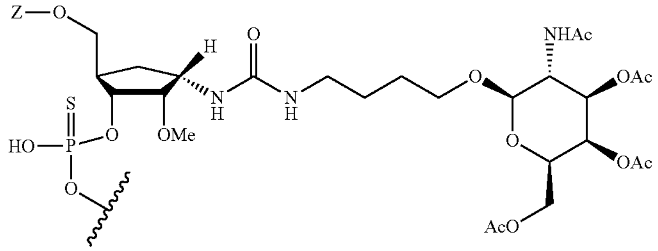 |
| C-93 | 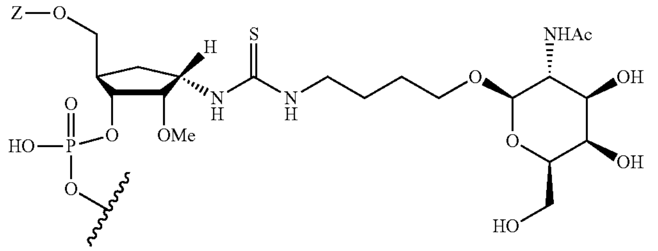 |

TABLE C-continued
| Compound No. | Structure |
| --- | --- |
| C-94 | 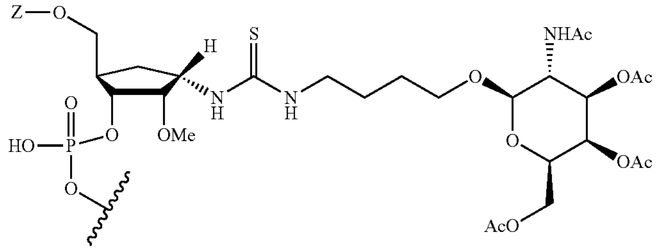 |
| C-95 | 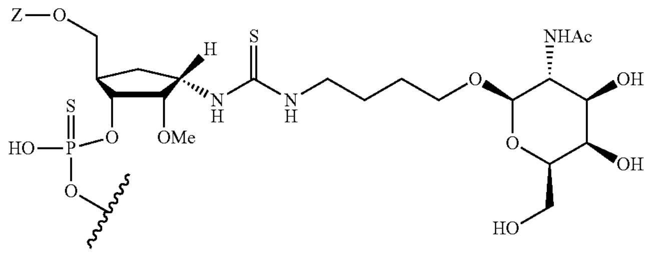 |
| C-96 | 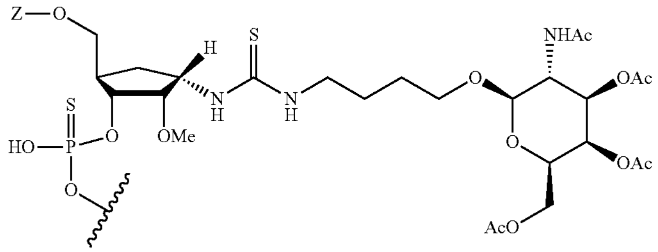 |
| C-97 | 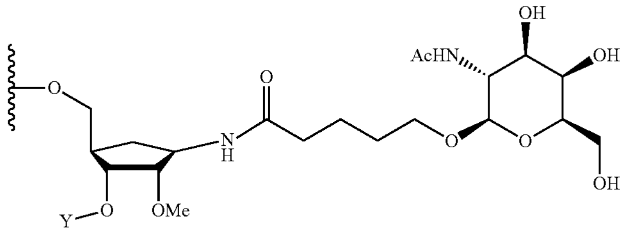 |
| C-98 | 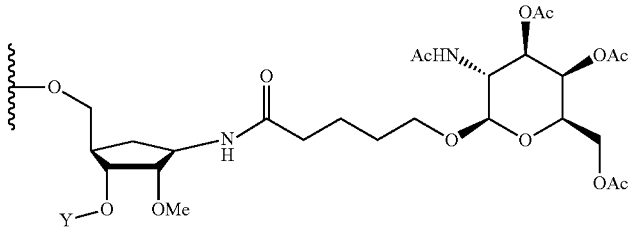 |
| C-99 | 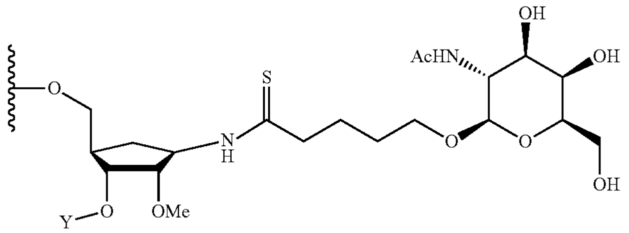 |

TABLE C-continued
| Compound No. | Structure |
|---|---|
| C-100 | 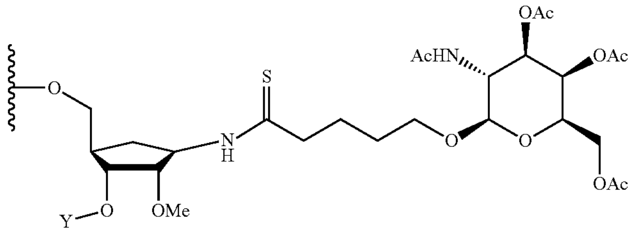 |
| C-101 | 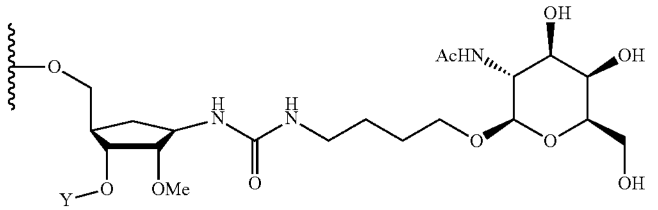 |
| C-102 | 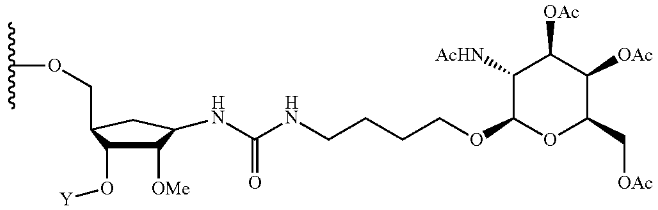 |
| C-103 | 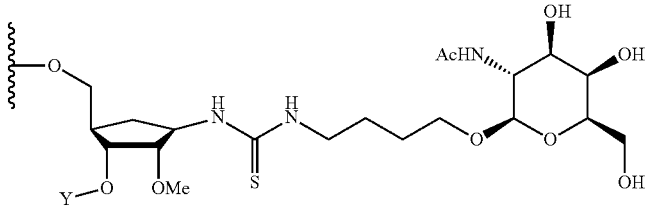 |
| C-104 | 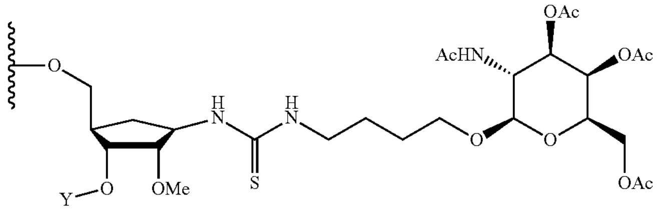 |
| C-105 | 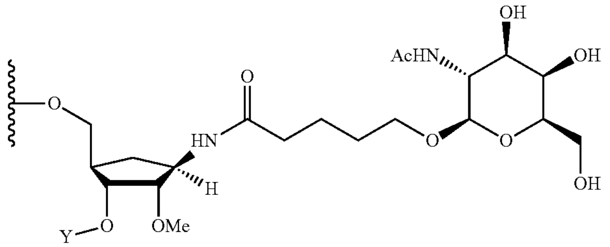 |

TABLE C-continued
| Compound No. | Structure |
| --- | --- |
| C-106 | 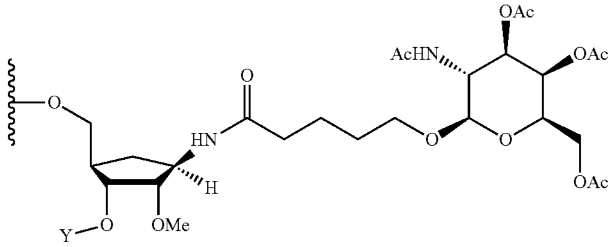 |
| C-107 | 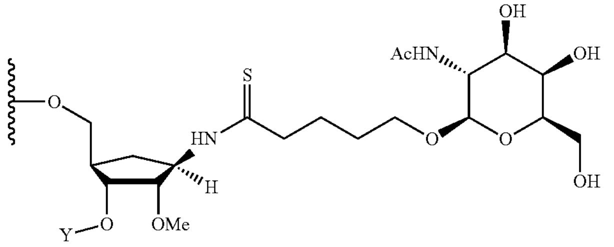 |
| C-108 | 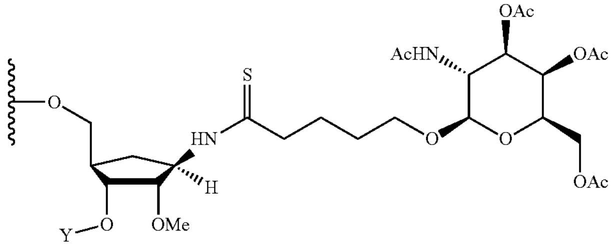 |
| C-109 | 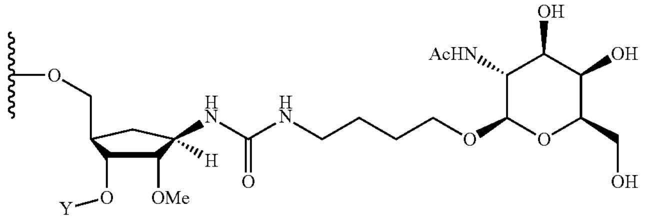 |
| C-110 | 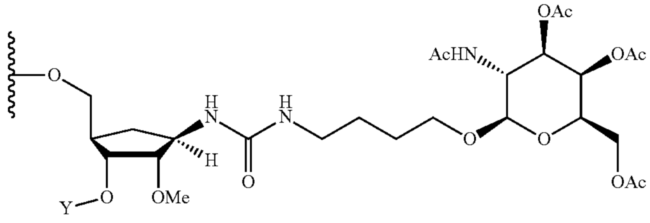 |
| C-111 | 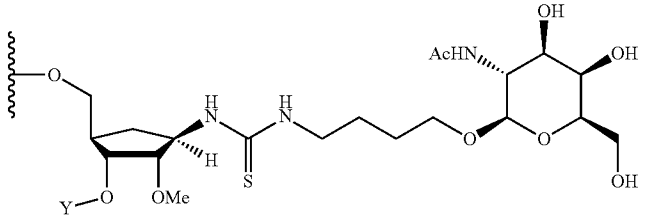 |

TABLE C-continued
| Compound No. | Structure |
| --- | --- |
| C-112 | 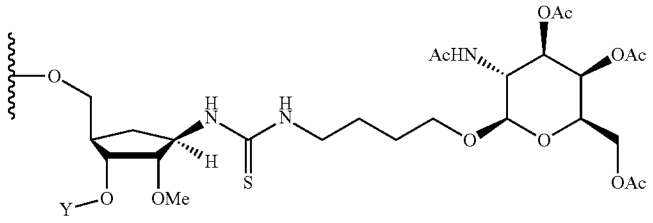 |
| C-113 | 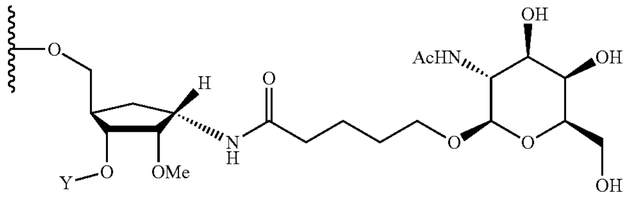 |
| C-114 | 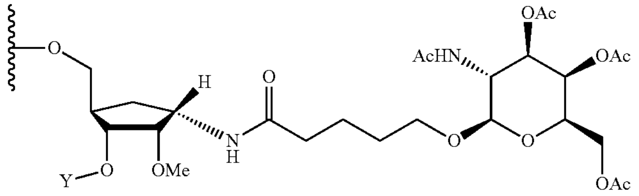 |
| C-115 | 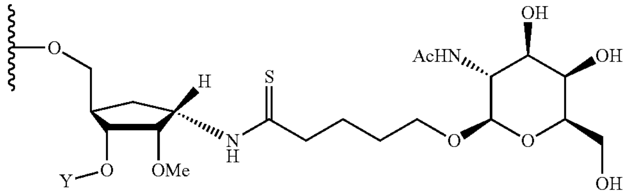 |
| C-116 | 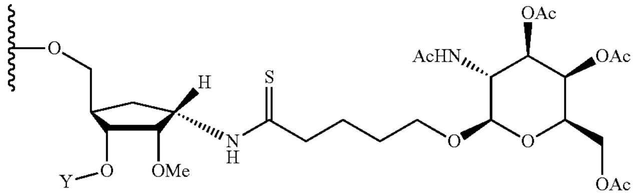 |
| C-117 | 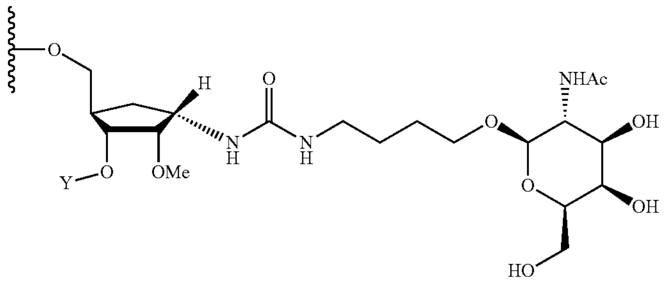 |

TABLE C-continued

| Compound No. | Structure |
| --- | --- |
| C-118 | 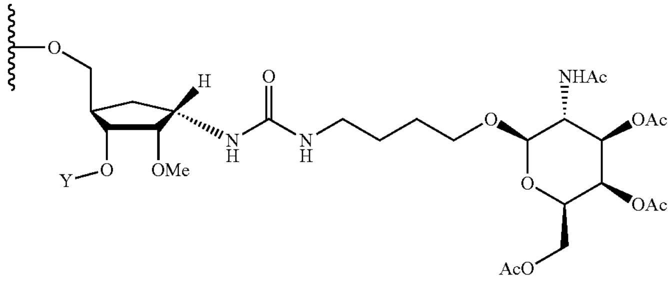 |
| C-119 | 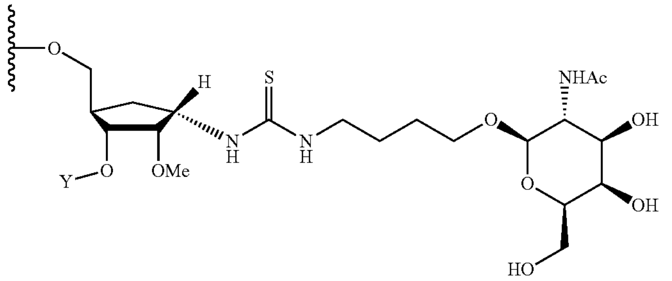 |
| C-120 | 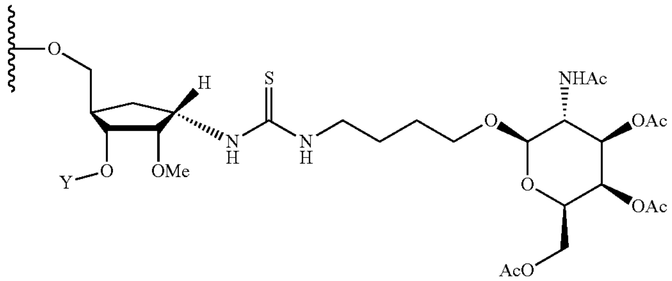 |

Linker Units

As used herein, a "Linker Unit" or "linker unit" refers to a moiety corresponding to a Linker Compound in which wherein W, Y, and/or Z is replaced with an attachment to a Ligand and/or a Nucleic Acid Agent.

In some embodiments, the Linker Unit is of Formula (I), wherein W is replaced with an attachment to the Ligand.

In some embodiments, the Linker Unit is of Formula (I), wherein Y and/or Z is replaced with an attachment to the Nucleic Acid Agent.

In some embodiments, the Linker Unit is of Formula (I), wherein:

W is replaced with an attachment to the Ligand; and

Y and/or Z is replaced with an attachment to the Nucleic Acid Agent.

In some embodiments, the Linker Unit is of Formula (I'-1), (I'-2), (II'-1), or (II'-2), wherein W is replaced with an attachment to the Ligand.

In some embodiments, the Linker Unit is of Formula (I'-1), (I'-2), (II'-1), or (II'-2), wherein Y and/or Z is replaced with an attachment to the Nucleic Acid Agent.

In some embodiments, the Linker Unit is of Formula (I-A) or (II-A), wherein W is replaced with an attachment to the Ligand.

In some embodiments, the Linker Unit is of Formula (I-A) or (II-A), wherein Y and/or Z is replaced with an attachment to the Nucleic Acid Agent.

In some embodiments, the Linker Unit is of Formula (I-A) or (II-A), wherein:

W is replaced with an attachment to the Ligand; and

Y and/or Z is replaced with an attachment to the Nucleic Acid Agent.

In some embodiments, the Linker Unit is of Formula (I-A'-1), (I-A'-2), (II-A'-1), or (II-A'-2), wherein W is replaced with an attachment to the Ligand.

In some embodiments, the Linker Unit is of Formula (I-A'-1), (I-A'-2), (II-A'-1), or (II-A'-2), wherein Y and/or Z is replaced with an attachment to the Nucleic Acid Agent.

In some embodiments, the Linker Unit is of Formula (I-A'-1), (I-A'-2), (II-A'-1), or (II-A'-2), wherein:

W is replaced with an attachment to the Ligand; and

Y and/or Z is replaced with an attachment to the Nucleic Acid Agent.

In some embodiments, the Linker Unit is of Formula (I-B) or (II-B), wherein W is replaced with an attachment to the Ligand.

In some embodiments, the Linker Unit is of Formula (I-B) or (II-B), wherein Y and/or Z is replaced with an attachment to the Nucleic Acid Agent.

In some embodiments, the Linker Unit is of Formula (I-B) or (II-B), wherein:

W is replaced with an attachment to the Ligand; and

Y and/or Z is replaced with an attachment to the Nucleic Acid Agent.

In some embodiments, the Linker Unit is of Formula (I-B'-1), (I-B'-2), (II-B'-1), or (II-B'-2), wherein W is replaced with an attachment to the Ligand.

In some embodiments, the Linker Unit is of Formula (I-B'-1), (I-B'-2), (II-B'-1), or (II-B'-2), wherein Y and/or Z is replaced with an attachment to the Nucleic Acid Agent.

In some embodiments, the Linker Unit is of Formula (I-B'-1), (I-B'-2), (II-B'-1), or (II-B'-2), wherein:

W is replaced with an attachment to the Ligand; and

Y and/or Z is replaced with an attachment to the Nucleic Acid Agent.

In some embodiments, the Linker Unit, prior to attachment, is a linker compound described herein.

In some embodiments, the Linker Unit, prior to attachment, is a compound of Formula (I) or a pharmaceutically acceptable salt thereof.

In some embodiments, the Linker Unit, prior to attachment, is a compound of Formula (I'-1), (I'-2), (II'-1), or (II'-2) or a pharmaceutically acceptable salt thereof.

In some embodiments, the Linker Unit, prior to attachment, is a compound of Formula (I-A) or (II-A), or a pharmaceutically acceptable salt thereof.

In some embodiments, the Linker Unit, prior to attachment, is a compound of Formula (I-A'-1), (I-A'-2), (II-A'-1), or (II-A'-2), or a pharmaceutically acceptable salt thereof.

In some embodiments, the Linker Unit, prior to attachment, is a compound of Formula (I-B) or (II-B), or a pharmaceutically acceptable salt thereof.

In some embodiments, the Linker Unit, prior to attachment, is a compound of Formula (I-B'-1), (I-B'-2), (II-B'-1), or (II-B'-2), or a pharmaceutically acceptable salt thereof.

In some embodiments, the Linker Unit, prior to attachment, is a compound selected from the compounds described in Table L and pharmaceutically acceptable salts thereof.

Ligands

As used herein, the term "ligand" refers to a moiety that, when being covalently attached to a Nucleic Acid Agent (e.g., an oligonucleotide), is capable of mediating its entry into, or facilitating its delivery to, a target site (e.g., a target cell or tissue).

In sone embodiments, the ligand comprises a sugar ligand moiety (e.g., N-acetylgalactosamine (GalNAc)) which may direct uptake of an oligonucleotide into the liver.

In some embodiments, the ligand binds to the asialoglycoprotein receptor (ASGPR). In some embodiments, the ligand binds to (e.g., through ASGPR) the liver, such as the parenchymal cells of the liver.

Suitable ligands include, but are not limited to, the ligands diclosed in Winkler (*Ther. Deliv.*, 2013, 4(7): 791-809), PCT Patent Appl'n Pub. Nos. WO/2016/100401, WO/2012/089352, and WO/2009/082607, and US. Patent Appl'n Pub. Nos. 2009/0239814, 2012/0136012, 2013/0158824, and 2009/0247608, each of which is incorporated by reference.

In some embodiments, the ligand comprises a carbohydrate moiety.

As used herein, "carbohydrate moiety" refers to a moiety which comprises one or more monosaccharide units each having at least six carbon atoms (which may be linear, branched or cyclic), with an oxygen, nitrogen or sulfur atom bonded to each carbon atom. In some embodiments, the carbohydrate moiety comprises a monosaccharide, a disaccharide, a trisaccharide, or a tetrasaccharide. In some embodiments, the carbohydrate moiety comprises an oligosaccharide containing from about 4-9 monosaccharide units. In some embodiments, the carbohydrate moiety comprises a polysaccharide (e.g., a starch, a glycogen, a cellulose, or a polysaccharide gum).

In some embodiments, the carbohydrate moiety comprises a monosaccharide, a disaccharide, a trisaccharide, or a tetrasaccharide.

In some embodiments, the carbohydrate moiety comprises an oligosaccharide (e.g., containing from about four to about nine monosaccharide units).

In some embodiments, the carbohydrate moiety comprises a polysaccharide (e.g., a starch, a glycogen, a cellulose, or a polysaccharide gum).

In some embodiments, the ligand is capable of binding to a human asialoglycoprotein receptor (ASGPR), e.g., human asialoglycoprotein receptor 2 (ASGPR2).

In some embodiments, the carbohydrate moiety comprises a sugar (e.g., one, two, or three sugar).

In some embodiments, the carbohydrate moiety comprises galactose or a derivative thereof (e.g., one, two, or three galactose or the derivative thereof).

In some embodiments, the carbohydrate moiety comprises N-acetylgalactosamine or a derivative thereof (e.g., one, two, or three N-acetylgalactosamine or the derivative thereof).

In some embodiments, the carbohydrate moiety comprises N-acetyl-D-galactosylamine or a derivative thereof (e.g., one, two, or three N-acetyl-D-galactosylamine or the derivative thereof).

In some embodiments, the carbohydrate moiety comprises N-acetylgalactosamine (e.g., one, two, or three N-acetylgalactosamine).

In some embodiments, the carbohydrate moiety comprises N-acetyl-D-galactosylamine (e.g., one, two, or three N-acetyl-D-galactosylamine).

In some embodiments, the carbohydrate moiety comprises mannose or a derivative thereof (e.g., mannose-6-phosphate).

In some embodiments, the carbohydrate moiety further comprises a linking moiety that connects the one or more sugar (e.g., N-acetyl-D-galactosylamine) with the Linker Unit.

In some embodiments the linking moiety comprises thioether (e.g., thiosuccinimide, or the hydrolysis analogue thereof), disulfide, triazole, phosphorothioate, phosphodiester, ester, amide, or any combination thereof.

In some embodiments, the linking moiety is a triantennary linking moiety.

Suitable ligands include, but are not limited to, the ligands disclosed in PCT Appl'n Pub. Nos. WO/2015/006740, WO/2016/100401, WO/2017/214112, WO/2018/039364, and WO/2018/045317, each of which is incorporated herein by reference.

In some embodiments, the ligand comprises
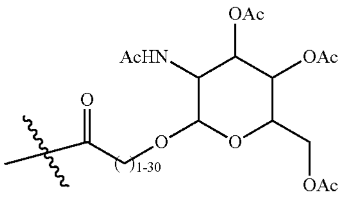
(e.g., one, two, or three
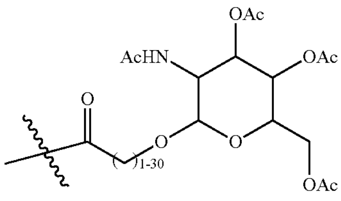
).
In some embodiments, the ligand comprises
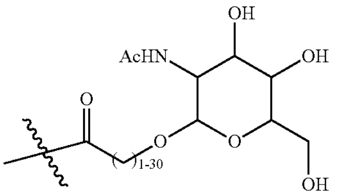
(e.g., one, two, or three
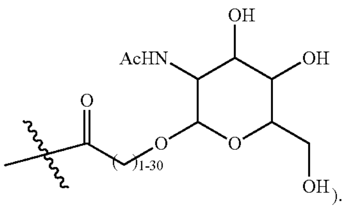
).
In some embodiments, the ligand comprises
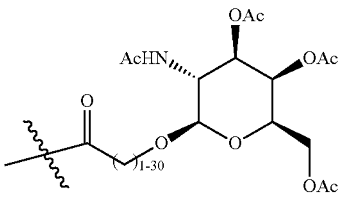
(e.g., one, two, or three
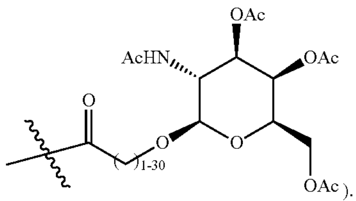
).
In some embodiments, the ligand comprises
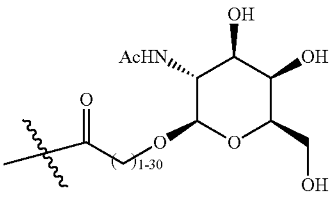
(e.g., one, two, or three
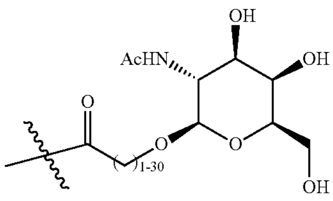
).
In some embodiments, the ligand comprises
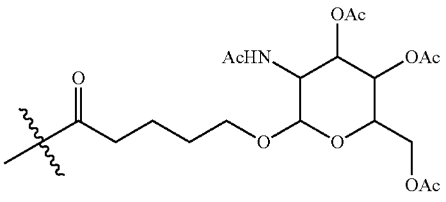 [SMILES: *C(=O)CCCCOC1OC(COC(C)=O)C(OC(C)=O)C(OC(C)=O)C1NC(C)=O]
(e.g., one, two, or three
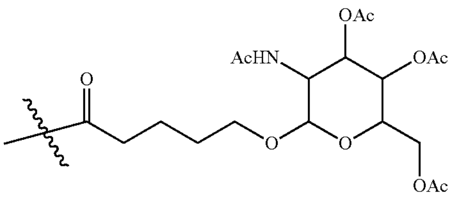
).

In some embodiments, the ligand comprises
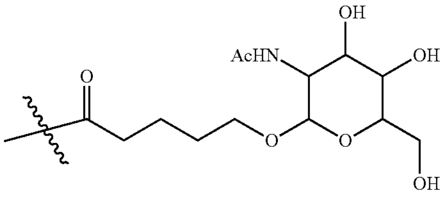 [SMILES: *C(=O)CCCCOC1OC(CO)C(O)C(O)C1NC(C)=O]
(e.g., one, two, or three
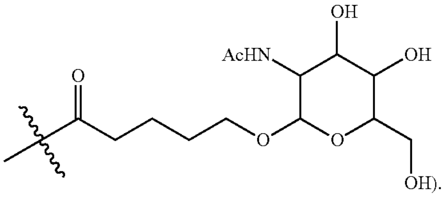
In some embodiments, the ligand comprises
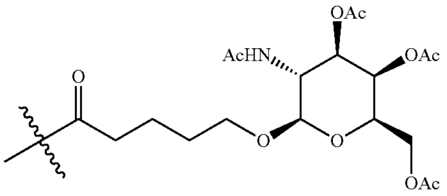 [SMILES: *C(=O)CCCCO[C@@H]1O[C@H](COC(C)=O)[C@H](OC(C)=O)[C@H](OC(C)=O)[C@H]1NC(C)=O]
(e.g., one, two, or three
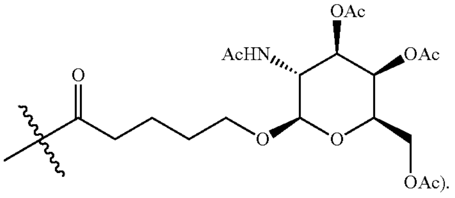
In some embodiments, the ligand comprises
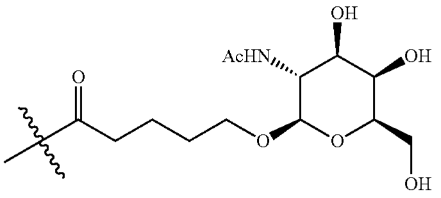 [SMILES: *C(=O)CCCCO[C@@H]1O[C@H](CO)[C@H](O)[C@H](O)[C@H]1NC(C)=O]
(e.g., one, two, or three
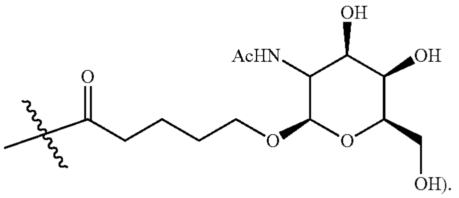
In some embodiments, the ligand comprises
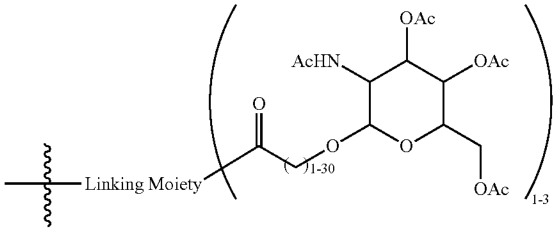
In some embodiments, the ligand comprises
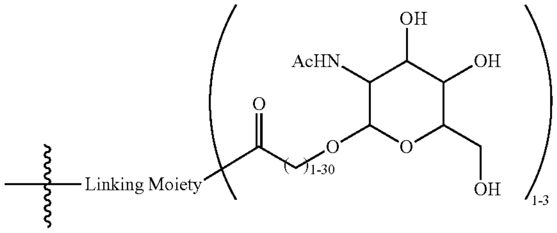
In some embodiments, the ligand comprises
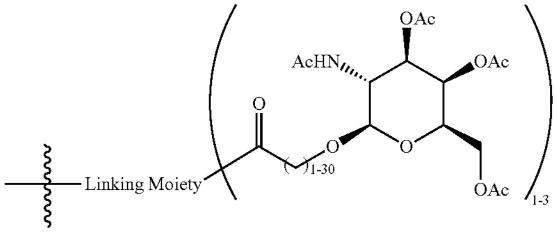
In some embodiments, the ligand comprises
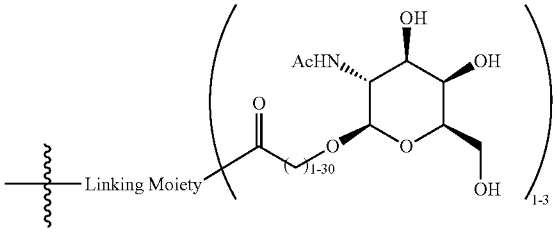

In some embodiments, the ligand comprises

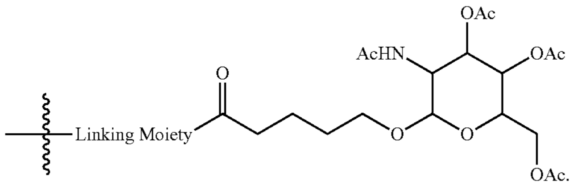

In some embodiments, the ligand comprises

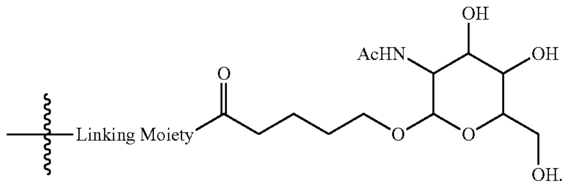

In some embodiments, the ligand comprises

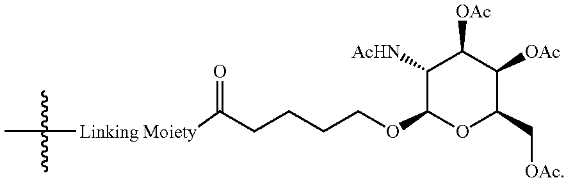

In some embodiments, the ligand comprises

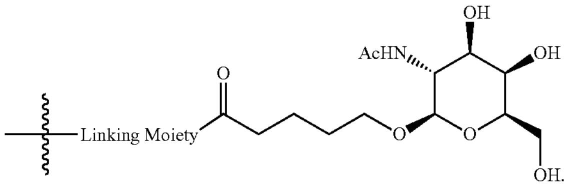

In some embodiments, the ligand comprises a lipid moiety (e.g., one, two, or three lipid moiety).

In some embodiments the lipid moiety comprises (e.g., one, two, of three of) $C_8$-$C_{24}$ fatty acid, cholesterol, vitamin, sterol, phospholipid, or any combination thereof.

In some embodiments, the ligand comprises a peptide moiety (e.g., one, two, or three peptide moiety).

In some embodiments, the peptide moiety comprises (e.g., one, two, or three of) integrin, insulin, glucagon-like peptide, or any combination thereof.

In some embodiments, the ligand comprises an antibody moiety (e.g., transferrin).

In some embodiments, the ligand comprises one, two, or three antibody moiety (e.g., transferrin).

In some embodiments, the ligand comprises an oligonucleotide (e.g., aptamer or CpG).

In some embodiments, the ligand comprises one, two, or three oligonucleotide (e.g., aptamer or CpG).

In some embodiments, the ligand comprises:

one, two, or three sugar (e.g., N-acetyl-D-galactosylamine);

one, two, or three lipid moieties;

one, two, or three peptide moieties;

one, two, or three antibody moieties;

one, two, or three oligonucleotides; or any combination thereof.

Nucleic Acid Agents

In some embodiments, the Nucleic Acid Agent comprises an oligonucleotide.

In some embodiments, the Nucleic Acid Agent (e.g., the oligonucleotide) comprises one or more one or more phosphate groups or one or more analogs of a phosphate group.

In some embodiments, the Linker Unit is attached to the Nucleic Acid Agent (e.g., the oligonucleotide) via a phosphate group, or an analog of a phosphate group, in the Nucleic Acid Agent.

In some embodiments, the oligonucleotide has a length of from 1 to 40 nucleotides, from 10 to 40 nucleotides, from 12 to 35 nucleotides, from 15 to 30 nucleotides, from 18 to 25 nucleotides, or from 20 to 23 nucleotides. In some embodiments, the oligonucleotide has a length of 18, 19, 20, 21, 22, 23, 24, or 25 nucleotides. In some embodiments, the oligonucleotide has a length of 20, 21, 22, or 23 nucleotides.

In some embodiments, the Nucleic Acid Agent comprises an RNA, a DNA, or a mixture thereof.

In some embodiments, the Nucleic Acid Agent comprises an RNA.

In some embodiments, the oligonucleotide is an siRNA (e.g., a single strand siRNA (e.g., a hairpin single strand siRNA) or a double strand siRNA), microRNA, antimicroRNA, microRNA mimics, antimiR, antagomir, dsRNA, ssRNA, aptamer, immune stimulatory oligonucleotide, decoy oligonucleotide, splice altering oligonucleotide, triplex forming oligonucleotide, G-quadruplexe, or antisense oligonucleotide.

In some embodiments, the Nucleic Acid Agent comprises a double stranded RNA (dsRNA), wherein the double stranded RNA comprises a sense strand and an antisense strand, as described herein.

In some embodiments, the Nucleic Acid Agent comprises a double stranded siRNA (ds-siRNA), wherein the double stranded siRNA comprises a sense strand and an antisense strand, as described herein.

It is understood that sense strand is also known as passenger strand, and the terms "sense strand" and "passenger strand" are used interchangeably herein.

It is understood that antisense strand is also known as guide strand, and the terms "antisense strand" and "guide strand" are used interchangeably herein.

In some embodiments, the oligonucleotide is an iRNA.

The term "iRNA" refers to an RNA agent which can down regulate the expression of a target gene (e.g., an siRNA), e.g., an endogenous or pathogen target RNA. While not wishing to be bound by theory, an iRNA may act by one or more of a number of mechanisms, including post-transcriptional cleavage of a target mRNA (referred to in the art as RNAi), or pre-transcriptional or pre-translational mechanisms. An iRNA can include a single strand or can include more than one strands, e.g., it can be a double stranded iRNA. If the iRNA is a single strand it can include a 5' modification which includes one or more phosphate groups or one or more analogs of a phosphate group. In some embodiments, the iRNA is double stranded. In some embodiments, one or both strands of the double stranded iRNA can be modified, e.g., 5' modification.

The iRNA typically includes a region of sufficient homology to the target gene, and is of sufficient length in terms of nucleotides, such that the iRNA, or a fragment thereof, can mediate down regulation of the target gene. The iRNA is or includes a region which is at least partially, and in some embodiments fully, complementary to the target RNA. It is not necessary that there be perfect complementarity between the iRNA and the target, but the correspondence may be sufficient to enable the iRNA, or a cleavage product thereof, to direct sequence specific silencing, e.g., by RNAi cleavage of the target RNA, e.g., mRNA.

The nucleotides in the iRNA may be modified (e.g., one or more nucleotides may include a 2'-F or 2'-$OCH_3$ group, or be nucleotide surrogates). The single stranded or double stranded regions of an iRNA may be modified or include nucleotide surrogates, e.g., the unpaired region or regions of a hairpin structure, e.g., a region which links two complementary regions, can have modifications or nucleotide surrogates. Modification to stabilize one or more 3'- or 5'-terminus of an iRNA, e.g., against exonucleases. Modifications can include C3 (or C6, C7, C12) amino linkers, thiol linkers, carboxyl linkers, non-nucleotidic spacers (C3, C6, C9, C12, abasic, triethylene glycol, hexaethylene glycol), special biotin or fluorescein reagents that come as phosphoramidites and that have another DMT-protected hydroxyl group, allowing multiple couplings during RNA synthesis. Modifications can also include, e.g., the use of modifications at the 2' OH group of the ribose sugar, e.g., the use of deoxyribonucleotides, e.g., deoxythymidine, instead of ribonucleotides, and modifications in the phosphate group, e.g., phosphothioate modifications. In some embodiments, the different strands will include different modifications.

In some embodiments, the strands are chosen such that the iRNA includes a single strand or unpaired region at one or both ends of the molecule. A double stranded iRNA may have an overhang, e.g., one or two 5' or 3' overhangs (e.g., at least a 3' overhang of 2-3 nucleotides). In some embodiments, the iRNA has overhangs, e.g., 3' overhangs, of 1, 2, or 3 nucleotides in length at each end. The overhangs can be the result of one strand being longer than the other, or the result of two strands of the same length being staggered.

In some embodiments, the length for the duplexed regions between the strands of the iRNA are between 6 and 30 nucleotides in length. In some embodiments, the duplexed regions are between 15 and 30, most preferably 18, 19, 20, 21, 22, and 23 nucleotides in length. In some embodiments, the duplexed regions are between 6 and 20 nucleotides, most preferably 6, 7, 8, 9, 10, 11 and 12 nucleotides in length.

The oligonucleotide may be that described in U.S. Patent Publication Nos. 2009/0239814, 2012/0136042, 2013/0158824, or 2009/0247608, each of which is hereby incorporated by reference.

In some embodiments, the oligonucleotide is an siRNA.

In some embodiments, the oligonucleotide is a single strand siRNA.

In some embodiments, the oligonucleotide is a double strand siRNA, for example, double strand siRNA described herein.

A "single strand siRNA" as used herein, is an siRNA which is made up of a single strand, which includes a duplexed region, formed by intra-strand pairing, e.g., it may be, or include, a hairpin or pan-handle structure. Single strand siRNAs may be antisense with regard to the target molecule.

A single strand siRNA may be sufficiently long that it can enter the RISC and participate in RISC mediated cleavage of a target mRNA. A single strand siRNA is at least 14, and in some embodiments at least 15, 20, 25, 29, 35, 40, or 50 nucleotides in length. In some embodiments, it is less than 200, 100, 80, 60, 50, 40, or 30 nucleotides in length.

In some embodiments, the single strand siRNA has a length of from 10 to 40 nucleotides, from 12 to 35 nucleotides, from 15 to 30 nucleotides, from 18 to 25 nucleotides, or from 20 to 23 nucleotides. In some embodiments, the single strand siRNA has a length of 18, 19, 20, 21, 22, 23, 24, or 25 nucleotides. In some embodiments, the single strand siRNA has a length of 20, 21, 22, or 23 nucleotides.

Hairpin siRNAs may have a duplex region equal to or at least 17, 18, 19, 20, 21, 22, 23, 24, or 25 nucleotide pairs. The duplex region may be equal to or less than 200, 100, or 50 nucleotide pairs in length. In some embodiments, ranges for the duplex region are 15-30, 17 to 23, 19 to 23, and 19 to 21 nucleotides pairs in length. The hairpin may have a single strand overhang or terminal unpaired region. In some embodiments, the overhangs are 2-3 nucleotides in length. In some embodiments, the overhang is at the sense side of the hairpin and in some embodiments on the antisense side of the hairpin.

In some embodiments, the oligonucleotide is a double strand siRNA.

A "double stranded siRNA" as used herein, is an siRNA which includes more than one, and in some cases two, strands in which interchain hybridization can form a region of duplex structure.

In some embodiments, the sense strand of a double stranded siRNA may be equal to or at least 14, 15, 16 17, 18, 19, 20, 21, 22, 23, 24, 25, 29, 40, or 60 nucleotides in length. It may be equal to or less than 200, 100, or 50 nucleotides in length. Ranges may be 17 to 25, 19 to 23, 19 to 21, 21 to 23, or 20 to 22 nucleotides in length.

In some embodiments, the sense strand has a length of from 10 to 40 nucleotides, from 12 to 35 nucleotides, from 15 to 30 nucleotides, from 18 to 25 nucleotides, or from 20 to 23 nucleotides. In some embodiments, the sense strand has a length of 18, 19, 20, 21, 22, 23, 24, or 25 nucleotides. In some embodiments, the sense strand has a length of 20, 21, 22, or 23 nucleotides.

In some embodiments, the sense strand has a length of 18, 19, 20, 21, or 22 nucleotides.

In some embodiments, the antisense strand of a double stranded siRNA may be equal to or at least, 14, 15, 16 17, 18, 19, 20, 21, 22, 23, 24, 25, 29, 40, or 60 nucleotides in length. It may be equal to or less than 200, 100, or 50 nucleotides in length. Ranges may be 17 to 25, 19 to 23, 19 to 21, 21 to 23, or 20 to 22 nucleotides in length.

In some embodiments, the antisense strand has a length of from 10 to 40 nucleotides, from 12 to 35 nucleotides, from 15 to 30 nucleotides, from 18 to 25 nucleotides, or from 20 to 23 nucleotides. In some embodiments, the antisense strand has a length of 18, 19, 20, 21, 22, 23, 24, or 25 nucleotides. In some embodiments, the antisense strand has a length of 20, 21, 22, or 23 nucleotides.

In some embodiments, the antisense strand has a length of 20, 21, 22, 23, or 24 nucleotides.

In some embodiments, the sense strand has a length of 18, 19, 20, 21, or 22 nucleotides, and the antisense strand has a length of 20, 21, 22, 23, or 24 nucleotides.

In some embodiments, the sense strand has a length of 18 nucleotides, and the antisense strand has a length of 20 nucleotides.

In some embodiments, the sense strand has a length of 19 nucleotides, and the antisense strand has a length of 21 nucleotides.

In some embodiments, the sense strand has a length of 20 nucleotides, and the antisense strand has a length of 22 nucleotides.

In some embodiments, the sense strand has a length of 21 nucleotides, and the antisense strand has a length of 23 nucleotides.

In some embodiments, the sense strand has a length of 22 nucleotides, and the antisense strand has a length of 24 nucleotides.

The double strand portion of a double stranded siRNA may be equal to or at least, 14, 15, 16 17, 18, 19, 20, 21, 22, 23, 24, 25, 29, 40, or 60 nucleotide pairs in length. It may be equal to or less than 200, 100, or 50 nucleotides pairs in length. Ranges may be 15 to 30, 17 to 23, 19 to 23, and 19 to 21 nucleotides pairs in length.

In some embodiments, the siRNA is sufficiently large that it can be cleaved by an endogenous molecule, e.g., by Dicer, to produce smaller siRNAs, e.g., siRNAs agents The sense and antisense strands may be chosen such that the double-stranded siRNA includes a single strand or unpaired region at one or both ends of the molecule. Thus, a double-stranded siRNA may contain sense and antisense strands, paired to contain an overhang, e.g., one or two 5' or 3' overhangs, or a 3' overhang of 1-3 nucleotides. The overhangs can be the result of one strand being longer than the other, or the result of two strands of the same length being staggered. Some embodiments will have at least one 3' overhang. In some embodiments, both ends of an siRNA molecule will have a 3' overhang. In some embodiments, the overhang is 2 nucleotides.

In some embodiments, the length for the duplexed region is between 15 and 30, or 18, 19, 20, 21, 22, and 23 nucleotides in length, e.g., in the ssiRNA range discussed above. ssiRNAs can resemble in length and structure the natural Dicer processed products from long dsiRNAs. Embodiments in which the two strands of the ssiRNA are attached, e.g., covalently attached are also included. Hairpin, or other single strand structures which provide the required double stranded region, and a 3' overhang are also contemplated.

The siRNAs described herein, including double-stranded siRNAs and single-stranded siRNAs can mediate silencing of a target RNA, e.g., mRNA, e.g., a transcript of a gene that encodes a protein. For convenience, such mRNA is also referred to herein as mRNA to be silenced. Such a gene is also referred to as a target gene. In general, the RNA to be silenced is an endogenous gene or a pathogen gene. In addition, RNAs other than mRNA, e.g., tRNAs, and viral RNAs, can also be targeted.

As used herein, the phrase "mediates RNAi" refers to the ability to silence, in a sequence specific manner, a target RNA. While not wishing to be bound by theory, it is believed that silencing uses the RNAi machinery or process and a guide RNA, e.g., an ssiRNA of 21 to 23 nucleotides.

In some embodiments, an siRNA is "sufficiently complementary" to a target RNA, e.g., a target mRNA, such that the siRNA silences production of protein encoded by the target mRNA. In another embodiment, the siRNA is "exactly complementary" to a target RNA, e.g., the target RNA and the siRNA anneal, for example to form a hybrid made exclusively of Watson-Crick base pairs in the region of exact complementarity. A "sufficiently complementary" target RNA can include an internal region (e.g., of at least 10 nucleotides) that is exactly complementary to a target RNA. Moreover, in some embodiments, the siRNA specifically discriminates a single-nucleotide difference. In this case, the siRNA only mediates RNAi if exact complementary is found in the region (e.g., within 7 nucleotides of) the single-nucleotide difference.

MicroRNAs: Micro RNAs (miRNAs) are a highly conserved class of small RNA molecules that are transcribed from DNA in the genomes of plants and animals, but are not translated into protein. Processed miRNAs are single stranded ~17-25 nucleotide (nt) RNA molecules that become incorporated into the RNA-induced silencing complex (RISC) and have been identified as key regulators of development, cell proliferation, apoptosis and differentiation. They are believed to play a role in regulation of gene expression by binding to the 3'-untranslated region of specific mRNAs. RISC mediates down-regulation of gene expression through translational inhibition, transcript cleavage, or both. RISC is also implicated in transcriptional silencing in the nucleus of a wide range of eukaryotes.

The number of miRNA sequences identified to date is large and growing, illustrative examples of which can be found, for example, in: "miRBase: microRNA sequences, targets and gene nomenclature" Griffiths-Jones S, Grocock R J, van Dongen S, Bateman A, Enright A J. NAR, 2006, 34, Database Issue, D140-D144; "The microRNA Registry" Griffiths-Jones S. NAR, 2004, 32, Database Issue, D109-D111.

Antisense Oligonucleotides: In some embodiments, a nucleic acid is an antisense oligonucleotide directed to a target polynucleotide. The term "antisense oligonucleotide" or simply "antisense" is meant to include oligonucleotides that are complementary to a targeted polynucleotide sequence. Antisense oligonucleotides are single strands of DNA or RNA that are complementary to a chosen sequence, e.g. a target gene mRNA. Antisense oligonucleotides are thought to inhibit gene expression by binding to a complementary mRNA. Binding to the target mRNA can lead to inhibition of gene expression either by preventing translation of complementary mRNA strands by binding to it, or by leading to degradation of the target mRNA. Antisense DNA can be used to target a specific, complementary (coding or non-coding) RNA. If binding takes places this DNA/RNA hybrid can be degraded by the enzyme RNase H. In some embodiments, antisense oligonucleotides contain from about 10 to about 50 nucleotides, more preferably about 15 to about 30 nucleotides. The term also encompasses antisense oligonucleotides that may not be exactly complementary to the desired target gene. Thus, instances where non-target specific-activities are found with antisense, or where an antisense sequence containing one or more mismatches with the target sequence is the most preferred for a particular use, are contemplated.

Antisense oligonucleotides have been demonstrated to be effective and targeted inhibitors of protein synthesis, and, consequently, can be used to specifically inhibit protein synthesis by a targeted gene. The efficacy of antisense oligonucleotides for inhibiting protein synthesis is well established. For example, the synthesis of polygalacturonase and the muscarine type 2 acetylcholine receptor are inhibited by antisense oligonucleotides directed to their respective mRNA sequences (U.S. Pat. Nos. 5,739,119 and 5,759,829 each of which is incorporated by reference). Further, examples of antisense inhibition have been demonstrated with the nuclear protein cyclin, the multiple drug resistance gene (MDG1), ICAM-1, E-selectin, STK-1, striatal GABAA receptor and human EGF (Jaskulski et al., Science. 1988 Jun. 10; 240(4858):1544-6; Vasanthakumar and Ahmed, Cancer Commun. 1989; 1(4):225-32; Peris et al., Brain Res Mol Brain Res. 1998 Jun. 15; 57(2):310-20; U.S.

Pat. Nos. 5,801,154; 5,789,573; 5,718,709 and 5,610,288, each of which is incorporated by reference). Furthermore, antisense constructs have also been described that inhibit and can be used to treat a variety of abnormal cellular proliferations, e.g. cancer (U.S. Pat. Nos. 5,747,470; 5,591,317 and 5,783,683, each of which is incorporated by reference).

Methods of producing antisense oligonucleotides are known in the art and can be readily adapted to produce an antisense oligonucleotide that targets any polynucleotide sequence. Selection of antisense oligonucleotide sequences specific for a given target sequence is based upon analysis of the chosen target sequence and determination of secondary structure, Tm, binding energy, and relative stability. Antisense oligonucleotides may be selected based upon their relative inability to form dimers, hairpins, or other secondary structures that would reduce or prohibit specific binding to the target mRNA in a host cell. Highly preferred target regions of the mRNA include those regions at or near the AUG translation initiation codon and those sequences that are substantially complementary to 5' regions of the mRNA. These secondary structure analyses and target site selection considerations can be performed, for example, using v.4 of the OLIGO primer analysis software (Molecular Biology Insights) and/or the BLASTN 2.0.5 algorithm software (Altschul et al., Nucleic Acids Res. 1997, 25(17):3389-402).

Antagomirs: Antagomirs are RNA-like oligonucleotides that harbor various modifications for RNAse protection and pharmacologic properties, such as enhanced tissue and cellular uptake. They differ from normal RNA by, for example, complete 2'-O-methylation of sugar, phosphorothioate backbone and, for example, a cholesterol-moiety at 3'-end. Antagomirs may be used to efficiently silence endogenous miRNAs by forming duplexes comprising the antagomir and endogenous miRNA, thereby preventing miRNA-induced gene silencing. An example of antagomir-mediated miRNA silencing is the silencing of miR-122, described in Krutzfeldt et al, Nature, 2005, 438: 685-689, which is expressly incorporated by reference herein in its entirety. Antagomir RNAs may be synthesized using standard solid phase oligonucleotide synthesis protocols. See U.S. Patent Application Publication Nos. 2007/0123482 and 2007/0213292 (each of which is incorporated herein by reference).

An antagomir can include ligand-conjugated monomer subunits and monomers for oligonucleotide synthesis. Exemplary monomers are described in U.S. Patent Application Publication No. 2005/0107325, which is incorporated by reference in its entirety. An antagomir can have a ZXY structure, such as is described in WO 2004/080406, which is incorporated by reference in its entirety. An antagomir can be complexed with an amphipathic moiety. Exemplary amphipathic moieties for use with oligonucleotide agents are described in WO 2004/080406, which is incorporated by reference in its entirety.

Aptamers: Aptamers are nucleic acid or peptide molecules that bind to a particular molecule of interest with high affinity and specificity (Tuerk and Gold, Science 249:505 (1990); Ellington and Szostak, Nature 346:818 (1990), each of which is incorporated by reference in its entirety). DNA or RNA aptamers have been successfully produced which bind many different entities from large proteins to small organic molecules. See Eaton, Curr. Opin. Chem. Biol. 1:10-16 (1997), Famulok, Curr. Opin. Struct. Biol. 9:324-9 (1999), and Hermann and Patel, Science 287:820-5 (2000), each of which is incorporated by reference in its entirety. Aptamers may be RNA or DNA based, and may include a riboswitch. A riboswitch is a part of an mRNA molecule that can directly bind a small target molecule, and whose binding of the target affects the gene's activity. Thus, an mRNA that contains a riboswitch is directly involved in regulating its own activity, depending on the presence or absence of its target molecule. Generally, aptamers are engineered through repeated rounds of in vitro selection or equivalently, SELEX (systematic evolution of ligands by exponential enrichment) to bind to various molecular targets such as small molecules, proteins, nucleic acids, and even cells, tissues and organisms. The aptamer may be prepared by any known method, including synthetic, recombinant, and purification methods, and may be used alone or in combination with other aptamers specific for the same target. Further, as described more fully herein, the term "aptamer" specifically includes "secondary aptamers" containing a consensus sequence derived from comparing two or more known aptamers to a given target.

Ribozymes: According to another embodiment, nucleic acid-lipid particles are associated with ribozymes. Ribozymes are RNA molecules complexes having specific catalytic domains that possess endonuclease activity (Kim and Cech, Proc Natl Acad Sci USA. 1987 December; 84(24):8788-92; Forster and Symons, Cell. 1987 Apr. 24; 49(2):211-20). For example, a large number of ribozymes accelerate phosphoester transfer reactions with a high degree of specificity, often cleaving only one of several phosphoesters in an oligonucleotide substrate (Cech et al., Cell. 1981 December; 27(3 Pt 2):487-96; Michel and Westhof, J Mol Biol. 1990 Dec. 5; 216(3):585-610; Reinhold-Hurek and Shub, Nature. 1992 May 14; 357(6374):173-6). This specificity has been attributed to the requirement that the substrate bind via specific base-pairing interactions to the internal guide sequence ("IGS") of the ribozyme prior to chemical reaction.

At least six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nucleic acid molecule may be formed in a hammerhead, hairpin, a hepatitis δ virus, group I intron or RNaseP RNA (in association with an RNA guide sequence) or *Neurospora* VS RNA motif, for example. Specific examples of hammerhead motifs are described by Rossi et al. Nucleic Acids Res. 1992 Sep. 11; 20(17):4559-65. Examples of hairpin motifs are described by Hampel et al. (Eur. Pat. Appl. Publ. No. EP 0360257), Hampel and Tritz, Biochemistry 1989 Jun. 13; 28(12):4929-33; Hampel et al., Nucleic Acids Res. 1990 Jan. 25; 18(2):299-304 and U.S. Pat. No. 5,631,359. An example of the hepatitis δ virus motif is described by Perrotta and Been, Biochemistry. 1992 Dec. 1; 31(47):11843-52; an example of the RNaseP motif is described by Guerrier-Takada et al., Cell. 1983 December; 35(3 Pt 2):849-57; *Neurospora* VS RNA ribozyme motif is described by Collins (Saville and Collins, Cell. 1990 May 18; 61(4):685-96; Saville and Collins, Proc Natl Acad Sci USA. 1991 Oct. 1; 88(19):8826-30; Collins and Olive, Biochemistry. 1993 Mar. 23; 32(11):2795-9); and an example of the Group I intron is described in U.S. Pat. No. 4,987,071. Important characteristics of enzymatic nucleic acid molecules used are that they have a specific substrate binding site which is complementary to one or more of the target gene DNA or RNA regions, and that they have nucleotide sequences within or surrounding that substrate binding site which impart an RNA cleaving activity to the molecule. Thus the ribozyme constructs need not be limited to specific motifs mentioned herein.

Methods of producing a ribozyme targeted to any polynucleotide sequence are known in the art. Ribozymes may be designed as described in Int. Pat. Appl. Publ. Nos. WO 93/23569 and WO 94/02595, each specifically incorporated herein by reference, and synthesized to be tested in vitro and in vivo, as described therein.

Ribozyme activity can be optimized by altering the length of the ribozyme binding arms or chemically synthesizing ribozymes with modifications that prevent their degradation by serum ribonucleases (see e.g., Int. Pat. Appl. Publ. Nos. WO 92/07065, WO 93/15187, and WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Immunostimulatory Oligonucleotides: Nucleic acids associated with lipid particles may be immunostimulatory, including immunostimulatory oligonucleotides (ISS; single- or double-stranded) capable of inducing an immune response when administered to a subject, which may be a mammal or other patient. ISS include, e.g., certain palindromes leading to hairpin secondary structures (see Yamamoto S., et al. (1992) J. Immunol. 148: 4072-4076, which is incorporated by reference in its entirety), or CpG motifs, as well as other known ISS features (such as multi-G domains, see WO 96/11266, which is incorporated by reference in its entirety).

The immune response may be an innate or an adaptive immune response. The immune system is divided into a more innate immune system, and acquired adaptive immune system of vertebrates, the latter of which is further divided into humoral cellular components. In some embodiments, the immune response may be mucosal.

In some embodiments, an immunostimulatory nucleic acid is only immunostimulatory when administered in combination with a lipid particle, and is not immunostimulatory when administered in its "free form." Such an oligonucleotide is considered to be immunostimulatory.

Immunostimulatory nucleic acids are considered to be non-sequence specific when it is not required that they specifically bind to and reduce the expression of a target polynucleotide in order to provoke an immune response. Thus, certain immunostimulatory nucleic acids may comprise a sequence corresponding to a region of a naturally occurring gene or mRNA, but they may still be considered non-sequence specific immunostimulatory nucleic acids.

In some embodiments, the immunostimulatory nucleic acid or oligonucleotide comprises at least one CpG dinucleotide. The oligonucleotide or CpG dinucleotide may be unmethylated or methylated. In another embodiment, the immunostimulatory nucleic acid comprises at least one CpG dinucleotide having a methylated cytosine. In some embodiments, the nucleic acid comprises a single CpG dinucleotide, wherein the cytosine in said CpG dinucleotide is methylated. In an alternative embodiment, the nucleic acid comprises at least two CpG dinucleotides, wherein at least one cytosine in the CpG dinucleotides is methylated. In a further embodiment, each cytosine in the CpG dinucleotides present in the sequence is methylated. In another embodiment, the nucleic acid comprises a plurality of CpG dinucleotides, wherein at least one of said CpG dinucleotides comprises a methylated cytosine.

Attachments Between Linker Unit, Nucleic Acid Agent, and Ligand

In some embodiments, the attachment between the Linker Unit and the Nucleic Acid Agent is a bond.

In some embodiments, the attachment between the Linker Unit and the Nucleic Acid Agent is a moiety (e.g., a moiety comprising a cleavable group).

In some embodiments, the attachment between the Linker Unit and the ligand is a bond.

In some embodiments, the attachment between the Linker Unit and the ligand is a moiety (e.g., a moiety comprising a cleavable group).

In some embodiments, the attachment between the Linker Unit and the ligand comprises —C(═O)— connected to the Linker Unit.

The group can be cleavable or non-cleavable. Suitable groups include, for example, —NR—, ~C(═O)—, —C(═O)NH—, —S(═O)—, —S(═O)—, —S(═O)NH— or a chain of atoms, such as, but not limited to, alkylene, alkenylene alkynylene arylalkylene arylalkenylene arylalkynylene heteroarylalkylene heteroarylalkenylene heteroarylalkynylene heterocyclylalkylene heterocyclylalkenylene heterocyclylalkynylene arylene heteroarylene heterocyclylene cycloalkylene cycloalkenylene alkylarylalkylene alkylarylalkenylene alkylarylalkynylene alkenylarylalkylene alkenylarylalkenylene alkenylarylalkynylene alkynylarylalkylene alkynylarylalkenylene alkynylarylalkynylene alkylheteroarylalkylene alkylheteroarylalkenylene alkylheteroarylalkynylene alkenylheteroarylalkylene alkenylbeteroarylalkenylene alkenylheteroarylalkynylene alkynylheteroarylalkylene alkynylheteroarylalkenylene alkynylheteroarylalkynylene alkylheterocyclylalkylene alkylheterocyclylalkenylene alkylhererocyclylalkynylene alkenylheterocyclylalkylene alkenylheterocyclylalkenylene alkenylheterocyclylalkynylene alkynylheterocyclylalkylene alkynylheterocyclylalkenylene alkynylheterocyclylalkynylene alkylarylene alkenylarylene alkynylarylene alkylheteroarylene alkenylheteroarylene alkynylhereroarylene each of which may be substituted or unsubstituted, and which one or more methylenes can be interrupted or terminated by —O—, —S—, —S(═O)—, —S(═O)—, —NR—, —C(═O)—, substituted or unsubstituted aryl, substituted or unsubstituted heteroaryl, or substituted or unsubstituted heterocyclic, where R is hydrogen, acyl, aliphatic or substituted aliphatic.

A cleavable group is one which is sufficiently stable outside the cell, but which upon entry into a target cell is cleaved to release the two parts the group is holding together. In a preferred embodiment, the cleavable group is cleaved at least 10 times or more, preferably at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable group by reduction; esterases; endosomes or agents that can create an acidic environment, e.g., those that result in a pH of five or lower; enzymes that can hydrolyze or degrade an acid cleavable group by acting as a general acid, peptidases (which can be substrate specific), and phosphatases.

A cleavable group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable group that is cleaved at a preferred pH, thereby releasing the cationic lipid from the ligand inside the cell, or into the desired compartment of the cell.

A conjugate can include a cleavable group that is cleavable by a particular enzyme. The type of cleavable group incorporated into a conjugate can depend on the cell to be targeted. For example, liver targeting ligands can be attached to the cationic lipids through a chemical moiety that includes an ester group. Liver cells are rich in esterases, and therefore the group will be cleaved more efficiently in liver cells than in cell types that are not esterase-rich. Other cell-types rich in esterases include cells of the lung, renal cortex, and testis.

Coupling groups that contain peptide bonds can be used when targeting cell types rich in peptidases, such as liver cells and synoviocytes.

In general, the suitability of a candidate cleavable group can be evaluated by testing the ability of a degradative agent (or condition) to cleave the candidate group. It will also be desirable to also test the candidate cleavable group for the ability to resist cleavage in the blood or when in contact with other non-target tissue. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals. In preferred embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

Redox Cleavable Groups. One class of cleavable groups are redox cleavable groups that are cleaved upon reduction or oxidation. An example of reductively cleavable group is a disulphide linking group (—S—S—). To determine if a candidate cleavable group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In a preferred embodiment, candidate compounds are cleaved by at most 10% in the blood. In preferred embodiments, useful candidate compounds are degraded at least 2, 4, 10 or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

Phosphate-Based Cleavable Groups. Phosphate-based cleavable groups are cleaved by agents that degrade or hydrolyze the phosphate group. An example of an agent that cleaves phosphate groups in cells are enzymes such as phosphatases in cells. In some embodiments, the phosphate-based linking group is —O—P(═O)($OR^k$)—O—, —O—P(═S($OR^k$)—O—, —O—P(═S)($SR^k$)—O—, —S—P—(═O)($OR^k$)—O—, —O—P(═O)($OR^k$)—S—, —S—P(═O)($OR^k$)—S—, —O—P(S)($OR^k$)—$_S$—, —S—P(═S)($OR^k$)—O—, —O—P(═O)($R^k$)—O—, —O—P(═S)($R^k$)—O—, —S—P(═O)($R^k$)—O—, —S—P(═S)($R^k$)—O—, —S—P(═O)($R^k$)—S—, or —O—P(═S)($R^k$)—S—. In some embodiments, the phosphate-based linking group is —O—P(═O)(OH)—O—, —O—P(═S)(OH)—O—, —O—P(═S)(SH)—O—, —S—P(═O)(OH)—O—, —O—P(O)(OH)—S—; —S—P(═O)(H)—S—, —O—P(═S)(OH)—S—; —S—P(═S)(OH)—O—, —S—P(═O)(H)—S—, or —O—P(═S)(H)—S—. In some embodiments, the phosphate-based linking group is —O—P(═O)(OH)—O—.

Acid Cleavable Groups. Acid cleavable groups are linking groups that are cleaved under acidic conditions. In preferred embodiments acid cleavable groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable groups include but are not limited to hydrazones, esters, and esters of amino acids. Acid cleavable groups can have the general formula —C═NN—, C(O) O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

Ester-Based Cleavable Groups. Ester-based cleavable groups are cleaved by enzymes such as esterases and amidases in cells. Examples of ester-based cleavable groups include but are not limited to esters of alkylene, alkenylene and alkynylene groups. Ester cleavable linking groups have the general formula —C(O)O—, or —OC(O)—. These candidates can be evaluated using methods analogous to those described above.

Peptide-Based Cleavable Groups. Peptide-based cleavable groups are cleaved by enzymes such as peptidases and proteases in cells. Peptide-based cleavable groups are peptide bonds formed between amino acids to yield oligopeptides (e.g., dipeptides, tripeptides etc.) and polypeptides. Peptide-based cleavable groups do not include the amide group (—C(O)NH—) The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula NHCHR$^A$C(O)NHCHR$^B$C(O)—, where R$^A$ and R$^B$ are the R groups of the two adjacent amino acids. These candidates can be evaluated using methods analogous to those described above. As used herein, "carbohydrate" refers to a compound which is either a carbohydrate per se made up of one or more monosaccharide units having at least 6 carbon atoms (which may be linear, branched or cyclic) with an oxygen, nitrogen or sulfur atom bonded to each carbon atom; or a compound having as a part thereof a carbohydrate moiety made up of one or more monosaccharide units each having at least six carbon atoms (which may be linear, branched or cyclic), with an oxygen, nitrogen or sulfur atom bonded to each carbon atom. Representative carbohydrates include the sugars (mono-, di-, tri- and oligosaccharides containing from about 4-9 monosaccharide units), and polysaccharides such as starches, glycogen, cellulose and polysaccharide gums. Specific monosaccharides include $C_5$ and above (preferably $C_5$-$C_8$) sugars; di- and trisaccharides include sugars having two or three monosaccharide units (preferably $C_5$-$C_8$).

Previously, it was reported that certain 1'-amino 2'-OTBS carbocyclic phosphoramidites were previously prepared and incorporated into natural oligonucleotides as a handle for the conjugation of fluorophore for the labelling of oligonucleotides (*Org. Lett.* 2021, 23, 6735-6739, incorporated herein by reference). Without wishing to be bound by theory, the linkers, scaffolds, and conjugates of the present disclosure may be distinct from the previously reported 1'-amino 2'-OTBS carbocyclic phosphoramidites in various aspects, including the chemical structures, the oligonucleotides being conjugated, the use of the conjugates, and/or the synthetic approaches.

Methods of Synthesis

In some aspects, the present disclosure provides a method of preparing a compound of the present disclosure.

In some aspects, the present disclosure provides a compound obtainable by, or obtained by, a method for preparing a compound as described herein.

In some aspects, the present disclosure provides an intermediate as described herein, being suitable for use in a method for preparing a compound as described herein.

The compounds of the present disclosure can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilized.

It will be appreciated that during the synthesis of the compounds of the disclosure in the processes defined herein, or during the synthesis of certain starting materials, it may be desirable to protect certain substituent groups to prevent their undesired reaction. The skilled chemist will appreciate when such protection is required, and how such protecting groups may be put in place, and later removed. For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule. Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl, or t-butoxycarbonyl group, an arylmethoxycarbonyl group, for example benzyloxycarbonyl, or an aroyl group, for example benzoyl. A suitable protecting group for an hydroxy or alkylhydroxy group can be, e.g., Acetyl (Ac), Benzoyl (Bz), Benzyl (Bn), β-Methoxyethoxymethyl ether (MEM), Dimethoxytrityl (DMT), Methoxymethyl ether (MOM), Methoxytrityl (MMT), p-Methoxybenzyl ether (PMB), p-Methoxyphenyl ether (PMP), Pivaloyl (Piv), Tetrahydropyranyl (THP), Tetrahydrofuran (THF), Trityl (triphenylmethyl, Tr), Silyl ether (e.g., trimethylsilyl (TMS), tert-butyldimethylsilyl (TBDMS), tri-iso-propylsilyloxymethyl (TOM), and triisopropylsilyl (TIPS) ethers), a Methyl ether, or an Ethoxyethyl ether (EE). A suitable protecting group for an 1,2-diol can be, e.g., acetal. A suitable protecting group for an 1,3-diol can be, e.g., tetraisopropyldisiloxanylidene (TIPDS).

The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium on carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium on carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium on carbon.

Conveniently, the reaction of the compounds is carried out in the presence of a suitable solvent, which is preferably inert under the respective reaction conditions. Examples of suitable solvents comprise but are not limited to hydrocarbons, such as hexane, petroleum ether, benzene, toluene or xylene; chlorinated hydrocarbons, such as trichlorethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF), 2-methyltetrahydrofuran, cyclopentylmethyl ether (CPME), methyl tert-butyl ether (MTBE) or dioxane; glycol ethers, such as ethylene glycol monomethyl or monoethyl ether or ethylene glycol dimethyl ether (diglyme); ketones, such as acetone, methylisobutylketone (MIBK) or butanone; amides, such as acetamide, dimethylacetamide, dimethylformamide (DMF) or N-methylpyrrolidinone (NMP); nitriles, such as acetonitrile; sulfoxides, such as dimethyl sulfoxide (DMSO); nitro compounds, such as nitromethane or nitrobenzene; esters, such as ethyl acetate or methyl acetate, or mixtures of the said solvents or mixtures with water.

The reaction temperature is suitably between about −100° C. and 300° C., depending on the reaction step and the conditions used.

Reaction times are generally in the range between a fraction of a minute and several days, depending on the reactivity of the respective compounds and the respective reaction conditions. Suitable reaction times are readily determinable by methods known in the art, for example reaction monitoring. Based on the reaction temperatures given above, suitable reaction times generally lie in the range between 10 minutes and 48 hours.

Moreover, by utilising the procedures described herein, in conjunction with ordinary skills in the art, additional compounds of the present disclosure can be readily prepared. Those skilled in the art will readily understand that known variations of the conditions and processes of the following preparative procedures can be used to prepare these compounds.

As will be understood by the person skilled in the art of organic synthesis, compounds of the present disclosure are readily accessible by various synthetic routes, some of which are exemplified in the accompanying examples. The skilled person will easily recognise which kind of reagents and reactions conditions are to be used and how they are to be applied and adapted in any particular instance—wherever necessary or useful —in order to obtain the compounds of the present disclosure. Furthermore, some of the compounds of the present disclosure can readily be synthesized by reacting other compounds of the present disclosure under suitable conditions, for instance, by converting one particular functional group being present in a compound of the present disclosure, or a suitable precursor molecule thereof, into another one by applying standard synthetic methods, like reduction, oxidation, addition or substitution reactions; those methods are well known to the skilled person. Likewise, the skilled person will apply—whenever necessary or useful—synthetic protecting (or protective) groups; suitable protecting groups as well as methods for introducing and removing them are well-known to the person skilled in the art of chemical synthesis and are described, in more detail, in, e.g., P. G. M. Wuts, T. W. Greene, "Greene's Protective Groups in Organic Synthesis", 4th edition (2006) (John Wiley & Sons).

General routes for the preparation of a compound of the application are described in Scheme 1 herein.

Scheme 1

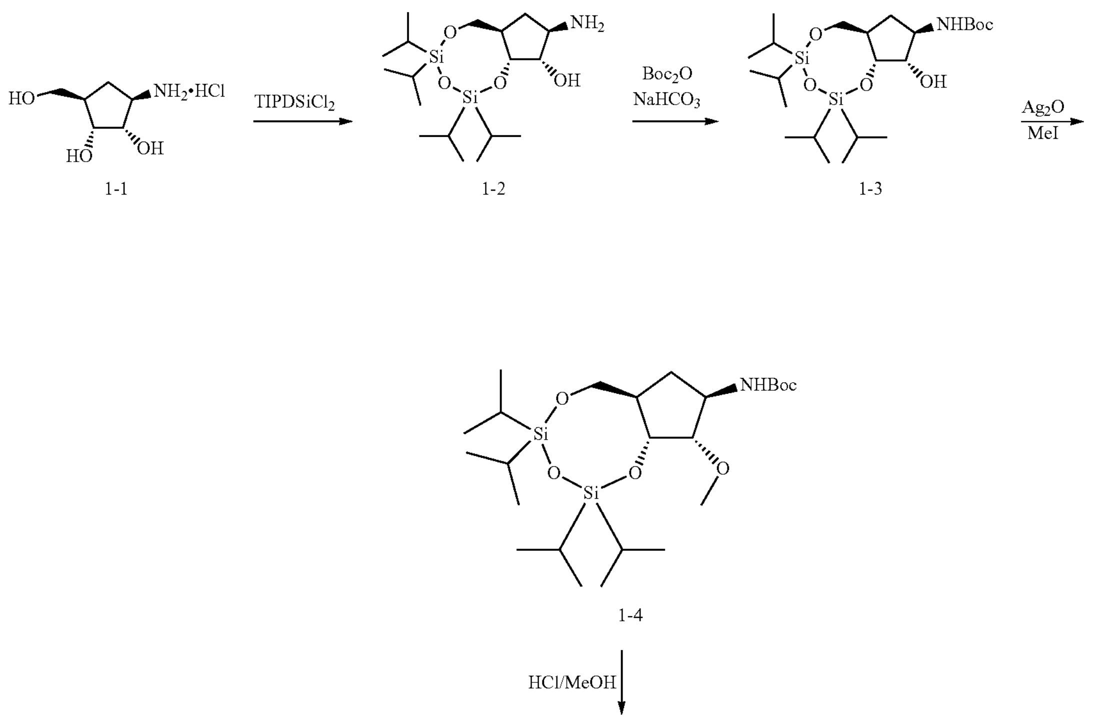

1-1 1-2 1-3 1-4

-continued

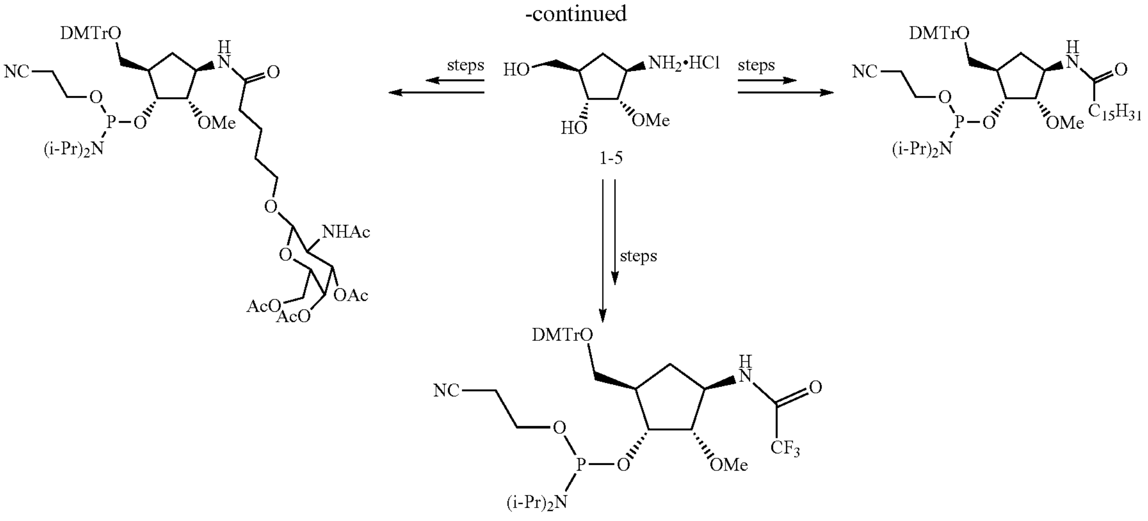

Biological Assays

Compounds, scaffolds, or conjugates designed, selected, prepared and/or optimized by methods described above, once produced, can be characterized using a variety of assays known to those skilled in the art to determine whether the compounds, scaffolds, or conjugates have biological activity. For example, the compounds, scaffolds, or conjugates can be characterized by conventional assays, including but not limited to those assays described below, to determine whether they have a desired activity, e.g., target binding activity and/or specificity and/or stability.

Furthermore, high-throughput screening can be used to speed up analysis using such assays. As a result, it may be possible to rapidly screen the molecules described herein for activity, using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

Various in vitro or in vivo biological assays may be suitable for detecting the effect of the compounds, scaffolds, or conjugates of the present disclosure. These in vitro or in vivo biological assays can include, but are not limited to, enzymatic activity assays, electrophoretic mobility shift assays, reporter gene assays, in vitro cell viability assays, and the assays described herein.

In some embodiments, the biological assays are described in the Examples herein.

Pharmaceutical Compositions

In some aspects, the present disclosure provides a pharmaceutical composition comprising a compound, scaffold, or conjugate of the present disclosure as an active ingredient.

As used herein, the term "composition" is intended to encompass a product comprising the specified ingredients in the specified amounts, as well as any product which results, directly or indirectly, from combination of the specified ingredients in the specified amounts.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilisation. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

The formulation of the present disclosure may be in the form of an aqueous solution comprising an aqueous vehicle. The aqueous vehicle component may comprise water and at least one pharmaceutically acceptable excipient. Suitable acceptable excipients include those selected from the group consisting of a solubility enhancing agent, chelating agent, preservative, tonicity agent, viscosity/suspending agent, buffer, and pH modifying agent, and a mixture thereof.

Any suitable solubility enhancing agent can be used. Examples of a solubility enhancing agent include cyclodextrin, such as those selected from the group consisting of hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, sulfated β-cyclodextrin (S-β-CD), maltosyl-β-cyclodextrin, β-cyclodextrin sulfobutyl ether, branched-β-cyclodextrin, hydroxypropyl-γ-cyclodextrin, randomly methylated-γ-cyclodextrin, and trimethyl-γ-cyclodextrin, and mixtures thereof.

Any suitable chelating agent can be used. Examples of a suitable chelating agent include those selected from the group consisting of ethylenediaminetetraacetic acid and metal salts thereof, disodium edetate, trisodium edetate, and tetrasodium edetate, and mixtures thereof.

Any suitable preservative can be used. Examples of a preservative include those selected from the group consisting of quaternary ammonium salts such as benzalkonium halides (preferably benzalkonium chloride), chlorhexidine gluconate, benzethonium chloride, cetyl pyridinium chloride, benzyl bromide, phenylmercury nitrate, phenylmercury acetate, phenylmercury neodecanoate, merthiolate, methylparaben, propylparaben, sorbic acid, potassium sorbate, sodium benzoate, sodium propionate, ethyl p-hydroxybenzoate, propylaminopropyl biguanide, and butyl-p-hydroxybenzoate, and sorbic acid, and mixtures thereof.

The aqueous vehicle may also include a tonicity agent to adjust the tonicity (osmotic pressure). The tonicity agent can be selected from the group consisting of a glycol (such as propylene glycol, diethylene glycol, triethylene glycol), glycerol, dextrose, glycerin, mannitol, potassium chloride, and sodium chloride, and a mixture thereof.

In order to adjust the formulation to an acceptable pH (typically a pH range of about 5.0 to about 9.0, more preferably about 5.5 to about 8.5, particularly about 6.0 to about 8.5, about 7.0 to about 8.5, about 7.2 to about 7.7, about 7.1 to about 7.9, or about 7.5 to about 8.0), the formulation may contain a pH modifying agent. The pH modifying agent is typically a mineral acid or metal hydroxide base, selected from the group of potassium hydroxide, sodium hydroxide, and hydrochloric acid, and mixtures thereof, and preferably sodium hydroxide and/or hydrochloric acid. These acidic and/or basic pH modifying agents are added to adjust the formulation to the target acceptable pH range. Hence it may not be necessary to use both acid and base—depending on the formulation, the addition of one of the acid or base may be sufficient to bring the mixture to the desired pH range.

The aqueous vehicle may also contain a buffering agent to stabilize the pH. When used, the buffer is selected from the group consisting of a phosphate buffer (such as sodium dihydrogen phosphate and disodium hydrogen phosphate), a borate buffer (such as boric acid, or salts thereof including disodium tetraborate), a citrate buffer (such as citric acid, or salts thereof including sodium citrate), and F-aminocaproic acid, and mixtures thereof.

According to a further aspect of the disclosure there is provided a pharmaceutical composition which comprises a compound of the disclosure as defined hereinbefore, or a pharmaceutically acceptable salt, hydrate or solvate thereof, in association with a pharmaceutically acceptable diluent or carrier.

The compositions of the disclosure may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the disclosure may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present disclosure for use in therapy is an amount sufficient to treat or prevent an inflammasome related condition referred to herein, slow its progression and/or reduce the symptoms associated with the condition.

An effective amount of a compound of the present disclosure for use in therapy is an amount sufficient to treat an inflammasome related condition referred to herein, slow its progression and/or reduce the symptoms associated with the condition.

The size of the dose for therapeutic or prophylactic purposes of a compound of Formula (I) or (II) will naturally vary according to the nature and severity of the conditions, the age and sex of the animal or patient and the route of administration, according to well-known principles of medicine.

Methods of Use

In some aspects, the present disclosure provides a method of modulating (e.g., reducing or eliminating) the expression of a target gene in a subject, comprising administering to the subject a conjugate of the present disclosure.

In some aspects, the present disclosure provides a method of modulating (e.g., reducing or eliminating) the expression of a target gene in a cell or tissue of a subject, comprising administering to the subject a conjugate of the present disclosure.

In some aspects, the present disclosure provides a method of delivering a Nucleic Acid Agent to a subject, comprising administering to the subject a conjugate of the present disclosure.

In some aspects, the present disclosure provides a method of treating or preventing a disease in a subject in need thereof, comprising administering to the subject a therapeutically effective amount of a conjugate of the present disclosure.

In some aspects, the present disclosure provides a conjugate of the present disclosure for modulating (e.g., reducing or eliminating) the expression of a target gene in a subject.

In some aspects, the present disclosure provides a conjugate of the present disclosure for modulating (e.g., reducing or eliminating) the expression of a target gene in a cell or tissue of a subject.

In some aspects, the present disclosure provides a conjugate of the present disclosure for delivering a Nucleic Acid Agent to a subject.

In some aspects, the present disclosure provides a conjugate of the present disclosure for treating or preventing a disease in a subject in need thereof.

In some aspects, the present disclosure provides use of a conjugate of the present disclosure in the manufacture of a medicament for modulating (e.g., reducing or eliminating) the expression of a target gene in a subject.

In some aspects, the present disclosure provides use of a conjugate of the present disclosure in the manufacture of a medicament for modulating (e.g., reducing or eliminating) the expression of a target gene in a cell or tissue of a subject.

In some aspects, the present disclosure provides use of a conjugate of the present disclosure in the manufacture of a medicament for delivering a Nucleic Acid Agent to a subject.

In some aspects, the present disclosure provides use of a conjugate of the present disclosure in the manufacture of a medicament for treating or preventing a disease in a subject in need thereof.

In some embodiments, the subject is a cell.

In some embodiments, the subject is a tissue.

In some embodiments, the subject is a human.

In some embodiments, the target gene is Factor VII, Eg5, PCSK9, TPX2, apoB, SAA, TTR, HBV, HCV, RSV, PDGF beta gene, Erb-B gene, Src gene, CRK gene, GRB2 gene, RAS gene, MEKK gene, JNK gene, RAF gene, Erk1/2 gene, PCNA(p21) gene, MYB gene, JUN gene, FOS gene, BCL-2 gene, Cyclin D gene, VEGF gene, EGFR gene, Cyclin A gene, Cyclin E gene, WNT-1 gene, beta-catenin gene, c-MET gene, PKC gene, NFKB gene, STAT3 gene, survivin gene, Her2/Neu gene, topoisomerase I gene, topoisomerase II alpha gene, p73 gene, p21(WAF1/CIP1) gene, p27(KIP1) gene, PPM1D gene, RAS gene, caveolin I gene, MIB I gene, MTAI gene, M68 gene, mutations in tumor suppressor genes, p53 tumor suppressor gene, LDHA, or any combination thereof.

In some embodiments, the disease characterized by unwanted expression of the target gene.

In some embodiments, the administration results in reduced or eliminated expression of the target gene in the subject.

In some embodiments, the disease is a viral infection, e.g., an HCV, HBV, HPV, HSV or HIV infection.

In some embodiments, the disease is cancer.

In some embodiments, the cancer is bilary tract cancer, bladder cancer, transitional cell carcinoma, urothelial carcinoma, brain cancer, gliomas, astrocytomas, breast carcinoma, metaplastic carcinoma, cervical cancer, cervical squamous cell carcinoma, rectal cancer, colorectal carcinoma, colon cancer, hereditary nonpolyposis colorectal cancer, colorectal adenocarcinomas, gastrointestinal stromal tumors (GISTs), endometrial carcinoma, endometrial stromal sarcomas, esophageal cancer, esophageal squamous cell carcinoma, esophageal adenocarcinoma, ocular melanoma, uveal melanoma, gallbladder carcinomas, gallbladder adenocarcinoma, renal cell carcinoma, clear cell renal cell carcinoma, transitional cell carcinoma, urothelial carcinomas, wilms tumor, leukemia, acute lymocytic leukemia (ALL), acute myeloid leukemia (AML), chronic lymphocytic (CLL), chronic myeloid (CML), chronic myelomonocytic (CMML), liver cancer, liver carcinoma, hepatoma, hepatocellular carcinoma, cholangiocarcinoma, hepatoblastoma, Lung cancer, non-small cell lung cancer (NSCLC), mesothelioma, B-cell lymphomas, non-Hodgkin lymphoma, diffuse large B-cell lymphoma, Mantle cell lymphoma, T-cell lymphomas, non-Hodgkin lymphoma, precursor T-lymphoblastic lymphoma/leukemia, peripheral T-cell lymphomas, multiple myeloma, nasopharyngeal carcinoma (NPC), neuroblastoma, oropharyngeal cancer, oral cavity squamous cell carcinomas, osteosarcoma, ovarian carcinoma, pancreatic cancer, pancreatic ductal adenocarcinoma, pseudopapillary neoplasms, acinar cell carcinomas. Prostate cancer, prostate adenocarcinoma, skin cancer, melanoma, malignant melanoma, cutaneous melanoma, small intestine carcinomas, stomach cancer, gastric carcinoma, gastrointestinal stromal tumor (GIST), uterine cancer, or uterine sarcoma.

In some embodiments, the cancer is liver cancer, liver carcinoma, hepatoma, hepatocellular carcinoma, cholangiocarcinoma, orhepatoblastoma.

In some embodiments, the disease is a proliferative, inflammatory, autoimmune, neurologic, ocular, respiratory, metabolic, dermatological, auditory, liver, kidney, or infectious disease. In some embodiments, the disease is a disease of the liver.

Definitions

Unless otherwise stated, the following terms used in the specification and claims have the following meanings set out below.

Without wishing to be limited by this statement, it is understood that, while various options for variables are described herein, the disclosure intends to encompass operable embodiments having combinations of the options. The disclosure may be interpreted as excluding the non-operable embodiments caused by certain combinations of the options.

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intends to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, i-pentyl, or n-hexyl. In some embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In some embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

As used herein, the term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

As used herein, the term "alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In some embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms. As used herein, "$C_2$-$C_6$ alkenylene linker" or "$C_2$-$C_6$ alkynylene linker" is intended to include $C_2$, $C_3$, $C_4$, $C_5$ or $C_6$ chain (linear or branched) divalent unsaturated aliphatic hydrocarbon groups. For example, $C_2$-$C_6$ alkenylene linker is intended to include $C_2$, $C_3$, $C_4$, $C_5$ and $C_6$ alkenylene linker groups.

As used herein, the term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

As used herein, the term "cycloalkyl" refers to a saturated or partially unsaturated hydrocarbon monocyclic or polycyclic (e.g., fused, bridged, or spiro rings) system having 3 to 30 carbon atoms (e.g., $C_3$-$C_{12}$, $C_3$-$C_{10}$, or $C_3$-$C_8$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, 1,2,3,4-tetrahydronaphthalenyl, and adamantyl. In the case of polycyclic cycloalkyl, only one of the rings in the cycloalkyl needs to be non-aromatic.

As used herein, the term "heterocycloalkyl" refers to a saturated or partially unsaturated 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, P, or Se), e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur, unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, 3-azabicyclo[3.1.0]hexanyl, 3-azabicyclo[3.1.0]hexan-3-yl, 1,4,5,6-tetrahydropyrrolo[3,4-c]pyrazolyl, 3,4,5,6,7,8-hexahydropyrido[4,3-d]pyrimidinyl, 4,5,6,7-tetrahydro-1H-pyrazolo[3,4-c]pyridinyl, 5,6,7,8-tetrahydropyrido[4,3-d]pyrimidinyl, 2-azaspiro[3.3]heptanyl, 2-methyl-2-azaspiro[3.3]heptanyl, 2-azaspiro[3.5]nonanyl, 2-methyl-2-azaspiro[3.5]nonanyl, 2-azaspiro[4.5]decanyl, 2-methyl-2-azaspiro[4.5]decanyl, 2-oxa-azaspiro[3.4]octanyl, 2-oxa-azaspiro[3.4]octan-6-yl, 5,6-dihydro-4H-cyclopenta[b]thiophenyl, and the like. In the case of multicyclic heterocycloalkyl, only one of the rings in the heterocycloalkyl needs to be non-aromatic (e.g., 4,5,6,7-tetrahydrobenzo[c]isoxazolyl).

As used herein, the term "aryl" includes groups with aromaticity, including "conjugated," or multicyclic systems with one or more aromatic rings and do not contain any heteroatom in the ring structure. The term aryl includes both monovalent species and divalent species. Examples of aryl groups include, but are not limited to, phenyl, biphenyl, naphthyl and the like. Conveniently, an aryl is phenyl.

As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, isothiazole, pyridine, pyrazine, pyridazine, pyrimidine, and the like. Heteroaryl groups can also be fused or bridged with alicyclic or heterocyclic rings, which are not aromatic so as to form a multicyclic system (e.g., 4,5,6,7-tetrahydrobenzo[c]isoxazolyl). In some embodiments, the heteroaryl is thiophenyl or benzothiophenyl. In some embodiments, the heteroaryl is thiophenyl. In some embodiments, the heteroaryl benzothiophenyl.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, quinoline, isoquinoline, naphthrydine, indole, benzofuran, purine, benzofuran, deazapurine, indolizine.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl such as benzo[d][1,3]dioxole-5-yl).

As used herein, the term "substituted," means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., R) occurs more than one time in any constituent or formula for a compound, its definition at each occurrence is independent of its definition at every other occurrence. Thus, for example, if a group is shown to be substituted with 0-2 R moieties, then the group may optionally be substituted with up to two R moieties and R at each occurrence is selected independently from the definition of R. Also, combinations of substituents and/or variables are permissible, but only if such combinations result in stable compounds.

As used herein, the term "hydroxy" or "hydroxyl" includes groups with an —OH or —O$^-$.

As used herein, the term "halo" or "halogen" refers to fluoro, chloro, bromo and iodo.

The term "haloalkyl" or "haloalkoxyl" refers to an alkyl or alkoxyl substituted with one or more halogen atoms.

As used herein, the term "optionally substituted haloalkyl" refers to unsubstituted haloalkyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "alkoxy" or "alkoxyl" includes substituted and unsubstituted alkyl, alkenyl and alkynyl groups covalently attached to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

As used herein, the expressions "one or more of A, B, or C," "one or more A, B, or C," "one or more of A, B, and C," "one or more A, B, and C," "selected from the group consisting of A, B, and C", "selected from A, B, and C", and the like are used interchangeably and all refer to a selection from a group consisting of A, B, and/or C, i.e., one or more As, one or more Bs, one or more Cs, or any combination thereof, unless indicated otherwise.

It is to be understood that the present disclosure provides methods for the synthesis of the compounds, scaffolds, and conjugates described herein. The present disclosure also provides detailed methods for the synthesis of various disclosed compounds, scaffolds, and conjugates according to the schemes herein as well as those shown in the Examples.

It is to be understood that, throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps order for performing certain actions is immaterial so long as the invention remains operable. Moreover, two or more steps or actions can be conducted simultaneously.

It is to be understood that the synthetic processes of the disclosure can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

It is to be understood that compounds, scaffolds, and conjugates of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure,* 5th edition, John Wiley & Sons: New York, 2001; Greene, T. W., Wuts, P. G. M., *Protective Groups in Organic Synthesis,* 3rd edition, John Wiley & Sons: New York, 1999; R. Larock, *Comprehensive Organic Transformations*, VCH Publishers (1989); L. Fieser and M. Fieser, *Fieser and Fieser's Reagents forganic Synthesis*, John Wiley and Sons (1994); and L. Paquette, ed., *Encyclopedia of Reagents forganic Synthesis*, John Wiley and Sons (1995), incorporated by reference herein, are useful and recognized reference textbooks of organic synthesis known to those in the art One of ordinary skill in the art will note that, during the reaction sequences and synthetic schemes described herein, the order of certain steps may be changed, such as the introduction and removal of protecting groups. One of ordinary skill in the art will recognise that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis,* 3rd edition, John Wiley & Sons: New York, 1999.

It is to be understood that, unless otherwise stated, any description of a method of treatment or prevention includes use of the compounds, scaffolds, and conjugates to provide such treatment or prevention as is described herein. It is to be further understood, unless otherwise stated, any description of a method of treatment or prevention includes use of the compounds, scaffolds, and conjugates to prepare a medicament to treat or prevent such condition. The treatment or prevention includes treatment or prevention of human or non-human animals including rodents and other disease models.

It is to be understood that, unless otherwise stated, any description of a method of treatment includes use of the compounds, scaffolds, and conjugates to provide such treatment as is described herein. It is to be further understood, unless otherwise stated, any description of a method of treatment includes use of the compounds, scaffolds, and conjugates to prepare a medicament to treat such condition. The treatment includes treatment of human or non-human animals including rodents and other disease models.

As used herein, the term "subject" is interchangeable with the term "subject in need thereof", both of which refer to a subject having a disease or having an increased risk of developing the disease. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In some embodiments, the mammal is a human. A subject in need thereof can be one who has been previously diagnosed or identified as having a disease or disorder disclosed herein. A subject in need thereof can also be one who is suffering from a disease or disorder disclosed herein. Alternatively, a subject in need thereof can be one who has an increased risk of developing such disease or disorder relative to the population at large (i.e., a subject who is predisposed to developing such disorder relative to the population at large). A subject in need thereof can have a refractory or resistant a disease or disorder disclosed herein (i.e., a disease or disorder disclosed herein that does not respond or has not yet responded to treatment). The subject may be resistant at start of treatment or may become resistant during treatment. In some embodiments, the subject in need thereof received and failed all known effective therapies for a disease or disorder disclosed herein. In some embodiments, the subject in need thereof received at least one prior therapy.

As used herein, the term "treating" or "treat" describes the management and care of a patient for the purpose of combating a disease, condition, or disorder and includes the administration of a compound of the present disclosure, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model. It is to be appreciated that references to "treating" or "treatment" include the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

It is to be understood that compounds, scaffolds, and conjugates of the present disclosure, or a pharmaceutically acceptable salt, polymorph or solvate thereof, can or may also be used to prevent a relevant disease, condition or disorder, or used to identify suitable candidates for such purposes.

As used herein, the term "preventing," "prevent," or "protecting against" describes reducing or eliminating the onset of the symptoms or complications of such disease, condition or disorder.

It is to be understood that the present disclosure also provides pharmaceutical compositions comprising any compound, scaffold, or conjugate described herein in combination with at least one pharmaceutically acceptable excipient or carrier.

As used herein, the term "pharmaceutical composition" is a formulation containing the compounds, scaffolds, or conjugates of the present disclosure in a form suitable for administration to a subject. In some embodiments, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In some embodiments, the active compound is mixed under sterile conditions with a pharmaceutically acceptable carrier, and with any preservatives, buffers, or propellants that are required.

As used herein, the term "pharmaceutically acceptable" refers to those compounds, scaffolds, conjugates, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

It is to be understood that a pharmaceutical composition of the disclosure is formulated to be compatible with its intended route of administration. Examples of routes of administration include parenteral, e.g., intravenous, intradermal, subcutaneous, oral (e.g., ingestion), inhalation, transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

It is to be understood that a compound or pharmaceutical composition of the disclosure can be administered to a subject in many of the well-known methods currently used for chemotherapeutic treatment. For example, a compound of the disclosure may be injected into the blood stream or body cavities or taken orally or applied through the skin with patches. The dose chosen should be sufficient to constitute effective treatment but not so high as to cause unacceptable side effects. The state of the disease condition (e.g., a disease or disorder disclosed herein) and the health of the patient should preferably be closely monitored during and for a reasonable period after treatment.

As used herein, the term "therapeutically effective amount", refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and therapeutic or combination of therapeutics selected for administration. Therapeutically effective amounts for a given situation can be determined by routine experimentation that is within the skill and judgment of the clinician.

As used herein, the term "therapeutically effective amount", refers to an amount of a pharmaceutical agent to treat or ameliorate an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and therapeutic or combination of therapeutics selected for administration. Therapeutically effective amounts for a given situation can be determined by routine experimentation that is within the skill and judgment of the clinician.

It is to be understood that, for any compound, therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present disclosure may be manufactured in a manner that is generally known, e.g., by means of conventional mixing, dissolving, granulating, dragee-making, levigating, emulsifying, encapsulating, entrapping, or lyophilising processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilisation. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, orange flavoring.

For administration by inhalation, the compounds are delivered in the form of an aerosol spray from pressured container or dispenser, which contains a suitable propellant, e.g., a gas such as carbon dioxide, or a nebuliser.

For intranasal administration, the compounds are delivered in solution or solid formulation. In some embodiments, the compounds are delivered in solution as a mist, a drip, or a swab. In some embodiments, the compounds are delivered as a powder. In some embodiments, the compound is included in a kit which further includes an intranasal applicator.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

In therapeutic applications, the dosages of the pharmaceutical compositions used in accordance with the disclosure vary depending on the agent, the age, weight, and clinical condition of the recipient patient, and the experience and judgment of the clinician or practitioner administering therapy, among other factors affecting the selected dosage. Generally, the dose should be sufficient to result in slowing, and preferably regressing, the symptoms of the disease or disorder disclosed herein and also preferably causing complete regression of the disease or disorder. Dosages can range from about 0.01 mg/kg per day to about 5000 mg/kg per day. An effective amount of a pharmaceutical agent is that which provides an objectively identifiable improvement as noted by the clinician or other qualified observer. Improvement in survival and growth indicates regression. As used herein, the term "dosage effective manner" refers to amount of an active compound to produce the desired biological effect in a subject or cell.

It is to be understood that the pharmaceutical compositions can be included in a container, pack, or dispenser together with instructions for administration.

It is to be understood that, for the compounds, scaffolds, or conjugates of the present disclosure being capable of further forming salts, all of these forms are also contemplated within the scope of the claimed disclosure.

As used herein, the term "pharmaceutically acceptable salts" refer to derivatives of the compounds of the present disclosure wherein the parent compound is modified by making acid or base salts thereof. Examples of pharmaceutically acceptable salts include, but are not limited to, mineral organic acid salts of basic residues such as amines, alkali organic salts of acidic residues such as carboxylic acids, and the like. The pharmaceutically acceptable salts include the conventional non-toxic salts or the quaternary ammonium salts of the parent compound formed, for example, from non-toxic inorganic organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

In some embodiments, the pharmaceutically acceptable salt is a sodium salt, a potassium salt, a calcium salt, a magnesium salt, a diethylamine salt, a choline salt, a meglumine salt, a benzathine salt, a tromethamine salt, an ammonia salt, an arginine salt, or a lysine salt.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ratio other than 1:1, e.g., 3:1, 2:1, 1:2, or 1:3.

It is to be understood that all references to pharmaceutically acceptable salts include solvent addition forms (solvates) or crystal forms (polymorphs) as defined herein, of the same salt.

The compounds, or pharmaceutically acceptable salts thereof, are administered orally, nasally, transdermally, pulmonary, inhalationally, buccally, sublingually, intraperitoneally, subcutaneously, intramuscularly, intravenously, rectally, intrapleurally, intrathecally and parenterally. In some embodiments, the compound is administered orally. One skilled in the art will recognise the advantages of certain routes of administration.

The dosage regimen utilising the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition. An ordinarily skilled physician or veterinarian can readily determine and prescribe the effective amount of the drug required to counter or arrest the progress of the condition.

Techniques for formulation and administration of the disclosed compounds of the disclosure can be found in *Remington: the Science and Practice of Pharmacy*, $19^{th}$ edition, Mack Publishing Co., Easton, PA (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous organic solutions. The compounds will be present in such pharmaceutical compositions in amounts sufficient to provide the desired dosage amount in the range described herein.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

In the synthetic schemes described herein, compounds may be drawn with one particular configuration for simplicity. Such particular configurations are not to be construed as limiting the disclosure to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXEMPLARY EMBODIMENTS

Exemplary Embodiment 1. A compound of Formula (I) or (II):

(I)

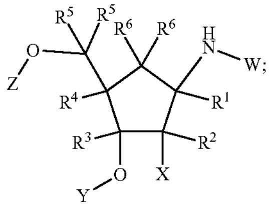

(II)

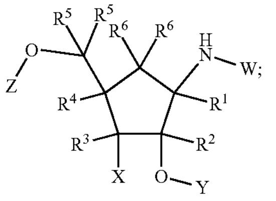

or a pharmaceutically acceptable salt thereof, wherein:

W is H, $C_1$-$C_6$ alkyl optionally substituted with one or more halogen, or an amino substitution group;

X is H, halogen, or —$OR^X$;

$R^X$ is H, $C_1$-$C_6$ alkyl, or —($C_1$-$C_6$ alkyl)-($C_6$-$C_{10}$ aryl), wherein the $C_1$-$C_6$ alkyl or —($C_1$-$C_6$ alkyl)-($C_6$-$C_{10}$ aryl) is optionally substituted with one or more $R^{Xa}$;

each $R^{Xa}$ independently is halogen, $C_1$-$C_6$ alkyl, or —O—($C_1$-$C_6$ alkyl), wherein the $C_1$-$C_6$ alkyl or —O—($C_1$-$C_6$ alkyl) is optionally substituted with one or more halogen;

Y is H, $C_1$-$C_6$ alkyl optionally substituted with one or more halogen, —$P(R^Y)_2$, —$P(OR^Y)(N(R^Y)_2)$, —$P(=O)(OR^Y)R^Y$, —$P(=S)(OR^Y)R^Y$, —$P(=O)(SR^Y)R^Y$, —$P(=S)(SR^Y)R^Y$, —$P(=O)(OR^Y)_2$, —$P(=S)(OR^Y)_2$, —$P(=O)(SR^Y)_2$, —$P(=S)(SR^Y)_2$, or a hydroxy protecting group;

each $R^Y$ independently is H or $C_1$-$C_6$ alkyl optionally substituted with one or more halogen or cyano;

Z is H, or $C_1$-$C_6$ alkyl optionally substituted with one or more halogen, —$P(R^Z)_2$, —$P(OR^Z)(N(R^Z)_2)$, —$P(=O)(OR^Z)R^Z$, —$P(=S)(OR^Z)R^Z$, —$P(=O)(SR^Z)R^Z$, —$P(=S)(SR^Z)R^Z$, —$P(=O)(OR^Z)_2$, —$P(=S)(OR^Z)_2$, —$P(=O)(SR^Z)_2$, —$P(=S)(SR^Z)_2$, or a hydroxy protecting group; each $R^Z$ independently is H or $C_1$-$C_6$ alkyl optionally substituted with one or more halogen or cyano;

or Y and Z in Formula (I), together form —$Si(R^L)_2$—O—$Si(R^L)_2$—, wherein each $R^L$ independently is H or $C_1$-$C_6$ alkyl;

$R^1$ is H, halogen, or $C_1$-$C_6$ alkyl optionally substituted with one or more halogen;

$R^2$ is H, halogen, or $C_1$-$C_6$ alkyl optionally substituted with one or more halogen;

$R^3$ is H, halogen, or $C_1$-$C_6$ alkyl optionally substituted with one or more halogen;

$R^4$ is H, halogen, or $C_1$-$C_6$ alkyl optionally substituted with one or more halogen; and each $R^5$ independently is H, halogen, or $C_1$-$C_6$ alkyl optionally substituted with one or more halogen; and each $R^6$ independently is H, halogen, or $C_1$-$C_6$ alkyl optionally substituted with one or more halogen.

Exemplary Embodiment 2. A scaffold or a pharmaceutically acceptable salt thereof, wherein the scaffold comprises:

(i) a Ligand; and (ii) a Linker Unit, wherein the Linker Unit is:

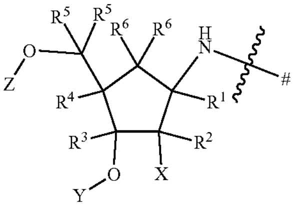

or

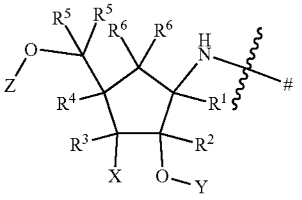

wherein variables $R^1$, $R^2$, $R^3$, $R^4$, $R^5$, $R^6$, X, Y, and Z are described in Exemplary Embodiment 1, and # indicates an attachment to the Ligand.

Exemplary Embodiment 3. A scaffold or a pharmaceutically acceptable salt thereof, wherein the scaffold comprises:

(i) one or more Nucleic Acid Agent; and (ii) one or more Linker Unit, wherein each Linker Unit independently is:

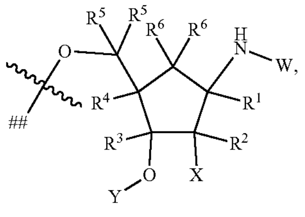

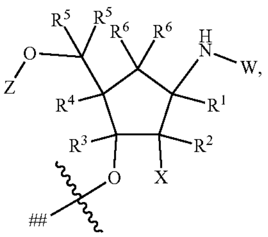

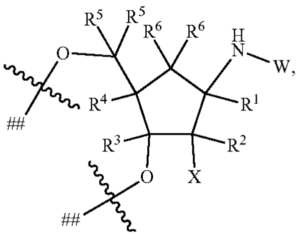

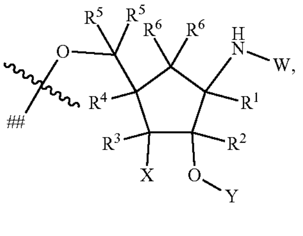

-continued

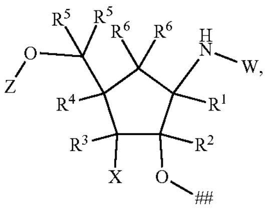

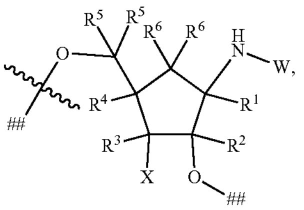

wherein variables $R^1$, $R^2$, $R^3$, $R^4$, $R^5$, $R^6$, W, X, Y, and Z are described in Exemplary Embodiment 1, and ## indicates an attachment to the Nucleic Acid Agent.

Exemplary Embodiment 4. A conjugate or a pharmaceutically acceptable salt thereof, wherein the conjugate comprises:

(i) one or more Nucleic Acid Agent;

(ii) one or more Ligand; and (iii) one or more Linker Unit, wherein each Linker Unit independently is:

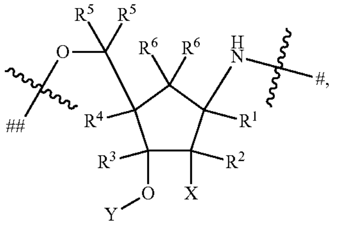

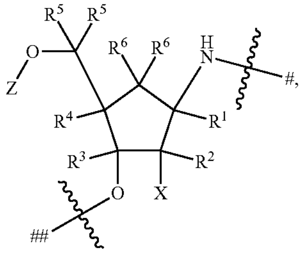

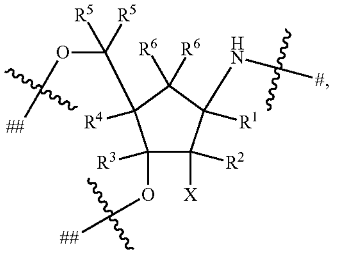

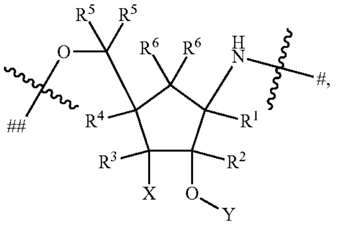

-continued

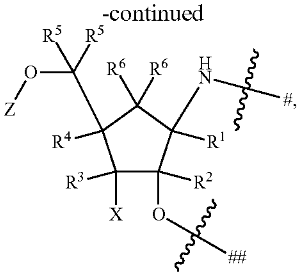

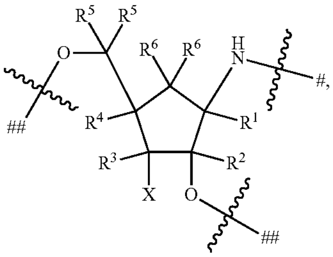

wherein variables $R^1$, $R^2$, $R^3$, $R^4$, $R^5$, $R^6$, X, Y, and Z are described in Exemplary Embodiment 1, # indicates an attachment to the Ligand, and ## indicates an attachment to the Nucleic Acid Agent.

Exemplary Embodiment 5. The compound, scaffold, or conjugate of any one of the previous Exemplary Embodiments, wherein W is H.

Exemplary Embodiment 6. The compound, scaffold, or conjugate of any one of the previous Exemplary Embodiments, wherein W is $C_1$-$C_6$ alkyl optionally substituted with one or more halogen.

Exemplary Embodiment 7. The compound, scaffold, or conjugate of any one of the previous Exemplary Embodiments, wherein W is an amino substitution group.

Exemplary Embodiment 8. The compound, scaffold, or conjugate of any one of the previous Exemplary Embodiments, wherein W is fluorenylmethyloxycarbonyl (Fmoc), tert-butyloxycarbonyl (BOC), benzyloxycarbonyl (Cbz), optionally substituted acyl, trifluoroacetyl (TFA), benzyl, triphenylmethyl (Tr), 4,4'-dimethoxytrityl (DMTr), or toluenesulfonyl (Ts).

Exemplary Embodiment 9. The compound, scaffold, or conjugate of any one of the previous Exemplary Embodiments, wherein W is optionally substituted acyl.

Exemplary Embodiment 10. The compound, scaffold, or conjugate of any one of the previous Exemplary Embodiments, wherein W is trifluoroacetyl (TFA).

Exemplary Embodiment 11. The compound, scaffold, or conjugate of any one of the previous Exemplary Embodiments, wherein X is H.

Exemplary Embodiment 12. The compound, scaffold, or conjugate of any one of the previous Exemplary Embodiments, wherein X is halogen.

Exemplary Embodiment 13. The compound, scaffold, or conjugate of any one of the previous Exemplary Embodiments, wherein X is —$OR^X$.

Exemplary Embodiment 14. The compound, scaffold, or conjugate of any one of the previous Exemplary Embodiments, wherein X is —OH.

Exemplary Embodiment 15. The compound, scaffold, or conjugate of any one of the previous Exemplary Embodiments, wherein X is —O—($C_1$-$C_6$ alkyl).

Exemplary Embodiment 16. The compound, scaffold, or conjugate of any one of the previous Exemplary Embodiments, wherein X is —O—($C_1$-$C_6$ alkyl)-O—($C_1$-$C_6$ alkyl).

Exemplary Embodiment 17. The compound, scaffold, or conjugate of any one of the previous Exemplary Embodiments, wherein X is —O—($C_1$-$C_6$ alkyl)-($C_6$-$C_{10}$ aryl) optionally substituted with one or more $R^{Xa}$.

Exemplary Embodiment 18. The compound, scaffold, or conjugate of any one of the previous Exemplary Embodiments, wherein X is —O—($C_1$-$C_6$ alkyl)-($C_6$-$C_{10}$ aryl).

Exemplary Embodiment 19. The compound, scaffold, or conjugate of any one of the previous Exemplary Embodiments, wherein $R^X$ is H.

Exemplary Embodiment 20. The compound, scaffold, or conjugate of any one of the previous Exemplary Embodiments, wherein $R^X$ is $C_1$-$C_6$ alkyl optionally substituted with one or more halogen or —O—($C_1$-$C_6$ alkyl) optionally substituted with one or more halogen.

Exemplary Embodiment 21. The compound, scaffold, or conjugate of any one of the previous Exemplary Embodiments, wherein $R^X$ is —($C_1$-$C_6$ alkyl)-($C_6$-$C_{10}$ aryl) optionally substituted with one or more halogen, $C_1$-$C_6$ alkyl, or —O—($C_1$-$C_6$ alkyl), wherein the $C_1$-$C_6$ alkyl or —O—($C_1$-$C_6$ alkyl) is optionally substituted with one or more halogen.

Exemplary Embodiment 22. The compound, scaffold, or conjugate of any one of the previous Exemplary Embodiments, wherein $R^X$ is —($C_1$-$C_6$ alkyl)-($C_6$-$C_{10}$ aryl).

Exemplary Embodiment 23. The compound, scaffold, or conjugate of any one of the previous Exemplary Embodiments, wherein Y is H.

Exemplary Embodiment 24. The compound, scaffold, or conjugate of any one of the previous Exemplary Embodiments, wherein Y is $C_1$-$C_6$ alkyl optionally substituted with one or more halogen.

Exemplary Embodiment 25. The compound, scaffold, or conjugate of any one of the previous Exemplary Embodiments, wherein Y is —P($R^Y$)$_2$, —P($OR^Y$)(N($R^Y$)$_2$), —P(═O)($OR^Y$)$R^Y$, —P(═S)($OR^Y$)$R^Y$, —P(═O)($SR^Y$)$R^Y$, —P(═S)($SR^Y$)$R^Y$, —P(═O)($OR^Y$)$_2$, —P(═S)($OR^Y$)$_2$, —P(═O)($SR^Y$)$_2$, —P(═S)($SR^Y$)$_2$.

Exemplary Embodiment 26. The compound, scaffold, or conjugate of any one of the previous Exemplary Embodiments, wherein Y is a hydroxy protecting group.

Exemplary Embodiment 27. The compound, scaffold, or conjugate of any one of the previous Exemplary Embodiments, wherein Y is silyl.

Exemplary Embodiment 28. The compound, scaffold, or conjugate of any one of the previous Exemplary Embodiments, wherein Y is triphenylmethyl (Tr) or 4,4'-dimethoxytrityl (DMTr).

Exemplary Embodiment 29. The compound, scaffold, or conjugate of any one of the previous Exemplary Embodiments, wherein Y is optionally substituted acyl or benzyl.

Exemplary Embodiment 30. The compound, scaffold, or conjugate of any one of the previous Exemplary Embodiments, wherein at least one $R^Y$ is H.

Exemplary Embodiment 31. The compound, scaffold, or conjugate of any one of the previous Exemplary Embodiments, wherein at least one $R^Y$ is $C_1$-$C_6$ alkyl optionally substituted with one or more halogen or cyano.

Exemplary Embodiment 32. The compound, scaffold, or conjugate of any one of the previous Exemplary Embodiments, wherein at least one $R^Y$ is H, and at least one $R^Y$ is $C_1$-$C_6$ alkyl optionally substituted with one or more halogen or cyano.

Exemplary Embodiment 33. The compound, scaffold, or conjugate of any one of the previous Exemplary Embodiments, wherein when X is —OH, then Y is not H or a hydroxy protecting group.

Exemplary Embodiment 34. The compound, scaffold, or conjugate of any one of the previous Exemplary Embodiments, wherein when X is —OH, then Y is $C_1$-$C_6$ alkyl optionally substituted with one or more halogen, —P($R^Y$)$_2$, —P($OR^Y$)(N($R^Y$)$_2$), —P(═O)($OR^Y$)$R^Y$, —P(═S)($OR^Y$)$R^Y$, —P(═O)($SR^Y$)$R^Y$, —P(═S)($SR^Y$)$R^Y$, —P(═O)($OR^Y$)$_2$, —P(═S)($OR^Y$)$_2$, —P(═O)($SR^Y$)$_2$, or —P(═S)($SR^Y$)$_2$.

Exemplary Embodiment 35. The compound, scaffold, or conjugate of any one of the previous Exemplary Embodiments, wherein when Y is H or a hydroxy protecting group, then X is not —OH.

Exemplary Embodiment 36. The compound, scaffold, or conjugate of any one of the previous Exemplary Embodiments, wherein when Y is H or a hydroxy protecting group, then X is H, halogen, or —$OR^X$, and $R^X$ is $C_1$-$C_6$ alkyl or —($C_1$-$C_6$ alkyl)-($C_6$-$C_{10}$ aryl), wherein the $C_1$-$C_6$ alkyl or —($C_1$-$C_6$ alkyl)-($C_6$-$C_{10}$ aryl) is optionally substituted with one or more $R^{Xa}$.

Exemplary Embodiment 37. The compound, scaffold, or conjugate of any one of the previous Exemplary Embodiments, wherein Z is H.

Exemplary Embodiment 38. The compound, scaffold, or conjugate of any one of the previous Exemplary Embodiments, wherein Z is $C_1$-$C_6$ alkyl optionally substituted with one or more halogen.

Exemplary Embodiment 39. The compound, scaffold, or conjugate of any one of the previous Exemplary Embodiments, wherein Z is —P($R^Z$)$_2$, —P($OR^Z$)(N($R^Z$)$_2$), —P(═O)($OR^Z$)$R^Z$, —P(═S)($OR^Z$)$R^Z$, —P(═O)($SR^Z$)$R^Z$, —P(═S)($SR^Z$)$R^Z$, —P(═O)($OR^Z$)$_2$, —P(═S)($OR^Z$)$_2$, —P(═O)($SR^Z$)$_2$, —P(═S)($SR^Z$).

Exemplary Embodiment 40. The compound, scaffold, or conjugate of any one of the previous Exemplary Embodiments, wherein Z is a hydroxy protecting group.

Exemplary Embodiment 41. The compound, scaffold, or conjugate of any one of the previous Exemplary Embodiments, wherein Z is silyl.

Exemplary Embodiment 42. The compound, scaffold, or conjugate of any one of the previous Exemplary Embodiments, wherein Z is triphenylmethyl (Tr) or 4,4'-dimethoxytrityl (DMTr).

Exemplary Embodiment 43. The compound, scaffold, or conjugate of any one of the previous Exemplary Embodiments, wherein Z is substituted acyl or benzyl.

Exemplary Embodiment 44. The compound, scaffold, or conjugate of any one of the previous Exemplary Embodiments, wherein at least one $R^Z$ is H.

Exemplary Embodiment 45. The compound, scaffold, or conjugate of any one of the previous Exemplary Embodiments, wherein at least one $R^Z$ is $C_1$-$C_6$ alkyl optionally substituted with one or more halogen or cyano.

Exemplary Embodiment 46. The compound, scaffold, or conjugate of any one of the previous Exemplary Embodiments, wherein at least one $R^Z$ is H, and at least one $R^Z$ is $C_1$-$C_6$ alkyl optionally substituted with one or more halogen or cyano.

Exemplary Embodiment 47. The compound, scaffold, or conjugate of any one of the previous Exemplary Embodiments, wherein Y and Z in Formula (I) together form —Si($R^L$)$_2$—O—Si($R^L$)$_2$—.

Exemplary Embodiment 48. The compound, scaffold, or conjugate of any one of the previous Exemplary Embodiments, wherein at least one $R^L$ is H.

Exemplary Embodiment 49. The compound, scaffold, or conjugate of any one of the previous Exemplary Embodiments, wherein each $R^L$ independently is $C_1$-$C_6$ alkyl.

Exemplary Embodiment 50. The compound, scaffold, or conjugate of any one of the previous Exemplary Embodiments, wherein $R^1$ is H.

Exemplary Embodiment 51. The compound, scaffold, or conjugate of any one of the previous Exemplary Embodiments, wherein $R^1$ is halogen.

Exemplary Embodiment 52. The compound, scaffold, or conjugate of any one of the previous Exemplary Embodiments, wherein $R^1$ is $C_1$-$C_6$ alkyl optionally substituted with one or more halogen.

Exemplary Embodiment 53. The compound, scaffold, or conjugate of any one of the previous Exemplary Embodiments, wherein $R^2$ is H.

Exemplary Embodiment 54. The compound, scaffold, or conjugate of any one of the previous Exemplary Embodiments, wherein $R^2$ is halogen.

Exemplary Embodiment 55. The compound, scaffold, or conjugate of any one of the previous Exemplary Embodiments, wherein $R^2$ is $C_1$-$C_6$ alkyl optionally substituted with one or more halogen.

Exemplary Embodiment 56. The compound, scaffold, or conjugate of any one of the previous Exemplary Embodiments, wherein $R^3$ is H.

Exemplary Embodiment 57. The compound, scaffold, or conjugate of any one of the previous Exemplary Embodiments, wherein $R^3$ is halogen.

Exemplary Embodiment 58. The compound, scaffold, or conjugate of any one of the previous Exemplary Embodiments, wherein $R^3$ is $C_1$-$C_6$ alkyl optionally substituted with one or more halogen.

Exemplary Embodiment 59. The compound, scaffold, or conjugate of any one of the previous Exemplary Embodiments, wherein $R^4$ is H.

Exemplary Embodiment 60. The compound, scaffold, or conjugate of any one of the previous Exemplary Embodiments, wherein $R^4$ is halogen.

Exemplary Embodiment 61. The compound, scaffold, or conjugate of any one of the previous Exemplary Embodiments, wherein $R^4$ is $C_1$-$C_6$ alkyl optionally substituted with one or more halogen.

Exemplary Embodiment 62. The compound, scaffold, or conjugate of any one of the previous Exemplary Embodiments, wherein $R^5$ is H.

Exemplary Embodiment 63. The compound, scaffold, or conjugate of any one of the previous Exemplary Embodiments, wherein $R^5$ is halogen.

Exemplary Embodiment 64. The compound, scaffold, or conjugate of any one of the previous Exemplary Embodiments, wherein $R^5$ is $C_1$-$C_6$ alkyl optionally substituted with one or more halogen.

Exemplary Embodiment 65. The compound, scaffold, or conjugate of any one of the previous Exemplary Embodiments, wherein $R^6$ is H.

Exemplary Embodiment 66. The compound, scaffold, or conjugate of any one of the previous Exemplary Embodiments, wherein $R^6$ is halogen.

Exemplary Embodiment 67. The compound, scaffold, or conjugate of any one of the previous Exemplary Embodiments, wherein $R^6$ is $C_1$-$C_6$ alkyl optionally substituted with one or more halogen.

Exemplary Embodiment 68. The compound, scaffold, or conjugate of any one of the previous Exemplary Embodiments, wherein each of $R^1$, $R^2$, $R^3$, $R^4$, $R^5$, and $R^6$ is H.

Exemplary Embodiment 69. The compound of any one of the preceding Exemplary Embodiments, wherein the compound is of Formula (I'-1), (I'-2), (II'-1), or (II'-2):

(I'-1)

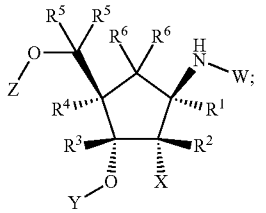

(I'-2)

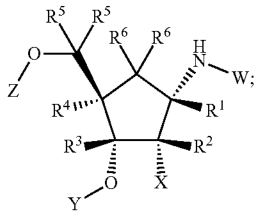

(II'-1)

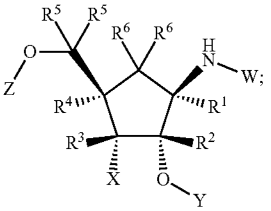

or (II'-2)

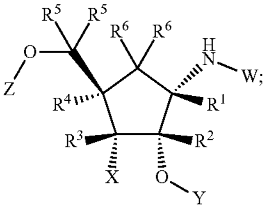

or a pharmaceutically acceptable salt thereof.

Exemplary Embodiment 70. The compound of any one of the preceding Exemplary Embodiments, wherein the compound is of Formula (I-A) or (II-A):

(I-A)

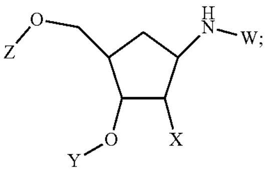

or (II-A)

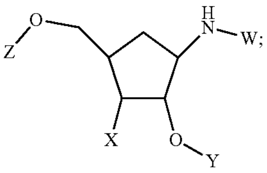

or a pharmaceutically acceptable salt thereof.

Exemplary Embodiment 71. The compound of any one of the preceding Exemplary Embodiments, wherein the compound is of Formula (I-A'-1), (I-A'-2), (II-A'-1), or (II-A'-2):

(I-A'-1)

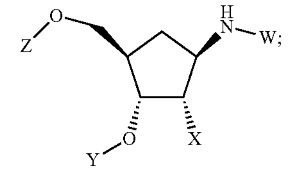

(I-A'-2)

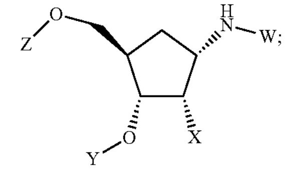

(II-A'-1)

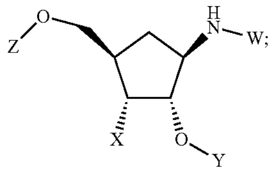

or (II-A'-2)

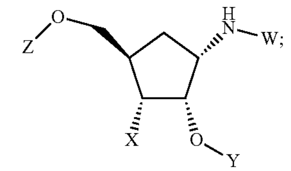

or a pharmaceutically acceptable salt thereof.

Exemplary Embodiment 72. The compound of any one of the preceding Exemplary Embodiments, wherein the compound is of Formula (I-B) or (II-B):

(I-B)

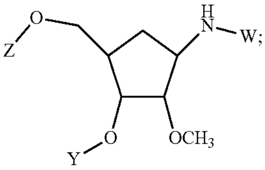

or (II-B)

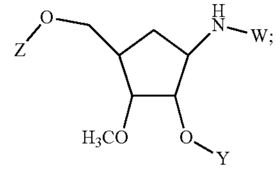

or a pharmaceutically acceptable salt thereof.

Exemplary Embodiment 73. The compound of any one of the preceding Exemplary Embodiments, wherein the compound is of Formula (I-B'-1), (I-B'-2), (II-B'-1), or (II-B'-2):

(I-B'-1)

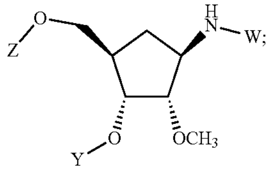

-continued (I-B'-2)

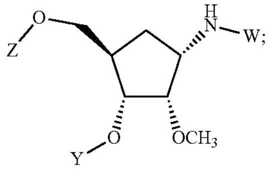

(II-B'-1)

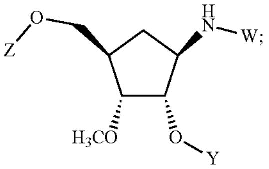

or (II-B'-2)

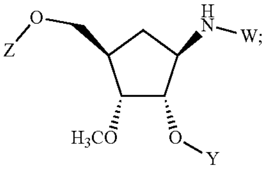

or a pharmaceutically acceptable salt thereof.

Exemplary Embodiment 74. The compound of any one of the preceding Exemplary Embodiments, wherein: Y is a hydroxy protecting group, and Z is a hydroxy protecting group; or Y and Z in Formula (I), (I'-1), (I'-2), (I-A), (I-A'-1), (I-A'-2), (I-B), (I-B'-1), or (I-B'-2) together form $—Si(R^L)_2—O—Si(R^L)_2—$, wherein each $R^L$ independently is H or $C_1$-$C_6$ alkyl.

Exemplary Embodiment 75. The compound of any one of the preceding Exemplary Embodiments, wherein the compound is:

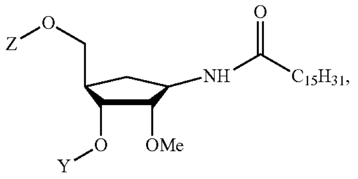

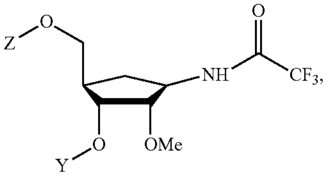

or

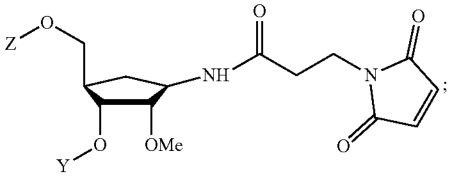

or a pharmaceutically acceptable salt thereof, wherein:

Y is $—P(R^Y)_2$, $—P(OR^Y)(N(R^Y)_2)$, $—P(=O)(OR^Y)R^Y$, $—P(=S)(OR^Y)R^Y$, $—P(=O)(SR^Y)R^Y$, $—P(=S)(SR^Y)R^Y$, $—P(=O)(OR^Y)_2$, $—P(=S)(OR^Y)_2$, $—P(=O)(SR^Y)_2$, $—P(=S)(SR^Y)_2$, or a hydroxy protecting group;

each $R^Y$ independently is H or $C_1$-$C_6$ alkyl optionally substituted with one or more halogen or cyano;

Z is $—P(R^Z)_2$, $—P(OR^Z)(N(R^Z)_2)$, $—P(=O)(OR^Z)R^Z$, $—P(=S)(OR^Z)R^Z$, $—P(=O)(SR^Z)R^Z$, $—P(=S)

$(SR^Z)R^Z$, $—P(═O)(OR^Z)_2$, $—P(═S)(OR^Z)_2$, $—P(═O)(SR^Z)_2$, $—P(═S)(SR^Z)_2$, or a hydroxy protecting group; and each $R^Z$ independently is H or $C_1$-$C_6$ alkyl optionally substituted with one or more halogen or cyano.

Exemplary Embodiment 76. The compound of any one of the preceding Exemplary Embodiments, wherein the compound is selected from the compounds described in Table L and pharmaceutically acceptable salts thereof.

Exemplary Embodiment 77. A compound being an isotopic derivative of the compound of any one of the preceding Exemplary Embodiments.

Exemplary Embodiment 78. The scaffold of any one of the preceding Exemplary Embodiments, wherein the scaffold is (Linker $Unit)_p$-((Nucleic Acid Agent)-(Linker $Unit)_s)_r$-(Nucleic Acid $Agent)_q$, wherein:

each Linker Unit is independent from another Linker Unit, and each Nucleic Acid Agent is independent from another Nucleic Acid Agent;

each r independently is an integer ranging from 0 to 10;

each s independently is an integer ranging from 0 to 10;

p is an integer ranging from 0 to 10;

q is 0 or 1; and the scaffold comprises at least one Linker Unit and at least one Nucleic Acid Agent.

Exemplary Embodiment 79. The scaffold of any one of the preceding Exemplary Embodiments, wherein the scaffold is

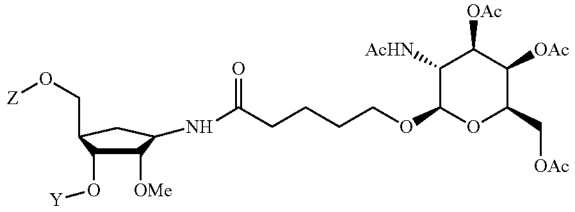

or a pharmaceutically acceptable salt thereof, wherein:

Y is $—P(R^Y)_2$, $—P(OR^Y)(N(R^Y)_2)$, $—P(═O)(OR^Y)R^Y$, $—P(═S)(OR^Y)R^Y$, $—P(═O)(SR^Y)R^Y$, $—P(═S)(SR^Y)R^Y$, $—P(═O)(OR^Y)_2$, $—P(═S)(OR^Y)_2$, $—P(═O)(SR^Y)_2$, $—P(═S)(SR^Y)_2$, or a hydroxy protecting group;

each $R^Y$ independently is H or $C_1$-$C_6$ alkyl optionally substituted with one or more halogen or cyano;

Z is $—P(R^Z)_2$, $—P(OR^Z)(N(R^Z)_2)$, $—P(═O)(OR^Z)R^Z$, $—P(═S)(OR^Z)R^Z$, $—P(═O)(SR^Z)R^Z$, $—P(═S)(SR^Z)R^Z$, $—P(═O)(OR^Z)_2$, $—P(═S)(OR^Z)_2$, $—P(═O)(SR^Z)_2$, $—P(═S)(SR^Z)_2$, or a hydroxy protecting group; and each $R^Z$ independently is H or $C_1$-$C_6$ alkyl optionally substituted with one or more halogen or cyano.

Exemplary Embodiment 80. The scaffold of any one of the preceding Exemplary Embodiments, wherein the scaffold is selected from the scaffolds described in Table Si.

Exemplary Embodiment 81. The scaffold of any one of the preceding Exemplary Embodiments, wherein the scaffold is

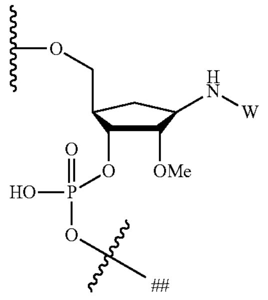

or

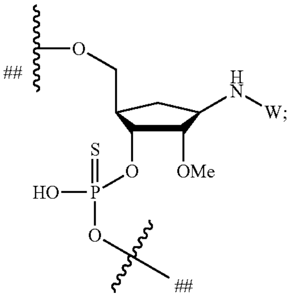

or a pharmaceutically acceptable salt thereof, wherein:

W is an amino substitution group.

Exemplary Embodiment 82. The scaffold of any one of the preceding Exemplary Embodiments, wherein the scaffold is selected from the scaffolds described in Table S2.

Exemplary Embodiment 83. The conjugate of any one of the preceding Exemplary Embodiments, wherein the conjugate is (Linker Unit-$(Ligand)_{0-1})_p$-((Nucleic Acid Agent)-(Linker Unit-$(Ligand)_{0-1})_s)_r$-(Nucleic Acid $Agent)_q$, wherein:

each Linker Unit is independent from another Linker Unit, each Nucleic Acid Agent is independent from another Nucleic Acid Agent, and each Ligand is independent from another Ligand;

each r independently is an integer ranging from 0 to 10;

each s independently is an integer ranging from 0 to 10;

p is an integer ranging from 0 to 10;

q is 0 or 1; and the conjugate comprises at least one Linker Unit, at least one Nucleic Acid Agent, and at least one Ligand.

Exemplary Embodiment 84. The conjugate of any one of the preceding Exemplary Embodiments, wherein the conjugate is selected from the conjugates described in Table C.

Exemplary Embodiment 85. The scaffold or conjugate of any one of the preceding Exemplary Embodiments, wherein the Linker Unit is of Formula (I), wherein W is replaced with an attachment to the Ligand.

Exemplary Embodiment 86. The scaffold or conjugate of any one of the preceding Exemplary Embodiments, wherein the Linker Unit is of Formula (I), wherein Y and/or Z is replaced with an attachment to the Nucleic Acid Agent.

Exemplary Embodiment 87. The scaffold or conjugate of any one of the preceding Exemplary Embodiments, wherein the ligand comprises a carbohydrate moiety.

Exemplary Embodiment 88. The scaffold or conjugate of any one of the preceding Exemplary Embodiments, wherein the carbohydrate moiety comprises a monosaccharide, a disaccharide, a trisaccharide, or a tetrasaccharide.

Exemplary Embodiment 89. The scaffold or conjugate of any one of the preceding Exemplary Embodiments, wherein the carbohydrate moiety comprises galactose or a derivative thereof.

Exemplary Embodiment 90. The scaffold or conjugate of any one of the preceding Exemplary Embodiments, wherein the ligand comprises

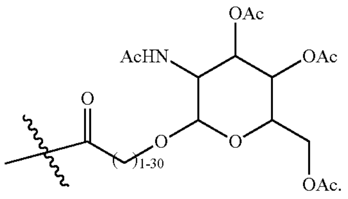

Exemplary Embodiment 91. The scaffold or conjugate of any one of the preceding Exemplary Embodiments, wherein the ligand comprises

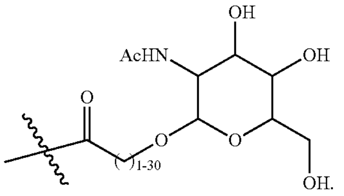

Exemplary Embodiment 92. The scaffold or conjugate of any one of the preceding Exemplary Embodiments, wherein the ligand comprises

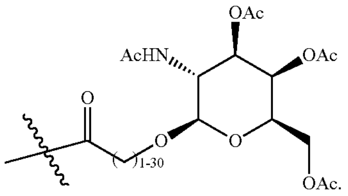

Exemplary Embodiment 93. The scaffold or conjugate of any one of the preceding Exemplary Embodiments, wherein the ligand comprises

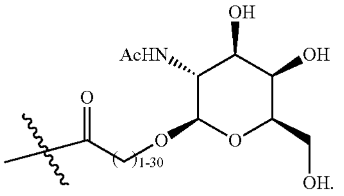

Exemplary Embodiment 94. The scaffold or conjugate of any one of the preceding Exemplary Embodiments, wherein the ligand comprises

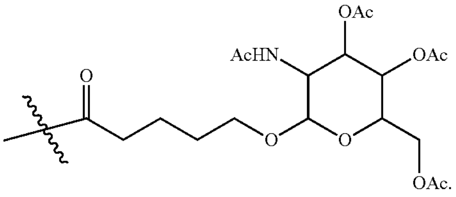 [SMILES: *C(=O)CCCCOC1OC(COC(C)=O)C(OC(C)=O)C(OC(C)=O)C1NC(C)=O]

Exemplary Embodiment 95. The scaffold or conjugate of any one of the preceding Exemplary Embodiments, wherein the ligand comprises

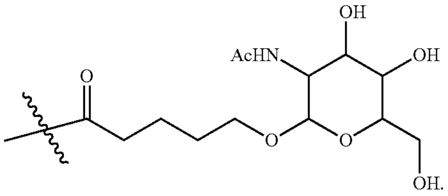 [SMILES: *C(=O)CCCCOC1OC(CO)C(O)C(O)C1NC(C)=O]

Exemplary Embodiment 96. The scaffold or conjugate of any one of the preceding Exemplary Embodiments, wherein the ligand comprises

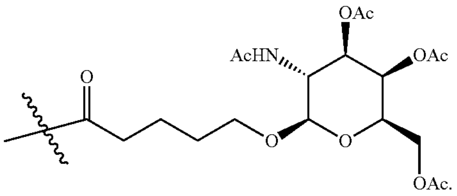 [SMILES: *C(=O)CCCCO[C@@H]1O[C@H](COC(C)=O)[C@H](OC(C)=O)[C@H](OC(C)=O)[C@H]1NC(C)=O]

Exemplary Embodiment 97. The scaffold or conjugate of any one of the preceding Exemplary Embodiments, wherein the ligand comprises

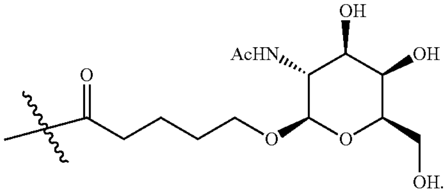 [SMILES: *C(=O)CCCCO[C@@H]1O[C@H](CO)[C@H](O)[C@H](O)[C@H]1NC(C)=O]

Exemplary Embodiment 98. The scaffold or conjugate of any one of the preceding Exemplary Embodiments, wherein the ligand comprises

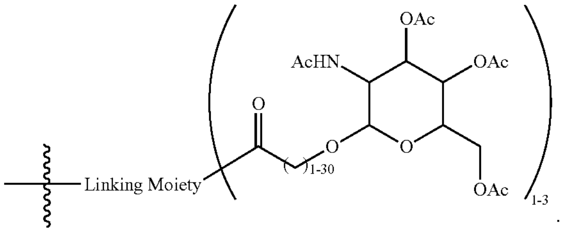

Exemplary Embodiment 99. The scaffold or conjugate of any one of the preceding Exemplary Embodiments, wherein the ligand comprises

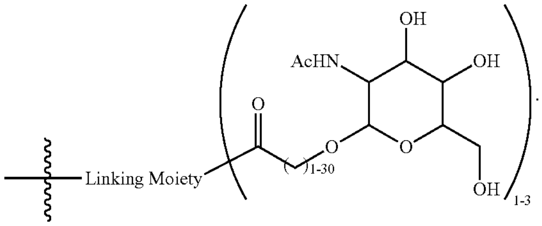

Exemplary Embodiment 100. The scaffold or conjugate of any one of the preceding Exemplary Embodiments, wherein the ligand comprises

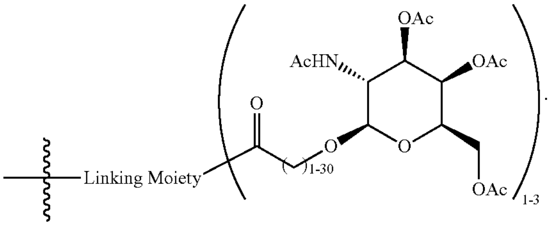

Exemplary Embodiment 101. The scaffold or conjugate of any one of the preceding Exemplary Embodiments, wherein the ligand comprises

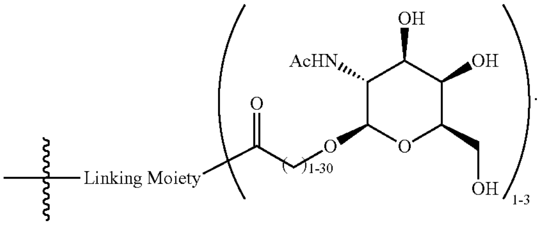

Exemplary Embodiment 102. The scaffold or conjugate of any one of the preceding Exemplary Embodiments, wherein the ligand comprises

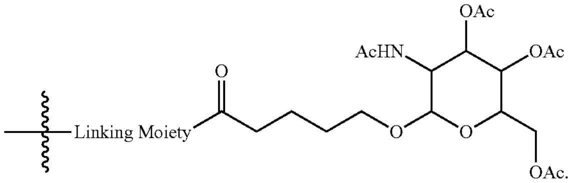

Exemplary Embodiment 103. The scaffold or conjugate of any one of the preceding Exemplary Embodiments, wherein the ligand comprises

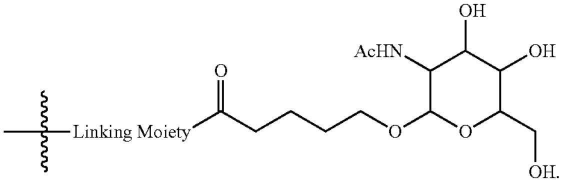

Exemplary Embodiment 104. The scaffold or conjugate of any one of the preceding Exemplary Embodiments, wherein the ligand comprises

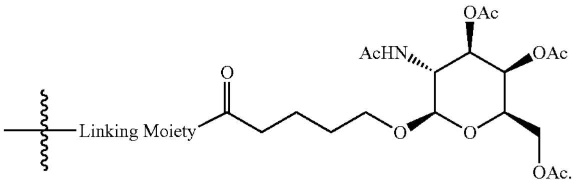

Exemplary Embodiment 105. The scaffold or conjugate of any one of the preceding Exemplary Embodiments, wherein the ligand comprises

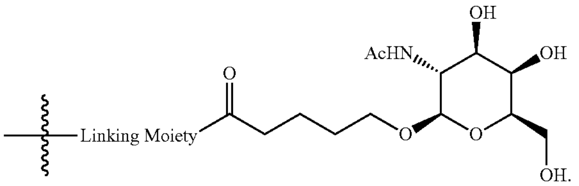

Exemplary Embodiment 106. The scaffold or conjugate of any one of the preceding Exemplary Embodiments, wherein the ligand comprises a lipid.

Exemplary Embodiment 107. The scaffold or conjugate of any one of the preceding Exemplary Embodiments, wherein the ligand comprises a peptide moiety.

Exemplary Embodiment 108. The scaffold or conjugate of any one of the preceding Exemplary Embodiments, wherein the ligand comprises an antibody moiety.

Exemplary Embodiment 109. The scaffold or conjugate of any one of the preceding Exemplary Embodiments, wherein the Nucleic Acid Agent comprises an oligonucleotide.

Exemplary Embodiment 110. The scaffold or conjugate of any one of the preceding Exemplary Embodiments, wherein the Nucleic Acid Agent comprises one or more one or more phosphate groups or one or more analogs of a phosphate group.

Exemplary Embodiment 111. The scaffold or conjugate of any one of the preceding Exemplary Embodiments, wherein the Linker Unit is attached to the Nucleic Acid Agent via a phosphate group, or an analog of a phosphate group, in the Nucleic Acid Agent.

Exemplary Embodiment 112. The scaffold or conjugate of any one of the preceding Exemplary Embodiments, wherein the Nucleic Acid Agent comprises an RNA.

Exemplary Embodiment 113. The scaffold or conjugate of any one of the preceding Exemplary Embodiments, wherein the oligonucleotide is an siRNA, microRNA, antimicroRNA, microRNA mimics, antimiR, antagomir, dsRNA, ssRNA, aptamer, immune stimulatory oligonucleotide, decoy oligonucleotide, splice altering oligonucleotide, triplex forming oligonucleotide, G-quadruplexe, or antisense oligonucleotide.

Exemplary Embodiment 114. A pharmaceutical composition comprising the compound, scaffold, or conjugate of the any one of the preceding Exemplary Embodiments.

Exemplary Embodiment 115. A method of modulating the expression of a target gene in a subject, comprising administering to the subject the conjugate of any one of the preceding Exemplary Embodiments.

Exemplary Embodiment 116. A method of delivering a Nucleic Acid Agent to a subject, comprising administering to the subject the conjugate of any one of the preceding Exemplary Embodiments.

Exemplary Embodiment 117. A method of treating or preventing a disease in a subject in need thereof, comprising administering to the subject a therapeutically effective amount of the conjugate of any one of the preceding Exemplary Embodiments.

Exemplary Embodiment 118. The conjugate of any one of the preceding Exemplary Embodiments for modulating the expression of a target gene in a subject.

Exemplary Embodiment 119. The conjugate of any one of the preceding Exemplary Embodiments for delivering a Nucleic Acid Agent to a subject.

Exemplary Embodiment 120. The conjugate of any one of the preceding Exemplary Embodiments for treating or preventing a disease in a subject in need thereof.

Exemplary Embodiment 121. Use of the conjugate of any one of the preceding Exemplary Embodiments in the manufacture of a medicament for modulating the expression of a target gene in a subject.

Exemplary Embodiment 122. Use of the conjugate of any one of the preceding Exemplary Embodiments in the manufacture of a medicament for delivering a Nucleic Acid Agent to a subject.

Exemplary Embodiment 123. Use of the conjugate of any one of the preceding Exemplary Embodiments in the manufacture of a medicament for treating or preventing a disease in a subject in need thereof.

Exemplary Embodiment 124. The method, conjugate, or use of any one of the preceding Exemplary Embodiments, wherein the subject is a human.

EXAMPLES

Example 1. Synthesis of GalNAc Compounds.

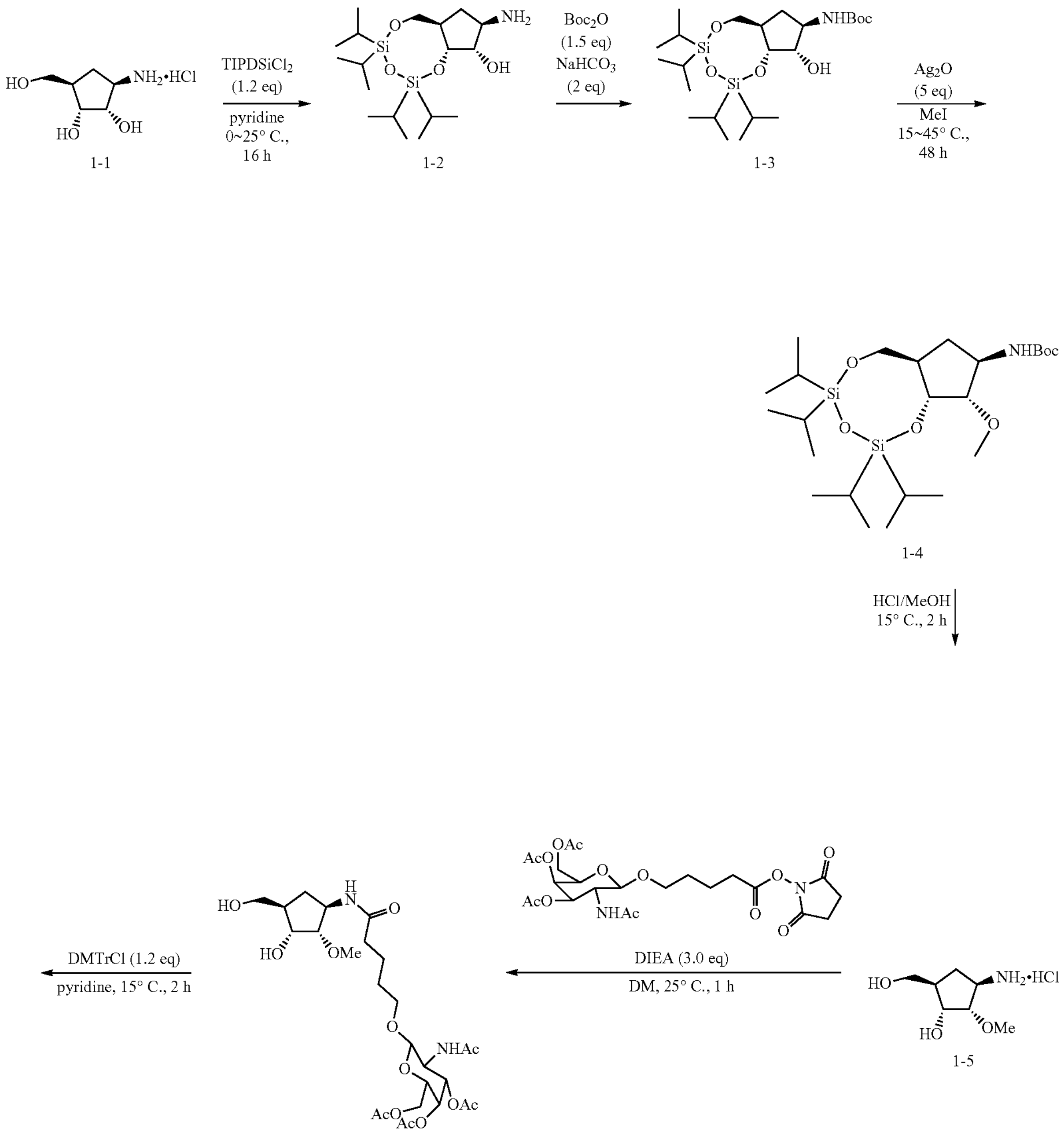

1-1 1-2 1-3 1-4 1-5 1-6

-continued

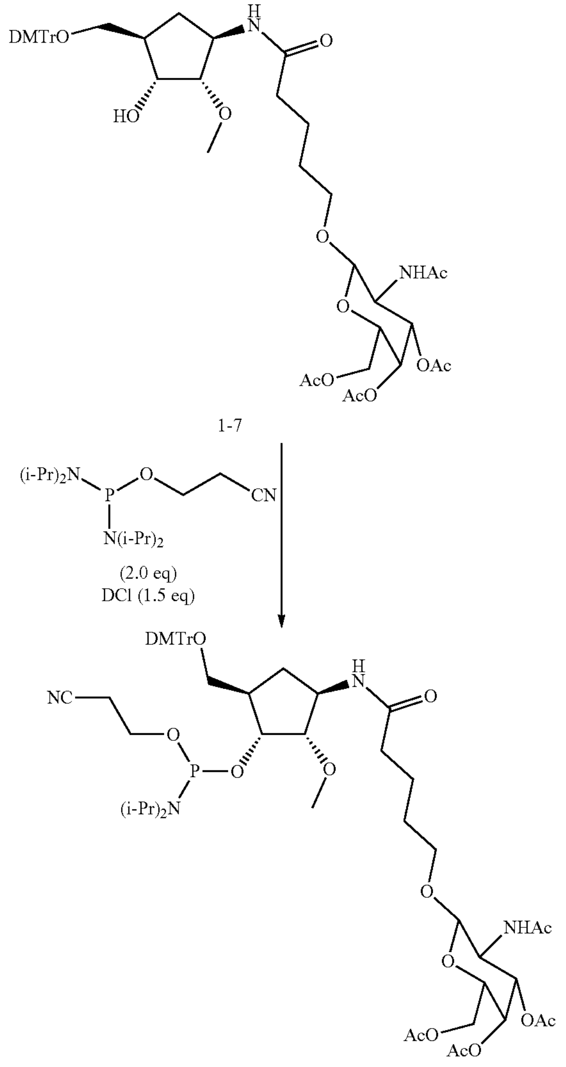

1-7

1-8

(6aR,8R,9S,9aR)-8-amino-2,2,4,4-tetraisopropylhexahydrocyclopenta[f][1,3,5,2,4]-trioxadisilocin-9-ol (1-2). To a solution of compound 1-1 (10.0 g, 54.5 mmol) in pyridine (100 mL) was added $TIPDSiCl_2$ (18.9 g, 59.9 mmol) at 0° C. and the mixture stirred at 25° C. for 16 hrs. The reaction was quenched with MeOH and concentrated in vacuum. The remaining residue was dissolved in EtOAc (200 mL), washed with aq. citric acid (200 mL×2) and brine (200 mL). The organic layer was dried with anhydrous $Na_2SO_4$, filtered and concentrated in vacuum to afford compound 1-2 (42.0 g, 99.0% yield) as a yellow oil. $^1$H NMR: 400 MHz, DMSO-$d_6$, δ 8.15 (s, 2H), 4.75 (d, J=4.4 Hz, 1H), 4.00-3.96 (m, 1H), 3.85 (d, J=3.2 Hz, 2H), 3.82-3.67 (m, 1H), 3.19-3.16 (m, 1H), 2.05-1.95 (m, 2H), 1.19-1.15 (m, 1H), 1.03-0.84 (m, 30H).

Tert-butyl ((6aR,8R,9S,9aR)-9-hydroxy-2,2,4,4-tetraisopropylhexahydrocyclopenta[f][1,3,5,2,4]trioxadisilocin-8-yl)carbamate (1-3). To a solution of compound 1-2 (21.0 g, 53.9 mol) in dioxane (210 mL) was added $Boc_2O$ (17.6 g, 80.8 mmol) and aq. $NaHCO_3$ (11.3 g, 135 mmol). The mixture was stirred at 20° C. for 16 hrs. The reaction mixture was quenched with aq. $NH_4Cl$ (400 mL) and extracted with EtOAc (400 mL×2). The organic layers were washed with brine (400 mL), and dried over $Na_2SO_4$, filtered and concentrated under vacuum. The residue was purified by column chromatography ($SiO_2$, petroleum ether/ethyl acetate=20/1 to 1/1) to afford compound 1-3 (37.3 g, 70.7% yield) as a colorless oil. $^1$H NMR: 400 MHz, DMSO-$d_6$, δ 6.96 (d, J=6.8 Hz, 1H), 4.22 (d, J=4.8 Hz, 1H), 3.92-3.91 (m, 1H), 3.82-3.78 (m, 1H), 3.67-3.57 (m, 2H), 3.34 (s, 1H), 1.99-1.96 (m, 1H), 1.38 (s, 9H), 1.17-0.89 (m, 29H).

Tert-butyl ((6aR,8R,9S,9aR)-2,2,4,4-tetraisopropyl-9 methoxyhexahydro-cyclopenta[f][1,3,5,2,4]trioxadisilocin-8-yl)carbamate (1-4). To a solution of compound 1-3 (12.4 g, 25.3 mmol) in Mel (124 mL) was added $Ag_2O$ (29.3 g, 126 mmol) at 25° C. and the mixture was stirred at 50° C. for 72 hrs. The reaction mixture was then filtered and concentrated in vacuum. The residue was purified by column chromatography ($SiO_2$, petroleum ether/ethyl acetate=20/1 to 1/1) to afford compound 1-4 (15.2 g, 39.7% yield) as a yellow oil. $^1$H NMR: 400 MHz, CDCl3, δ 4.36 (s, 1H), 3.98-3.94 (m, 2H), 3.92 (s, 1H), 3.72-3.68 (m, 2H), 3.54 (s, 3H), 3.41 (s, 1H), 2.22-2.13 (m, 2H), 1.46 (d, J=5.2 Hz, 9H), 1.08-0.91 (m, 29H).

(1R,2S,3R,5R)-3-amino-5-(hydroxymethyl)-2-methoxycyclopentan-1-ol hydrochloride (1-5). To a solution of compound 1-4 (13.2 g, 26.2 mmol) in MeOH (10 ml) was added HCl/MeOH (4 M, 264 mL, 1.06 mol). The mixture was stirred at 25° C. for 2 hrs and concentrated under vacuum to afford compound 1-5 (13.6 g, crude) as a yellow oil, which was used for the next step without further purification.

(2S,3S,4S,5S,6S)-5-acetamido-2-(acetoxymethyl)-6-((5-(((1R,2S,3R,4R)-3-hydroxy-4-(hydroxymethyl)-2-methoxycyclopentyl)amino)-5-oxopentyl)oxy)tetrahydro-2H-pyran-3,4-diyl diacetate (1-6). To a solution of compound 1-5 (5.18 g, 32.1 mmol) and the GalNAc-NHS ester (17.5 g, 32.1 mmol) in DMF (52 mL) was added DIPEA (12.5 g, 96.4 mmol) to achieve a pH of 8. The mixture was stirred at 25° C. for 1 h, quenched with aq. $NaHCO_3$ (200 mL), and extracted with EtOAc (100 mL×2). The organic layers were washed with brine (100 mL), and dried over $Na_2SO_4$, filtered and concentrated under vacuum. The residue was purified by column chromatography ($SiO_2$, petroleum ether/ethyl acetate=10/1 to 1/1) to afford compound 1-6 (14.3 g, 75.4% yield) as a yellow oil. $^1$H NMR: 400 MHz, DMSO-$d_6$, δ 9.11 (s, 1H), 7.85 (d, J=9.2 Hz, 1H), 7.76 (d, J=8.0 Hz, 1H), 5.21 (d, J=3.2 Hz, 1H), 4.98-4.94 (m, 1H), 4.56 (t, J=2.6 Hz, 1H), 4.48 (d, J=8.8 Hz, 1H), 4.31 (d, J=5.6 Hz, 1H), 4.02-4.01 (m, 4H), 3.75-3.74 (m, 3H), 3.30 (s, 3H), 3.28-3.17 (m, 3H), 2.10 (s, 3H), 2.04-1.98 (m, 6H), 1.89 (s, 3H), 1.77 (s, 3H), 1.47-1.45 (m, 4H), 1.30-1.27 (m, 8H), 1.20-0.97 (m, 1H).

(2S,3S,4S,5S,6S)-5-acetamido-2-(acetoxymethyl)-6-((5-(((1R,2S,3R,4R)-4-((bis(4-methoxyphenyl)(phenyl)methoxy)methyl)-3-hydroxy-2-methoxycyclopentyl)amino)-5-oxopentyl)oxy)tetrahydro-2H-pyran-3,4-diyl diacetate (1-7). To a solution of compound 1-6 (8.00 g, 13.55 mmol) in pyridine (80 mL) was added DMTrCl (5.05 g, 14.9 mmol) and the mixture was stirred at 25° C. for 2 hrs. The reaction was quenched with aq. citric acid (100 mL) and extracted with EtOAc (100 mL×2). The organic layers were washed with brine (100 mL), dried over $Na_2SO_4$, filtered and concentrated under vacuum. The residue was purified by column chromatography ($SiO_2$, petroleum ether/ethyl acetate=2/1 to 0/1) to afford compound 1-7 (8.40 g, 40.0% yield) as a yellow oil. $^1$H NMR: 400 MHz, DMSO-$d_6$, δ 7.82 (d, J=9.2 Hz, 1H), 7.75 (d, J=8.0 Hz, 1H), 7.38-7.21 (m, 9H), 6.88 (d, J=8.4 Hz, 4H), 5.21 (d, J=3.2 Hz, 1H), 4.98-4.94 (m, 1H), 4.47 (d, J=8.8 Hz, 1H), 4.40 (d, J=6.4 Hz, 1H), 4.05-4.00 (m, 5H), 3.88 (s, 1H), 3.73-3.71 (m, 8H), 3.33 (s, 3H), 3.31-2.85 (m, 3H), 2.12-1.99 (m, 11H), 1.89 (s, 3H), 1.76 (s, 3H), 1.46-1.45 (m, 4H), 1.03-1.00 (s, 1H).

(2S,3S,4S,5S,6S)-5-acetamido-2-(acetoxymethyl)-6-((5-(((1R,2S,3R,4R)-4-((bis(4-methoxyphenyl)(phenyl)methoxy)methyl)-3-(((2-cyanoethoxy)(diisopropylamino)phosphaneyl)oxy)-2-methoxycyclopentyl)amino)-5-oxopentyl)oxy)tetrahydro-2H-pyran-3,4-diyl diacetate (1-8). To a solution of compound 1-7 (7.40 g, 8.29 mmol) in DCM (74 mL) was added DCI (1.47 g, 12.4 mmol) and 2-cyanoethyl-N,N,N',N'-tetraisopropylphosphoro-diamidite (5.00 g, 16.6 mmol) at 25° C. The reaction was stirred at 25° C. for 1 hr. The mixture was then poured into aq. $NaHCO_3$ (100 mL) and extracted with DCM (100 mL×3). The organic layers were washed with brine (100 mL), dried over sodium sulfate, filtered and concentrated in vacuum. The mixture was purified by column chromatography ($SiO_2$, petroleum ether:ethyl acetate=3/1 to 0/1, 0.1% TEA) to afford the GalNAc amidite compound 1-8 (6.90 g, 68.0% yield) as a white solid. $^1$H NMR: 400 MHz, $CD_3CN$, δ 7.44-7.22 (m, 9H), 6.88-6.85 (m, 4H), 6.48-6.46 (m, 2H), 5.28 (d, J=3.6 Hz, 1H), 5.01-4.97 (m, 1H), 4.50 (d, J=8.4 Hz, 1H), 4.15-4.05 (m, 6H), 3.92 (s, 9H), 3.65-3.45 (m, 4H), 3.36 (t, J=4.8 Hz, 4H), 3.19-2.95 (m, 2H), 2.64-2.30 (m, 3H), 2.17 (s, 2H), 2.05-1.98 (m, 2H), 1.94 (s, 3H), 1.91 (s, 3H), 1.81 (s, 3H), 1.51-1.49 (m, 4H), 1.16-1.12 (m, 9H), 1.04 (d, J=6.8 Hz, 4H).

Example 2. MRNA Knockdown Activity of Exemplary siRNA Duplexes Conjugated with GalNAc G3 to Target Gene 1

The gene silencing activities were studied with exemplary siRNA duplexes listed in Table 1. These siRNA duplexes were conjugated with either GalNAc L96 or GalNAc G3 for hepatic delivery to target gene 1. As shown in FIG. 1, GalNAc G3 provides comparable delivery efficiency and KD activities with GalNAc L96.

CD-1 female mice were administrated subcutaneously with 0.5 mg/kg siRNA duplexes conjugated with GalNAc. A control group was dosed with phosphate buffered saline (PBS). Four days post treatment, animals were then hydrodynamically injected (HDI) through tail vein with 10 μg human gene 1 in pcDNA3.1 (+). The mice were sacrificed one day post-treatment. Liver tissues were collected, stored in RNAlater® overnight at 4° C., and transferred to −80° C. after RNA later removal, for mRNA analysis. Reduction of target mRNA was measured by qPCR using CFX384 TOUCH™ Real-Time PCR Detection System (BioRad Laboratories, Inc., Hercules, CA). All samples were normalized to the PBS treated control animals and plotted using GraphPad Prism software (GraphPad Software Inc., La Jolla, CA).

TABLE 1

Sequence Information of Exemplary siRNA duplexes Tested in FIG. 1.

| | |
|---|---|
| Duplex 1 | [mUs][mAs][mG][mA][mC][fC][mU][fG][fU][fU][fU][mU][mG][mC][mU][mU][mU][mU][mG][mA][L96] [EPmUs][fCs][fA][mA][fA][mA][fG][mC][mA][fA][mA][mA][mC][fA][mG][fG][mU][mC][mU][mAs][mGs][mA] |
| Duplex 2 | [mUs][mAs][mG][mA][mC][fC][mU][fG][fU][fU][fU][mU][mG][mC][mU][mU][mU][mU][mG][mA] [G3s][G3s] [G3] [EPmUs][fCs][fA][mA][fA][mA][fG][mC][mA][fA][mA][mA][mC][fA][mG][fG][mU][mC][mU][mAs][mGs][mA] |
| Duplex 3 | [mUs][mAs][mG][mA][mC][fC][mU][fG][fU][fU][fU][mU][mG][mC][mU][mU][mU][mU][mG][mA] [G3][G3][G3] [EPmUs][fCs][fA][mA][fA][mA][fG][mC][mA][fA][mA][mA][mC][fA][mG][fG][mU][mC][mU][mAs][mGs][mA] |
| Duplex 4 | [mUs][mAs][mG][mA][mC][fC][mU][fG][fU][fU][fU][mU][mG][mC][mU][mU][mU][mUs][mGs][mA] [G3][G3][G3] [EPmUs][fCs][fA][mA][fA][mA][fG] [mC][mA][fA][mA][mA][mC][fA][mG][fG][mU][mC][mU][mAs][mGs][mA] |

The lower-case letters of "f" and "m" indicate 2'-deoxy-2'-fluoro (2'-F), and 2-O-methyl (2'-OMe) sugar modifications, respectively, to adenosine, cytidine, guanosine and uridine; the letter "s" indicates phosphorothioate (PS) linkage; "EP" indicates ethyl phosphonate modification at 5'-end; L96 and G3 indicate the GalNAc structures as shown below:

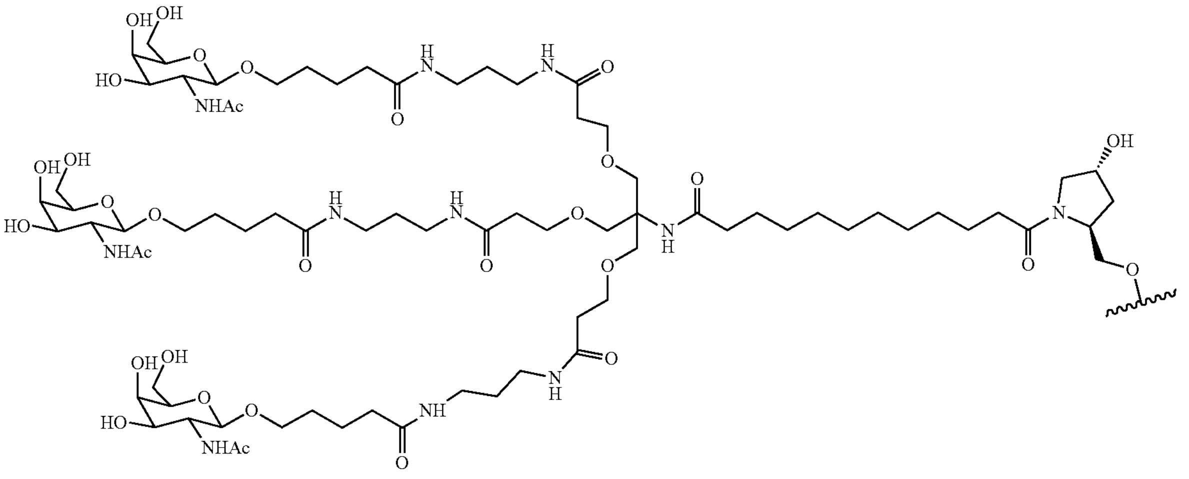

GalNAc L96

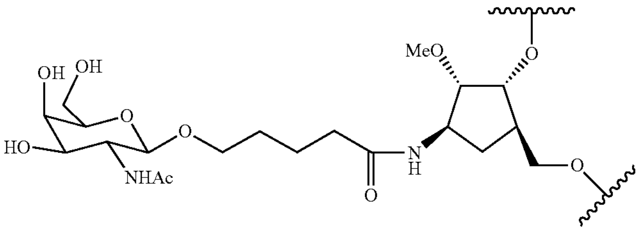

GalNAc G3

EQUIVALENTS

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the disclosure to the precise form disclosed, but by the claims appended hereto.

The invention claimed is:

1. A conjugate, or a pharmaceutically acceptable salt thereof, wherein the conjugate comprises:

(i) one or more Nucleic Acid Agents; and (ii) one or more moieties selected from:

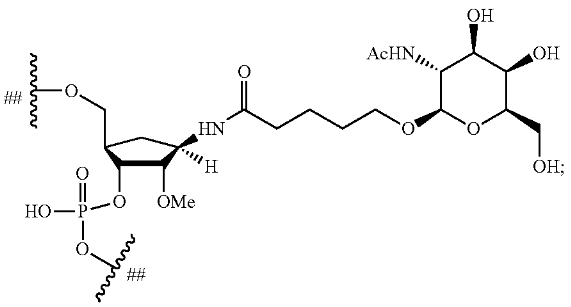

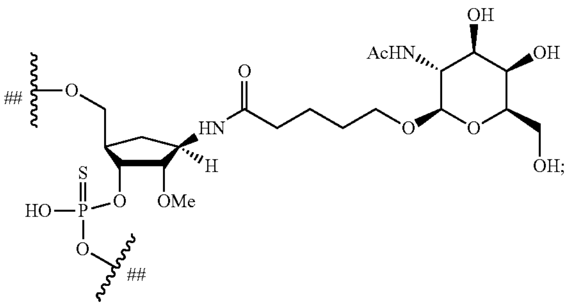

-continued

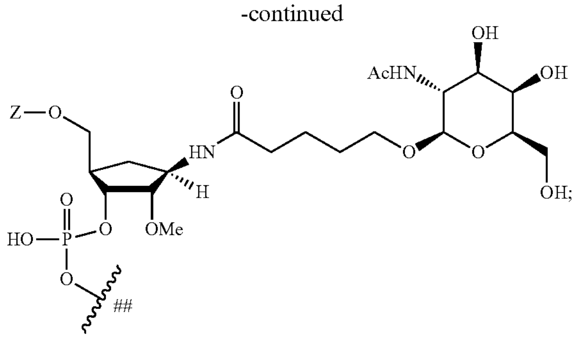

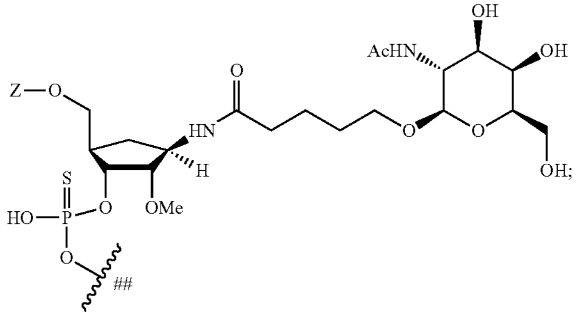

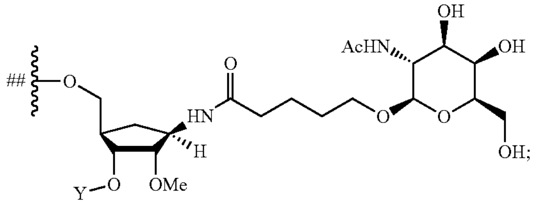

and

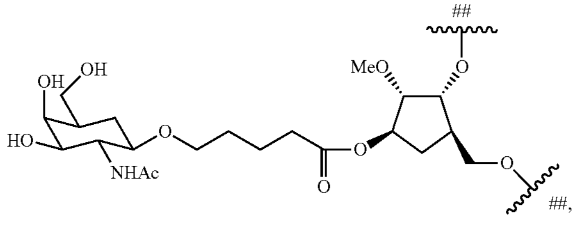

wherein:

Y is H, $C_1$-$C_6$ alkyl optionally substituted with one or more halogen, —P($R^Y$)$_2$, —P($OR^Y$)(N($R^Y$)$_2$), —P(═O)($OR^Y$)$R^Y$, —P(═S)($OR^Y$)$R^Y$, —P(═O)($SR^Y$)$R^Y$, —P(═S)($SR^Y$)$R^Y$, —P(═O)($OR^Y$)$_2$, —P(═S)($OR^Y$)$_2$, —P(═O)($SR^Y$)$_2$, —P(═S)($SR^Y$)$_2$, or a hydroxy protecting group;

each $R^Y$ independently is H or $C_1$-$C_6$ alkyl optionally substituted with one or more halogen or cyano;

Z is H, or $C_1$-$C_6$ alkyl optionally substituted with one or more halogen, —P($R^Z$)$_2$, —P($OR^Z$)(N($R^Z$)$_2$), —P(═O)($OR^Z$)$R^Z$, —P(═S)($OR^Z$)$R^Z$, —P(═O)($SR^Z$)$R^Z$, —P(═S)($SR^Z$)$R^Z$, —P(═O)($OR^Z$)$_2$, —P(═S)($OR^Z$)$_2$, —P(═O)($SR^Z$)$_2$, —P(═S)($SR^Z$)$_2$, or a hydroxy protecting group;

each $R^Z$ independently is H or $C_1$-$C_6$ alkyl optionally substituted with one or more halogen or cyano;

and each ## independently indicates an attachment to the rest of the conjugate.

2. The conjugate of claim 1, wherein Y is H.

3. The conjugate of claim 1, wherein Y is $C_1$-$C_6$ alkyl optionally substituted with one or more halogen.

4. The conjugate of claim 1, wherein Y is —P($R^Y$)$_2$, —P($OR^Y$)(N($R^Y$)$_2$), —P(═O)($OR^Y$)$R^Y$, —P(═S)($OR^Y$)$R^Y$, —P(═O)($SR^Y$)$R^Y$, —P(═S)($SR^Y$)$R^Y$, —P(═O)($OR^Y$)$_2$, —P(═S)($OR^Y$)$_2$, —P(═O)($SR^Y$)$_2$, or —P(═S)($SR^Y$)$_2$.

5. The conjugate of claim 1, wherein Y is a hydroxy protecting group.

6. The conjugate of claim 1, wherein Z is H.

7. The conjugate of claim 1, wherein Z is $C_1$-$C_6$ alkyl optionally substituted with one or more halogen.

8. The conjugate of claim 1, wherein Z is —P($R^Z$)$_2$, —P($OR^Z$)(N($R^Z$)$_2$), —P(═O)($OR^Z$)$R^Z$, —P(═S)($OR^Z$)$R^Z$, —P(═O)($SR^Z$)$R^Z$, —P(═S)($SR^Z$)$R^Z$, —P(═O)($OR^Z$)$_2$, —P(═S)($OR^Z$)$_2$, —P(═O)($SR^Z$)$_2$, or —P(═S)($SR^Z$)$_2$.

9. The conjugate of claim 1, wherein Z is a hydroxy protecting group.

10. The conjugate of claim 1, wherein the conjugate further comprises a lipid moiety, a peptide moiety, or an antibody moiety.

11. The conjugate of claim 1, wherein each Nucleic Acid Agent independently comprises an oligonucleotide.

12. A pharmaceutical composition comprising the conjugate of claim 1, and at least one pharmaceutically acceptable excipient or carrier.

13. A method of reducing the expression of a target gene in a subject or delivering a Nucleic Acid Agent to a subject, comprising administering to the subject the conjugate of claim 1.

14. The conjugate of claim 1, wherein the conjugate comprises

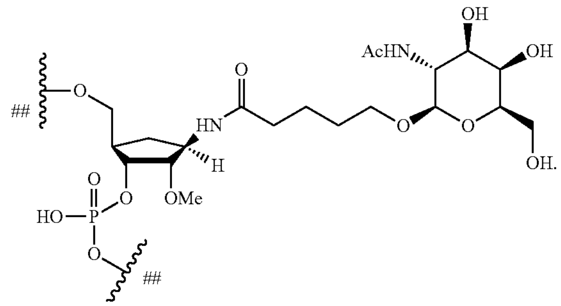

15. The conjugate of claim 1, wherein the conjugate comprises

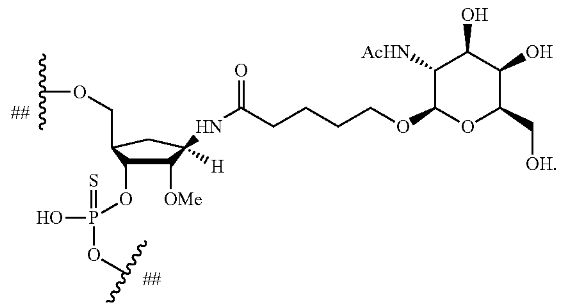

16. The conjugate of claim 1, wherein the conjugate comprises
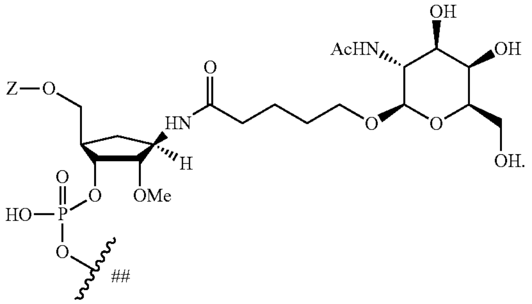
17. The conjugate of claim 1, wherein the conjugate comprises
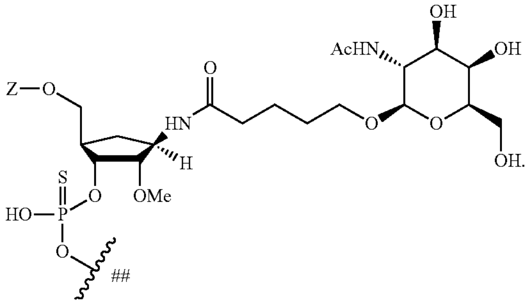
18. The conjugate of claim 1, wherein the conjugate comprises
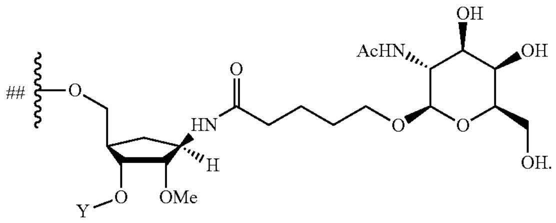
19. The conjugate of claim 1, wherein the conjugate comprises
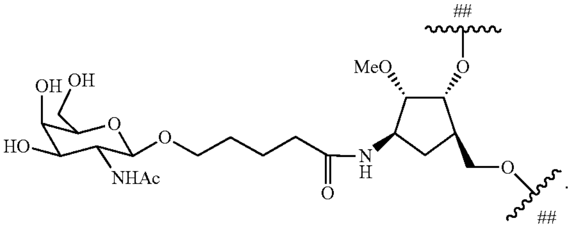 [SMILES: *OC[C@H]1C[C@@H](NC(=O)CCCCOC2OC(CO)C(O)C(O)C2NC(C)=O)[C@H](OC)[C@@H]1O*]
* * * * *